United States Patent
Hawley-Nelson et al.

(10) Patent No.: US 8,058,068 B2
(45) Date of Patent: *Nov. 15, 2011

(54) PEPTIDE-ENHANCED TRANSFECTIONS

(75) Inventors: Pamela Hawley-Nelson, Silver Spring, MD (US); Jianqing Lan, Germantown, MD (US); PoJen Shih, Columbia, MD (US); Joel A. Jessee, Mt. Airy, MD (US); Kevin P. Schifferli, Germantown, MD (US); Gulilat Gebeyehu, Silver Springs, MD (US); Valentina C. Ciccarone, Gaithersburg, MD (US); Krista L. Evans, Germantown, MD (US)

(73) Assignee: Life Technologies Corporation, Carlsbad, CA (US)

( * ) Notice: Subject to any disclaimer, the term of this patent is extended or adjusted under 35 U.S.C. 154(b) by 315 days.

This patent is subject to a terminal disclaimer.

(21) Appl. No.: 10/200,879

(22) Filed: Jul. 23, 2002

(65) Prior Publication Data

US 2003/0144230 A1 Jul. 31, 2003

Related U.S. Application Data

(63) Continuation of application No. 09/911,569, filed on Jul. 23, 2001, now abandoned, which is a continuation of application No. 09/039,780, filed on Mar. 16, 1998, now Pat. No. 6,376,248, which is a continuation-in-part of application No. 08/818,200, filed on Mar. 14, 1997, now Pat. No. 6,051,429, which is a continuation-in-part of application No. 08/658,130, filed on Jun. 4, 1996, now Pat. No. 5,736,392, which is a continuation-in-part of application No. 08/477,354, filed on Jun. 7, 1995, now abandoned.

(51) Int. Cl.
 *C12N 15/88* (2006.01)
 *C07K 14/00* (2006.01)
 *C07K 14/025* (2006.01)
 *C07H 21/02* (2006.01)
 *C07H 21/04* (2006.01)

(52) U.S. Cl. .............. 435/458; 530/324; 428/402.2; 536/23.1

(58) Field of Classification Search ................ None
See application file for complete search history.

(56) References Cited

U.S. PATENT DOCUMENTS

| | | | |
|---|---|---|---|
| 4,235,871 A | 11/1980 | Papahadjopoulous | |
| 4,897,355 A | 1/1990 | Eppstein et al. | |
| 4,946,787 A | 8/1990 | Eppstein et al. | |
| 4,959,217 A | 9/1990 | Sanders et al. | |
| 5,165,925 A | 11/1992 | Leong | |
| 5,166,320 A | 11/1992 | Wu et al. | |
| 5,196,510 A | 3/1993 | Rodwell et al. | |
| 5,198,423 A | 3/1993 | Taguchi et al. | |
| 5,264,618 A | 11/1993 | Felgner et al. | |
| 5,266,106 A | 11/1993 | Breton | |
| 5,279,833 A | 1/1994 | Rose | |
| 5,283,185 A | 2/1994 | Epand et al. | |
| 5,328,984 A | 7/1994 | Pastan et al. | |
| 5,334,761 A | 8/1994 | Gebeyehu et al. | |
| 5,338,532 A | 8/1994 | Tomalia et al. | |
| 5,342,921 A | 8/1994 | Cousens et al. | |
| 5,354,844 A | 10/1994 | Beug et al. | |
| 5,491,074 A | 2/1996 | Aldwin et al. | |
| 5,521,291 A | 5/1996 | Curiel et al. | |
| 5,527,524 A | 6/1996 | Tomalia et al. | |
| 5,532,142 A | 7/1996 | Johnston et al. | |
| 5,545,412 A | 8/1996 | Eppstein et al. | |
| 5,547,932 A | 8/1996 | Curiel et al. | |
| 5,560,929 A | 10/1996 | Hedstrand et al. | |
| 5,574,142 A | 11/1996 | Meyer, Jr. et al. | |
| 5,578,475 A | 11/1996 | Jessee | |
| 5,583,198 A | 12/1996 | Whittaker | |
| 5,587,441 A | 12/1996 | Frechet et al. | |
| 5,587,446 A | 12/1996 | Frechet et al. | |
| 5,589,392 A | 12/1996 | Short | |
| 5,589,466 A | 12/1996 | Felgner et al. | |
| 5,595,897 A | 1/1997 | Midoux et al. | |
| 5,595,899 A | 1/1997 | Sato et al. | |
| 5,627,159 A | 5/1997 | Shih et al. | |
| 5,631,329 A | 5/1997 | Yin et al. | |
| 5,650,096 A | 7/1997 | Harris et al. | |
| 5,658,776 A | 8/1997 | Flotte et al. | |
| 5,661,025 A | 8/1997 | Szoka, Jr. et al. | |
| 5,670,347 A | 9/1997 | Gopal | |

(Continued)

FOREIGN PATENT DOCUMENTS

AU    B-26526/92    9/1992

(Continued)

OTHER PUBLICATIONS

Verma et al. Gene Therapy—promises, problems and prospects. Nature. vol. 389, No. 6648, pp. 239-242, Sep. 1997.*
Palu et al. In pursuit of new developments for gene therapy of human diseases. J Biotechnol. vol. 68, No. 1, pp. 1-13, Feb. 1999.*
Luo et al. Synthetic DNA delivery systems. Nat Biotechnol. vol. 18, No. 1, pp. 33-37, Jan. 2000.*
Edelstein et al. Gene therapy clinical trials worldwide 1989-2004—an overview. J Gene Med. vol. 6, No. 6):597-602, Jun. 2004.*
Remy et al. Targeted gene transfer into hepatoma cells with lipopolyamine-condensed DNA particles presenting galactose ligands: a stage toward artificial viruses. PNAS, USA. vol. 92, No. 5, pp. 1744-1748, Feb. 28, 1995.*

(Continued)

*Primary Examiner* — Jennifer Dunston

(57) ABSTRACT

The present invention provides compositions useful for transfecting eukaryotic cells comprising nucleic acid complexes with peptides, wherein the peptide is optionally covalently coupled to a nucleic acid-binding group, and cationic lipids or dendrimers as transfection agents. The invention also provides transfection compositions in which a peptide is covalently linked to the transfection agent (lipid, cationic lipid or dendrimer). Inclusion of peptides or modified-peptides in transfection compositions or covalent attachment of peptides to transfection agents results in enhanced transfection efficiency. Methods for the preparation of transfection compositions and methods of using these transfection compositions as intracellular delivery agents and extracellular targeting agents are also disclosed.

25 Claims, 16 Drawing Sheets

U.S. PATENT DOCUMENTS

| | | | |
|---|---|---|---|
| 5,674,908 A * | 10/1997 | Haces et al. | 514/642 |
| 5,674,977 A | 10/1997 | Gariepy | |
| 5,693,509 A | 12/1997 | Cotten et al. | |
| 5,703,055 A | 12/1997 | Felgner et al. | |
| 5,714,166 A | 2/1998 | Tomalia et al. | |
| 5,719,131 A | 2/1998 | Harris et al. | |
| 5,736,387 A | 4/1998 | Paul et al. | |
| 5,736,392 A | 4/1998 | Hawley-Nelson et al. | |
| 5,744,335 A | 4/1998 | Wolff et al. | |
| 5,747,641 A | 5/1998 | Frankel et al. | |
| 5,759,805 A | 6/1998 | Feldhaus et al. | |
| 5,773,527 A | 6/1998 | Tomalia et al. | |
| 5,783,565 A | 7/1998 | Lee et al. | |
| 5,795,587 A | 8/1998 | Gao et al. | |
| 5,807,746 A | 9/1998 | Lin et al. | |
| 5,811,297 A | 9/1998 | Gopal | |
| 5,827,703 A | 10/1998 | Debs et al. | |
| 5,830,430 A | 11/1998 | Unger et al. | |
| 5,830,878 A | 11/1998 | Gorman et al. | |
| 5,831,397 A | 11/1998 | Stevens et al. | |
| 5,834,439 A | 11/1998 | Haces et al. | |
| 5,837,533 A | 11/1998 | Boutin | |
| 5,844,107 A | 12/1998 | Hanson et al. | |
| 5,854,224 A | 12/1998 | Lockett et al. | |
| 5,869,606 A | 2/1999 | Whittaker | |
| 5,877,302 A | 3/1999 | Hanson et al. | |
| 5,891,648 A | 4/1999 | Martin et al. | |
| 5,906,922 A | 5/1999 | Whittaker et al. | |
| 5,908,635 A | 6/1999 | Thierry | |
| 5,908,777 A | 6/1999 | Lee et al. | |
| 5,922,859 A | 7/1999 | Birnstiel et al. | |
| 5,948,925 A | 9/1999 | Keynes et al. | |
| 5,955,365 A | 9/1999 | Szoka et al. | |
| 5,972,900 A | 10/1999 | Ferkol, Jr. et al. | |
| 5,972,901 A | 10/1999 | Ferkol et al. | |
| 5,976,567 A | 11/1999 | Wheeler et al. | |
| 5,994,109 A | 11/1999 | Woo et al. | |
| 6,008,202 A | 12/1999 | Huang et al. | |
| 6,008,336 A | 12/1999 | Hanson et al. | |
| 6,017,735 A | 1/2000 | O'Hare et al. | |
| 6,020,202 A | 2/2000 | Jessee | |
| 6,022,874 A | 2/2000 | Wheeler | |
| 6,022,950 A | 2/2000 | Murphy | |
| 6,033,884 A | 3/2000 | Woo et al. | |
| 6,051,429 A | 4/2000 | Hawley-Nelson et al. | |
| 6,056,938 A | 5/2000 | Unger et al. | |
| 6,075,012 A | 6/2000 | Gebeyehu et al. | |
| 6,077,835 A | 6/2000 | Hanson et al. | |
| 6,086,913 A | 7/2000 | Tam et al. | |
| 6,110,662 A | 8/2000 | Foung et al. | |
| 6,110,916 A | 8/2000 | Haces et al. | |
| 6,126,964 A * | 10/2000 | Wolff et al. | 424/450 |
| 6,150,168 A | 11/2000 | Woo et al. | |
| 6,177,554 B1 | 1/2001 | Woo et al. | |
| 6,214,804 B1 | 4/2001 | Felgner | |
| 6,300,317 B1 | 10/2001 | Szoka et al. | |
| 6,335,199 B1 | 1/2002 | Bischoff et al. | |
| 6,376,248 B1 | 4/2002 | Hawley-Nelson et al. | |
| 6,399,663 B1 | 6/2002 | Haces et al. | |
| 6,521,456 B1 | 2/2003 | Siebenkotten et al. | |
| 6,716,882 B2 | 4/2004 | Haces et al. | |
| 6,773,920 B1 | 8/2004 | Dalby et al. | |
| 6,989,434 B1 | 1/2006 | Gebeyehu et al. | |
| RE39,220 E | 8/2006 | Gopal | |
| 7,166,298 B2 | 1/2007 | Jessee et al. | |
| 7,335,509 B2 | 2/2008 | Huang et al. | |
| 7,361,640 B2 | 4/2008 | Huang et al. | |
| 7,479,573 B2 | 1/2009 | Chu et al. | |
| 2002/0077305 A1 | 6/2002 | Jessee et al. | |
| 2002/0086849 A1 | 7/2002 | Gebeyehu et al. | |
| 2003/0069173 A1 | 4/2003 | Hawley-Nelson et al. | |
| 2004/0102606 A1 | 5/2004 | Balicki et al. | |
| 2004/0152770 A1 | 8/2004 | Haces et al. | |
| 2004/0176282 A1 | 9/2004 | Dalby et al. | |
| 2005/0260757 A1 | 11/2005 | Gebeyehu et al. | |
| 2006/0229246 A1 | 10/2006 | Hawley-Nelson et al. | |
| 2008/0153166 A1 | 6/2008 | Huang et al. | |

FOREIGN PATENT DOCUMENTS

| | | |
|---|---|---|
| EP | 0 304 111 B1 | 7/1988 |
| EP | 0 359 347 B1 | 8/1989 |
| EP | 0 359 347 | 3/1990 |
| EP | 0424688 | 5/1991 |
| EP | 0 544 292 | 11/1992 |
| EP | 1 236 473 A2 | 9/2002 |
| WO | WO 87/02061 | 4/1987 |
| WO | WO 90/09736 | 9/1990 |
| WO | WO 90/11092 | 10/1990 |
| WO | WO 91/04753 | 4/1991 |
| WO | WO 91/07947 | 6/1991 |
| WO | WO-91/08191 | 6/1991 |
| WO | WO-91/09958 | 7/1991 |
| WO | WO 91/15501 | 10/1991 |
| WO | WO 91/16024 | 10/1991 |
| WO | WO 91/17424 | 11/1991 |
| WO | WO92/13570 | 8/1992 |
| WO | WO 92/15694 | 9/1992 |
| WO | WO 92/21752 | 12/1992 |
| WO | WO 92/22635 | 12/1992 |
| WO | WO 93/05162 | 3/1993 |
| WO | WO93/07282 | 4/1993 |
| WO | WO93/07283 | 4/1993 |
| WO | WO-93/18759 | 9/1993 |
| WO | WO 9319768 A1 * | 10/1993 |
| WO | WO-93/23425 | 11/1993 |
| WO | WO94/04696 | 3/1994 |
| WO | WO-94/05624 | 3/1994 |
| WO | WO94/23751 | 10/1994 |
| WO | WO-94/23751 | 10/1994 |
| WO | WO 94/27435 | 12/1994 |
| WO | WO95/02397 | 1/1995 |
| WO | WO-95/02397 | 1/1995 |
| WO | WO-95/02698 | 1/1995 |
| WO | WO95/17373 | 6/1995 |
| WO | WO-95/20682 | 8/1995 |
| WO | WO 95/21259 | 8/1995 |
| WO | WO95/24221 | 9/1995 |
| WO | WO95/31557 | 11/1995 |
| WO | WO96/01841 | 1/1996 |
| WO | WO 9605218 A1 * | 2/1996 |
| WO | WO96/10038 | 4/1996 |
| WO | WO 96/15811 | 5/1996 |
| WO | WO96/22321 | 7/1996 |
| WO | WO96/22765 | 8/1996 |
| WO | WO96/31549 | 10/1996 |
| WO | WO-96/40961 | 12/1996 |
| WO | WO 97/05265 | 2/1997 |
| WO | WO-97/11683 | 4/1997 |
| WO | WO 97/28817 A1 | 8/1997 |
| WO | WO-98/00110 | 1/1998 |
| WO | WO 98/02190 | 1/1998 |
| WO | WO 98/32866 | 7/1998 |
| WO | WO-98/40499 | 9/1998 |
| WO | WO-98/40502 | 9/1998 |
| WO | WO 99/29712 | 6/1999 |
| WO | WO-99/58694 | 11/1999 |
| WO | WO-00/03694 | 1/2000 |
| WO | WO 02/34879 | 5/2002 |
| WO | WO-2004/105697 | 12/2004 |

OTHER PUBLICATIONS

Kamata et al. Amphiphilic peptides enhance the efficiency of liposome-mediated DNA transfection. Nucleic Acids Research. vol. 22, No. 3, pp. 536-537, Feb. 11, 1994.*

Lappidot et al. Fusion-mediated microinjection of liposome-enclosed DNA into cultured cells with the aid of influenza virus glycoproteins. vol. 189, No. 2, pp. 241-246, Aug. 1990.*

Felgner et al. Enhanced gene delivery and mechanism studies with a novel series of cationic lipid formulations. J Biol Chem. vol. 269, No. 4, pp. 2550-2561, Jan. 1994.*

Barthel et al. Gene transfer optimization with lipospermine-coated DNA. DNA Cell Biol. vol. 12, No. 6, pp. 553-560, Jul.-Aug. 1993.*

GenBank Accession No. CAA76847, GI: 3336842, publicly available Jul. 1998.*

Fischer-Fantuzzi et al. Cell-dependent efficiency of reiterated nuclear signals in a mutant simian virus 40 oncoprotein targeted to the nucleus. Molecular and Cellular Biology, vol. 8, No. 12, pp. 5495-5503, Dec. 1988.*

Abremski, K. et al. (1983), "Studies on the Properties of P1 Site-Specific Recombination: Evidence for Topologically Unlinked Products following Recombination," Cell 32:1301-1311.

Balicki, D. et al. (Oct. 2000), "Histone H2A-mediated Transient Cytokine Gene Delivery Induces Efficient Antitumor Responses in Murine Neuroblastoma," Proc. Natl. Acad. Sci. USA 97:11500-11504.

Behr, J-P. (1994), "Gene Transfer with Synthetic Cationic Amphiphiles: Prospects for Gene Therapy," Bioconjug. Chem. 5:382-389.

Bonfanti, M. et al. (Apr. 1997), "p21$^{WAFT}$-derived Peptides Linked to an Internalization Peptide Inhibit Human Cancer Cell Growth," Cancer Res. 57;1442-1446.

Bottger, M. et al. (1988), "Condensation of vector DNA by the chromosomal protein HMG1 results in efficient transfection," Biochim. Biophys. Acta 950:221-228.

Bottger, M. et al. (1990), "Transfection by DNA-nuclear protein HMG1 complexes: Raising of efficiency and role of DNA topology," Arch. Geschwulstforsch. 60:265-270.

Chen, X. et al. (1994), "A self-initiating eukaryotic transient gene expression system based on cotransfection of bacteriophage T7 RNA polymerase and DNA vectors containing a T7 autogene," Nucl. Acids Res. 22(11):2114-2120.

Cheng, S. et al. (Jun. 1994), "Effective amplification of long targets from cloned inserts and human genomic DNA," Proc. Natl. Acad. Sci. USA 91:5695-5699.

Cotten, M. and Wagner, E. (1993), "Non-viral approaches to gene therapy," Curr. Opin. Biotechnol. 4:705-710.

Derer et al. (1999), "Direct protein transfer to terminally differenitated muscle cells," J. Mol. Medicine 77:609-613.

Derossi, D. et al. (1994), "The Third Helix of the Antennapedia Homeodomain Translocates through Biological Membranes," J. Biol. Chem. 269(14):10444-10450.

Derossi, D. et al. (1996), "Cell Internalization of the Third Helix of the Antennapedia Homeodomain is Receptor-independent," J. Biol. Chem. 271(30):18188-18193.

Elliott, G. and O'Hare, P. (Jan. 1999), "Intercellular trafficking of VP22-GFP fusion proteins," Gene Therapy 6:149-151.

Elliott, G. and O'Hare, P. (1997), "Intercellular Trafficking and Protein Delivery by a Herpesvirus Structural Protein," Cell 88:223-233.

Fischer, U. et al. (1995), "The HIV-1 Rev Activation Domain is a Nuclear Export Signal That Accesses an Export Pathway Used by Specific Cellular RNAs," Cell 82:475-483.

Fritz, J.D. et al. (Aug. 1996), "Gene Transfer into Mammalian Cells Using Histone-Condensed Plasmid DNA," Human Gene Therapy 7:1395-1404.

Giles, R.V. (Jun. 2000), "Antisense oligonucleotide technology: From EST to therapeutics," Curr. Opin. Mol. Therap. 2:238-252.

Guo, F. et al. (Sep. 1997), "Structure of Cre recombinase complexed with DNA in a site-specific recombination synapse," Nature 389:40-46.

Invitrogen Corp. (1999), "Voyager™—The Power of Translocation," catalog, (1999), pp. 5.1-5.6.

Hall, H. et al. (1996), "Inhibition of FGF-stimulated phosphatidylinositol hydrolysis and neurite outgrowth by a cell-membrane permeable phosphopeptide," Curr. Biol. 6(5):580-587.

Hart, S. et al. (Mar. 1998), "Lipid-Mediated Enhancement of Transfection by a Nonviral Integrin-Targeting Vector,"Human Gene Therapy 9:575-585.

Hoess, R.H. et al. (1982), "P1 site-specific recombination: Nucleotide sequence of the recombining sites," Proc. Natl. Acad. Sci. USA 79:3398-3402.

Langel, U. et al. (Jul. 1997), "Cell Penetrating PNA Constructs," J. Neurochem. (Supplement) 69:S260.

Life Technologies Inc. catalogue and reference guide, (1993-1994), p. 9-19.

Life Technologies Inc. catalogue, Spectrum, pp. 1-8 (Sep. 1999).

Mack, K.D. et al. (1994), "Cationic Lipid Enhances in vitro Receptor-mediated Transfection," Am. J. Med. Sci. 307:138-143.

Mazur, W. et al. (1993), "The Efficiency of Lipofectin-Mediated Gene Transfer into Porcine and Human Coronary Smooth Muscle Cells is Dramatically Improved by the Influenza Virus Hemagglutinin Antigen," J. Am. Coll. Cardial. 21:186A abstract #889-31.

Morham, S.G. and Shuman, S. (1992), "Covalent and Noncovalent DNA Binding by Mutants of Vaccinia DNA Topoisomerse I," J. Biol. Chem. 267(22):15984-15992.

Murphy, A.L. and Murphy, S. (Jan. 1999), "Catch VP22: the hitch-hiker's ride to gene therapy?" Gene Therapy 6:4-5.

Neckers, L.M. (1993), "Cellular Internalization of Oligodeoxynucleotides," in Antisense Research and Applications, Crooke, S.T. and Leblue, B., eds., CRC Press, LLC, Boca Raton, FL, pp. 451-460.

Neurath, et al. (1990), "B cell epitope mapping of human immunodeficiency virus envelope glycoproteins with long (19- to 36-residue) synthetic peptides," J. Gen. Virol. 71:85-95.

Niidome et al. (Jun. 1997) "Binding of Cationic α-Helical Peptides to Plasmid DNA and Their Gene Transfer Abilities into Cells," *The Journal of Biological Chemistry* 272(24):15307-15312.

Perez, F. et al. (1994), "Rab3A and Rab3B Carboxy-Terminal Peptides Are Both Potent and Specific Inhibitors of Prolactin Release by Rat Cultured Anterior Pituitary Cells," Mol. Endocrinol. 8(9):1278-1287.

Perez, F. et al. (1992), "Antennapedia homeobox as a signal for the cellular internalization and nuclear addressing of a small exogenous peptide," J. Cell Sci. 102:717-722.

Prochiantz, A. (1996), "Getting hydrophilic compounds into cells: lessons from homeopeptides," Current Opinion in Neurobiology 6:629-634.

Prochiantz, A. (1998), "Peptide nucleic acid smugglers," Nature Biotechnol. 16:819-820.

Richardson, J.H. et al. (Apr. 1995), "Phenotypic knockout of the high-affinity human interleukin 2 receptor by intracellular single-chain antibodies against the α subunit of the receptor," Proc. Natl. Acad. Sci. USA 92:3137-3141.

Rothenberg, M. et al. (1989), "Oligodeoxynucleotides as Anti-Sense Inhibitors of Gene Expression: Therapeutic Implications," J. Natl. Can. Inst. 81:1539-1544.

Shuman, S. and Moss, B. (1987), "Identification of a vaccinia virus gene encoding a type I DNA topoisomerase," Proc. Natl. Acad. Sci. USA 84:7478-7482.

Sigma Catalog, 1993 pp. 1028-1034.

Troy, C.M. et al. (1996), "Downregulation of Cu/Zn Superoxide Dismutase Leads to Cell Death via the Nitric Oxide-Peroxynitrite Pathway," J. Neurosci. 16(1):253-161.

Trubetskoy, V.S. et al. (1992), "Cationic Liposomes Enhance Targeted Delivery and Expression of Exogenous DNA Mediated by N-terminal Modified Poly(L-lysine)-antibody Conjugate in Mouse Lung Endothelial Cells," Biochim. Biophys. Acta.1131:311-313.

Trubetskoy, V.S. et al. (1992), "Use of N-Terminal Modified Poly(L-lysine)-Antibody Conjugates as a Carrier for Targeted Gene Delivery in Mouse Lung Endothelial Cells," Bioconjugate Chem. 3:323-327.

van der Krol, A.R. et al. (1988), "Modulation of Eukaryotic Gene Expression by Complementary RNA or DNA Sequences," Biotechniques 6:958-976.

Wang et al. (1997), "Positive and negative regulation of gene expression in eukaryotic cells with an inducible transcriptional regulator," Gene Therapy 4:432-441.

Wen, W. et al. (Aug. 1995), "Identification of a Signal for Rapid Export of Proteins from the Nucleus," Cell 82:463-473.

Wilke, M. et al. (1996), "Efficacy of a peptide-based gene delivery system depends on mitotic activity," Gene Therapy 3:1133-1142.

Zabner, J. et al. (1995), "Cellular and Molecular Barriers to Gene Transfer by a Cationic Lipid," J. Biol. Chem. 270(32):18997-19007.

Zaitsev, S.V. et al. (Jun. 1997), "H1 and HMG17 extracted from calf thymus nuclei are efficient DNA carriers in gene transfer," Gene Therapy 4:586-592.

Aumailley, M. et al. (1989), "Cell Attachment Properties of Collagen Type VI and Arg-Gly-Asp Dependent Binding to its α2(VI) and α3(VI) Chains," Exp. Cell Res. 181:463-474.

Behr, J-P. et al. (1989), "Efficient gene transfer into mammalian primary endocrine cells with lipopolyamine-coated DNA," Proc. Natl. Acad. Sci. USA 86:6982-6986.

Bielinska, A. et al. (1996), "Regulation of in vivo gene expression using antisense oligonucleotides or antisense expression plasmids transfected using starburst PAMAM dendrimers," Nucl. Acids Res. 24(11):2176-2182.

Bonifaci, N. et al. (1995), "Nuclear translocation of an exogenous fusion protein containing HIV Tat requires unfolding," AIDS 9(9):995-1000.

Braunlin et al., "Equilibrium dialysis studies of polyamine binding to DNA," Biopolymers 21:1301-1314.

Carrasco, L. et al. (1982),"Modification of Membrane Permeability in Vaccinia Virus-Infected Cells," J. Virol. 117:62-69.

Ciccarone et al. (1993), "Cationic Liposome-Mediated Transfection of Eukaryotic Cells: High Efficiency Nucleic Acid Delivery with Lipofectin, Lipofectace™, and Lipofectamine™ Reagents," FASEB J., Abstracts, 7(7):A1131, Abstract No. 454.

Ciccarone et al., "DMRIE-C reagent for transfection of suspension cells and for RNA transfections," Focus 17:84-87.

Cotton et al. (1992), "High-efficiency receptor-mediated delivery of small and large 48 kilobase gene constructs using the endosome-disruption activity of defective or chemically inactivated adenovirus particles," Proc. Natl. Acad. Sci. USA 89:6094-6098.

Curiel, D.T. et al. (1992), "High-Efficiency Gene Transfer Mediated by Adenovirus Coupled to DNA-Polylysine Complexes," Hum. Gene Therapy 3:147-154.

Curiel, D.T. et al. (1991), "Adenovirus enhancement of transferrin-polylysine-mediated gene delivery," Proc. Natl. Acad. Sci. USA 88:8850-8854.

Dayhoff, M.O. et al. (1978), "Model of Evolutionary Change in Proteins," in *Atlas of Protein Sequence and Structure*, vol. 5, Supp. 3, Chapter 22, pp. 345-352.

Dedhar, S. et al. (1987), "A Cell Surface Receptor Complex for Collagen Type I Recognizes the Arg-Gly-Asp Sequence," J. Cell Biol. 104:585-593.

DeRobertis et al. (1978),"Intracellular migration of nuclear proteins in *Xenopus oocytes*," Nature 272:254-256.

Dingwall, C. and Laskey, R.A. (1991), "Nuclear targeting sequences—a consensus?" TIBS 16:478-481.

Epand et al. (1992), "Peptide models for the membrane destabilizing actions of viral fusion proteins," Biopolymers 32:309-314.

Eytan, G.D. (1982), "Use of Liposomes for Reconstitution of Biological Functions," Biochem. Biophys. Acta 694:185-202.

Fawell, S. et al. (1994), "Tat-mediated delivery of heterologous proteins into cells," Proc. Natl. Acad. Sci. USA 91:664-668.

Felgner, P.L. and Ringold, G.M. (1989), "Cationic liposome-mediated transfection," Nature 337:387-388.

Felgner, P.L. et al. (1987), "Lipofection: A highly efficient, lipid-mediated DNA-transfection procedure," Proc. Natl. Acad. Sci. USA 84:7413-7417.

FitzGeraid, D.J.P. et al. (1983), "Adenovirus-Induced Release of Epidermal Growth Factor and Pseudomonas Toxin into the Cytosol of KB Cells during Receptor-Mediated Endocytosis," Cell 32:607-617.

Frankel, A.D. et al. (1989), "Activity of synthetic peptides from the Tat protein of human immunodeficiency virus type 1," Proc. Natl. Acad. Sci. USA 86:7397-7401.

Friedlander, D.R. et al. (1988), "Functional Mapping of Cytotactin: Proteolytic Fragments Active in Cell-Substrate Adhesion," J. Cell Biol. 107:2329-2340.

Gao, X. and Huang, L. (1996), "Potentiation of Cationic Liposome-Mediated Gene Delivery by Polycations," Biochemistry 35:1027-1036.

Gardner, J.M. and Hynes, R.O. (1985), "Interaction of Fibronectin with its Receptor on Platelets," Cell 42:439-448.

Gould-Fogerite, S. et al. (1989), "Chimerasome-mediated gene transfer in vitro and in vivo," Gene 84:429-438.

Grant, D.S. et al. (1989), "Two Different Laminin Domains Mediate the Differentiation of Human Endothelial Cells into Capillary-like Structures in Vitro," Cell 58:933-943.

Haensler, J. and Szoka, R. (1993), "Polyamidoamine Cascade Polymers Mediate Efficient Transfection of Cells in Culture," Bioconjugate Chem. 4:372-379.

Hagstrom, J.E. et al. (1996), "Complexes of non-cationic liposomes and histone HI mediate efficient transfection of DNA without encapsulation," Biochim. Biophys. Acta 1284:47-55.

Haverstick, D.M. et al. (1986), "Inhibition of Platelet Adhesion to Fibronectin, Fibrinogen, and von Willebrand Factor Substrates by a Synthetic Tetrapeptide Derived From the Cell-Binding Domain of Fibronectin," Blood 86(4):946-952.

Hawley-Nelson, P. et al. (1993) FOCUS vol. 15, 17pp.

Humphries, M.J. et al. (1986), "Identification of an Alternatively Spliced Site in Human Plasma Fibronectin That Mediates Cell Type-specific Adhesion," J. Cell Biol. 103:2637-2647.

Humphries, M.J. et al. (1987), "Identification of Two Distinct Regions of the Type III Connecting Segment of Human Plasma Fibronectin That Promote Cell Type-specific Adhesion," J. Biol. Chem. 262(14):6886-6892.

Ito, A. et al. (1990), "Synthetic Cationic Amphiphiles for Liposome-Mediated DNA Transfection," Biochem. Internatl. 22(2):235-241.

Kalderon et al. (1984), "A Short Amino Acid Sequence Able to Specify Nuclear Location," Cell 39:499-509.

Kaneda et al. (1989), "Introduction and Expression of the Human Insulin Gene in Adult Rat Liver," J. Biol. Chem. 264(21):12126-12129.

Kaneda et al. (1987), "The Improved Efficient Method for Introducing Macromolecules into Cells Using HVJ (Sendai virus) Liposomes with Gangliosides," Exp. Cell Res. 173:56-69.

Kielian, J. and Helenius, A. (1986), "Entry of Alphaviruses," in *The Togaviridae and Flaviviradae*, Schlesinger & Schlesinger (eds.), Plenum Press, N.Y., pp. 91-119.

Kirsch, T. et al. (1996), "Cloning, High-Yield Expression in *Escherichia coli*, and Purification of Biologically Active HIV-1 Tat Protein," Protein Expr. Purif. 8:75-84.

Klappe, K. et al. (1986), "Parameters Affecting Fusion Between Sendai Virus and Liposomes. Role of Viral Proteins, Liposome Composition, and pH," Biochemistry 25:8252-8260.

Konopka, K. et al. (1991), "Enhancement of human immunodeficiency virus type I infection by cationic liposomes: the role of CD4, serum and liposome-cell interactions," J. Gen. Virol. 72:2685-2696.

Kraaijeveld, S.A. et al. (1984), "The Effect of liposomal charge on the neutralizing antibody response against inactivated encephalomyocarditis and Simiki Forest Viruses," Clin. Exp. Immunol. 56:509-514.

Kukowska-Latallo, J.F. et al. (1996), "Efficient transfer of genetic material into mammalian cells using Starburst polyamidoamine dendrimers," Proc. Natl. Acad. Sci. USA 93:4897-4902.

Lanford et al. (1986), "Induction of Nuclear Transport with a Synthetic Peptide Homologous to the SV40 T Antigen Transport Signal," Cell 46:575-582.

Lawler, J. et al. (1988), "Cell Attachment to Thrombospondin: The Role of ARG-GLY-ASP, Calcium, and Integrin Receptors," J. Cell Biol. 107:2351-2361.

Life Technologies Catalog, (1993) 10 pp.

Liljistrom, P. and Garoff, H. (1991), "A New Generation of Animal Cell Expression Vectors Based on the Semliki Forest Virus Replicon," Biotech. 9:1356-1361.

Mann, D.A. and Frankel, A.D. (1991), "Endocytosis and targeting of exogenous HIV-1 Tat protein," EMBO J. 10(7):1733-1739.

Marsh, M. (1983), "Interactions of Simiki Forest Virus Spike Glycoprotein Rosettes and Vesicles with Cultured Cells," J. Cell Biol. 96:455-461.

Mason, P.W. et al. (1994), "RGD sequence of foot-and-mouth disease virus is essential for infecting cells via the natural receptor but can be bypassed by an antibody-dependent enhancement pathway," Proc. Natl. Acad. Sci. USA 91:1932-1936.

Miyanohara, A. et al. (1998), "Partial Cell-Free Assembly of VSV-G Pseudotyped Retrovirus Particles," Molecular and Cellular Biology of Gene Therapy Symposium, Keystone, Colorado, Jan. 19-25, 1998, #007, p. 34.

Murata et al. (1991), "Modification of the N-Terminus of Membrane Fusion-Active Peptides Blocks the Fusion Activity," Biochem. Biophys. Res. Commun. 179(2):1050-1055.

Neugebauer, J. (1990), "Detergents: An Overview," Meth. Enzymol. 182:239-253.

Otero, M.J. and Carrasco, L. (1987), "Proteins are Cointernalized with Virion Particles during Early Infection," J. Virol. 160:75-80.

Pastan, I.H. and Willingham, M.C. (1981), "Journey to the Center of the Cell: Role of the Receptosome," Science 214:504-509.

Pepinsky, R.B. et al. (1994), "Specific Inhibition of a Human Papillomavirus E2 Trans-Activator by Intracellular Delivery of its Repressor," DNA and Cell Biology 13(10), Mary Ann Liebert, Inc., Publishers, pp. 1011-1019.

Phalen et al. (1991), "Cholesterol is Required for Infection by Semliki Forest Virus," J. Cell Biol. 112(4):615-623.

Pierschbacher, M.D. and Ruoslahti, E. (1987), "Influence of Stereochemistry of the Sequence Arg-Gly-Asp-Xaa on Binding Specificity in Cell Adhesion," J. Biol. Chem. 262(36):17294-17298.

Pierschbacher, M.D. and Ruoslahti, E. (1984), "Cell attachment activity of fibronectin can be duplicated by small synthetic fragments of the molecule," Nature 309:30-33.

Pinnaduwage, P. et al. (1989), "Use of a quaternary ammonium detergent in liposome mediated DNA transfection of mouse L-cells," Biochim. Biophys. Acta 985:33-37.

Promega Catalog, p. 251.

Rihs, H.-P. et al. (1991), "The rate of nuclear cytoplasmic protein transport is determined by the casein kinase II site flanking the nuclear localization sequence of the SV40 T-antigen," EMBO J. 10(3):633-639.

Rihs, H-P. and Peters, R. (1989), "Nuclear transport kinetics depend on phosphorylation-site-containing sequences flanking the karyophilic signal of the Simian virus 40 T-antigen," EMBO J. 8(5):1479-1484.

Rose, J.K. et al. (1991), "A New Cationic Liposome Reagent Mediating Nearly Quantitative Transfection of Animal Cells," BioTechniques 10(4):520-525.

Rosenthal, A.F. and Geyer, R.P. (1960), "A Synthetic Inhibitor of Venom Lecithinase A," J. Biol. Chem. 235(8):2202-2206.

Ruoslahti, E. and Pierschbacher, M.D. (1987), "New Perspectives in Cell Adhesion: RGD and Integrins," Science 238:491-497.

Sands, J.A. (1936), "Virucidal Activity of Ceryltrimethylammonium Bromide Below the Critical Micelle Concentration," FEMS Microbiol. Lett. 36:261-263.

Scheule (1986), "Novel Preparation of Functional Sindbis Virosomes," Biochemistry 25:4223-4232.

Schlegel, R. et al. (1983), "Inhibition of VSV Binding and Infectivity by Phosphatidylserine: Is Phosphatidylserine a VSV-Binding Site?" Cell 32:639-646.

Schlegel, R and Wade, M. (1985), "Biologically Active Peptides of the Vesicular Stomatitus Virus Glycoprotein," J. Virol. 53(1):319-323.

Seth, et al., "Pathway of Adenovirus Entry into Cells," (1986) in Virus Attachment and Entry into Cells, Crowell, R.L. and Lonberg-Holm, K. (eds.), Am. Soc. Microbiology, Washington, pp. 191-195.

Stegmann, T. et al. (1989), "Protein-mediated membrane fusion," Ann. Rev. Biophys. Biophys. Chem. 18:187-211.

Suzuki, S. et al. (1985), "Complete amino acid sequence of human vitronectin deduced from cDNA. Similarity of cell attachment sites in vitronectin and fibronectin," EMBO J. 4(10):2519-2524.

Tang, M.X. et al. (1996), "In Vitro Gene Delivery by Degraded Polyamidoamine Dendrimers," Bioconjugate Chem. 7:703-714.

Tikchonenko, T. et al. (1988), "Transfer of condensed viral DNA into eukaryotic cells using proteoliposomes," Gene 63:321-330.

"Transfection Reagent," Genet. Eng. News (Jun. 15, 1993), p. 12, col. 4.

Väänänen et al., (1980), "Fusion and Haemolysis of Erthrocytes Caused by Three Togaviruses: Semliki Forest, Sindbis, and Rubella," J. Gen. Virology 46:467-475.

Vives, E. et al. (1997), "A Truncated HIV-1 Tat Protein Basic Domain Rapidly Translocates through the Plasma Membrane and Accumulates in the Cell Nucleus," J. Biol Chem. 272(25):16010-16017.

Wagner, E. et al. (1992), "Coupling of adenovirus to transferrin-polylysine/DNA complexes greatly enhances receptor-mediated gene delivery and expression of transfected genes," Proc. Natl. Acad. Sci. USA 89:6099-6103.

Wagner, E. et al. (1992), "Influenza virus hemagglutinin HA-2 N-terminal fusogenic peptides augment gene transfer by transferrin-polylysine-DNA complexes: Toward a synthetic virus-like gene-transfer vehicle," Proc. Natl. Acad. Sci. USA 89:7934-7938.

Walker et al. (1992), "Cationic lipids direct a viral glycoprotein into the class I major histocompatibility complex antigen-presentation pathway," Proc. Natl. Acad. Sci. USA 89:7915-7918.

Wayner, E.A. et al. (1989), "Identification and Characterization of the T Lymphocyte Adhesion Receptor for an Alternative Cell Attachment Domain (CS-I) in Plasma Fibronectin," J. Cell Biol. 109:1321-1330.

Wickham, T.J. et al. (1995), "Targeting of adenovirus penton base to new receptors through replacement of its RGD motif with other receptor-specific peptide motifs," Gene Therapy 2:750-756.

Yoshimura et al. 91993), "Adenovirus-mediated Augmentation of Cell Transfection with Unmodified Plasmid Vectors," J. Biol. Chem. 268:2300.

Young et al. (1983), "Interaction of Enveloped Viruses with Planar Bilayer Membranes: Observations on Sendai, Influenza, Vesicular Stomatitis, and Simiki Forest Viruses," Virology 128:186-194.

Zhou, X. et al. (1991), "Lipophilic polylysines mediate efficient DNA transfection in mammalian cells," Biochim. Biophys. Acta 1065:8-14.

Zhou, X. and Huang, L. (1994), "DNA transfection mediated by cationic liposomes containing lipopolylysine: characterization and mechanism of action," Biochim. Biophys. Acta 1189:195-203.

Behr, J.-P., "Synthetic Gene-Transfer Vectors," (1993) Accounts of Chemical Research 26:274-278.

Caminati, G. et al., "Photophysical Investigation of Starburst Dendrimers and Their Interactions with Anionic and Cationic Surfactants," (1990) J. Am. Chem. Soc. 112:8515-8522.

Citovsky, V. et al., "Nuclear localization of agrobacteririum VirE2 protein in plant cells," (1992) Science 256:1802.

Cotten, M. et al., "Transferrin-polycation-mediated introduction of DNA into human leukemic cells: Stimulation by agents that affect the survival of transfected DNA or modulate transferrin receptor levels," (1990) Proc. Natl. Acad. Sci. 87:4033-4037.

Curiel, D.T. et al., "Gene transfer to respiratory epithelial cells via the receptor-mediated endocytosis pathway," (1992) Am. J. Respir. Cell. Mol. Biol. 6:247-252.

Demeneix, B.A. et al., "Gene transfer into intact vertebrate embryos," (1991) Int. J. Dev. Biol. 35:481-484.

Dingwall et al., "Human Immunodeficiency virus 1 tat protein binds trans-activation-responsive region (TAR) RNA in vitro," Proc. Natl. Acad. Sic. USA 86:6925-6929.

Dwarki, V.J., "Cationic liposome-mediated RNA transfection," (1993) Methods in Enzymology 217:644-654.

Finlay, D.R. et al., "Nuclear transport in vitro," (1989) J. Cell Sci. Suppl. II p. 225-242.

Gao, X and Huang, L., "A novel cationic liposome reagent for efficient transfection of mammalian cells," (1991) Biochem. and Biophys. Res. Communications 179(1):280-285.

Garcia-Bustos, J. et al., "Nuclear protein localization," (1991) Biochimica et Biophysica Acta 1071:83-101.

Goldfarb, D.S. et al., "Synthetic peptides as nuclear localization signals," (1986) Nature 322:641-644.

Goldfarb, D.S. and Michaud, N., "Pathways for the nuclear transport of proteins and RNAs," (1991) Trends in Cell Biology 1:20-24.

Harbottle, R. et al. (1995), "RGD-mediated gene delivery and expression in epithelial cells," Keystone Symposium on Gene Therapy and Molecular Medicine, Steamboat Springs, CO, Mar. 26-Apr. 1, 1995, Abstract No. C6-321.

Huckett, B. et al., "Evidence for targeted gene transfer by receptor-mediated endocytosis," Biochem. Pharmacology 40(2):253-263.

Kaneda, Y. et al., "Increased expression of DNA cointroduced with nuclear protein in adult rat liver," (1939) Science 243:375-378.

Karlsson, S. et al., "Transfer of genes into hematopoietic cells using recombinant DNA viruses," (1985) Proc. Natl. Acad. Sci. USA 82:158-162.

Lanford, R.E. et al., "Comparison of diverse transport signals in synthetic peptide-induced nuclear transport," (1990) Exp. Cell Res. 186:32-38.

Ledley, F.D., "Clinical considerations in the design of protocols for somatic gene therapy," (1991) Human Gene Therapy 2:77-83.

Legendre, J.-Y. and Szoka, F.C., Jr., "Delivery of plasmid DNA into mammalian cell lines using pH-sensitive liposomes: Comparison with cationic liposomes," (1992) *Pharm. Res.* 9(10):1235-1242.

Legendre, J.-Y. and Szoka, F.C., Jr., "Cyclic amphipathic peptide-DNA complexes mediate high-efficiency transfection of adherent mammalian cells," (1993) *Proc. Natl. Acad. Sci. USA* 90:893-897.

Loyter, A. et al., "Mechanisms of DNA uptake by mammalian cells: Fate of exogenously added DNA monitored by the use of fluorescent dyes," (1982) *Proc. Natl. Acad. Sci. USA* 79:422-426.

Malone, R.W. et al., "Cationic liposome-mediated RNA transfection," (1989) *Proc. Natl. Acad. Sci. USA* 86:6077-6081.

Parente, R.A. et al., "Association of a pH-sensitive peptide with membrane vesicles: Role of amino acid sequence," (1990) *Biochemistry* 29:8713-8719.

Parente, R.A. et al., "Mechanism of leakage of phospholipid vesicle contents induced by the peptide GALA," (1990) *Biochemistry* 29:8720-8728.

Poste, G. et al., "Lipid vesicles as carriers for introducing biologically active materials into cells," (1976) *Methods in Cell Biology* 14:33-71.

Rosenkranz, A.A. et al., "Receptor-mediated endocytosis and nuclear transport of a transfecting DNA construct," (1992) *Exp. Cell Res.* 199:323-329.

Schmid, N. and Behr, J.-P., "Location of spermine and other polyamines on DNA as revealed by photoaffinity cleavage with polyaminobenzenediazonium salts," (1991) *Biochemistry* 30:4357-4361.

Silver, P.A., "How proteins enter the nucleus," (1991) *Cell* 64:489-497.

Smull, C.E. and Ludwig, E.H., "Enhancement of the plaque-forming capacity of poliovirus ribonucleic acid with basic proteins," (1962) *J. Bacteriology* 84:1035-1040.

Sugawa, H. et al., "Large macromolecules can be introduced into cultured mammalian cells using erythrocyte membrane vesicles," (1985) *Exp. Cell Res.* 159:410-418.

Trubetskoy, V.S. et al., "Use of N-terminal modified poly (L-lysine)-antibody conjugate as a carrier for targeted gene delivery in mouse lung endothelial cells," (1992) *Bioconjugate Chem.* 3:323-327.

van Zee, K. et al., "A hydrophobic protein sequence can override a nuclear localization signal independently of protein context," (1991) *Mol. and Cellular Biol.* 11(10):5137-5146.

Wagner, E. et al., "DNA-binding transferrin conjugates as functional gene-delivery agents: Synthesis by linkage of polylysine or ethidium homodimer to the transferrin carbohydrate moiety," (1991) *Bioconjugate Chem.* 2:226-231.

Wagner, E. et al., "Transferrin-polycation conjugates as carriers for DNA uptake into cells," (1990) *Proc. Natl. Acad. Sci. USA* 87:3410-3414.

Wilson, J.M. et al., "Hepatocyte-directed gene transfer in vivo leads to transient improvement of hypercholesterolemia in low density lipoprotein receptor-deficient rabbits," (1992) *J. Biol. Chem.* 267(2):963-967.

Wolff, J.A. et al., "Direct gene transfer into mouse muscle in vivo," (1990) *Science* 247:1465-1463.

Wu, C.H. et al., "Targeting genes: Delivery and persistent expression of a foreign gene driven by mammalian regulatory elements in vivo," (1989) *J. Biol. Chem.* 265(29):16985-16987.

Wu, G.Y. et al., "Receptor-mediated gene delivery in vivo: Partial correction of genetic analbuminemia in nagase rats," (1991) *J. Biol. Chem.* 266(22):14338-14342.

Wu, G.Y. and Wu, C.H., "Receptor-mediated gene delivery and expression in vivo," (1988) *J. Biol. Chem.* 263(29):14621-14624.

Wu, G.Y. and Wu, C.H., "Evidence for targeted gene delivery to Hep G2 hepatoma cells in vitro," (1983) *Biochemistry* 27:887-892.

Yagi, K. et al., "Incorporation of histone into liposomes increases the efficiency of liposome-mediated gene transfer," (1991) *J. Clin. Biochem. Nutr.* 10:21-25.

Zenke, M. et al., "Receptor-mediated endocytosis of transferrin-polycation conjugates: An efficient way to introduce DNA into hematopoietic cells," (1990) *Proc. Natl. Acad. Sci. USA* 37:3655-3659.

Zhu, Z. et al., "Transformation of tobacco protoplasts with DNA entrapped in pH-sensitive liposomes," (1990) *Plant Cell Tissue and Organ Culture* 22:135-145.

Budker et al. (Jul. 1997), "Protein/Amphipatic Polyamine Complexes Enable Highly Efficient Transfection with Minimal Toxicity," Biotechniques 23:139-147.

Wagner et al. (May 1991), "Transferrin-polycation-DNA complexes: The effect of polycations on the structure of the complex and DNA delivery to cells," Proc. Natl Acad Sci. 88:4255-4259.

Adam, et al., "Identification of specific binding proteins for a nuclear localization sequence", Nature, 337,(1989),246-279.

Andrews, et al., "Erythroid Transcription Factor NF-E2 is a Haematopoietic-Specific Basic-Leucine Zipper Protein", Nature, 362(6422),(Apr. 22, 1993),722-728.

Behr, "Synthetic gene transfer vectors", Pure & Appl. Chem, 66,(1994),827-835.

Benditt, et al., "Interaction of a NLS with isolated nuclear envelopes and idenetification of signal-binding proteins by photoaffinity labeling", PNAS, 86,(1989),9327-9331.

Boulikas, "Nuclear Localization Signals (NLS)", Critical Reviews in Eukaryotic Gene Expression, 3,(1993),193-227.

Boulikas, "Putative NLS in protein transcription factors", J. Cellular Biochem., 55,(1994),32-58.

Branden, et al., "PNA-NLS fusion that mediates transport of DNA", Nature Biotechnology, 17,(1999),784.

Brokx, et al., "Designing peptide-based scaffolds as drug delivery vehicles", J. Controlled release, 78,(78),115-123, 2002.

Bronstein, et al., "Chemiluminescent and Bioluminescent reporter gene assays", Analytical Biochemistry, 219,(1994),169-181.

Chan, et al., "Supramolecular structure and nculear targeting efficeince determine the enhancement of transfection of polylysines", Gene Therapy, 7,(2000),1690-1697.

Cheetham, et al., "Choleterol sulfate inhibits the fusion of sendai virus to biological and model membranes", J. Biol. Chem., 265,(1990),12404-12409.

Chelsky, et al., "Sequence requirements for peptide-mediated translocation to the nucleus", Molecular and Cellular Biology, 9,(1989),2487-2492.

Citovsky, et al., "Nuclear localization of Agrobacterium VirE2 protein in plant cells", Science, 256,(1992),1802-1805.

Clever, et al., "Identification of a DNA binding domain in SV40 capsid proteins Vp2 and Vp3", J. Cell Biol., 268,(268),20877-20883, 1993.

Clever, et al., "Simian virus 40 Vp2/3 small structural proteins harbor their own nuclear transport signal", Virology, 181,(1991),78-90.

Coleman, et al., "The Matrix Protein of Newcastle Disease Virus Localizes to the Nucleus via a Bipartite Nuclear Localization Signal", Virology, 195,(1993),596-607.

Cotten, et al., "Chicken Adenovirus Augment Receptor Mediated DNA Delivery to Mammalian Cells and Yield Exceptional Levels of Stable Transformants", J., Vir., 67,(1993),3777-3785.

Cotten, et al., "High-Efficiency Receptor-Mediated Delivery of Small and Large (48 Kilobase Gene Constructs Using the Endosome-Disruption Activity of Defective or Chemically Inactivated Adenovirus Particles", PNAS, 89,(1992),6094-6098.

Cristiano, et al., "Hepatic Gene Therapy: Adenovirus Enhancement of Receptor Mediated Gene Delivery and Expression in Primary Hepatocytes", PNAS, 90,(1993),2122-2126.

Dang, et al., "Identification of Human cMyc Protein Nuclear Translocation Signal", Molecular and Cellular Biol., 8,(1988),4048-4054.

Dang, et al., "Nuclear and Nucleolar Targeting Sequences of c-erb-A, c-myb, N-myc, p53, HSP70, and HIV Tat Proteins", J. Biol Chem., 264(30),(Oct. 25, 1989),18019-18023.

Davey, et al., "Identification of the Sequence Responsible for the Nuclear Accumulation of Influenza Virusnucleoprotein in *Xenopus oocytes*", Cell, 40,(1985),667-675.

De Roberts, et al., "Intracellular Mirgration of Nuclear Proteins in *Xenopus oocytes*", Nature, 272,(1978),254-256.

Dingwall, et al., "A Polypeptide Domain That Specifies Migration of Nucleoplasmin into the Nucleus", Cell, 30,(1982),449-458.

Dingwall, et al., "The Nuclear Membrane", Science, 258,(1992),942-947.

Dworetzky, et al., "The Effects of Variations in the Number and Sequence of Targeting Signals on Nuclear Uptake", J. Cell Biol., 107,(1988),1279-1287.

Dworetzky, et al., "Translocation of RNA-Coated Gold Particles Through Nuclear Pores of Oocytes", J. Cell Biol, 106,(1988),575-584.

Friedberg, "Nuclear Targeting Sequences", TIBS, 17,(1992),347.

Goldfarb, et al., "Karyophillic Peptides: Aplication to the Study of Nuclear Transport", Cell Biology International Report, 12,(1988),809-833.

Green, et al., "Autonomous Functional Domains of Chemically Synthesized Human Immunodeficiency Virus Tat Trans-Activator Protein", Cell, 55(6),(1988),1179-1188.

Haensler, et al., "Synthesis and Characterization of Trigalactosylated Bisacridine Compound to Target DNA Hepatocytes", Bioconjugate Chem., 4,(1993),85-93.

Hauber, et al., "Mutational Analysis of the Conserved Basic Domain of Human Immunodeficiency Virus Tat Protein", J Virol. 63(3),(Mar. 1989),1181-1187.

Hicks, et al., "Specific Binding of Nuclear Localization Sequences to Plant Nuclei", The Plant Cell, 5,(1993),983-994.

Isaka, et al., "Glomerlosclerosis Induced by in vivo Transfection of Transforming Growth Factor-B or Platelet-Derived Grwoth Factor Gene into Rat Kidney", J. Clinical Inves., 92,(1993),2597-2601.

Johnson, et al., "Expression of Transcription Factor E2F1 Induces Quiescent Cells to Enter S Phase", Nature, 365,(1993),349-352.

Kalderon, et al., "Sequence Requirements for Nuclear Location of SV40 Large T-Antigen", Nature, 311,(1984),33-38.

Kleinschmidt, et al., "Identification of Domains Involved in Nuclear Uptake and Histone Binding of Protein N1 of *Xenopus laevis*", EMBO, 7,(1988),1605-1614.

Lanford, et al., "Effect of Basic and Nonbasic Amino Acid Substitutions on Transport Induced by SV50 Synthetic Peptide Nuclear Transport Signals", Molecular and Cellular Biology, 8,(1988),2722-2729.

Leonetti, et al., "Biological Activity of OligonucleotidepOly(L-Lysine) Conjugates: mechanism of Cell Uptake", Biconjugate Chem., 1,(1990),149-153.

Li, et al., "Xenopus Nuclear Factor 7 Possess an NLS That Functions Efficiently in Both Oocytes and Embryos", Journal of Cell Science, 105,(1993),389-395.

Marchuk, et al., "Remarkable Conservation of Structure Among Inetrmediate Filament Genes", Cell, 39,(1984),491-498.

Matheny, et al., "The NLS of NGF-1-A Located Within the Zinc Finger DNA Binding Domain", J. Biol. Chem., 269,(1994),8176-8181.

Michaud, et al., "Microinjected U snRNAs are Imported to oocoyte Nuclei Via the Nuclear Porecomplex by Three Distinguishable Targeting Pathways", J. Cell Biology, 116,(1992),851-861.

Mohler, et al., "Segmentally Restricted, Cephalic Expression of a leucine Zipper Gene During Drosphila Embryogenesis", Mech Dev. 34(1),(Mar. 1991),3-9.

Mooreland, et al., "Amino Acid Sequence That Determine the NLS of Yeast Histone 2B", Molecular and Cellular Biol., 7,(1987),4048-4057.

Morin, et al., "Nuclear Localization of the Adenovirus DNA-Binding Protein: Requiremenet for Two Signals and Complementation During Viral Infection", Molecular and Cellular Biol., 9,(1989),4372-4380.

Mulligan, "The Basic Science of Gene Therapy", Science, 260,(1993),926-932.

Nath, et al., "Function of Two Discrete Regions is Required for Nuclear Localization of Polymerase Basic Protein 1 of A/WSN/33 Influenza Virus (H1 N1)", Molecular and Cellular Biol., 8,(1990),4139-4145.

Pearson, et al., "A Transdominant Tat Mutant That Inhibits Tat-Induced Gene Expression From the Human Immunodeficiency Virus Long Terminal Repeat", Proc Natl Acad Sci U.S.A. 87(13),(1990),5079-5083.

Plank, et al., "Gene Transfer Into Hepatocytes Using Asiaglycoproyeinrceptor Mediated Endocytosis of DNA Complexed With an Artificial Tetra-Antennary Galactose Ligand", Bioconjugate Chem, 3,(1992),533-539.

Raikhel, "Nuclear Targeting in Plants", Plant Physiol., 100,(1992),1627-1632.

Robbins, et al., "Two Interdependent Basic Domains in Nucleoplasmin Nuclear Targeting Sequence: Identification of a Class of Bipartite Nuclear Targeting Sequence", Cell, 64,(1991),615-623.

Roberts, "Nuclear Localization Signal-Mediated Protein Transport", Biochim. Biophysica Acta,(1989),263-280.

Roberts, et al., "The Effect of Protein Context on NLS Function", Cell, 50,(1987),465-475.

Ruben, et al., "Structural and Functional Characterization of Human . Immunodeficiency Virus Tat Protein", J. Virol, 63,(1989),1-8.

Schlegel, et al., "Biologically Active Peptides of the Vesicular Stomatitis Virus Glycoprotein", J. Virol., 53,(1985),319-323.

Schmolke, et al., "Nuclear Targeting of the Tegument Protein pp65 (UL83) of Human Cytomegalovirus: an Unusual bipartite Nuclear Localization Signal Functions With One Portion of the Protein to Mediate its Efficient Nuclear Transport", J. Virology, 69,(1995),1071-1078.

Schreiber, et al., "The Human Poly(ADP-ribose) Polymerase Nuclear Localization Signal is ia Bipartite Element Functionally Separate from DNA Binding and Catalytic Activity", EMBO, 11,(1992),3263-32698.

Schwarzbaum, et al., "The Generation of Macrophage-Like Cell Lines by Transfection With SV40 Origin Defective DNA", J. Immunology, 132,(1984),1158-1162.

Sheldon, et al., "Loligomers: Design of De Novo Peptide-Based Intracellular Vehicles", PNAS, 92,(1995),2056-2060.

Short, et al., "Modification of *E. coli* Lac Repressor for Expression in Eukaryotic Cells: Effects of Nuclear Signal Sequences on Protein Activity and Nuclear Accumulation", Nucleic Acid Research, 20,(1992),1785-1791.

Singh, et al., "Penetration and Intracellular Routing of Nucleus-Directed Peptide-Based Shuttles (Loligomers) in Eukaryotici Cells", Biochemistry, 37,(1998),5798-5809.

Siomi, et al., "Sequence Requirements for Nuclear Localization of Human T Cell Luekemia Virus Type I pX Protein, Which Regulates Viral RNA Processing", Cell, 55,(1988),197-202.

Svinarchuk, et al., "Nuclear Pore Specifically Interacting With Oligonucleotides", Nucleic Acid Research, 24,(1991),316.

Takai, et al., "DNA Transfection of Mouse Lympoid Cells by the Combination of DEAE-Dextran-Mediated DNA Uptake and Osmotic Shock Procedure", Biochimic et Biophysica Acta, 1048,(1990),105-109.

Trubetskoy, et al., "Use of N-Terminal Modified Poly(L-Lysine)-Antibody Conjugates as a Carrier for Targeted Gene Delivery in Mounse Lung Endothelial Cells", Bioconj. Chem., 3,(1992),323-327.

Varagona, et al., "Nuclear Localization Signal(s) Required for Nuclear Targeting of the Maize Regulatory Protein Opaque-2", The Plant Cell, 4,(1992),1213-1227.

Wagner, et al., "Nuclear Protein Transport is Funcitionally Conserved Between yeast and Higher Eukaryotes", FEBS, 321,(1993),261-266.

Weeks, et al., "Fragments of the HIV-1 Tat Protein Specifically Bid TAR RNA", Science, 249,(1990),1281-1285.

Wu, et al., "Receptor Mediated In Vitro Gene Transformation by a Soluble DNA Carrier System", J. Biol. Chem., 262,(1987),4429-4432.

Xia, et al., "Characterization of Nuclear Targeting Signal of Hepatitis Delta Antigen: Nuclear Transport as a Protein Complex", J. Virol., 66,(1992),914-921.

Yamasaki, et al., "Identification of Four Nuclear Transport Signal-Binding Proteins That Interact With Divers Transport Signals", Molecular and Cellular Biol., 9,(1989),3028-3036.

Ylikomi, et al., "Cooperation of Proto-Signals for Nuclear Accumulation of Estrogen and Progesterone Receptors", EMBO, 11,(1992),3681-3694.

Yoneda, et al., "A Long Synthetic Peptides Containing a Nuclear Localization Signal and its Flanking Sequences of SV40 T-Antigen Directs Transport of IgM Into the Nucleus Efficiently", Exp. Cell Res., 201,(1992),313-320.

Yoneda, et al., "Synthetic Peptides Containing a Region of SV40 Large T-Antigen Involved in Nuclear Localization Direct the Transport of Proteins Into the Nucleus", Exp. Cell Res., 170,(1987),439-452.

Zacksenhaus, et al., "A Bipartite Nuclear Localization Signal in the Retinblastoma Gene Product and its Importance for Biological Activity", Molecular and Cellularl Biol, 13,(1993),4588-4599.

Zanta, et al., "Gene Delivery: A Single NLS Peptide is Sufficient to Carry DNA to the Cell Nucleus", PNAS, 96,(1999),91-96.

Zhang, et al., "A Transfecting Peptide Derived From Adenovirus Fiber Protein", Gene Therapy, 6,(1999),171-181.

Zhao, et al., "Nuclear Transport of Adenovirus DNA Polymeraseis Facilitated by Ineraction With Preterminal Protein", Cell, 55,(1988),1005-1015.

Zhou, et al., "A Ligand Dependent bipartite Nuclear Targeting Signal in human Andogen Receptor", J. Biol. Chem., 269,(1994),13115-13123.

Zhou, et al., "Lipophilic Polylysines Mediate Efficient DNA Transfection in Mammalian Cells", Biochim Biophys Acta 1065(1),(May 31, 1991),8-14.

Zwiebel, et al., "High-Level Recombinant Gene Expression in Rabbit Endothelial Cells Transduced by Retroviral Vectors", Science, 243,(1989),220-222.

Curtain, et al., "Fusogenic activity of amino-terminal region of HIV type 1 Nef protein", *AIDS Research and Human Retroviruses* vol. 10, No. 10, 1994, pp. 1231-1240.

Felgner, et al., "Keystone Symposium on Genetic Targeted Research and Therapeutics: Antisense and Gene Therapy, Keystone, CO", *J. Cell. Biochem. Supply* 0 (17 Part E) 1993, p. 206, S306.

Garrigues, B. and Vidaud, L., "Synthesis of Spermine and Spermidine Selectively Substituted on the Secondary Amine Functions", American Chemical Society, 1989, Chemical Abstracts 111:593; Abstract No. 23282t.

Liebert, Mary A., "Transfection Reagent", *Genetic Engineering News, Inc.* col. 4, 1993, p. 12.

Stewart, et al., "Solid Phase Peptide Synthesis", *Pierce Chemical Co.*, 1969, p. 80.

Zhang, et al., "Cationic liposomes-protamine-DNA complexes for gene delivery", *Liposomes: Methods in Enzymology*, vol. 373, Liposomes Part C Ed. Duzgunes.N., Academic Press, 2003, pp. 332-342.

International Search Report and Written Opinion for PCT Patent Application No. PCT/US98/05232, mailed Sep. 17, 1998, 2.

International Search Report received for PCT Application No. PCT/US96/00816 mailed on Aug. 1, 1996, 3.

International Search Report received for PCT Application No. PCT/US96/08723 dated Jul. 17, 1996, 2.

Office Action received for Canadian Patent Application No. 2,211,118 mailed on Nov. 19, 2007, 7.

Response to Office Action received for Canadian Patent Application No. 2,211,118 mailed on May 15, 2008, 9.

Notice of Allowance for Canadian Patent Application No. 2,221,118 Mailed on Feb. 5, 2009.

Office Action received for Japanese Application No. 9-501227 mailed on Apr. 22, 2008, 4.

Response Office Action mailed Apr. 22, 2008 for Japanese Patent Application No. 9-501227 filed on Oct. 22, 2008.

Dialog Abstract of JP 6080560A, vol. 18, No. 337 Jun. 27, 1994, 5.

Office Action received for Japanese Patent Application No. 10-539899 mailed on Jun. 17, 2008, 4.

European Search Report for EP Application No. 96902747.3 mailed Oct. 28, 1999.

European Search Received for EP Patent Application No. 96917118 mailed on Mar. 10, 1999.

European Search Report received for EP Application No. 98911737.9 mailed on Feb. 28, 2001, 1.

Anderson, W F. et al., "Human Gene Therapy", *Nature* vol. 392, Suppl Apr. 30, 1998, 25-30.

Bernard, Gordon R. , "The adult respiratory distress syndrome", *Annual Review of Medicine* vol. 36 1985, 195-200.

Bongartz, Jean-Pierre et al., "Improved Biological Activity of Antisense Oligonucleotides Coniuqated to a Fusoqenic Peptide", *Nucleic Acids Research* vol. 22 No. 22 1994, 4681-4688.

Brisson, Marni et al., "Improved gene delivery formulations and expression systems for enhanced transfection efficiency", *Pure and Applied Chemistry* vol. 70, No. 1 1998, 83-88.

Brunette, Elisa et al., "Lipofection does not require the removal of serum", *Nucleic Acids Research* vol. 20, No. 5 Mar. 11, 1992, 1151.

Ciccarone, Valentina et al., "Cationic Lipsome-Mediated Transfecftion: Effect of Serum on Expression and Efficiency", *Focus* vol. 15, No. 3 1993 , 80-83.

De Wet, Jeffrey R. et al., "Firefly luciferase gene: structure and expression in mammalian cells.", *Molecular and Cellular Biology* vol. 7, No. 2 Feb. 1987, 725-737.

Demeneix, B. A. et al., "Temporal and Spatial Expression of Lipospermine-Compacted Genes Transferred into Chick Embryos in Vivo", *Biotechniques* vol. 16, No. 3 Mar. 1994, 496-501.

Gao, X et al., "Cationic liposome-mediated gene transfer", *Gene Therapy* 2 1995, 710-722.

Hawley-Nelson, Pamela et al., "Lipofectamine Reagent: A New, Higher Efficiency Polycationic Liposome Transfection Reagent", *Focus* vol. 15, No. 3, Life Technologies Inc. 1993, 73-79.

Lee, et al., "Folate-targeted, Anionic Liposome-entrapped Polylysine-condensed DNA for Tumor Cell-specific Gene Transfer", *Journal of Biological Chemistry* vol. 271 1996, 8481-8487.

Lee, Robert J. et al., "Lipidic Vector Systems for Gene Transfer", *Critical Reviews in Therapeutic Drug Carrier Systems* vol. 14, No. 2 1997, 173-206.

Li, S. et al., "Characterization of Cationic Lipid-Protamine-DNA(LPD) Complexes for Intravenous Gene Delivery", *Gene Ther* vol. 5 1998, pp. 930-937.

Li, S et al., "In vivo gene transfer via intravenous administration of cationic lipid/protamine/DNA (LPD) complexes", *Gene Therapy* vol. 4, No. 9 Sep. 1997, 891-900.

Liu, F et al., "Factors controlling efficiency of cationic lipid-mediated transfection in vivo via intravenous administration", *Gene Therapy* vol. 4, No. 6 Jun. 1997, 517-523.

Miller, Nicholas et al., "Targeted vectors for gene therapy.", *The FASEB Journal* vol. 9, No. 2 Feb. 1995, 190-199.

Neumann, J. R. et al., "A Novel Rapid Assay for Chloramphenicol Acetyltransferease Gene Expression", *BioTechniques* May 1987, 444-446.

Schifferli, et al., "Optimization of Cationic Lipid Reagent-Mediated Transfection for Suspension Cell Lines", *FOCUS*, vol. 18 1996, 45-47.

Stamatatos, Leonidas et al., "Interactions of cationic lipid vesicles with negatively charged phospholipid vesicles and biological membranes", *Biochemisty* vol. 27 1988, 3917-3925.

Brigham, K. L., et al., "Expression of a Prokaryotic Gene in Cultural Lung Endothelial Cells After Lipofection with a Plasmid Vector", *American Journal of Respiratory Cell and Molecular Biology*, vol. 1, No. 2,(Aug. 1989),95-100.

Deonarain, M P., "Ligand-targeted receptor-mediated vectors for gene delivery", *Expert Opinions on Therapeutic Patents*, vol. 8, No. 1,(Jan. 1998),53-69.

Felgner, P.I. et al., "Cationic Lipid/Polynucleotide Condenstaes for In Vitro and In Vivo Polynucleotide Delivery—The Cytofectins", *J. Liposome Res.* 3 (1), (1993),3-16.

Gao, X. et al., "Cationic Liposomes and Polymers for Gene Transfer", *J. Liposome Res*, vol. 3, No. 1,(1993),17-30.

Gao, X. and Huang L., "Cytoplasmic Expression of a Reporter Gene by Co-Delivery of T7 RNA Polymerase and T7 Promoter Sequence with Cationic Liposomes", *Nucl. Acids Res.* 21(12), (1993),2867-2872.

Gorman, Cornelia M., "High Efficiency Gene Transfer into Mammalian Cells", *DNA Cloning*, vol. II,(Jul. 1985),143-190.

Hofland, et al., "Formulation and Delivery of Nucleic Acids. In: Handbook of Experimental Pharmacology", *Novel Therapeutics from Modern Biotechnology*, vol. 137, Chapter 8,(1998).

Huang, L et al., "Targeted delivery of drugs and DNA with liposomes", *Journal of Liposome Research*, vol. 3, No. 3,(1993),505-515.

Huang, Leaf "Target-sensitive liposomes", *Journal of Liposome Research*, vol. 4, No. 1,(1994),397-412.

Hui, Kam M., et al., "Induction of alloreactive cytotoxic T lymphocytes by intrasplenic immunization with allogeneic class I Major Histocompatibility Complex DNA and DC-chol cationic liposomes", *Journal of Liposome Research*, vol. 4, No. 3,(Nov. 1994),1075-1090.

Ibanez, Miguel et al., "Spermidine-condensed DNA and cone-shaped lipids improve delivery and expression of exogenous DNA transfer by liposomes", *Biochemistry and Cell Biology*, vol. 74, No. 5,(Sep. 1996),633-643.

Lee, et al., "Ch 16: Gene transfer by liposome-entrapped polycation-condensed DNA-LPDI and LPDI", *Conference Proceedings, Artificial Self-Assembling Systems for Gene Delivery*, eds., Feigner, Heller, Lehn, Behr and Szoka, Jr., America Chemical Society, Washington, D.C.,,(1996), 169-176.

Li, et al., "Targeted delivery of antisense oligodeoxynucleotides by LPD II", *Journal of Liposome Research*, vol. 7,(1997),63-76.

Li, et al., "Targeted delivery of antisense oligodeoxynucleotides formulated in a novel lipidic vector", *Journal of Liposome Research*, vol. 8,(1998),239-250.

Nebel, Elizabeth G., et al., "Gene transfer in vivo with DNA-liposome complexes: lack of autoimmunity and gonadal localization", *Human Gene Therapy*, vol. 3, No. 6,(Dec. 1992), 649-656.

Roitt, et al., *Immunology, Second Edition*, J.B. Lippincott Co.,(1989).

Zhu, et al., "Effects of 5'azacytidine on transformation and gene expression in *Nicotiana tabacum*", *In Vitro Cell. Dev. Biol.*, vol. 27, (1991),77-83.

U.S. Appl. No. 08/477,354, Non-Final Office Action received for U.S. Appl. No. 08/477,354 mailed on Apr. 29, 1996, 13.

U.S. Appl. No. 09/376,395, Final Office Action received for U.S. Appl. No. 09/376,395 mailed on Dec. 11, 2001, 11.

U.S. Appl. No. 09/376,395, Final Office Action received for U.S. Appl. No. 09/376,395 mailed on Sep. 21, 2004, 30.

U.S. Appl. No. 09/376,395, Non-Final Office Action received for U.S. Appl. No. 09/376,395 mailed on Feb. 26, 2003, 27.

U.S. Appl. No. 09/376,395, Non-Final Office Action received for U.S. Appl. No. 09/376,395 mailed on Dec. 19, 2003, 33.

U.S. Appl. No. 09/376,395, Non-Final Office Action received for U.S. Appl. No. 09/376,395 mailed on Mar. 15, 2001, 22.

U.S. Appl. No. 09/376,395, Non-Final Office Action received for U.S. Appl. No. 09/376,395 mailed on Aug. 9, 2002, 15.

U.S. Appl. No. 09/376,395, Response to Non-Final Office Action received for U.S. Appl. No. 09/376,395 mailed on Dec. 9, 2002, 9.

U.S. Appl. No. 09/376,395, Response to Non-Final Office Action received for U.S. Appl. No. 09/376,395 mailed on Jun. 21, 2004, 24.

U.S. Appl. No. 09/376,395, Response to Non-Final Office Action received for U.S. Appl. No. 09/376,395 mailed on Aug. 26, 2003, 27.

U.S. Appl. No. 09/376,395, Response to Non-Final Office Action received for U.S. Appl. No. 09/376,395 mailed on Sep. 24, 2001, 29.

U.S. Appl. No. 09/376,395, Response to Restriction Requirement received for U.S. Appl. No. 09/376,395 mailed on Dec. 27, 2000, , 15.

U.S. Appl. No. 09/376,395, Restriction Requirement received for U.S. Appl. No. 09/376,395 mailed on Oct. 20, 2000, 6.

U.S. Appl. No. 09/911,569, Non-Final Office Action received for U.S. Appl. No. 09/911,569 mailed on Oct. 21, 2004, 37.

U.S. Appl. No. 09/911,569, Non-Final Office Action received for U.S. Appl. No. 09/911,569 mailed on Jul. 14, 2005, 20.

U.S. Appl. No. 09/911,569, Response to Non-Final Office Action received for U.S. Appl. No. 09/911,569 mailed on Apr. 21, 2005.

U.S. Appl. No. 09/911,569, Response to Restriction Requirement received for U.S. Appl. No. 09/911,569 mailed on Aug. 18, 2004, 16.

U.S. Appl. No. 09/911,569, Restriction Requirement received for U.S. Appl. No. 09/911,569 mailed on Mar. 18, 2004, 11.

U.S. Appl. No. 10/850,873, Office Action issued Feb. 1, 2007 for U.S. Appl. No. 10/850,873, filed May 20, 2004, by P. Harvie, 16.

U.S. Appl. No. 11/333,982, Non-Final Office Action received for U.S. Appl. No. 11/333,982 mailed on Sep. 18, 2008, 16.

U.S. Appl. No. 11/333,982, Response to Restriction Requirement received for U.S. Appl. No. 11/333,982 mailed on Jul. 21, 2008, 41.

U.S. Appl. No. 11/333,982, Restriction Requirement received for U.S. Appl. No. 11/333,982 mailed on Mar. 21, 2008, 6.

U.S. Appl. No. 11/943,434, Non-Final office action mailed on Mar. 18, 2009, 34 pgs.

U.S. Appl. No. 11/943,434, Response to Non-Final office action dated Mar. 18, 2009, filed Jul. 7, 2009.

Partial European Search Report mailed Jun. 4, 2010 in EP 091781179.

Remy, J. S. et al., "Targeted gene transfer into hepatoma cells with Lipopolyamine-condensed DNA particles presenting galactose ligands: a stage toward artificial viruses", *Proceedings of the National Academy of Sciences of USA*, vol. 92, No. 5, National Academy of Science. Washington, Feb. 1, 1995; pp. 1744-1748.

EP 091781179, "Extended European Search Report mailed Nov. 4, 2010".

U.S. Appl. No. 12/637,544, "Office action mailed Apr. 1, 2011".

U.S. Appl. No. 12/637,544, "Response to Aug. 19, 2010 Office Action filed Feb. 14, 2011".

Wang, Jiahong, et al., "Targeted neutralization of calmodulin in the nucleus blocks DNA synthesis and cell cycle progression", *Biochimica et Biophysica Acta*, Elsevier, NL, vol. 1313, No. 3, Jan. 1, 1996; pp. 223-228.

* cited by examiner

SCHEME 1

SCHEME 2

SCHEME 3

SCHEME 4

L = any lipid

PEPTIDE-ENHANCED TRANSFECTIONS

CROSS-REFERENCE TO RELATED APPLICATIONS

This application is a continuation of U.S. application Ser. No. 09/911,569, filed Jul. 23, 2001, now abandoned, which is a continuation of U.S. application Ser. No. 09/039,780, filed Mar. 16, 1998, now U.S. Pat. No. 6,376,248, which is a continuation-in-part of U.S. application Ser. No. 08/818,200, filed Mar. 14, 1997, now U.S. Pat. No. 6,051,429, which is a continuation-in-part of U.S. application Ser. No. 08/658,130, filed Jun. 4, 1996, now U.S. Pat. No. 5,736,392, which is a continuation-in-part of U.S. application Ser. No. 08/477,354, filed Jun. 7, 1995, now abandoned, all of which are incorporated by reference in their entirety herein to the extent not inconsistent with the disclosure herewith.

FIELD OF THE INVENTION

Compositions containing peptides, optionally conjugated to nucleic acid-binding groups, to lipids or to dendrimers, and transfection agents, including cationic lipids and dendrimer polymers, useful for transfecting eukaryotic cells are disclosed. Also disclosed are methods of transfecting eukaryotic cells employing such compositions.

BACKGROUND OF THE INVENTION

Lipid aggregates such as liposomes can function to facilitate introduction of macromolecules, such as DNA, RNA, and proteins, into living cells. Lipid aggregates comprising cationic lipid components can be effective for delivery and introduction of large anionic molecules, such as nucleic acids, into certain types of cells. See Felgner, P. L. and Ringold, G. M. (1989) Nature 337:387-388 and Felgner, P. L. et al. (1987) Proc. Natl. Acad. Sci. USA 84:7413. Since the membranes of most cells have a net negative charge, anionic molecules, particularly those of high molecular weight, are not readily taken up by cells. Cationic lipids aggregate to and bind polyanions, such as nucleic acids, tending to neutralize the negative charge. The effectiveness of cationic lipids in transfection of nucleic acids into cells is thought to result from an enhanced affinity of cationic lipid-nucleic acid aggregates for cells, as well as the function of the lipophilic components in membrane fusion.

Dendrimers are a new type of synthetic polymer with regular, dendric branching with radial symmetry composed of an initiator core, interior layers (or generations) of repeating units, radially attached to the core and an exterior surface of terminal functional groups. See: D. A. Tomalia and H. D. Durst (1993) in E. Weber (ed.) Topics in Current Chemistry, Vol. 165: Supramolecular Chemistry I-Directed Synthesis and Molecular Recognition, Springer-Verlag, Berlin, pp. 193-313. The size, shape and surface charge density of the dendrimer is controlled by choice of core, repeating unit, number of generations and terminal functional group. See: U.S. Pat. Nos. 5,527,524; 5,338,532; 4,694,064; 4,568,737; 4,507,466; and PCT patent applications; WO8801179; WO8801178; WO9524221; and WO9502397. "STARBURST" (Trademark, Dendritech, Inc.) or dense star polyamidoamine dendrimers have been reported to mediate efficient transfection of DNA into mammalian cells (J. F. Kukowska-Latolla et al. (1996) Proc. Natl. Acad. Sci. USA 93:4897-4902 and A. Bielinska et al. (1996) Nucleic Acids Res. 24(11):2176-2182). "SUPERFECT" (Trademark, Qiagen, Inc.) or activated dendrimers have been reported to mediate efficient transfection of DNA into mammalian cells (J. Haensler and R. Szoka (1993) Bioconjugate Chem. 4:372-379 and M. X. Tang et al., (1996) Bioconjugate Chem. 7P703-714). PCT patent application WO9524221 relates to bioactive or targeted dendrimer conjugates. PCT patent applications WO9319768 and WO9502397 relate to polynucleotide delivery systems comprising dendrimers.

Transfection agents, including cationic lipids and dendrimers, are not universally effective for transfection of all cell types. Effectiveness of transfection of different cells depends on the particular transfection agent composition and the type of lipid aggregate or dendrimer-complex formed. In general, polycationic lipids are more efficient than monocationic lipids in transfecting eukaryotic cells. Behr, J-P. et al. (1989) Proc. Natl. Acad. Sci. 86:6982-6986, Hawley-Nelson, P., et al. (1993) FOCUS 15:73 and U.S. Pat. No. 5,334,761 (Gebeyehu et al.). Behr et al. and EPO published application 304 111 (1990), for example, describe improved transfection using carboxyspermine-containing cationic lipids including 5-carboxyspermylglycine dioctadecyl-amide (DOGS) and dipalmitoylphosphatidylethanolamine 5-carboxyspermylamide (DPPES). The polycationic liposomal transfection reagents 1,3 dioleoyloxy-2-(6-carboxyspermyl)-propylamid (DOSPER, Boehringer-Mannheim) and "MULTIFECTOR" (Trademark, VennNova, Inc.) are other examples. For transfection, the optimal charge ratio of DNA/dendrimer was found to be between 1:5 and 1:50 and G5 (generation 5)-G10 (generation 10) dendrimers were reported capable of mediating transfection. Transfection efficiency of a given dendrimer varied with cell type, as has been observed with cationic lipid-mediated transfection (J. F. Kukowska-Latolla et al. (1996) Proc. Natl. Acad. Sci. USA 93:4897-4902).

Many biological materials are taken up by cells via receptor-mediated endocytosis. See: Pastan and Willingham (1981) Science 214:504-509. This mechanism involves binding of a ligand to a cell-surface receptor, clustering of ligand-bound receptors, and formation of coated pits followed by internalization of the ligands into endosomes. Both enveloped viruses, like influenza virus and alphaviruses, and non-enveloped viruses, like Adenovirus, infect cells via endocytotic mechanisms. See: Pastan, I. et al. (1986) in *Virus Attachment and Entry into Cells*, (Crowell, R. L. and Lonberg-Holm, K., eds.) Am. Soc. Microbiology, Washington, p. 141-146; Kielian, M. and Helenius, A. (1986) "Entry of Alphaviruses" in *The Togaviridae and Flaviviridae*, (Schlesinger, S. and Schlesinger, M. J., eds.) Plenum Press, New York p. 91-119; FitzGerald, D. J. P. et al. (1983) Cell 32:607-617. Enhancement of dendrimer-mediated transfection of some cells by chloroquine (a lysosomotropic agent) suggests that endocytosis is involved in at least some dendrimer-mediated transfections.

Despite their relative effectiveness, however, successful transfection of eukaryotic cell cultures using polycationic lipid reagents often requires high dosages of nucleic acid (approximately $10^5$ DNA molecules per cell). The introduction of foreign DNA sequences into eukaryotic cells mediated by viral infection is generally orders of magnitude more efficient than transfection with cationic lipid or dendrimer transfection agents. Viral infection of all the cells in a culture requires fewer than 10 virus particles per cell. Although the detailed mechanism of fusion is not fully understood and varies among viruses, viral fusion typically involves specific fusagenic agents, such as viral proteins, viral spike glycoproteins and peptides of viral spike glycoproteins. Vesicular stomatitis virus (VSV) fusion, for example, is thought to involve interaction between the VSV glycoprotein (G protein) and membrane lipids (Schlegel, R. et al. (1983) Cell 32:639-646).

The VSV G protein reportedly binds preferentially to saturable receptors such as acidic phospholipid phosphatidylserine (Schlegel, R. and M. Wade (1985) J. Virol. 53(1): 319-323). Fusion of influenza virus involves hemagglutinin HA-2 N-terminal fusagenic peptides. See Kamata, H. et al. (1994) Nucl. Acids Res. 22(3):536-537.

Cell binding and internalization can also be enhanced, accelerated or made selective with peptides that bind cell receptors. For example, the penton-base protein of the Adenovirus coat contains the peptide motif RGD (Arg-Gly-Asp) which mediates virus binding to integrins and viral internalization via receptor-mediated endocytosis (Wickham, T. J. et al. (1995) Gene Therapy 2:750-756).

The efficiency of cationic lipid transfections has recently been shown to be enhanced by the addition of whole virus particles to the transfection mixture. See Yoshimura et al. (1993) J. Biol. Chem. 268:2300. Certain viral components may also enhance the efficiency of cationic lipid-mediated transfection. See: U.S. patent application Ser. No. 08/090, 290, filed Jul. 12, 1993; and Ser. No. 08/274,397, filed Jul. 12, 1994, now U.S. Pat. No. 5,578,475; incorporated by reference in their entirety herein. The use of peptides from viral proteins to enhance lipid-mediated transfections was also recently suggested by Kamata et al. (1994) Nucl. Acids Res. 22:536. Kamata et al. suggest that "LIPOFECTIN"-mediated transfections may be enhanced 3-4-fold by adding influenza virus hemagglutinin peptides to the transfection mixture. Despite these positive early indications, results vary as to the effectiveness of including fusagenic or nuclear localization peptides in lipidic transfection compositions. Remy et al. (1995) Proc. Natl. Acad. Sci. USA 92:1744 report that "[a]ddition of lipids bearing a fusagenic or a nuclear localization peptide head group to the (polycationic lipid-DNA complex) particles does not significantly improve an already efficient system."

SUMMARY OF THE INVENTION

The present invention is based on the discovery that peptide sequences from viral, bacterial or animal proteins and other sources, including peptides, proteins or fragments or portions thereof can significantly enhance the efficiency of transfection of eukaryotic cells mediated by transfection agents, including cationic lipids and dendrimers. The compositions and methods of the invention comprise peptides, proteins and fragments thereof, modified peptides, modified proteins and modified fragments thereof, peptide conjugates, protein conjugates and conjugates of fragments thereof, including those of fusagenic, membrane-permeabilizing, receptor-ligand, and/or nuclear-localization peptides or proteins, or peptides or proteins that localize to other sub-cellular locations (e.g., mitochondrial localization peptides or proteins), which significantly improve the efficiency of transfection when bound to nucleic acid. In preferred embodiments, peptides, proteins, fragment thereof, or modified peptides, proteins and fragments thereof are bound or added to nucleic acid prior to adding the transfection reagent, although such peptides, proteins, fragments and modifications thereof may be added or complexed with the transfection reagent prior to addition of the nucleic acid. Alternatively, the nucleic acid is combined with the transfection agent prior to addition of the peptide, protein, fragments and modifications thereof. These fusagenic, receptor-ligand, nuclear localization, transport or trafficking, or other peptides can form a noncovalent association or complex with the nucleic acid that is to be introduced into a cell. Complex formation can be enhanced by covalent coupling of the peptide or protein to a DNA-binding group, which can bind to the nucleic acid through conformational or charge interactions and facilitate binding of the peptide to DNA. More generally, nucleic acid-peptide or protein complex formation can be enhanced by covalent coupling of the peptide or protein to a nucleic acid-binding group. Nucleic acids (DNA and RNA and variants thereof) are more efficiently transported into the cell by the transfection agent when bound to peptides or proteins of this invention and can with appropriate choice of peptide or protein be directed to the cell nucleus or to other sub-cellular locations, thus requiring less nucleic acid starting material.

This invention also relates to the covalent coupling of peptides or proteins to the transfection agent, e.g., directly or via an appropriate linking or spacer group to a lipid of the cationic lipid transfection composition (a cationic or neutral lipid) or directly or via an appropriate linking or spacer group to a dendrimer. Of particular interest are conjugated lipids and dendrimers that are covalently linked to fusagenic peptides or proteins, transport or trafficking peptides or proteins, membrane-permeabilizing peptides or proteins and receptor-ligand peptides or proteins. A variety of spacer groups may be used dependent upon the transfection agent and the peptide or protein. For example, spacers may be alkyl, ether, thioether, ester or amide groups.

The cationic lipid compositions of the present invention and the dendrimer compositions of this invention provide significant advantages over, prior art compositions, including enhanced transformation frequency.

The present invention provides compositions and methods for transfecting eukaryotic cells, particularly higher eukaryotic cells, with nucleic acids. Nucleic acids, both DNA and RNA, are introduced into cells such that they retain their biological function. Compositions for transfecting eukaryotic cells comprising a peptide-nucleic acid complex or protein-nucleic acid complex and a transfection agent are provided. Transfection compositions of this invention include those in which the transfection agent is any lipid, preferably a cationic lipid, a mixture of cationic lipids or a mixture of cationic lipids and neutral lipids. Transfection compositions of this invention also include those in which the transfection agent is a dendrimer or mixture of dendrimers, as well as mixtures of dendrimers and neutral or cationic lipids. Transfection compositions comprise a peptide or modified-peptide, e.g., a peptide-conjugate, or protein or fragment or portion thereof, modified or conjugated, which may bind nucleic acid and which are fusagenic, membrane-permeabilizing, or which function for nuclear localization, function for transport or trafficking, function for localization to another sub-cellular location, and/or function as a receptor-ligand. Receptor-ligand peptides or proteins of this invention include those that bind to cell surface receptors, membrane receptors or cytosolic receptors and that can function for cell targeting or cell adhesion, and include those that trigger internalization or endocytosis. The peptide- or protein-nucleic acid complex is formed by interacting a peptide or protein or modified peptide or modified protein with nucleic acid or by interacting the peptide or protein with a nucleic acid-transfection agent complex. Modified peptides or proteins include peptides or proteins covalently conjugated to nucleic acid-binding groups. Peptide- or protein-conjugates of this invention also include peptide- or protein-lipid (neutral or cationic) and peptide- or protein-dendrimer conjugates in which the peptide or protein is covalently linked to the transfection agent or a component of the transfection agent.

For non-covalent peptide- or protein-enhanced lipid transfection, the peptide- or protein-nucleic acid complex is subsequently combined with a lipid, preferably a cationic lipid (or a mixture of a cationic lipid and neutral lipid) to form a peptide- or protein-nucleic acid-lipid aggregate which facilitates introduction of the anionic nucleic acid through cell membranes, including the nuclear membrane, or targets the nucleic acid to a particular cell or sub-cellular location. Transfection compositions of this invention comprising peptide- or protein-nucleic acid complexes and lipid can further include other non-peptide agents that are known to further enhance transfection.

For lipid transfection employing a covalent peptide- or protein-lipid conjugate, the peptide- or protein-lipid conjugate is combined with nucleic acid, as is conventional for cationic lipid transfection. The peptide- or protein-lipid conjugate may be first combined in a mixture of non-conjugated cationic and/or neutral lipids and then combined with nucleic acid to form a peptide- or protein-lipid-nucleic acid lipid aggregate which facilitates introduction of the anionic nucleic acid through cell membranes, including the nuclear membrane, or targets the nucleic acid to a particular cell or to a sub-cellular location. Transfection compositions of this invention comprising peptide- or protein-lipid conjugates and nucleic acids can further include other non-peptide or non-protein agents that are known to further enhance transfection.

In an alternative transfection method of this invention employing fusagenic peptides or proteins covalently conjugated to lipids, the peptide- or protein-lipid conjugate is complexed with non-conjugated cationic lipids (or a mixture of cationic and neutral lipids). A sub-cellular localization peptide or protein, preferably a nuclear localization peptide or protein, is complexed to the nucleic acid and the nucleic acid-peptide or protein complex is admixed with the cationic lipid-containing complex comprising covalently conjugated fusagenic peptides or proteins. The resulting mixture exhibits enhanced transfection efficiency.

For dendrimer transfection, the covalent peptide- or protein-dendrimer conjugate is subsequently combined with nucleic acid, as is known in the art for dendrimer-mediated transfection, to form a peptide- or protein-dendrimer-nucleic acid aggregate that facilitates introduction of the anionic nucleic acid through cell membranes, including the nuclear membrane, or targets the nucleic acid to a particular cell or sub-cellular location. When a peptide- or protein-dendrimer conjugate is employed, the peptide or protein is believed, for the most part, to be concentrated at the outer surface of the dendrimer aggregate formed. Transfection compositions of this invention comprising peptide- or protein-dendrimer conjugates and nucleic acid can further include other non-peptide agents that are known to further enhance dendrimer transfection, for example dendrimer transfection can be enhanced by addition of DEAE-dextran and/or chloroquin.

In alternative transfection compositions of this invention employing fusagenic peptides or proteins conjugated to dendrimers, the peptide- or protein-dendrimer conjugate is admixed with a nucleic acid that is itself complexed to a sub-cellular localization peptide or protein, preferably a nuclear localization peptide or protein. The new complex (e.g., Sp-NLS-nucleic acid complexed to VSVG or RGD or E5-dendrimer) is optionally admixed with non-conjugated dendrimers or optionally admixed with a cationic lipid-containing composition. The resulting mixture exhibits enhanced transfection efficiency.

Peptides useful in transfection compositions include, but are not limited to, functional portions of proteins and or polypeptides that are fusagenic, function for nuclear or other sub-cellular localization, function for transport or trafficking, are receptor ligands, comprise cell-adhesive signals, cell-targeting signals, cell-internalization signals or endocytosis signals as well as peptides or functional portions thereof of viral fusagenic proteins, of viral nuclear localization signals, of receptor-ligands, of cell adhesion signals, of cell-targeting signals or of internalization- or endocytosis-triggering signals. Peptides useful in this invention include naturally-occurring peptides, peptides derived from synthetic or engineered proteins or polypeptides, and synthetic analogs or functional equivalents of naturally-occurring peptides. Peptides of this invention include those comprised of the twenty commonly occurring amino acids, as well as rare amino acids, such as homocysteine and ornithine, or D-amino acids or amino acid analogs. Peptides and proteins or this invention can include polyamines such as carboxy spermine. Transfection compositions comprising viral peptides or functional portions of viral peptides of influenza virus, vesicular stomatitis virus, adenovirus and simian virus 40 are of particular interest. Transfecting compositions containing viral peptides (as well as proteins and polypeptides) modified so that they are covalently conjugated to DNA-binding groups, for example, spermine or related polyamines, are also useful in the methods of this invention.

Any proteins (or fragments or portions thereof) may be used in accordance with this invention, either singly or in combination with other proteins or peptides. In a preferred aspect, two or more, three or more, four or more, five or more, six or more, etc. proteins and/or peptides are used in the invention. Additionally, such single or multiple proteins and/or peptides may be used in combination with one or more, two or more, three or more, four or more, five or more, six or more, etc. transfection agents. In another preferred aspect, at least two peptides and/or proteins are used in combination with a transfection agent, preferably at least two transfection agents such as lipids and/or dendrimers.

Proteins useful in transfection compositions include, but are not limited to, receptor ligands, membrane binding and fusion proteins, transport or trafficking proteins, nuclear localizing proteins, nuclear proteins, including proteins derived from chromatin, bacterial internalization-mediating proteins, bacterial toxins or portions of toxins (with toxin portion inactivated), which enter cells and localize to subcellular compartments, membrane-disturbing proteins and anti-microbial proteins. Proteins include those derived from viral, bacterial, animal and other sources. Receptor-ligand proteins which are useful include, but are not limited to, insulin, transferrin, epidermal growth factor, fibroblast growth factor, lactoferrin, and fibronectin. Useful viral membrane binding and fusion proteins include, but are not limited to, the adenoviral proteins penton base, knob, and hexon, the vesicular stomatitis virus glycoprotein (VSVG), the coat proteins from semliki forest virus and the influenza hemagglutinin (HA). Viral transport or trafficking proteins include, but are not limited to, HIV Tat, hepatitis B virus core protein, and herpes simplex virus VP22. A list of nuclear and chromatin proteins which are useful includes, but is not limited to, the histone proteins, especially H1 and H2, the "high mobility group" proteins, especially HMG 1 and 17, protamine and hn RNP A1. Bacterial internalization proteins include, but are not limited to, invasin and internalin and proteins with similar functions derived from *Listeria* and *Myobacterium tuberculosis*. Bacterial toxins which enter cells and localize to sub-cellular compartments include, but are not limited to, Pseudomonas endotoxin A, Diphtheria toxin, and Shigella toxin. In each case, the bacterial toxin function of these proteins and polypeptides is inactivated to avoid detriment to transfected cells. Membrane-disturbing and anti-microbial proteins (some derived from venoms) include, but are not limited to, melittin, magainin, gramicidin, cecropin, defensins, protegrins, tachyplesins, thionins, indolicidin, bactenecin, drosomycin, apidaecins, cathelicidin, bacteriacidal/permeability-increasing protein (BPI), nisin, and buforin.

Inclusion of a peptide- or protein-nucleic acid complex or a modified peptide- or protein-nucleic acid complex in a cationic lipid transfection composition can significantly enhance transfection (by 2-fold or more) of the nucleic acid compared to transfection of the nucleic acid mediated by the cationic lipid alone. Enhancement of dendrimer transfection by peptides or proteins or modified peptides or modified proteins or fragments thereof is pronounced in a wide variety of cell lines, including human primary cell lines and in cell lines that are generally considered by those in the art to be "hard-to-transfect."

Monovalent or polyvalent cationic lipids are employed in cationic lipid transfecting compositions. Preferred monovalent cationic lipids are DOTMA (N-[1-(2,3-dioleoyloxy)-propyl]-N,N,N-trimethyl ammonium chloride), DOTAP (1,2-bis(oleoyloxy)-3-3-(trimethylammonium)propane), DMRIE (1,2-dimyristyloxypropyl-3-dimethyl-hydroxy ethyl ammonium bromide) or DDAB (dimethyl dioctadecyl ammonium bromide). Preferred polyvalent cationic lipids are lipospermines, specifically DOSPA (2,3-dioleyloxy-N-[2 (sperminecarboxamido)ethyl]-N,N-dimethyl-1-propanaminium trifluoro-acetate) and DOSPER (1,3-dioleoyloxy-2-(6carboxy spermyl)-propyl-amid, and the di- and tetra-alkyl-tetra-methyl spermines, including but not limited to TMTPS (tetramethyltetrapalmitoyl spermine), TMTOS (tetramethyltetraoleyl spermine), TMTLS (tetramethyltetralauryl spermine), TMTMS (tetramethyltetramyristyl spermine) and TMDOS (tetramethyldioleyl spermine). Cationic lipids are optionally combined with non-cationic lipids, particularly neutral lipids, for example lipids such as DOPE (dioleoylphosphatidylethanolamine), DPhPE (diphytanoylphosphatidylethanolamine) or cholesterol. A cationic lipid composition composed of a 3:1 (w/w) mixture of DOSPA and DOPE or a 1:1 (w/w) mixture of DOTMA and DOPE are generally useful in transfecting compositions of this invention. Preferred transfection compositions are those which induce substantial transfection of a higher eukaryotic cell line.

Inclusion of a peptide- or protein-nucleic acid or modified peptide- or protein-nucleic acid complex in a dendrimer transfection composition can significantly enhance transfection (by 2-fold or more) of the nucleic acid compared to transfection of the nucleic acid mediated by the dendrimer alone or in combination with DEAE-dextran or chloroquine or both. Enhancement of transfection by peptides, proteins, modified peptides or modified proteins is pronounced in a wide variety of cell lines, including human primary cell lines and in cell lines that are generally considered by those in the art to be "hard-to-transfect."

In general, any dendrimer that can be employed to introduce nucleic acid into any cell, particularly into a eukaryotic cell, is useful in the improved transfection compositions and methods of this invention. Dendrimers of generation 5 or higher (G5 or higher) are preferred, with those of generation between G5-G10 being of particular interest. Dendrimers of this invention include those with $NH_3$ or ethylenediamine cores, GX($N1H_3$) or GX(EDA), where X=the generation number. Dendrimers where X=5-10 being preferred. Dendrimers of this invention include those in which the repeating unit of the internal layers is a amidoamine (to form polyamidoamines, i.e. PAMAMs). Dendrimers of this invention include those in which the terminal functional groups at the outer surface of the dendrimer provides a positive charge density, e.g., as with terminal amine functional groups. The surface charge and the chemical nature of the outer dendrimer surface can be varied by changing the functional groups on the surface, for example, by reaction of some or all of the surface amine groups. Of particular interest are dendrimers that are functionalized by reaction with cationic amino acids, such as lysine or arginine. Grafted dendrimers as described, for example in PCT applications WO 9622321 and WO9631549 and noted in U.S. Pat. No. 5,266,106, can be employed in the compositions and methods of this invention. Activated dendrimers (J. Haensler and R. Szoka (1993) Bioconjugate Chem. 4:372-379 and M. X. Tang et al., (1996) Bioconjugate Chem. 7P703-714) can also be employed in the composition and methods of this invention.

The methods of the present invention involve contacting any cell, preferably a eukaryotic cell, with a transfection composition comprising a peptide, a protein or fragment or portion thereof, including a fusagenic, membrane-permeabilizing, transport or trafficking sub-cellular-localization, or receptor-ligand peptide or protein, optionally conjugated to a nucleic acid-binding group, or optionally conjugated to the transfection agent (lipid or dendrimer) wherein said peptide or protein or modified peptide or protein is non-covalently associated with the nucleic acid. In one embodiment, a peptide- or protein-nucleic acid complex (where the peptide or protein can be conjugated to a nucleic-acid binding group) is formed and then combined with a cationic lipid for transfection. In a related embodiment, a peptide- or protein-lipid conjugate is combined optionally with other lipids, including any appropriate cationic lipid, and then combined with nucleic acid for transfection. In another related embodiment, a nucleic acid-lipid complex is formed and then combined with a peptide or protein for transfection. In a second embodiment, a peptide- or protein-nucleic acid complex (where the peptide or protein can be conjugated to a nucleic-acid binding group) is formed and then combined with a dendrimer for transfection. In a related embodiment, a peptide-dendrimer conjugate is combined optionally with other dendrimers and then combined with nucleic acid for transfection. In another related embodiment, a nucleic acid-dendrimer complex is formed and then combined with a peptide or protein for transfection. Dendrimers and/or peptide-conjugated dendrimers can be combined with cationic lipids and cationic lipid composition to obtain improved nucleic acid transfection compositions. In accordance with the invention, multiple peptides and/or proteins may be added to accomplish transfection.

Methods of this invention employ among others, viral peptides or proteins of influenza virus, adenovirus, Semliki forest virus, HIV, hepatitis, herpes simplex virus, vesicular stomatitis virus or simian virus 40 and more specifically an RGD-peptide sequence, an NLS peptide sequence and/or a VSVG-peptide sequence and to modified peptides or proteins of each of the foregoing. Methods of this invention are applicable to transfection of adherent or suspension cell lines, in general to animal cell lines, specifically to mammalian, avian, reptilian, amphibian and insect cell lines and more specifically to animal primary cell lines, human primary cell lines, stem cell lines, and fibroblasts, as well as to cells in vivo in living organisms.

In one specific embodiment, a transfection-enhancing peptide or protein is first bound to a nucleic acid to be introduced into a cell. The peptide- or protein-nucleic acid complexes are then admixed with a transfection agent (or mixture thereof) and the resulting mixture is employed to transfect cells. Preferred transfection agents are cationic lipid compositions, particularly monovalent and polyvalent cationic lipid compositions, more particularly "LIPOFECTIN," "LIPOFEC- TACE," "LIPOFECTAMINE," "CELLFECTIN," DMRIE-C, DMRIE, DOTAP, DOSPA, and DOSPER, and dendrimer compositions, particularly G5-G10 dendrimers, including dense star dendrimers, PAMAM dendrimers, grafted dendrimers, and dendrimers known as dendrigrafts and "SUPERFECT."

In a second specific transfection method, a transfection-enhancing peptide or protein is conjugated to a nucleic acid-binding group, for example a polyamine and more particularly a spermine, to produce a modified peptide or protein which is then bound to the nucleic acid to be introduced into the cell. The modified peptide-nucleic acid complex is then admixed with a transfection agent (or mixture thereof) and the resulting mixture is employed to transfect cells. In particular, the peptide or protein is covalently conjugated to a spermine, the spermine-modified peptide or protein is complexed with nucleic acid and admixed with a cationic lipid. Preferred transfection agents are cationic lipid compositions, particularly monovalent and polyvalent cationic lipid compositions, more particularly "LIPOFECTIN," "LIPOFECTACE," "LIPOFECTAMINE," "CELLFECTIN," DMRIE-C, DMRIE, DOTAP, DOSPA, and DOSPER, and dendrimer compositions, particularly G5-G10 dendrimers, including dense star dendrimers, PAMAM dendrimers, grafted dendrimers, and including dendrimers known as dendrigrafts.

In a third specific embodiment, a mixture of one or more transfection-enhancing peptides, proteins, or protein fragments, including fusagenic peptides or proteins, transport or trafficking peptides or proteins, receptor-ligand peptides or proteins, or nuclear localization peptides or proteins and/or their modified analogs (e.g., spermine modified peptides or proteins) or combinations thereof are mixed with and complexed with nucleic acid to be introduced into a cell. The peptide-nucleic acid complexes are then admixed with transfection agent and the resulting mixture is employed to transfect cells.

In another specific embodiment, a component of a transfection agent (lipids, cationic lipids or dendrimers) are covalently conjugated to selected peptides, proteins, or protein fragments directly or via a linking or spacer group. Of particular interest in this embodiment are peptides or proteins that are fusagenic, membrane-permeabilizing, transport or trafficking, or which function for cell-targeting. The peptide- or protein-transfection agent complex is combined with nucleic acid and employed for transfection.

The transfection compositions and methods of the present invention can be applied to in vitro and in vivo transfection of cells, particularly of eukaryotic cells, and more particularly to transfection of higher eukaryotic cells, including animal cells. The methods of this invention can be used to generate transfected cells which express useful gene products. The methods of this invention can also be employed as a step in the production of transgenic animals. The methods of this invention are useful as a step in any therapeutic method requiring introduction of nucleic acids into cells including methods of gene therapy and viral inhibition and for introduction of antisense or antigene nucleic acids or ribozymes or RNA regulatory sequences or related inhibitory or regulatory nucleic acids into cells. In particular, these methods are useful in cancer treatment, in in vivo and ex vivo gene therapy, and in diagnostic methods.

The transfection compositions and methods of this invention comprising peptides, proteins, peptide or protein fragments or modified peptides or modified proteins, can also be employed as research reagents in any transfection of eukaryotic cells done for research purposes. The transfection compositions can, with appropriate choice of physiologic medium, be employed in therapeutic and diagnostic applications.

Transfection agents and transfection-enhancing agents of this invention can be provided in a variety of pharmaceutical compositions and dosage forms for therapeutic applications. For example, injectable formulations, intranasal formulations and formulations for intravenous and/or intralesional administration containing these complexes can be used therapy.

In general the pharmaceutical compositions of this invention should contain sufficient transfection agent and any enhancing agents (peptide, protein, etc.) to provide for introduction of a sufficiently high enough level of nucleic acid into the target cell or target tissue such that the nucleic acid has the desired therapeutic effect therein. The level of nucleic acid in the target cell or tissue that will be therapeutically effective will depend on the efficiency of inhibition or other biological function and on the number of sites the nucleic acid must affect.

The dosage of transfection agent administered to a patient will depend on a number of other factors including the method and site of administration, patient age, weight and condition. Those of ordinary skill in the art can readily adjust dosages for a given type of administration, a given patient and for a given therapeutic application.

It will be appreciated by those of ordinary skill in the art that the transfection composition should contain minimal amounts of inhibitory components, such as serum or high salt levels, which may inhibit introduction of nucleic acid into the cell, or otherwise interfere with transfection or nucleic acid complexation. It will also be appreciated that any pharmaceutical or therapeutic compositions, dependent upon the particular application, should contain minimal amounts of components that might cause detrimental side-effects in a patient.

Components of the transfection compositions of this invention can be provided in a reagent kit. In general, the kit comprises a transfection agent and a transfection-enhancing peptide, protein or fragment thereof. In one embodiment, a kit comprises individual portions of cationic lipid and peptide, protein or fragment thereof or modified peptide, protein or fragment thereof. In a second embodiment, a kit comprises individual portions of dendrimer and peptide, protein or fragments thereof or modified peptide, protein or fragments thereof. Cationic lipid transfection kits can optionally include neutral lipid as well as other transfection-enhancing agents or other additives, and the relative amounts of components in the kit may be adjusted to facilitate preparation of transfection compositions. Kit components can include appropriate medium or solvents for other kit components. Cationic lipid transfection kits comprising a monocationic or polycationic lipid composition including a neutral lipid and a modified peptide or protein are preferred. Dendrimer transfection kits can optionally include other transfection enhancing agents, such as DEAE-dextran and/or chloroquine, as well as other additives and the relative amounts of components in the kit may be adjusted to facilitate preparation of transfection compositions. Dendrimer transfection kits comprising a G5-G10 dendrimer or a Lys- or Arg-modified dendrimer or dendrigraft or an activated dendrimer in combination with a peptide or protein or a modified peptide or protein are preferred. Kits provided by this invention include those comprising an individual portion of a polycationic lipid composition comprising DOSPA and DOPE or a monocationic lipid composition comprising DOTMA and DOPE and a portion of modified peptide, particularly a spermine-modified peptide. Kits provided by this invention include those comprising an individual portion of a dendrimer and a portion of a spermine-modified peptide.

In related embodiments, kits of this invention can comprise a peptide- or protein-lipid conjugate or a peptide- or protein-dendrimer conjugate in combination with non-conjugated lipids, non-conjugated dendrimers and other agents to facilitate transfection.

Kits of this invention can include those useful in diagnostic methods, e.g., diagnostic kits which in addition to transfection agent and transfection-enhancing agents (e.g., proteins, peptides, and fragments and modifications of peptides and proteins) can contain a diagnostic nucleic acid. A diagnostic nucleic acid is a general term for any nucleic acid which can be employed to detect the presence of another substance (most generally an analyte) in a cell. For example, when transfected into a cell a diagnostic nucleic acid may increase or decrease expression of a gene therein in response to the presence of another substance in the cell (e.g., a protein, small molecule, steroid, hormone, or another nucleic acid). Diagnostic nucleic acids also include those nucleic acids that carry some label or otherwise detectable marker to a particular target cell or target tissue for detection of the target cell or tissue or for detection of a substance in the target cell or tissue.

Nucleic acids that can be transfected by the methods of this invention include DNA and RNA of any size from any source comprising natural bases or non-natural bases, and include those encoding and capable of expressing therapeutic or otherwise useful proteins in cells, those which inhibit undesired expression of nucleic acids in cells, those which inhibit undesired enzymatic activity or activate desired enzymes, those which catalyze reactions (ribozymes), and those which function in diagnostic assays (e.g., diagnostic nucleic acids). Thereapeutic nucleic acids include those nucleic acids that encode or can express therapeutically useful proteins, peptides or polypeptides in cells, those which inhibit undesired expression of nucleic acids in cells, those which inhibit undesired enzymatic activity or activate desired enzymes in cells.

The compositions and methods provided herein can also be readily adapted in view of the disclosure herein to introduce biologically-active macromolecules other than nucleic acids including, among others, polyamines, polyamine acids, polypeptides and proteins into eukaryotic cells. Other materials useful, for example as therapeutic agents, diagnostic materials, research reagents, which can be bound to the peptides and modified peptides and introduced into eukaryotic cells by the methods of this invention.

BRIEF DESCRIPTION OF THE FIGURES

FIG. 3A, C, E, and G: no Sp-NLSNLS; FIG. 3B, D, F and H: 1-4 µg Sp-NLSNLS/well, precomplexed with DNA.

DETAILED DESCRIPTION OF THE INVENTION

Figure 1:
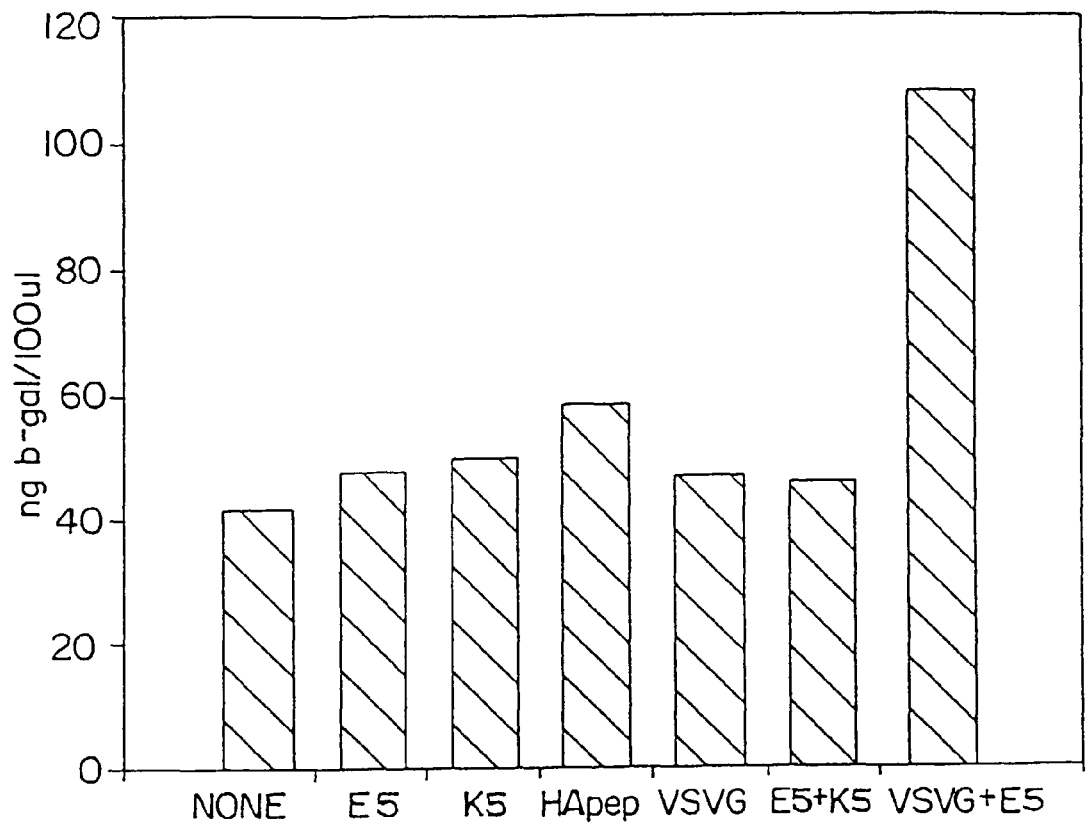
FIG. 1 is a bar graph showing enhancement of transfection of human fibroblast cells with various peptides added to "LIPOFECTAMINE"-DNA transfection mixtures.

The present invention provides improved methods for transfecting any cell, preferably eukaryotic cells with nucleic acids by employing peptides, proteins, or fragments thereof, modified peptides or modified proteins, or modified fragments thereof, in combination with transfection agents, e.g., cationic lipids and dendrimers. The improvement relates in one aspect to the use of a peptide- or protein-nucleic acid complex to enhance the efficiency of cationic lipid-mediated or dendrimer-mediated transfection. The peptide- or protein-nucleic acid complex comprises peptide bound to nucleic acid or a peptide modified to be covalently conjugated to a nucleic acid-binding group which is then bound to nucleic acid. Alternatively, the peptide or protein is used in combination with a nucleic acid-transfection agent complex. This invention has significant advantages over prior art methods of transfection which employ cationic lipids or dendrimers for transfection.

The peptides of this invention include fusagenic peptides, membrane-permeabilizing peptides, transport or trafficking peptides, nuclear localization peptides, and receptor-ligand peptides, among others. Receptor-ligand peptides include among others cell-adhesion peptides, cell-targeting peptides, internalization-triggering peptides, and endocytosis-triggering peptides. Peptides useful in this invention can include peptide sequences functional for fusion (fusagenic sequences), transport, sub-cellular localization or which mediate binding to a receptor. Peptides can include those that are functional fragments of polypeptides or proteins, and may be synthetic or derived from synthetic or engineered proteins or polypeptides. A peptide may be multi-functional comprising sequences with more than one of these functions. Peptides are optionally covalently coupled to a nucleic-binding group, including a polyamine, and form a complex with the nucleic acid. Peptide-complexed nucleic acids are more efficiently transported into the cells and the cell nucleus, thus enhancing the efficiency of cationic lipid- or dendrimer-mediated cell transfection. Because of the improved efficiency of transfection, considerably less nucleic acid is required for effective transfection. Transfection compositions of this invention, by virtue of complex formation between the nucleic acid and peptide or modified peptide, provide enhanced transfection as compared to prior art cationic lipid and dendrimer transfection compositions.

The proteins of this invention include fusagenic proteins, membrane-permeabilizing proteins, transport or trafficking proteins, nuclear localization proteins, and receptor-ligand proteins, among others. Receptor-ligand proteins include among others cell-adhesion proteins, cell-targeting proteins, internalization-triggering proteins, and endocytosis-triggering proteins. Proteins useful in this invention can include peptide sequences functional for fusion (fusagenic sequences), transport, sub-cellular localization or which mediate binding to a receptor. Proteins can include those that are functional fragments of polypeptides or proteins, and may be synthetic or engineered proteins or comprise synthetic or engineered polypeptides. A protein may be multi-functional comprising sequences having more than one of these functions. Proteins are optionally covalently coupled to a nucleic-binding group, including a polyamine, and form a complex with the nucleic acid. Protein-complexed nucleic acids are more efficiently transported into the cells and the cell nucleus, thus enhancing the efficiency of cationic lipid- or dendrimer-mediated cell transfection. Because of the improved efficiency of transfection, considerably less nucleic acid is required for effective transfection. Transfection compositions of this invention, by virtue of complex formation between the nucleic acid and protein or modified protein, provide enhanced transfection as compared to prior art cationic lipid and dendrimer transfection compositions.

Another aspect of this invention relates to improved efficiency of transfection using peptide or protein conjugates in which a selected peptide (protein or protein fragment) is covalently linked to a dendrimer or to a lipid that will be a component in a cationic lipid transfection composition. The peptide- or protein-conjugated transfection agent is then employed in transfections as is known in the art for the non-conjugated transfection agent.

The following definitions are employed in the specification and claims.

The term "transfection" is used herein generally to mean the delivery and introduction of biologically functional nucleic acid into a cell, e.g., a eukaryotic cell, in such a way that the nucleic acid retains its function within the cell. Transfection methods of this invention may be applied to cells in vitro or in vivo. The term transfection includes the more specific meaning of delivery and introduction of expressible nucleic acid into a cell such that the cell is rendered capable of expressing that nucleic acid. The term expression means any manifestation of the functional presence of the nucleic acid within a cell, including both transient expression and stable expression. Nucleic acids include both DNA and RNA without size limits from any source comprising natural and non-natural bases. Nucleic acids can have a variety of biological functions. They may encode proteins, comprise regulatory regions, function as inhibitors of gene or RNA expression (e.g., antisense DNA or RNA), function as inhibitors of proteins, function to inhibit cell growth or kill cells, catalyze reactions or function in a diagnostic or other analytical assay.

Transfection efficiency is "enhanced" when an improvement of at least about 5 percent, preferably about 10 percent, and more preferably about 20 percent in efficiency is shown using the protocols for measuring nucleic acid biological function set forth in the examples hereof. Transfection is substantially enhanced when at least about a 2-fold (i.e. 100% or more) improvement of efficiency is measured as described herein.

The term "nucleic acid-binding group" is used herein generally to mean a protein, peptide, polypeptide or polyamine which is capable of non-covalently associating with nucleic acids. Nucleic acid-binding groups include DNA-binding groups. Binding of the nucleic acid-binding group to the nucleic acid can be specific to the sequence of the nucleic acid, or non-specific to its sequence. Although the mechanism of association depends upon the particular binding group, sequence specificity generally results from an ensemble of mutually favorable interactions between a binding group and its target DNA. Some DNA-binding groups, for example, interact with the DNA's paired bases and sugar-phosphate chains through direct contacts, including hydrogen bonds, salt bridges and van der Waals forces. Other groups function through sequence-specific conformational variations in DNA (or more generally nucleic acid) rather than from sequence-specific hydrogen bonding interactions between nucleic acid and protein. It will be understood that the term "nucleic acid-binding group" includes any protein, peptide, polypeptide or polyamine which is capable of binding nucleic acid, without regard to the mechanism of binding. Nucleic acid-binding groups are known to the art and widely available in commerce.

The term "peptide" as used herein is intended to be a generic term which broadly includes short peptides (typically less than 100 amino acids). Peptide used generically herein also includes peptides modified with nucleic acid-binding groups or peptides which retain amino acid protecting groups, such as the Mtr group. Longer polypeptides (typically more than 100 amino acids), and proteins which contain one or more polypeptide chains which function as transfection enhancing agents having fusagenic, cell-receptor ligand, transport or sub-cellular localization function, can be substituted for the peptides of this invention and can also be modified with nucleic acid-binding groups. The peptides of this invention typically have more than two amino acids; preferred peptides have more than 4 amino acids.

The peptides of this invention have biological function as fusagenic peptides, membrane-permeabilizing peptides, sub-cellular-localization peptides, cellular transport, and receptor-ligand peptides. Two or more peptide functions can be combined into the same peptide, for example, by automated peptide synthesis. Peptides include dimers, multimers and contatimers of peptide sequences that have one or more desired functionalities.

The term spermine is used to describe the molecule spermine, but also to describe peptides that are modified to be covalently linked to a spermine, as in the term "spermine-modified" peptide. Spermine may be linked directly or indirectly through intervening covalent bonds to the peptide. Spermine-modified peptide can be used generically to describe modified peptides containing a linker to spermine. For example, the term spermine-modified also refers to peptides that are linked to carboxyspermine.

Receptor-ligand proteins or peptides of this invention include those peptides, proteins or protein fragments which bind to cell-surface or other membranes or which bind to soluble receptor molecules and which optionally have another biological function and which optionally trigger internalization or endocytosis. Receptor-ligand proteins or peptides include cell-adhesion proteins or peptides, and cell targeting proteins or peptides.

Receptor-ligand proteins or peptides also include adhesion proteins or peptides. Adhesion proteins or peptides do not typically trigger endocytosis. Adhesion proteins or peptides include or can be derived from adhesion proteins including fibronectin, vitronectin, tenascin, laminins, collagens, thrombospondins, fibrinogens and functional equivalents. Such receptor-ligand peptides also include fragments of adhesion proteins including, but not limited to, fibronectin fragments such as "RETRONECTIN" (obtainable from Takara, Japan; see U.S. Pat. No. 5,198,423, which is incorporated by reference in its entirety herein). Table 1 provides examples of adhesion proteins and peptides.

Fragments of adhesion proteins include RGD sequence-containing peptides (RGD peptides) as listed in Table 1. The CS-1 peptide, sequence given in Table 1, is obtained from a 38 kD tryptic fragment of plasma fibronectin containing the carboxyl-terminal Heparin II domain and part of the type III connecting segment (IIICS) (Wayner, E. A. et al. (1989) "Identification and Characterization of T Lymphocyte Adhesion Receptor for an Alternative Cell Attachment Domain (CS-1) in Plasma Fibronectin" J. Cell Biol. 109:1321-1330.)

Receptor ligand proteins or peptides also include those that trigger internalization and/or endocytosis. For example, Penton Base is a pentamer coat protein of adenovirus that contains five copies of the integrin receptor binding motif, Arg-Gly-Asp (RGD). Penton Base is used by the virus to bind integrins $\alpha_v\beta_3$ and $\alpha_v\beta_5$. Following adenovirus attachment to cells by the fiber coat protein, the integrin receptors mediate virus internalization in to the host cells. The Penton Base (wild-type) RGD sequence is HAIRGDTFAT [SEQ ID NO:1] (Wickham, T. J. et al. (1995) Gene Therapy 2:750-756.)

Adhesive peptides include RGD peptides which are peptides containing the tripeptide sequence Arg-Gly-Asp which can duplicate or inhibit the cell attachment promoting effects of fibronectin or vitronectin (Pierschbacher, M. D., and Ruoslahti, E. (1987) J. Biol. Chem. 262:17294-8), or other peptides with similar binding motifs.

Receptor-ligand proteins or peptides of this invention include those proteins or peptides that have an affinity for or binding to, receptor molecules that are broadly expressed in a variety of cell types, such as those proteins or peptides that bind to integrin $\alpha_v\beta_5$. Receptor-ligand peptides of this invention also include those proteins or peptides that bind to receptor molecules that are specifically expressed in a limited number of cell types (e.g. tissue-specific) or highly expressed in a particular cell type (e.g., in cancer cells, such as those that bind to the integrin $\alpha_v\beta_5$, which is highly expressed in certain melanomas and glioblastoma).

Sub-cellular localization proteins or peptides include those that recognize, target or are directed to a particular sub-cellular component, e.g., the nucleus, mitochondria, etc. See: C. Dingwall et al. (1991) TIBS 16:478-481.

Several proteins have been shown to be involved in transport or trafficking within eukaryotic cells. This is an important cell function for the delivery of cellular components to their appropriate compartments. Proteins that have the capability to cross cellular membranes in reverse direction and reach the nucleus include Interleukin-1 β, HIV Tat protein, acidic and basic fibroblast growth factors, angiogenin, homeoprotein Antennapedia, Schwannoma derived growth factor, and the Herpes Simplex Virus VP22 protein. These proteins are able to cross the cell membrane and reach the nucleus. Two of these proteins, HIV-Tat and HSV-VP22 have also been shown to mediate the uptake of other proteins when synthesized as fusions. The transport functions of the Tat protein were shown to be contained within an 11-12 amino acid peptide, and fusions of heterologous proteins with these peptides were transported into cells. (Vives, E. et al. (1997), "A truncated HIV-1 tat protein basic domain rapidly translocates through the plasma membrane and accumulates in the cell nucleus," J. Biol. Chem. 272:16010-16017; Kirsch, T. et al. (1996), "Cloning, high yield expression in *Escherichia coli*, and purification of biologically active HIV-1 Tat protein," Protein Expr. Purif. 8:75-84; Bonifaci, N. et al. (1995), "Nuclear translocation of an exogenous fusion protein containing HIV Tat requires unfolding," AIDS 9:995-1000; Fawell, S. et al. (1994), "Tat-mediated delivery of heterologous proteins into cells," Proc. Natl. Acad. Sci. (USA) 91:664-668; Pepinsky, R. B. et al. (1994), "Specific inhibition of a human papillomavirus E2 Trans-activator by intracellular delivery of its receptor," DNA and Cell Biol. 13:1011-1019; Mann, D. A. and Frankel, A. D. (1991), "Endocytosis and targeting of exogenous HIV-1 Tat protein," EMBO J. 10:1733-1739; Frankel, A. D. et al. (1989), "Activity of synthetic peptides from the Tat protein of human immunodeficiency virus type I," Proc. Natl. Acad. Sci. (USA) 86:7397-7401.

Most generally, any of the sequences exemplified in Tables 1-3, or functional equivalents thereof can be employed as peptides or modified peptides to enhance transfection activity in the transfection compositions and methods of this invention. Specific examples of spermine-modified peptides are provided in Table 4.

Table 2 lists a variety of peptides that are useful in the present invention, including peptides with a single functional region and peptides combining two or more functional regions. Concatemers of single function peptides and mixed concatemers combining sequential repetitions of dual (or more) function peptides are listed and are useful in the present invention. The peptide formulas in Table 2 combine generic regions, e.g., spacers and linker groups with conserved amino acid sequence associated with a particular function. Not specifically listed in Table 2 are dimers and multimers of functional peptides, for example, dimers formed between two cysteine residues of peptides. Dimers and multimers of functional peptides are useful in this invention.

Table 2 also lists cyclic peptides and cysteine peptide precursors of cyclic peptides that contain a functional peptide sequence of this invention (NLS, VSVG, RGD, LDV, E5, K5, etc.).

Table 3 provides a number of specific peptide sequences that are useful in the methods and compositions of this invention for enhancement of transfection. The table includes a number of specific combinations of two functional peptide sequences with optional spacers and optional cationic tails (for binding to nucleic acids). One entry in the table, "NLS phosphorylation" relates to an NLS sequence coupled to a phosphorylation-site-containing sequence. This fusion has been described in H-P. Rihs et al. (1989) EMBO J. 8:1479-1484 and H-P Rihs et al. (1991) EMBO J. 10:633-639. The presence of the phosphorylation site enhances transport to the nucleus.

Table 3 also contains precursors to transfection enhancing peptides, HIS-TEV-peptides. These peptides contain a HIS tail and a TEV (Tobacco Etch Virus) protease recognition sequence in addition to the peptide sequence useful for transfection enhancement. TEV protease will specifically cleave the HIS tail from the peptide leaving the functional peptide sequence. This combination can be employed for the isolation and purification of fusion polypeptides as has been described in U.S. Pat. No. 5,532,142 which is incorporated by reference herein. Peptides with HIS tails can be selectively purified on Ni columns.

Table 3 also includes examples of peptides having $(D)_n$ tails, i.e., tails of anionic amino acids. These peptides are of particular interest for binding to the surface of positively charged lipid-nucleic acid aggregates to enhance transfection of the aggregates and the nucleic acid that is carried therein. One transfection method for use of these peptides with anionic tails involves initial formation of cationic lipid aggregates with nucleic acid by conventional methods, followed by complexation to the anionic tailed peptide. A second transfection method for use of these peptides with anionic tails involves complexation of anionic peptide tails to lipid, followed by addition of DNA. These peptides can also be employed with dendrimer-nucleic acid complexes.

Those of ordinary skill in the art will appreciate that some amino acid sequence variation in functional peptides or modified peptides, such as those listed in Tables 1, 2 and 3, can be tolerated without significant loss of function. In many cases, substitutions of like amino acids, e.g., basic (cationic) amino acid for basic amino acid (e.g., K for R or R for K) or acidic (anionic) amino acid for acidic amino acid, in a given functional peptide will not significantly affect peptide function. In functional peptides containing a string of like amino acids, e.g., PKKKRKV [SEQ ID NO:2], addition or deletion of one or more amino acids from the string may be tolerated, e.g., PKKKKRKV [SEQ ID NO:3], without significant loss of peptide function.

Generally, conservative amino acid substitutions or substitutions of similar amino acids are tolerated without affecting protein or peptide function. Similar amino acids can be those that are similar in size and/or charge properties, for example, Lysine and arginine, aspartate and glutamate and isoleucine and valine are pairs of similar amino acids. Similarity between amino acid pairs has been assessed in the art in a number of ways. For example, Dayhoff et al. (1978) in Atlas of Protein Sequence and Structure, Volume 5, Supplement 3, Chapter 22, pages 345-352, which is incorporated by reference herein, provides frequency tables for amino acid substitutions which can be employed as a measure of amino acid similarity. Dayhoff et al.'s frequency tables are based on comparisons of amino acid sequences for proteins having the same function from a variety of evolutionarily different sources. Furthermore, for a given peptide, protein, or fragment thereof of this invention having a function for cell binding, adherence, cell internalization, membrane permeabilization, nuclear localization and like functions, there can be specific data currently and readily available to the art regarding amino acid substitution that does not effect peptide and/or protein function. All such peptides, proteins and fragments thereof having similar or conservative amino acid substitutions to the peptide, proteins and fragments thereof as listed in the Tables and description herein are encompassed by this invention and re useful in the compositions and methods of this invention. Peptides, proteins and fragments thereof having similar or identical function, for example for cell binding, cell adherence, cell internalization, membrane permeabilization, nuclear localization and like functions, to those listed in the Tables herein or described herein can also be employed in the compositions and methods of this invention.

Variations that diverge the least from exemplified or art-known functional peptide or protein sequences are generally preferred. For use in this invention, functional peptides can contain flanking strings of amino acids (preferably glycines) that do not affect function of the core peptide sequence. In an analogous way, a functional peptide sequence of this invention can be embedded within a larger peptide or protein wherein the nature of the sequence external to the core functional sequence does not affect function of the core. This invention includes peptides which contain more than one distinct functional sequence, e.g., NLSVSVG or RGDNLS. In these peptides, the functional sequences can be separated by linker peptide regions (preferably one or more Gs). Peptides of this invention can include amino acids that are not part of a functional region which are added to the peptide to provide a site for chemical linkage to another species, e.g., cysteine can be used as a site for binding to spermine. In some cases, amino acids external to the functional core sequence can act as spacers or linker regions between the functional peptide and the species (lipid, dendrimer, polyamine, spermine, etc.) to which it is covalently attached. These amino acids may function in optimal configuration of the peptide. For example, cysteine residues included in a peptide can be oxidized to form —S—S— dimers or larger multimer (trimers, etc.) by oxidization. Two cysteines placed distal to each other in a peptide can be oxidized to prepare a cyclic peptide containing one or more functional amino acid sequences. A heterogenous dimer with greater stability can be formed by incorporating penicillamine (Pen) in place of cysteine (Pierschbacher et al. (1987) J. Biol. Chem. 262).

This invention also includes peptides or proteins containing functional groups that enhance transfection and also contain amino acids or amino acid sequences that are useful in the preparation, isolation and purification of the peptides and proteins themselves. For example, aromatic amino acids can be included in a peptide or protein sequence to provide a UV absorption marker to allow convenient measurement of peptide or protein concentration. Alternatively, transfection-enhancing peptides and proteins can be provided with amino acid sequences that specifically bind to certain column materials to facilitate peptide or protein purification. Certain transfection-enhancing peptides or proteins may be more easily produced through expression of DNA in bacteria or other expression systems. Peptides or proteins of this invention can include amino acid sequences (or parts thereof) that are sites for selective proteases that are useful in isolation of the peptide or protein from an expression system.

The terms "modified-peptide" and "modified-protein" are used herein generally to mean a peptide or protein which has been chemically modified to include a nucleic acid-binding group covalently attached thereto. The term "modified-peptide" as used herein includes "polyamine-peptide conjugate" wherein the covalently attached nucleic acid-binding, or more specifically a DNA-binding group, is a polyamine, including "spermine-modified peptide" wherein the DNA-binding group is spermine. In some cases, a peptide or protein may itself bind to nucleic acid; in other cases modification of the peptide is necessary for or enhances binding to nucleic acid. For example, strings of cationic amino acids can be added to a functional peptide (at the C- or N-terminus) to facilitate binding to nucleic acid. These sequences can be written as $(Uaa)_u$, where u is an integer ranging typically from 1 to about 20 (and more preferably ranges from 8-20) and Uaa, independently of other Uaa's in the peptide, is a cationic amino acid, e.g., $(K)_u$[SEQ ID NO:4], $(R)u$ [SEQ ID NO:5], or $(KR)_u$[SEQ ID NO:6]. More generally, cationic amino acid strings for binding to nucleic acids can include non-cationic amino acids (preferably Gs) so long as the binding function is not significantly decreased.

Naturally-occurring peptides or proteins may require additional modification to allow conjugation to spermine or other polyamines. For example, cysteines may be added to the C-terminals or N-terminals of peptides or introduced within a peptide to facilitate conjugation. Likewise a string of spacer amino acids, i.e. $(G)_n$ [SEQ ID NO:7], where n is an integer ranging most generally from 1- about 20, can be added between a peptide and the species to which it is covalently linked. Any peptide modification used to facilitate conjugation preferably does not substantially affect peptide binding or function.

The term "peptide-nucleic acid complex" generally refers to the noncovalent association between a peptide or protein and a nucleic acid. The peptide or protein of this complex may be a modified peptide as defined above. As used herein in certain embodiments of transfection methods, a "peptide-nucleic acid complex" is formed prior to the addition of cationic lipid or dendrimer to a transfection composition.

"Lipid aggregate" is a generic term that includes liposomes of all types both unilamellar and multilamellar as well as vesicles, micelles and more amorphous aggregates. A cationic lipid aggregate is a lipid aggregate comprising sufficient cationic lipid, optionally in combination with non-cationic (e.g., neutral) lipids, such that the lipid aggregate has a net positive charge. Cationic lipids and lipid aggregates are capable of aggregating the peptide-nucleic acid complexes of the invention.

Cationic lipid composition includes those compositions comprising a cationic lipid or a mixture of cationic lipids, which can be either monovalent or polyvalent cationic lipids. The cationic lipid composition optionally contains neutral lipids. Of particular interest are cationic lipid compositions recognized in the art as useful in transfection methods. Preferred cationic lipid compositions comprise monovalent or polyvalent cationic lipids; more preferred are those compositions containing DOTMA, DOTAP, DDAB, DMRIE, DOSPA, DOSPER, TMTPS and their analogs or homologs; the most preferred cationic compositions are "LIPOFECTIN" and "LIPOFECTAMINE."

Transfection activity or efficiency is measured by detecting the presence of the transfected nucleic acid in a cell. This is often assessed by measuring the biological function of the nucleic acid in the cell, and most often assessed by measuring the level of transient or stable expression of a reporter gene comprised in the transfected nucleic acid. Reporter gene expression depends among other things on the amount of nucleic acid transfected as well as promoter function in the cell. Transfection activity can also be assessed by determining the percent of cells in a sample that have been transfected, for example, by assessing reporter gene expression using cell counting or in situ staining methods. The transfection methods of this invention employing peptides in combination with cationic lipids can display significant enhancement of transfection (2-fold or more) over transfection methods employing comparable cationic lipids alone.

The method of this invention involves contacting a eukaryotic cell with a transfection composition comprising a peptide-nucleic acid complex (or a modified peptide-nucleic acid complex) and a transfection agent, a cationic lipid or a dendrimer. A cationic lipid transfection composition optionally comprises a non-cationic lipid, preferably a neutral lipid. Cationic lipid transfection compositions can optionally comprise known transfection enhancing agents in addition to peptides or modified peptides, including, for example chloroquine, a lysosomotrophic agent. Dendrimers or mixtures thereof can be employed in transfection compositions. Dendrimer transfection compositions may include agents other than peptides or modified peptides that are known to enhance dendrimer-mediated transfection, e.g., DEAE-dextran and/or chloroquine. The peptide or protein can be a fusagenic peptide or protein of a virus. A preferred fusagenic peptide or protein is that of influenza virus hemagglutinin or vesicular stomatitis virus G-protein, or VSVG. The peptide or protein can be a sub-cellular localization signal peptide or protein. A preferred nuclear localization signal peptide is that of simian virus 40, particularly the nuclear localization sequence (NLS) of the SV40 large T antigen (Kalderon et al. (1984) Cell 39:499; and Lanford et al. (1986) Cell 46:575). There is some diversity in the sequences of nuclear localization signals as reported in C. Dingwell and R. A. Laskey (1991) TIBS:478-481, which is incorporated by reference herein for the sequences disclosed. This invention includes peptides or proteins comprising nuclear localization sequences as disclosed therein. The peptide or protein of this invention can be a receptor-ligand peptide or protein. Preferred receptor-ligand peptides are cell adhesion peptides, particularly RGD peptides or other integrin-binding peptides. Transfecting compositions comprising peptides or proteins of viral proteins conjugated to a nucleic acid-binding group are particularly preferred. Preferred nucleic acid-binding groups are spermines and the cationic amino acid strings $(K)_u$ and $(R)_U$ where u is an integer from 1 to about 20 and more preferably is about 8 to about 20.

Enhanced transfection methods of this invention are demonstrated with the prototype nuclear localization signal peptide from simian virus 40 and the prototype fusagenic peptides from influenza (HApep; E5 and K5 amphophilic peptides), vesicular stomatitis virus (G protein) and an RGD peptide (GRGDSPC, SEQ ID NO:8) taken from the cell attachment site of fibronectin. The DNA-binding group that has been employed is a polyamine capable of forming a noncovalent association with the base pairs of the nucleic acid. Enhanced transfection methods of this invention have been further exemplified using the prototype DNA-binding group, spermine.

In some cases, the peptides or proteins form a direct noncovalent association or complex with the nucleic acid. This peptide-nucleic acid complex forms as a consequence of conformational or charge interactions between the peptide and the base pairs of the DNA. A peptide-nucleic acid complex forms spontaneously in an appropriate medium. Transfection compositions comprising these peptide-nucleic acid complexes are prepared by first interacting the nucleic acid with the peptide or protein followed by addition of the resulting complex to a cationic lipid composition or a dendrimer.

The peptides or proteins of this invention, when covalently coupled to a nucleic acid-binding group (modified-peptide), can form a noncovalent association or complex with the nucleic acid. This modified-peptide-nucleic acid complex forms as a consequence of conformational or charge interactions between the nucleic acid-binding group and the nucleic acid (DNA or RNA). For example, the prototype spermine-peptide-nucleic acid complex likely forms as a consequence of charge interactions between the amines of spermine and the phosphates on the DNA backbone. A modified-peptide-nucleic acid complex forms spontaneously in an appropriate medium. Transfection compositions comprising these modified-peptide-nucleic acid complexes are prepared by first interacting the nucleic acid with the modified peptide to form complexes followed by addition of a cationic lipid composition.

In one embodiment, a composition containing the peptide-nucleic acid or modified-peptide-nucleic acid complex is admixed with a cationic lipid, alone or in combination with a non-cationic lipid, to form a peptide-nucleic acid-lipid aggregate. A peptide-nucleic acid-lipid aggregate forms spontaneously in an appropriate medium or various well-known techniques may also be employed to produce a desired type of lipid aggregate. The relative amounts of cationic lipid and non-cationic lipid employed depends on a number of factors, including the cell type to be transfected, toxicity of the lipids to the cell and the environment (e.g., medium) in which the aggregate is to be employed. The kinds and amounts of lipids employed is typically balanced for a given cell type to minimize cell toxicity and maximize transfection efficiency.

In another embodiment, peptide-nucleic acid or modified-peptide-nucleic acid complexes are admixed with a dendrimer (or mixture of dendrimers) to form a peptide-nucleic acid-dendrimer aggregate. This aggregate forms spontaneously in an appropriate medium. The relative amounts of dendrimer to nucleic acid are adjusted to optimize transfection in a given cell type in a given environment. The chemical type, size and shape of the dendrimer is also selected to optimize transfection in a given cell type.

Nucleic acid delivery can be enhanced by the use of cell targeting, cell adhesion or binding peptides or proteins. Peptides containing the RGD sequence can be coupled to the polycation spermine which acts as a DNA binding group. The RGD-spermine peptide is believed to enhance transfection via cell targeting, and more importantly, cell adhesion. Attachment to adhesion proteins, and in some cases to other cells, is often mediated by integrins. Many adhesive proteins present in extracellular matrices and in the blood contain the tripeptide arginine-glycine-aspartic acid (RGD), as their cell recognition site (Ruoslahti, E. and Pierschbacher, D. (1987) Science 238:491). Pathogens such as bacteria, and more specifically, foot and mouth disease virus (FMDV) (Mason et al. (1994), Proc. Natl. Acad. Sci. 91, 1932-1936) and Adenovirus (Wickham, T. J. et al (1995), "Targeting of adenovirus penton base to new receptors through replacement of its RGD motif with other receptor-specific peptide motifs," in Gene Therapy 2-750-756) have RGD containing proteins expressed on their surface, which interact with integrins on the host cell and facilitate internalization. RGD, (K)u RGD [SEQ ID NO:9] (particularly where u=16 [SEQ ID NO: 10]) and RGD-spermine peptide can enhance "LIPOFECTIN-," "LIPOFECTAMINE-" or DOSPER-mediated transfection or dendrimer-mediated transfections.

Viral peptides or proteins can be isolated by a variety of well-known techniques, for example using the cationic detergent DTAB as described in Glushakova, S. E., et al. (1985) "Influenza viral glycoproteins isolation using cationic detergent dodecylmethylammonium bromide and its subsequent internalization into liposomal membrane" Mol. Genet. Microbiol. Virol. 4:39-44. Alternatively, viral peptides or proteins, as well as functional peptides or proteins from other sources, can be produced by a variety of standard chemical synthetic methods. Functional peptides, for example, can be synthesized using automated solid phase peptide synthesis as described, e.g., in Stewart et al. (1984) *Solid Phase Peptide Synthesis*, Pierce Chemical Company, Rockford, Ill. Fusagenic peptides from influenza and vesicular stomatitis virus, including the exemplified hemagglutinin peptide, K5 and E5 amphophilic peptides and G protein, are particularly useful in the methods of this invention. Nuclear localization signal peptides from simian virus 40, including the exemplified NLS peptide, are also preferred. Peptides or proteins can be used alone or in combination with other functional peptides or proteins in the methods of this invention. As illustrated in Table 2, two or more functional peptide sequences (optionally separated by linkers or spacers) can be combined in a given peptide.

Modified-peptides or proteins can be prepared by a variety of well-known coupling techniques, for example using a heterobifunctional cross-linking agent as described in the Examples hereof. A variety of cross-linking agents are known to the art and widely available in commerce including, without limitation, succinimidyl or maleimidyl cross-linkers, such as Sulfosuccinimidyl 4-(p-maleimidophenyl)butyrate (Sulfo-SMPB), disuccinimidyl suberate, succinimidyl 4-(p-maleimidophenyl)butyrate (SMPB), 4-succinimidyloxycarbonyl-α-methyl-α-(2-pyridyldithio)-toluene (SMPT), Sulfosuccinimidyl 6-[3-(2-pyridyldithio)propionamido]hexanoate (Sulfo-LC-SPDP), Succinimidyl 6-[3-(2-pyridyldithio)propionamido]hexanoate (LC-SPDP), N-Succinimidyl 3-(2-pyridyldithio)propionate (SPDP), Sulfosuccinimidyl 4-(N-maleimidomethyl)cyclohexane-1-carboxylate (Sulfo-SMCC), Succinimidyl 4-(N-maleimidomethyl)cyclohexane-1-carboxylate (SMCC); m-Maleimidobenzoyl-N-hydroxysulfosuccinimide ester (Sulfo-MBS), m-Maleimidobenzoyl-N-hydroxysuccinimide ester (MBS), Sulfosuccinimidyl(4-iodoacetyl)aminobenzoate (Sulfo-SIAB), N-Succinimidyl(4-iodoacetyl)aminobenzoate (SIA). Methods for conjugating peptides or proteins and polyamines are well-known in the art. Representative methods are disclosed in Staros, J. V. (1982) Biochemistry 21:3990. Any of the functional peptides or proteins exemplified herein, or functional equivalents thereof, can be modified by covalent coupling to a nucleic acid-binding agent, e.g., to a polyamine and preferably to spermine.

Covalent linking of a peptide or protein to a lipid or a dendrimer can be performed by a variety of conventional methods using known coupling agents and known derivatization methods.

Media employed in transfections should preferably be free of components, like serum or high salt levels, that can inhibit cationic lipid-mediated or dendrimer-mediated transfection of cells.

A variety of cationic lipids is known in the art. Generally, any cationic lipid, either monovalent or polyvalent, can be used in the compositions and methods of this invention. Polyvalent cationic lipids are generally preferred. Cationic lipids include saturated and unsaturated alkyl and alicyclic ethers and esters of amines, amides or derivatives thereof. Straight-chain and branched alkyl and alkene groups of cationic lipids can contain from 1 to about 25 carbon atoms. Preferred straight-chain or branched alkyl or alkene groups have six or more carbon atoms. Alicyclic groups can contain from about 6 to 30 carbon atoms. Preferred alicyclic groups include cholesterol and other steroid groups. Cationic lipids can be prepared with a variety of counter ions (anions) including among others: $Cl^-$, $Br^-$, $I^-$, $F^-$, acetate, trifluoroacetate, sulfate, nitrite, triflate, and nitrate.

A well-known cationic lipid is N-[1-(2,3-dioleoyloxy)-propyl]-N,N,N-trimethylammonium chloride (DOTMA). See Felgner, P. L. et al. (1987) Proc. Natl. Acad. Sci. USA 84:7413-7417. DOTMA and the analogous diester DOTAP (1,2-bis(oleoyloxy)-3-3-(trimethylammonium)propane) are commercially available. Additional cationic lipids structurally related to DOTMA are described in U.S. Pat. No. 4,897,355, which is incorporated by reference in its entirety herein.

Other useful groups of cationic lipids related to DOTMA and DOTAP are commonly called DORI-ethers or DORI-esters. DORI lipids differ from DOTMA and DOTAP in that one of the methyl groups of the trimethylammonium group is replaced with a hydroxyethyl group. The DORI lipids are similar to the Rosenthal Inhibitor (RI) of phospholipase A (Rosenthal, A. F. and Geyer, R. P. (1960) J. Biol. Chem. 235:2202-2206). The oleoyl groups of DORI lipids can be replaced with other alkyl or alkene groups, such as palmitoyl or stearoyl groups. The hydroxyl group of the DORI-type lipids can be used as a site for further functionalization, for example for esterification and/or for ether formation.

Additional cationic lipids which can be employed in the compositions and methods of this invention include those described as useful for transfection of cells in PCT application WO 91/15501 published Oct. 17, 1991, Pinnaduwage, P. et al. (1989) Biochem. Biophys. Acta. 985:33-37; Rose, J. K. et al. (1991) BioTechniques 10:520-525; Ito, A et al. (1990) Biochem, Intern, 22:235-241.

The polycationic lipid formed by conjugating polylysine to DOPE (Zhou, X. et al. (1991) Biochem. Biophys. Acta 1065: 8-14), as well as other lipopolylysines, can also be employed in the methods and compositions of this invention.

Polycationic lipids containing carboxyspermine are also useful in the compositions and methods of this invention. Behr, J-P. et al. (1989) Proc. Natl. Acad. Sci. 86:6982-6986 and EPO published application 304 111 (1990) describe carboxyspermine-containing cationic lipids including 5-carboxyspermylglycine dioctadecyl-amide (DOGS) and dipalmitoylphosphatidylethanolamine 5-carboxyspermylamide (DPPES). Additional cationic lipids can be obtained by replacing the octadecyl and palmitoyl groups of DOGS and DPPES, respectively, with other alkyl or alkene groups. Polycationic lipids designated DOSPER (See: Formula B for specific and generic formula) are also useful in the methods of this invention. U.S. Pat. No. 5,334,761, which is incorporated by reference in its entirety herein, also describes cationic lipids, including DOSPA (see: Formula A for specific and generic formula) which are useful in this invention. Also, U.S. Pat. No. 5,674,908, which is incorporated by reference in its entirety herein, describes polycationic lipids, including TMTPS, which are useful in this invention.

phatidylserines, such as dioleoyl- or dipalmitoylphosphatidylserine; diphosphatidylglycerols; fatty acid esters; glycerol esters; sphingolipids; cardolipin; cerebrosides; and ceramides; and mixtures thereof. Neutral lipids also include cholesterol and other 3βOH-sterols.

Dendrimers can be prepared by several now well-documented methods. See: WO95/24221; D. A. Tomalia and H. D. Durst (1993) in E. Weber (ed.) Topics in Current Chemistry, Vol. 165: Supramolecular Chemistry I-Directed Synthesis and Molecular Recognition, Springer-Verlag, Berlin, pp. 193-313; U.S. Pat. Nos. 5,527,524; 5,338,532; 4,694,064; 4,568,737; 4,507,466; and PCT patent applications;

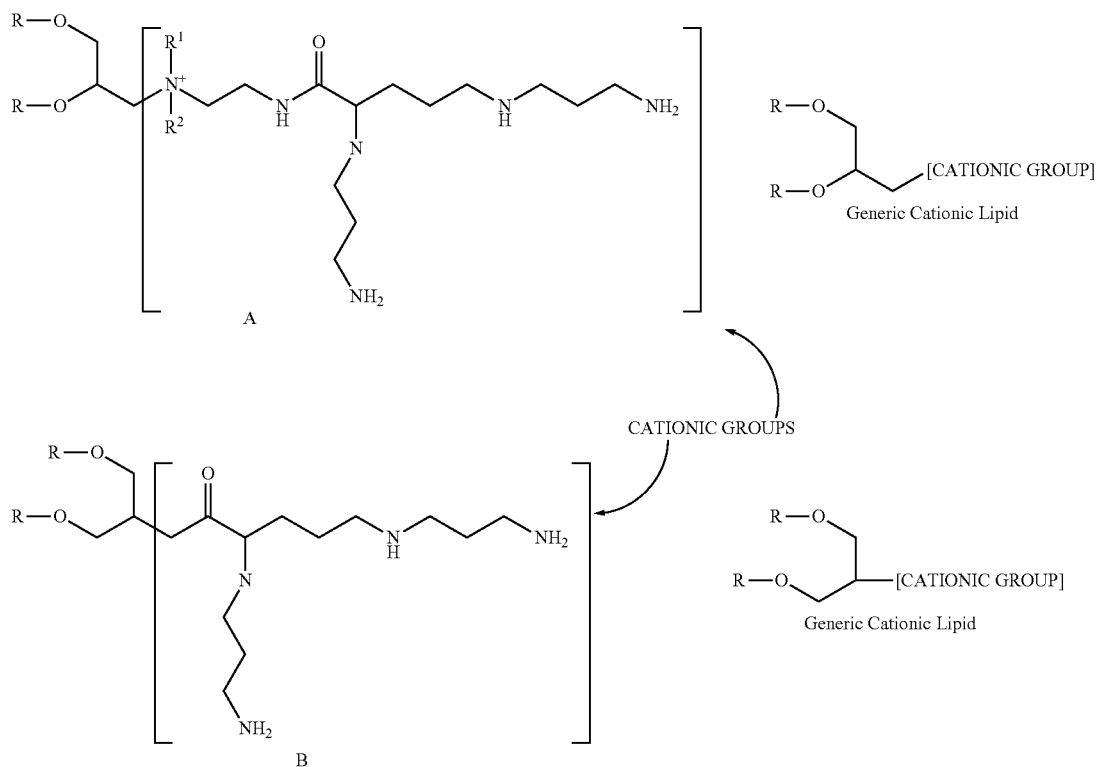

PCT application WO 95/17373 describes highly packed polycationic ammonium, sulfonium and phosphonium lipids that are useful for transfection. These cationic lipids are useful in methods of this invention.

In the transfection compositions of this invention cationic lipids can optionally be combined with non-cationic lipids, preferably neutral lipids, to form lipid aggregates that bind to the modified-peptide-nucleic acid complex. Neutral lipids useful in this invention include, among many others: lecithins; phosphotidylethanolamine; phosphatidylethanolamines, such as DOPE (dioleoylphosphatidylethanolamine), DPhPE (diphytanoylphosphatidylethanolamine), DPPE (dipalmitoylphosphatidylethanolamine), dipalmiteoylphosphatidylethanolamine, POPE (palmitoyloleoylphosphatidylethanolamine) and distearoylphosphatidylethanolamine; phosphotidylcholine; phosphatidylcholines, such as DOPC (dioleoylphosphidylcholine), DPPC (dipalmitoylphosphatidylcholine) POPC (palmitoyloleoylphosphatidylcholine) and distearoylphosphatidylcholine; phosphatidylglycerol; phosphatidylglycerols, such as DOPG (dioleoylphosphatidylglycerol), DPPG (dipalmitoylphosphatidyl-glycerol), and distearoylphosphatidylglycerol; phosphatidylserine; phos- WO8801179; WO8801178; and WO9502397. "STARBURST" (Trademark, Dendritech, Inc.) or dense star polyamidoamine (PAMAM) dendrimers including those having cationic amino acids or other cationic species at their outer surface or "SUPERFECT" (Trademark, Qiagen, Inc.) or activated dendrimers are preferred for transfection methods of this invention. Transfection protocols for use with dendrimers and a discussion of the choice of a given dendrimer for a given transfection is given in J. F. Kukowska-Latolla et al. (1996) Proc. Natl. Acad. Sci. USA 93:4897-4902; A. Bielinska et al. (1996) Nucleic Acids Res. 24(11):2176-2182; WO9524221; WO9319768; WO9502397; and J. Haensler and R. Szoka (1993) Bioconjugate Chem. 4:372-379 and M. X. Tang et al., (1996) Bioconjugate Chem. 7P703-714.

The present invention is based on the discovery that certain peptides or proteins or modified peptides or proteins can significantly enhance the efficiency of transfection of eukaryotic cells with nucleic acids. The peptide or protein or modified peptide or protein binds to the DNA and functions as a fusagenic peptide or protein, functions for sub-cellular localization or for cell adhesion. Peptides or proteins, optionally modified, if necessary or desirable, to enhance binding to nucleic acids, that function as internalization-triggering signals or endocytosis-triggering signals or transport signals, also function in the transfection methods of this invention. The compositions and methods of the invention comprise peptides or proteins, optionally modified covalently with a nucleic acid-binding group, which significantly improve the efficiency of transfection when bound to nucleic acid prior to adding the transfection reagent. These bound nucleic acids are more efficiently transported into the cell and to the cell nucleus, thus requiring less nucleic acid starting material. Although the present invention is exemplified using a cationic lipid delivery system or a dendrimer delivery system, fusagenic, sub-cellular localization peptides and cell-targeting peptides are effective in enhancing transfection using a variety of known delivery systems. The present invention thus provides improved methods of transfection using these peptides and modified peptide, including peptides covalently conjugated to dendrimers or peptides covalently conjugated to lipids, to enhance transfection by other nucleic acid delivery means including, without limitation, electroporation (T. K. Wong and E. Neumann (1982) *Biochem. Biophys. Res. Commun.* 107:584 and E. Neumann et al. (1982) *EMBO J.* 1:841), calcium phosphate (F. L. Graham and A. J. Vander Eb (1973) *Virology* 52:456), microinjection (M. R. Capecchi (1920) 22:479), ballistic transformation using microscopic particles coated with DNA (D. T. Tomes et al. (1990) *Plant Mol. Biol. Manual A*13:1-22 and G. N. Ye et al. (1990) *Plant. Molec. Biol.* 15:809) DEAE-dextran (A. Vaheri and J. S. Pagano (1965) *Science* 175:434), and polybrene-DMSO (S. Kawai and M. Nishizawa (1984) *Molec. Cell. Biol.* 4:1172).

Transfection compositions of this invention include compositions for transfecting eukaryotic cells using a peptide or protein comprising a nuclear localization sequence, a fusagenic peptide or transport peptide, receptor-ligand peptide or transport peptide sequence covalently attached to a polycation. Peptides or proteins having a nuclear localization sequence, fusagenic peptide, transport peptide or receptor-ligand signal attached to a polycation, are also a part of the invention. Preferred linkers include, for example, heterobifunctional crosslinkers. The polycation is preferably a polyamine and most preferably, spermine. As previously discussed, the transfection compositions and peptides of the invention are useful with a wide variety of delivery systems including, without limitation, electroporation, calcium phosphate, microinjection, ballistic transformation, DEAE-dextran and polybrene-DMSO. The present invention thus includes methods for transfecting a eukaryotic cell with a nucleic acid, the method generally comprising the steps of (1) admixing a peptide or protein or modified peptide or protein with a nucleic acid to form a peptide-nucleic acid complex; and (2) introducing the peptide-nucleic acid complex from step (1) into the cell using a known delivery means. Alternatively, the method of the invention may comprise (1) admixing a transfection agent with a nucleic acid and (2) introducing a peptide or protein, optionally covalently conjugated to a nucleic acid binding group. Additionally, both methods may be combined using any number of proteins or peptides. One of ordinary skill in the art, based on knowledge generally available to the art including the present disclosure, can use the compositions and peptides or proteins of the present invention with any delivery system without the expense of undue experimentation.

This invention includes pharmaceutical compositions, therapeutic compositions and diagnostic compositions. In each case these compositions comprise an amount of transfection composition of this invention sufficient for effecting introduction of a selected nucleic acid into a target cell or target tissue. Pharmaceutical and therapeutic compositions of this invention comprise suitable pharmaceutical carriers. Any cationic or polycationic species in these pharmaceutical or therapeutic compositions can be provided as salts with pharmaceutically appropriate counter ions.

Kits comprising components of the transfection compositions of this invention can be employed to facilitate preparation and use of transfection compositions. Such kits can be provided and employed as research reagents for any transfection of eukaryotic cells done for research purposes. Such kit may also be used for diagnostic and therapeutic applications. Kits can be configured with components adequate for use in single transfection or for multiple transfections. In one embodiment, kit components comprise a cationic lipid composition and a peptide or protein or modified-peptide or protein to enhance transfection. The cationic lipid composition comprises a cationic lipid and preferably a neutral lipid. Preferred cationic lipid compositions comprise a monocationic or polycationic lipid. More preferred cationic lipid compositions comprise the monocationic lipids DOTMA and DOTAP, the polycationic lipid DOSPA, or analogs and homologs of DOSPA, including DOSPER. Preferred neutral lipids include DOPE or DPhPE and analogs or homologs thereof.

The level of transfection enhancement effected by a given peptide or protein or modified peptide or protein may vary dependent upon the cell type, components of the transfection agent, transfection method used, the order of addition of components to or the order of complexation of components in a transfection composition, among other factors. Those of ordinary skill in the art using the guidance and methods provided herein and with knowledge of procedures, assays and methods for transfection well-known in the art can select, without undue experimentation, a particular peptide or protein or modified peptide or protein of this invention for enhancement of transfection in a given system.

It will be readily apparent to those of ordinary skill in the art that a number of parameters are important for optimal transfection. For cationic lipid-mediated transfection, these parameters include cationic lipid concentration, relative amounts of cationic and non-cationic lipid, the concentration of nucleic acid, the medium employed for transfection, the length of time the cells are incubated with transfection composition, the amount of peptide employed, the amount of DNA-binding group or polyamine employed, and the way, e.g., order, in which the components of the transfection composition are combined. For dendrimer-mediated transfection, these parameters include dendrimer size, shape and chemical composition, the relative amount of dendrimer and nucleic acid, the addition of other transfection agents (DEAE-dextran, chloroquine), the concentration of nucleic acid, the medium employed for transfection, the length of time the cells are incubated with transfection composition, the amount of peptide employed, the amount of DNA-binding group or polyamine employed, and the way (e.g., order) in which the components of the transfection composition are combined. It may be necessary to optimize these parameters for each cell type (for each kind of transfection system) to be transfected. Such optimization is routine employing the guidance provided herein and transfection assays as described in the Examples herein.

It will also be apparent to those of ordinary skill in the art that alternative methods, reagents, procedures and techniques other than those specifically detailed herein can be employed or readily adapted to produce the transfection compositions of this invention and practice the transfection methods of this invention. Such alternative methods, reagents, procedures and techniques are within the spirit and scope of this invention.

The transfection compositions and methods of this invention are further illustrated in the following non-limiting Examples. All abbreviations used herein are standard abbreviations in the art. Specific procedures not described in detail in the Examples are well-known in the art.

All publications and patents referred to herein are specifically incorporated by reference in their entirety.

EXAMPLES

Example 1

Peptides and Peptide Conjugates

Peptides were synthesized using automated solid phase peptide synthesis as described, e.g., in Stewart et al. (1984) *Solid Phase Peptide Synthesis*, Pierce Chemical Company, Rockford, Ill. Peptides were synthesized using a polyamide-Kieselguhr composite resin and a Milligen 9050 peptide synthesizer (Milligen/Biosearch, Burlington, Mass.). Coupling cycles were performed according to the manufacturer's recommendations. 9-Fluorenyl-methyloxy-carbonyl (Fmoc) amino acid was activated as a pentafluorophenyl ester (-OPfp ester); Peptides were deblocked using; (1) 20% piperidine in N,N-dimethylformamide (DMF) for alpha-amino groups; Peptides were cleaved from the resin and deprotected using 95% trifluoroacetic acid (TFA), (2) Reagent R [TFA (90%), thioanisol (5%), ethylene dithiole (3%) and anisole (2%)], Reagent B [TFA (88%), phenol (5%), triisopropylsilane (2%) and water (5%)] or Reagent T [TFA (95%), triisopropylsilane (5%); Deprotection agent being chosen as is understood in the art based on the protecting groups used and the type of amino acid residues in the peptide; Crude peptides were precipitated and washed with ether. Peptides were purified by high pressure liquid chromatography on a Vydac C-18 reverse-phase column using a Waters HPLC system. The mobile phase consisted of a gradient from 0.01% TFA in 95% water/acetonitrile to 0.01% TFA in 25% water/acetonitrile. Peptides were characterized by HPLC, amino acid analysis and mass spectrometry (ES or MALDI-TOF). Exemplary peptide sequences useful in this invention are listed in Tables 1-3.

It was found that certain peptides that were only partially deblocked, i.e., at least one amino acid protecting group had not been removed, showed significant enhancement of transfection. Appropriate choice of deprotection agent allows selective synthesis of peptides which retain a desired protecting group. For example, deprotection with Reagent T does not remove the Mtr protecting group on arginines allowing the synthesis of partially deblocked peptides with Mtr groups remaining on R residues.

Synthesis of Polyamine Conjugated Peptides

Figure 5:
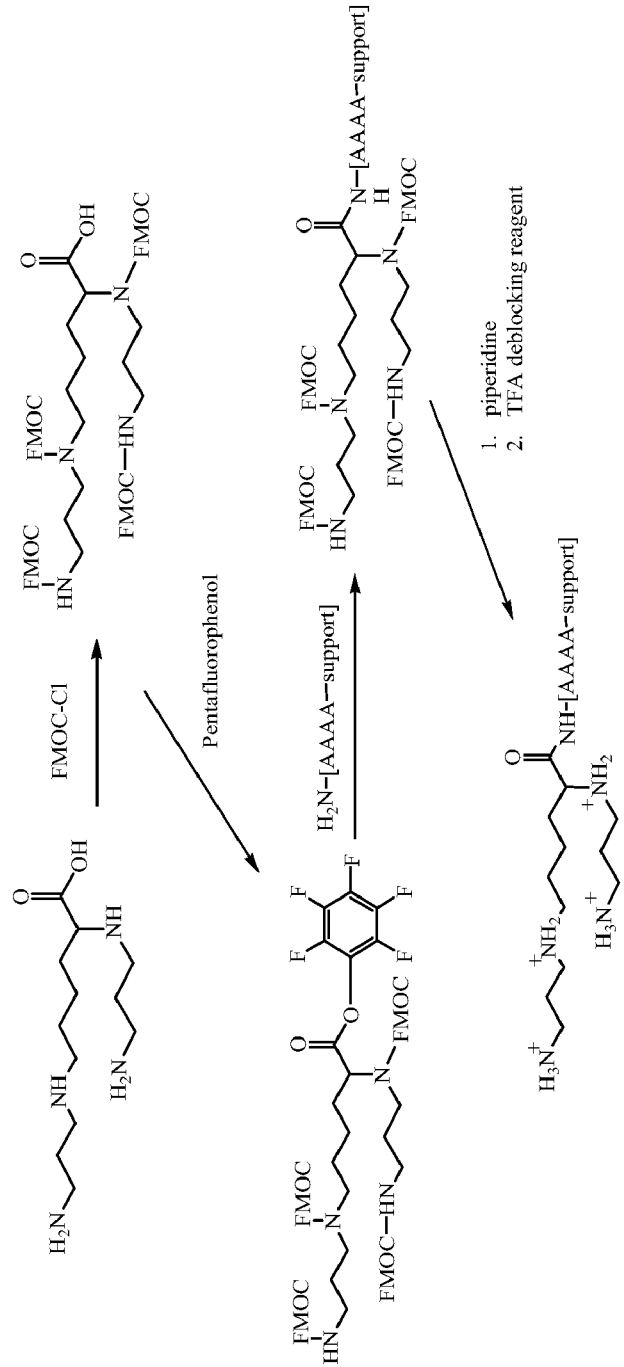
FIG. 5 shows a reaction scheme for the synthesis of polyamine conjugated peptides.

Peptides can be modified with polyamines, such as spermine, using an automated peptide synthesizer. Either the Fmoc or Boc chemistries can be used. For example, spermine can be attached to the N-terminus of a peptide as illustrated in Scheme 1 of FIG. 5. 5-Carboxy spermine and Boc-protected 5-carboxy spermine can be synthesized as described in Behr, J-P. et al. (1989) Proc. Natl. Acad. Sci., 86:6982-6986. Fmoc-carboxy spermine can be synthesized by treating carboxy spermine with 9-fluorenylmethyl chloroformate. Fmoc-carboxy spermine or the pentafluorophenyl ester can be used in the synthesizer to obtain spermine-modified peptides. More than one polyamine can be attached in this manner to a given peptide using an appropriate combination of protecting groups.

$N^I$, $N^{II}$, $N^{III}$, $N^{IV}$-tetra(9-fluorenylmethoxycarbonyl)-5-carboxyspermine (Fmoc-carboxyspermine)

5-Carboxy spermine (11.0 g) was dissolved in 100 ml water. The solution was chilled on ice and diluted with 200 ml dioxane and flushed with argon. A solution of 50 g of 9-fluorenylmethyl chloroformate (Fmoc-Cl) in 200 ml of dioxane was slowly added to the chilled carboxy spermine. The reaction mixture was stirred under argon at 4° C. for an hour and at room temperature overnight under argon. The reaction was monitored by TLC (silica Gel, $CHCl_3$/MeOH: 9/1). The reaction mixture was poured into 1.5 L ice cold water (1.5 L) and extracted with ethyl acetate (2 L). The organic layer was separated and sequentially extracted with 400 ml of 1 N HCl (2×) and 300 ml saturated NaCl. The organic layer was dried over $Na_2SO_4$ and concentrated on a rotary evaporator. The resultant gummy material was subjected to flash chromatography (silica, $CHCl_3$/MeOH: 95/5) to yield 25.5 g of the desired material as a white fluffy solid.

Fmoc-carboxy-spermine-OPfp Ester

A solution of pentafluorophenol (4.2 g) in 3 ml of dioxane solution, followed by 2 ml of dioxane, was added to a solution of Fmoc-carboxy-spermine (8.0 g) in 10 ml of dioxane. The resulting mixture was chilled in an ice water bath and flushed with argon. Freshly distilled dicyclohexylcarbodiimide (DCC, 1.6 g) in 4 ml of dioxane was added to the chilled reaction mixture. The mixture was stirred at 4° C. for about an hour and at room temperature overnight under argon. Precipitated dicyclohexyl urea (DCU) was filtered out of the reaction mixture, which was then concentrated to dryness on a rotary evaporator. The residue was dried under high vacuum overnight. The ester was obtained in quantitative yield as a slightly yellowish gum, which was used without further purification in the peptide synthesizer.

Synthesis of Spermine-Modified Peptides

Spermine-modified peptides were synthesized using Fmoc chemistry on a Milligen 9050 synthesizer using the protocol suggested by the manufacturer. Peptides were synthesized conventionally and carboxyspermine was attached at the N-terminus of the synthesized peptide using Fmoc-carboxyspermine-OPfp ester as the last amino acid to be added on the synthesizer, as illustrated in Scheme 1. Deprotection reagents used were selected as discussed above. The peptide-spermine conjugates were stored frozen until use. Table 4 lists several examples of spermine-conjugated peptides that were synthesized using FMOC-carboxy-spermine. Modified peptides were analyzed and purified using HPLC on a Vydac C-18 column. Modified peptides were characterized by HPLC, amino acid analysis and mass spectrometry (ES or MALDI-TOF). This method can be employed or readily adapted in view of well-known techniques for synthesis of polyamine-peptide conjugates.

Figure 6:
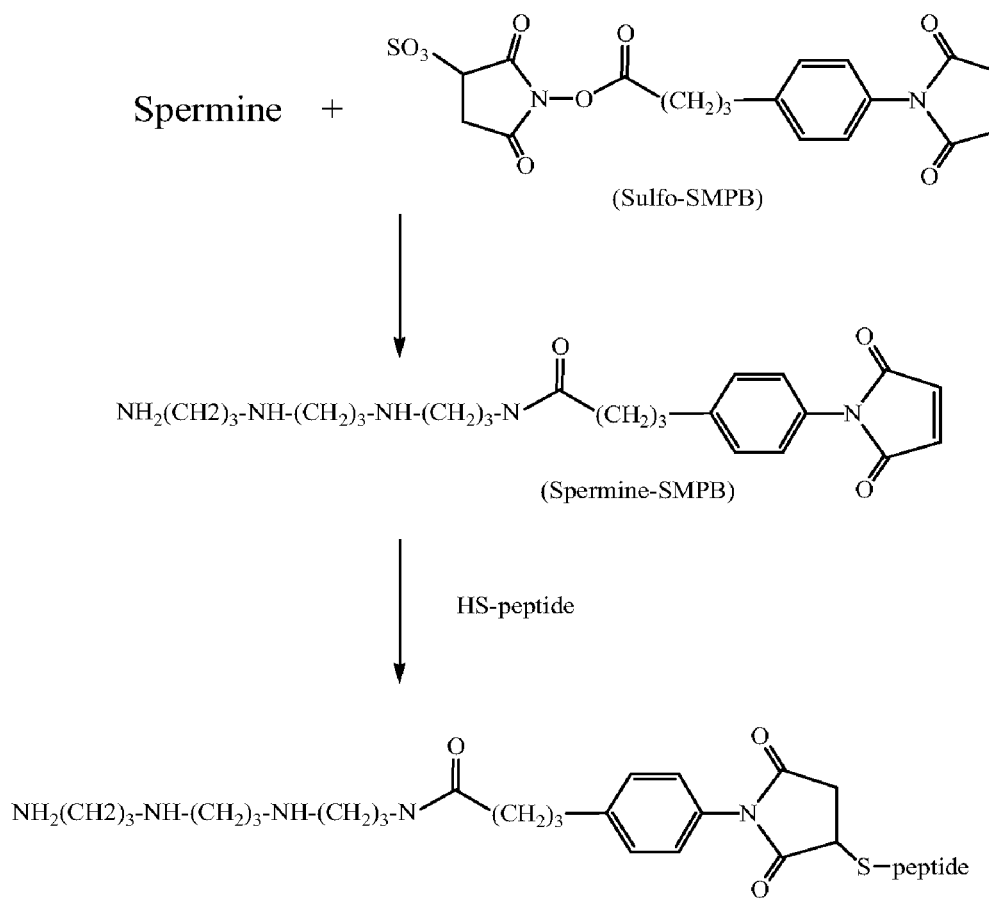
FIG. 6 shows a reaction scheme for the synthesis of spermine-modified peptides.

Peptide-spermine conjugates can also be prepared using a heterobifunctional cross-linking agent sulfo-SMPB (Pierce Chemical Co., Rockford, Ill.) as illustrated in Scheme 2 of FIG. 6. See: S. S. Wong "Heterobifunctional Cross-linkers" in Chemistry of Protein Conjugation and Cross-linking CRC Press p. 147-194. Briefly, 100 mg/mL sulfo-SMPB in DMF is diluted to 20 mg/mL using 50 mM sodium phosphate buffer (pH 7.5). Spermine (50 mg/mL in 50 mM sodium phosphate buffer) was then added to the sulfo-SMPB solution at a 3:1 molar ratio. After 1 hour at room temperature, the reaction mixture is fractionated (LH-20 column) using the sodium phosphate buffer. The first major peak (spermine-MPB) was collected. Spermine-MPB is mixed at a 1:1.5 to 1:2 ratio with a synthetic (or naturally-occurring) peptide with terminal cysteine (HS–), either in pure powder form or in acetonitrile/water solution. Excess peptide is separated on a LH-20 column eluted with water. The peptide-spermine conjugate is stored frozen until use. The reaction of spermine-MPB with HS-peptide should be performed under appropriate reducing conditions to avoid peptide dimmer formation. This method can be employed or readily adapted in view of well-known techniques for synthesis of polyamine-peptide conjugates.

Peptide dimers of peptides containing cysteine residues can be formed, if desired, by oxidative coupling to form a disulfide bond between two peptides. Concatemers and mixed concatemers of this invention can be prepared by automated peptide synthesis and if desired the concatemers, mixed concatemers and peptide oligomers (dimers, etc.) can be conjugated to nucleic acid-binding groups by methods described herein.

Figure 7:
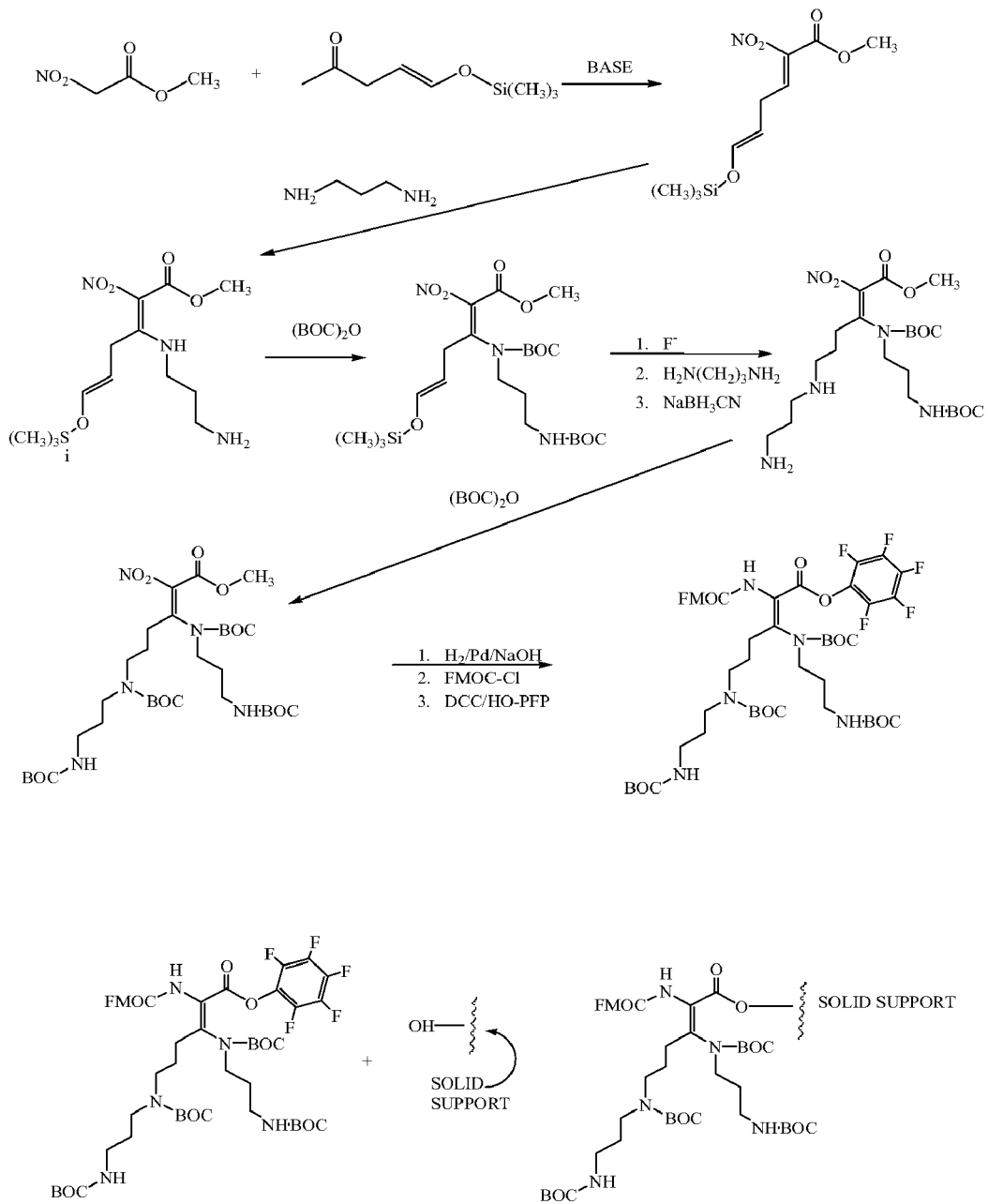
FIG. 7 shows a reaction scheme for the synthesis of protected polyamine species.

Scheme 3 of FIG. 7 illustrates appropriately protected polyamine species that can be used in automated peptide synthesizers to introduce polyamines at the carboxy terminus of peptides (e.g., Structure II, for carboxyspermine conjugation). The scheme illustrates a synthesis of the carboxyspermine derivative of Structure II, which can be readily generalized for the synthesis of any analogous polyamine derivatives. The compound of Structure II, activated by removal of the pentafluorophenol group, can be conjugated to the solid support to provide a carboxy spermine group at a peptide carboxy terminus. Standard automated peptide synthesis is performed using the support of Structure I. The fully protected carboxy spermine of Structure II can itself be employed as a reagent for addition of the carboxy spermine group at any position along a synthetic peptide chain. These methods can be readily and routinely adapted for conjugation of any polyamine.

Peptide-Lipid Conjugates

Figure 8:
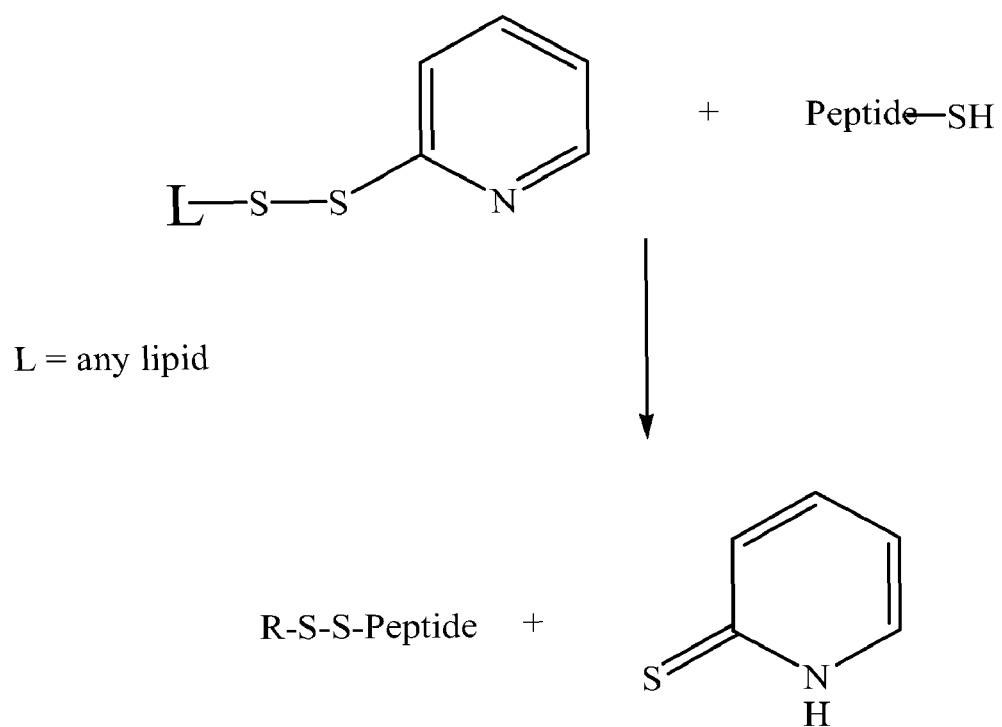
FIG. 8 shows a reaction scheme for the synthesis of peptide-lipid conjugates.

Peptide-lipid conjugates are prepared as follows: A lipid with a reactive head group, for example a group such as 1,2-dioleoyl-S,N-glycero-1-3-phosphoethanolamine-N-[3-(2-pyridyldithio)propionate] (N-PDP-PE, Avanti Polar Lipids, Inc. Alabaster, Ala.) is reacted with a cysteine-peptide (e.g., cysteine at either end of the functional peptide). Reaction can be performed at RT and followed by measuring the released chromophore. See Scheme 4 of FIG. 8. For example, N-PDP-PE is dissolved in methanol to a concentration of 0.2 M (about 200 mg/mL). Cys-peptides, including VSVG-Cys, (e.g., KFTIVFC, SEQ ID NO:11); RGD-Cys (e.g., GRGD-SPC, SEQ ID NO:8); or Cys-NLS (e.g., CGWGP-KKKRKVG, SEQ ID NO 12), are dissolved in an appropriate solvent, e.g., DMF, to a concentration of 100 mg/mL and mixed with the N-PDP-PE solution at a molar ratio of 1.5-2:1. Peptide-lipid conjugates can be purified by HPLC using a Vydac protein and peptide C18 reverse phase column with an acetonitrile/water/TFA and methanol solvent system. The conjugate can be characterized by UV and MS analysis.

Example 2

Enhancement of Cationic Lipid Transfection of Human Fibroblast Cells with Viral Peptides Added into Transfection Medium The following viral peptides were synthesized using automated solid phase peptide synthesis as described in Example 1: the membrane fusion region of influenza virus (HApep) (see, Epand et al. (1992) Biopolymers 32:309); modifications of FluHa to yield hemagglutinin peptides E5 and K5 (see, Kamata, H. et al. (1994) Nucleic Acids Res. 22:536-537); and vesicular stomatitis virus G-protein, VSVG (see, Schlegel, R. and Wade, M. (1985) J. Virol. 53:319). The nuclear localization signal (NLS) of SV40 large T antigen, NLS (see, Lanford et al. (1986) Cell 46:575) and the RGD peptide (Ruoslahti, E. and Pierschbacher, D. (1987) Science 238:491) were also synthesized. The sequences of the peptides synthesized is given in Table 5.

Newborn human fibroblasts (NHF) were isolated from neonatal foreskin dermis and prepared as described in, Hawley-Nelson, P., et al. (1993) Focus 15:73, incorporated by reference herein, and cultured for up to 20 passages. Cultures of adherent cells were grown in Dulbecco's-modified Eagle's medium (DMEM) containing 0.1 mM MEM Non-Essential Amino Acids (NEAA), 10% (v/v) fetal bovine serum (FBS), 100 U/mL penicillin (PEN) and 100 μg/mL streptomycin (STREP). Cultures were passaged at confluence using 0.25% (v/v) trypsin, 0.1 mM EDTA.

The plasmid vectors pCMVβgal and pCMVSPORTpgal are commercially available (Clontech, CA and GIBCO-BRL, respectively) mammalian reporter vectors containing the *E. coli* β-galactosidase (β-gal) gene under the control of the Cytomegalovirus promoter. See: MacGregor et al. (1989) Nucleic Acids Res. 17: 2365; Norton et al. (1985) Mol. and Cell Biol. 5:281; Alam (1990) Anal. Biochem. 188:245. Plasmid DNA was purified by standard cesium chloride methods.

Human fibroblasts were plated the day before transfection at $8\times10^4$ per well on a 24-well dish. Before transfection, the cells were rinsed with serum-free DMEM. Two 25 μl aliquots of "OPTI-MEM"-I medium, one containing 3 μg "LIPOFECTAMINE" and the other containing 0.2 μg pCMVβgal DNA, were combined to form complexes for 30 min at room temperature. "LIPOFECTAMINE" (Gibco/BRL: Life Technologies, Inc., Gaithersburg, Md.) is a 3:1 (w/w) mixture of the polycationic lipid, 2,3-dioleyloxy-N-[2(sperminecarboxamido)ethyl]-N,N-dimethyl-1-propanaminium trifluoroacetate (DOSPA), and DOPE. Peptides were dissolved in dimethylsulfoxide (DMSO) at 250× the final concentration (see Table 5). Peptide solution (1 μL) was added to 250 μl serum-free DMEM transfection medium and added to the rinsed cells. Treatments containing the E5, K5, HApep, and VSVG alone, and E5+K5 and VSVG+K5 in combination with each other were compared to a transfection sample containing no peptide ("LIPOFECTAMINE"+DNA only). For treatments that combined two peptides, E5, K5 and VSVG were all used at 5 μM concentrations. The DNA-lipid aggregates in "OPTI-MEM"-I were then added to the transfection medium with added peptide(s) on the cells. After 24 hours incubation at 37° C., cells were harvested, extracted and assayed for β-galactosidase activity as described above.

Enzyme activity of lysed cell extracts was used to compare levels of expression resulting from different treatment protocols. One to two days following transfection, cells were rinsed once with PBS and frozen at −70° C. in 0.15 mL/well 0.1% "TRITON" X-100 (t-octylphenoxypolyethoxyethanol; Sigma Chemical Co., St. Louis, Mo.; "TRITON" is a trademark of Union Carbide, Inc.) and 0.1M Tris, pH 8.0. After rapid thawing at 37° C., the lysate was cleared by centrifugation. Lysed cell extracts were assayed for β-galactosidase activity employing the method essentially as described in Sambrook et al. (1989) Molecular Cloning A Laboratory Manual, 2nd Ed., Cold Spring Harbor Laboratory Press, p. 16.66. Briefly, soluble cell extract containing 2-6 μg protein was added to 100 μl 0.1M sodium phosphate buffer (pH 7.5) containing 1 mM $MgCl_2$, 50 mM β-mercaptoethanol and 0.88 mg/mL o-nitrophenyl-β-D-galacatopyranoside (ONPG) in a 96-well microtiter plate. A standard curve of 10-70 ng β-galactosidase (Gibco/BRL: Life Technologies, Inc., Gaithersburg, Md.) was included on the plate. Yellow color developed in 5-20 minutes at 37° C. The reaction was stopped when necessary by adding 150 µl 1 M $Na_3CO_2$; $OD_{420}$ was determined on a microtiter plate reader.

FIG. 1 shows the effect of peptides added into the DMEM transfection medium after lipid has been complexed to DNA. As shown in FIG. 1, relatively minor enhancements of transfection compared to the control were observed, except for HApep and the combination of VSVG and E5. The VSVG+ E5 combination showed greater than 2-fold enhancement compared to "LIPOFECTAMINE" alone. Peptide concentrations that resulted in optimal transfection are listed in Table 5. It was later found that the order of addition of components had a significant effect upon transfection enhancement by peptides. Initial complexation of the peptide with the nucleic acid prior to contact of the DNA with the cationic lipid composition in general gave significantly higher transfection enhancement.

Example 3

Transfection Enhancement of Sp-NLSNLS Pre-Complexed to DNA in Combination with "LIPOFECTAMINE"

Sp-NLSNLS (the peptide (NLSNLS): GYGP-KKKRKVGGGGYGPKKKRKVGG [SEQ ID NO:13] conjugated to spermine) enhances transfection efficiency in combination with "LIPOFECTAMINE" in human fibroblasts, NIH 3T3, MDCK and BHK-21 cells when the peptide is pre-complexed to the DNA prior to addition of "LIPOFECTAMINE."

In this example, all media, sera, and reagents were from GIBCO BRL unless otherwise noted. All cells were cultured in Dulbecco's MEM (DMEM, high glucose: 4,500 mg/L D-glucose, with L-glutamine and phenol red) with 0.1 mM Non-Essential Amino Acids (NEAA), 100 U/mL penicillin and 100 µg/mL streptomycin. Human fibroblasts, MDCK, and BHK-21 cells were cultured with 10% Fetal Bovine Serum (FBS). NIH 3T3 cells were cultured with 10% Calf Serum. Human fibroblast cells were obtained as described in Example 2. NIH 3T3 (NIH Swiss mouse embryo, contact-inhibited fibroblasts), MDCK (dog kidney cells) and baby hamster kidney (BHK-21) cells were obtained from the American Type Culture Collection (Rockville, Md.). All cultures were maintained at 37° C. with 5% $CO_2$. Human fibroblasts at $6 \times 10^4$, BHK-21 at $4 \times 10^4$, MDCK at $6 \times 10^4$, and NIH 3T3 at $5 \times 10^4$ cells per well were plated the day before transfection in 24-well plates. On transfection day, the cell cultures were 50-80% confluent.

For each well on a 24-well plate, 0.5-4 µL "LIPOFECTAMINE" Reagent and 0.1-0.8 µg pCMV·SPORT-β-gal or pCMVβ DNA (G. R. McGregor and C. T. Caskey (1989) Nucleic Acids Res. 17:2365) were diluted into separate 25 µL aliquots of serum-free medium ("OPTIMEM-1" or D-MEM with added 0.1 mM NEAA). Sp-NLSNLS (1-4 µg, as a 1 mg/ml solution in water) was added into the DNA solution, and incubated at RT for 15 min to allow pre-complexation. The DNA-Sp-NLSNLS solution was mixed together with diluted "LIPOFECTAMINE", then incubated at RT for 30 min. The cells were rinsed with serum-free DMEM with NEAA, then 0.2 ml per well of serum-free DMEM with NEAA was added to the cells. The DNA-Sp-NLSNLS-lipid complex was added to the serum-free D-MEM on the cells, incubated at 37° C. for 5 hrs, then 1 ml of D-MEM containing FBS (final concentration 10%) was added. Cultures were incubated 24 hrs, then fixed and stained in-situ with X-gal (J. R. Sanes et al. (1986) EMBO J. 5:3133, see below) or harvested for ONPG assay (as described in Example 2).

Figure 2:
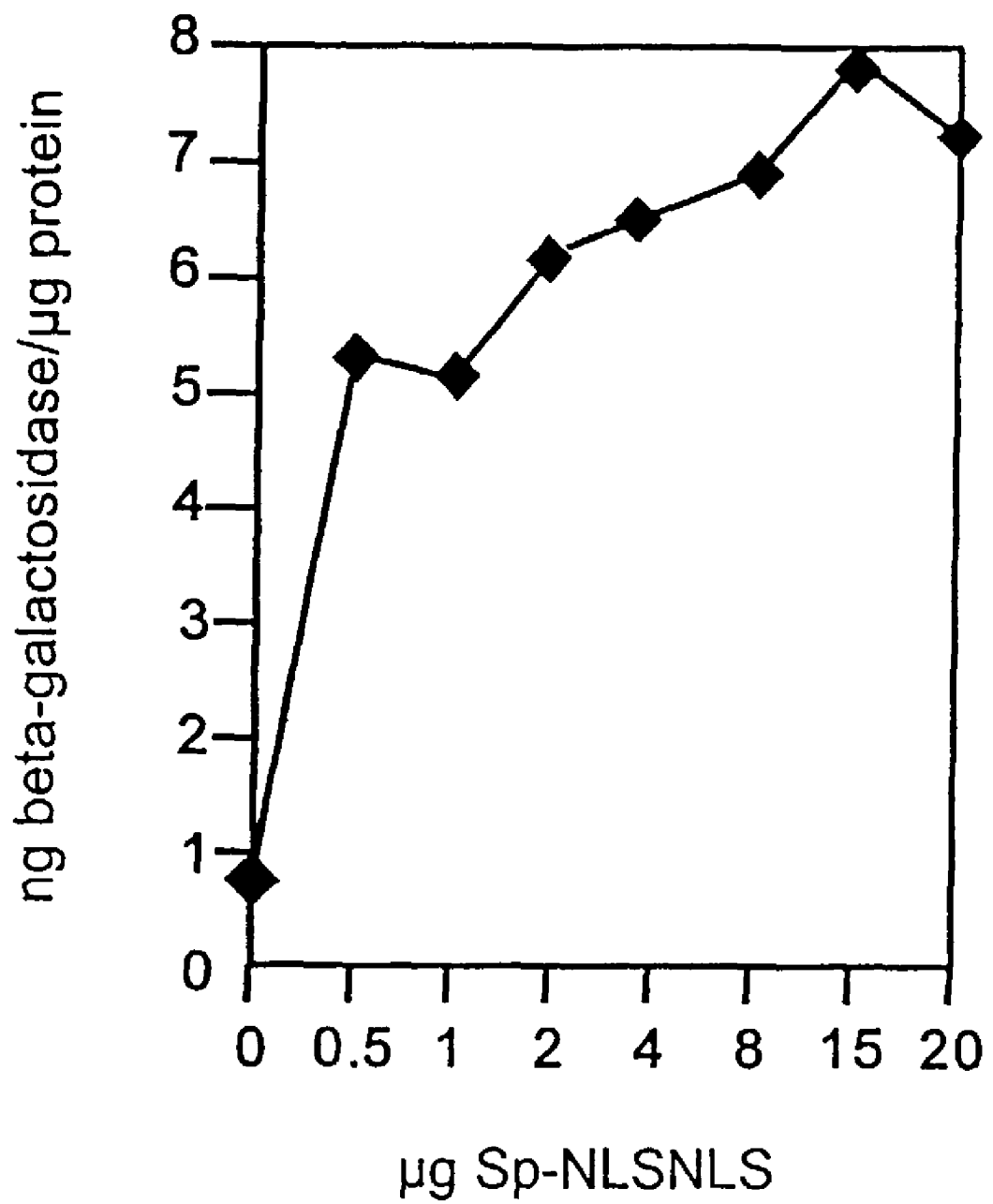
FIG. 2 is a graph showing the effect of Sp-NLSNLS concentration on enhancement of "LIPOFECTAMINE" transfection activity. Human fibroblasts were transfected with 0.4 µg DNA, 2 µL "LIPOFECTAMINE" and Sp-NLSNLS as indicated in serum-free medium. Cells were harvested and assayed for β-galactosidase activity 24 h after transfection.

In order to test enhancement of transfection efficiency, human fibroblasts were transfected with pCMV-SPORT-β-gal DNA using "LIPOFECTAMINE" and Sp-NLSNLS. Increasing concentrations of Sp-NLSNLS were tested and β-galactosidase activity was assayed with ONPG (FIG. 2). In this transfection, 2-20 µg Sp-NLSNLS precomplexed with 0.4 µg DNA resulted in a plateau of enhanced activity. Enhancement levels between 5-8-fold were routinely observed at 2-4 µg Sp-NLSNLS per 0.4 µg DNA in similar experiments (data not shown).

Human fibroblasts similarly transfected were stained in-situ with X-gal. The results of the most active concentration of Sp-NLSNLS (2 µg) and lipid (2 µL) with DNA (0.4 µg) was photographed and positive cells counted. Percent positive cells (mean of 3 determinations +/−half the range) was determined: "LIPOFECTAMINE" (4+/−2%), "LIPOFECTAMINE" with Sp-NLSNLS (18+/−6%). This is a four-fold enhancement in percent transfected cells.

In situ staining was used to demonstrate β-galactosidase expression. Cells were rinsed with PBS, fixed for 5 min in 2% (v/v) formaldehyde, 0.2% glutaraldehyde in PBS, rinsed twice with PBS, and stained overnight with 0.1% X-gal (Gibco/BRL: Life Technologies, Inc., Gaithersburg, Md.), 5 mM potassium ferrocyanide, 5 mM potassium ferricyanide, 2 mM $MgCl_2$ in PBS. Rinsed cells were photographed using a 10× objective on a Nikon inverted microscope with Hoffman optics. Transfection efficiency was evaluated by counting or estimating the number of β-gal positive (blue-stained) cells.

Analyses of transfection enhancement by Sp-NLSNLS were performed in human fibroblasts, BHK-21, NIH3T3, and MDCK cells using wide ranges of lipid and DNA concentrations. The data are presented in FIGS. 3A-3H. In each case, the whole platform of activity is raised, not just the activity at the optimum of lipid and DNA concentrations. Enhancement of this type facilitates the reproducibility of high efficiency transfections, broadening the spectrum of activity of polycationic lipid-mediated transfection (particularly transfection using "LIPOFECTAMINE" and resulting in high activity over a broader range of DNA and lipid concentrations. The use of spermine-derivatized peptides, such as Sp-NLSNLS, in transfections decreases the amount of detailed optimization of lipid and DNA concentration previously required to achieve high activity cationic lipid transfections in a given system.

By increasing the platform of activity across the ranges of lipid and DNA concentrations with Sp-NLSNLS and other peptides and spermine-derivatized peptides, it is possible to achieve high level transfections with lower amounts of lipid and DNA resulting in higher cell yield from equivalent or higher efficiency transfection.

Figure 3A:
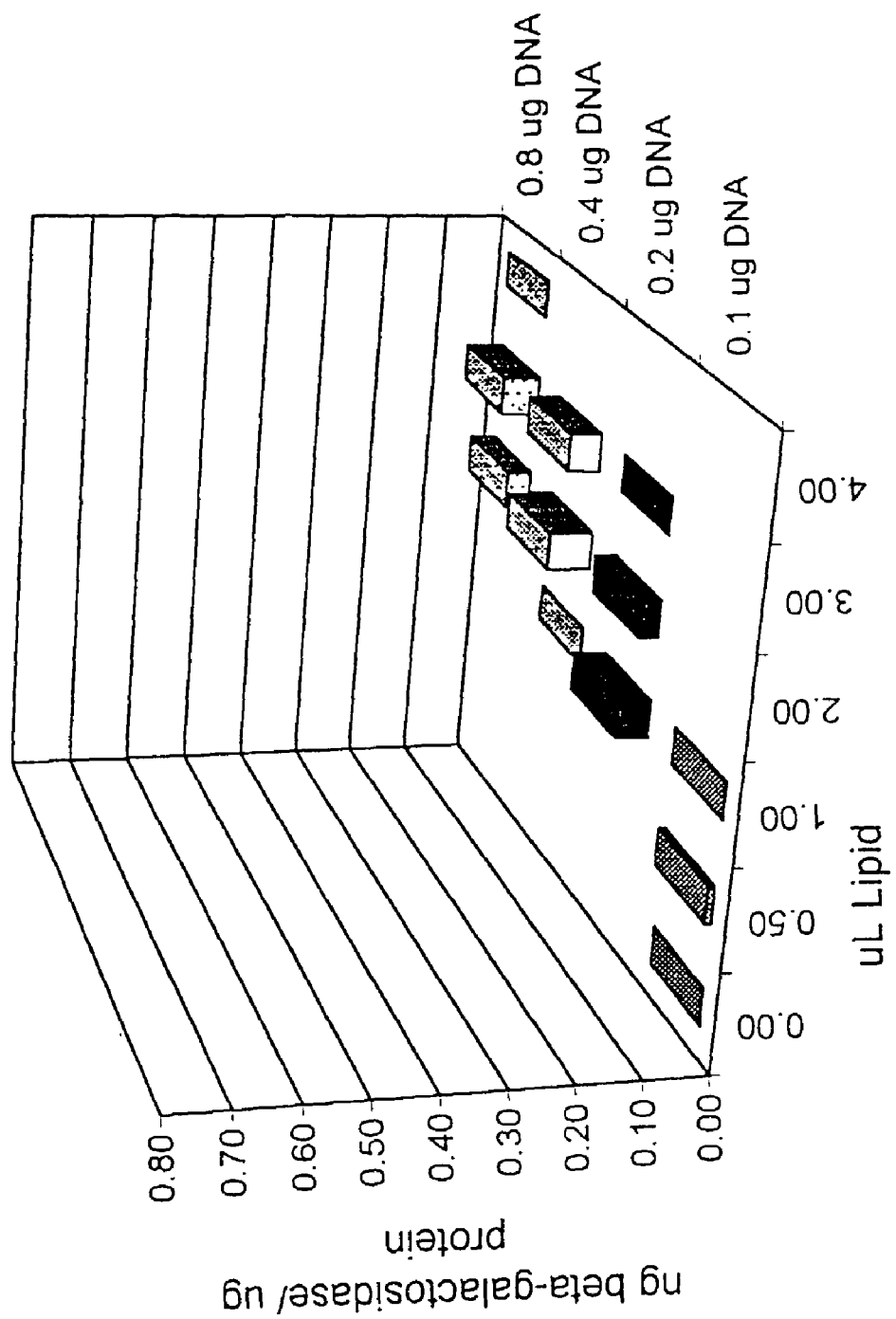
FIGS. 3A-H provide comparisons of lipid transfection with and without Sp-NLSNLS precomplexed with DNA in 4 cell types. Human fibroblast (3A and 3B); BHK-1(3C and 3D); NIH 3T3 (3E and 3F); MDCK (3G and 3H) cells were transfected in 24-well plates with "LIPOFECTAMINE" and DNA as shown.
Figure 3B:
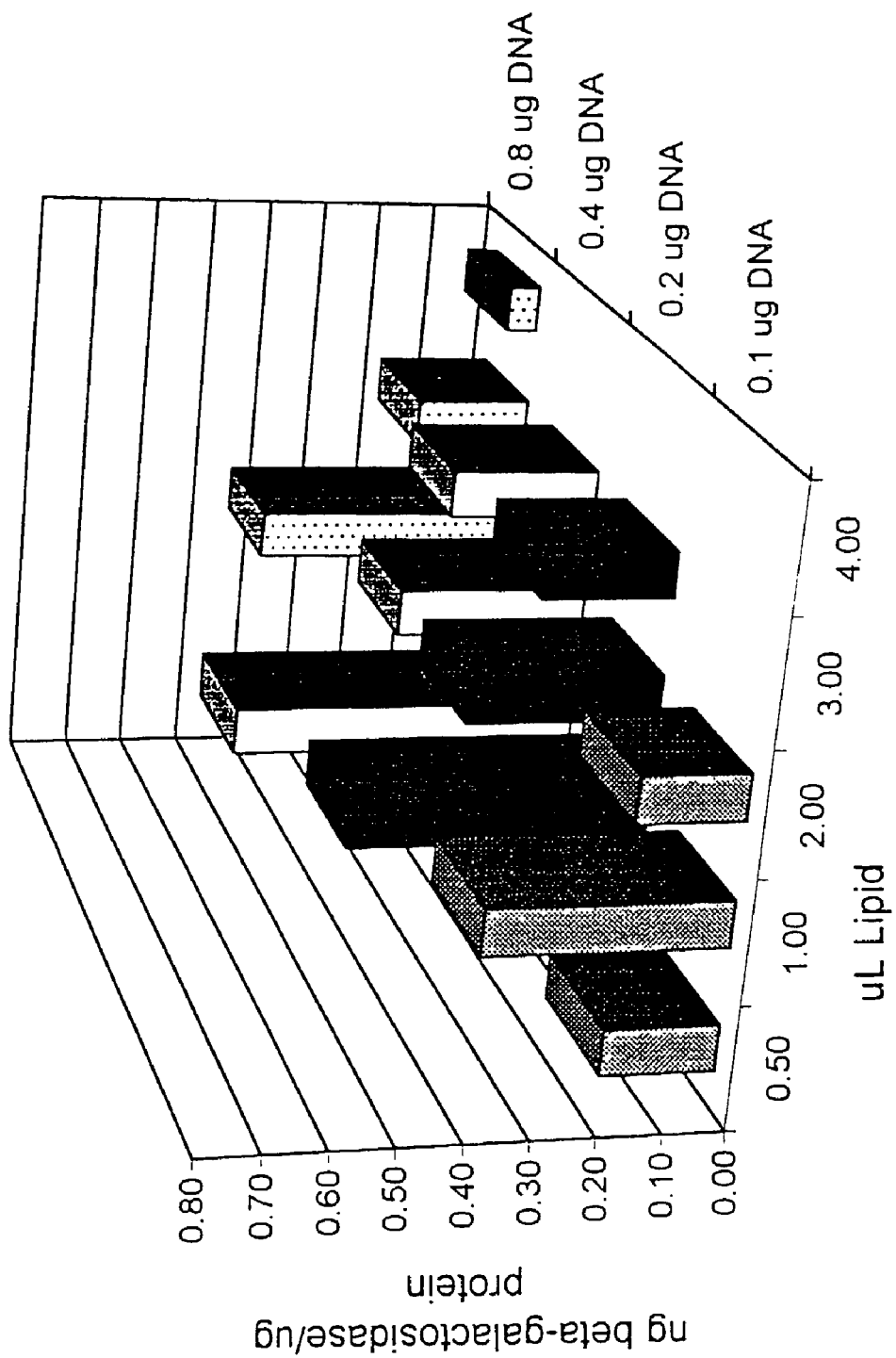
Figure 3C:
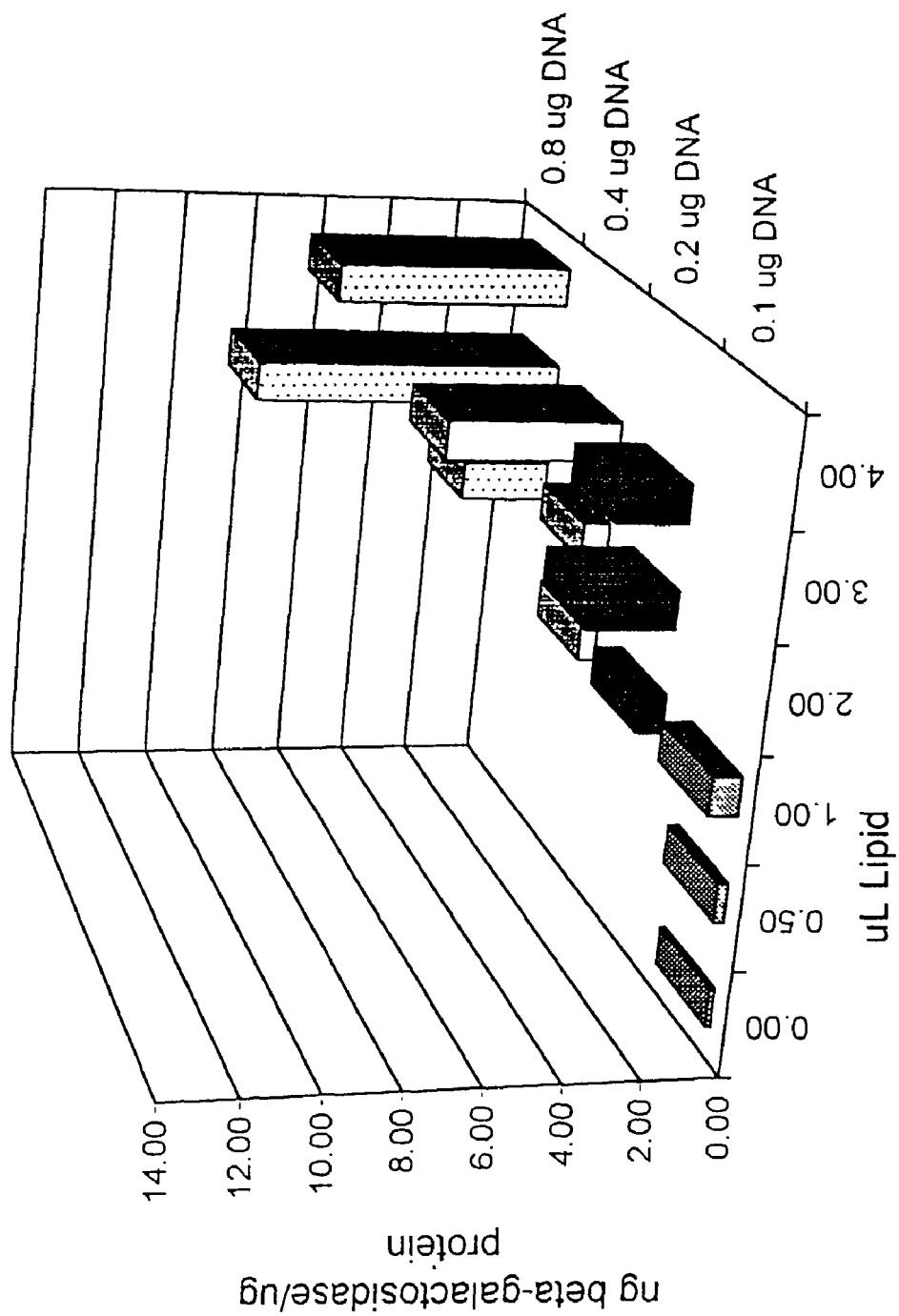
Figure 3D:
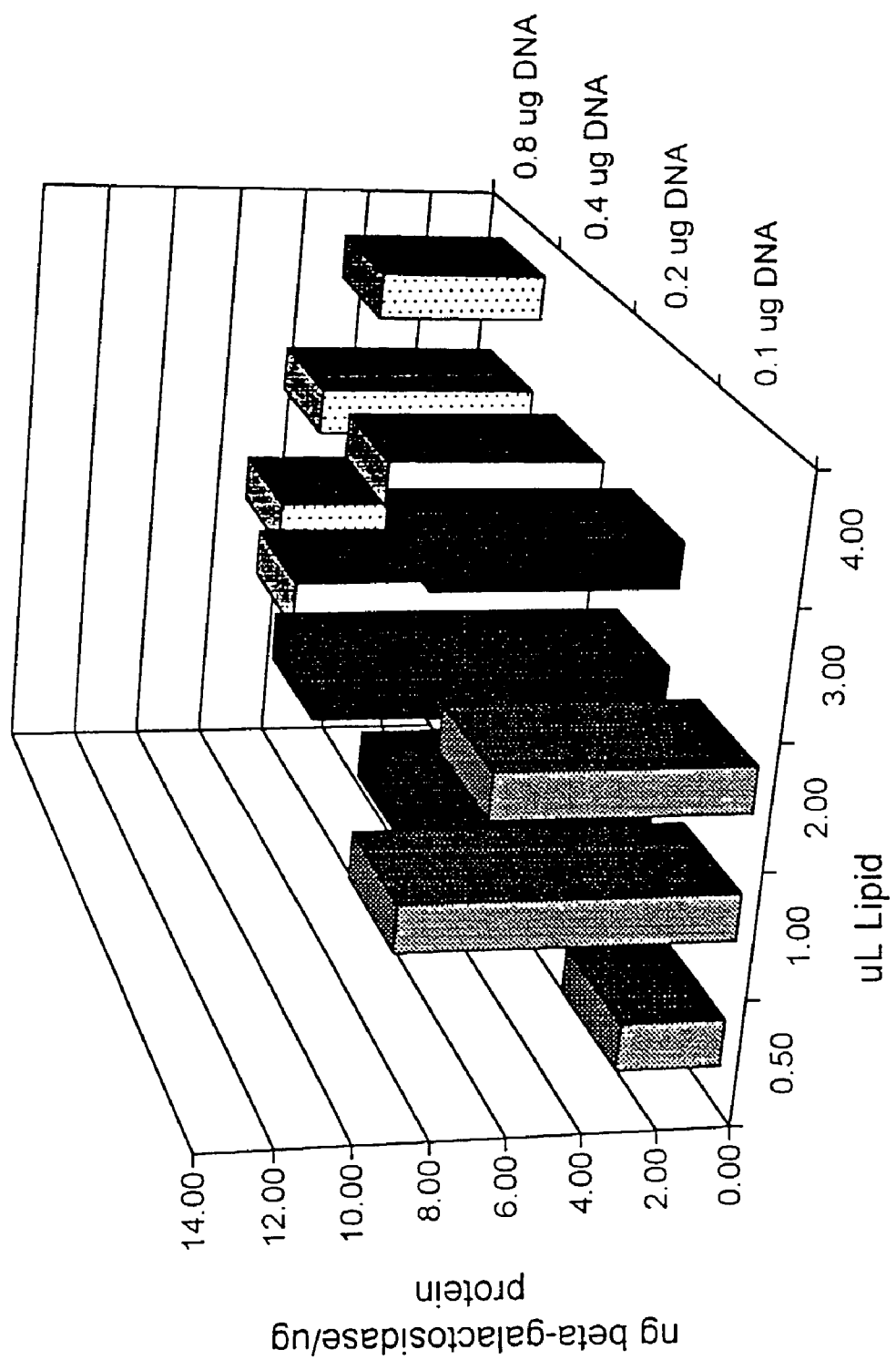
Figure 3E:
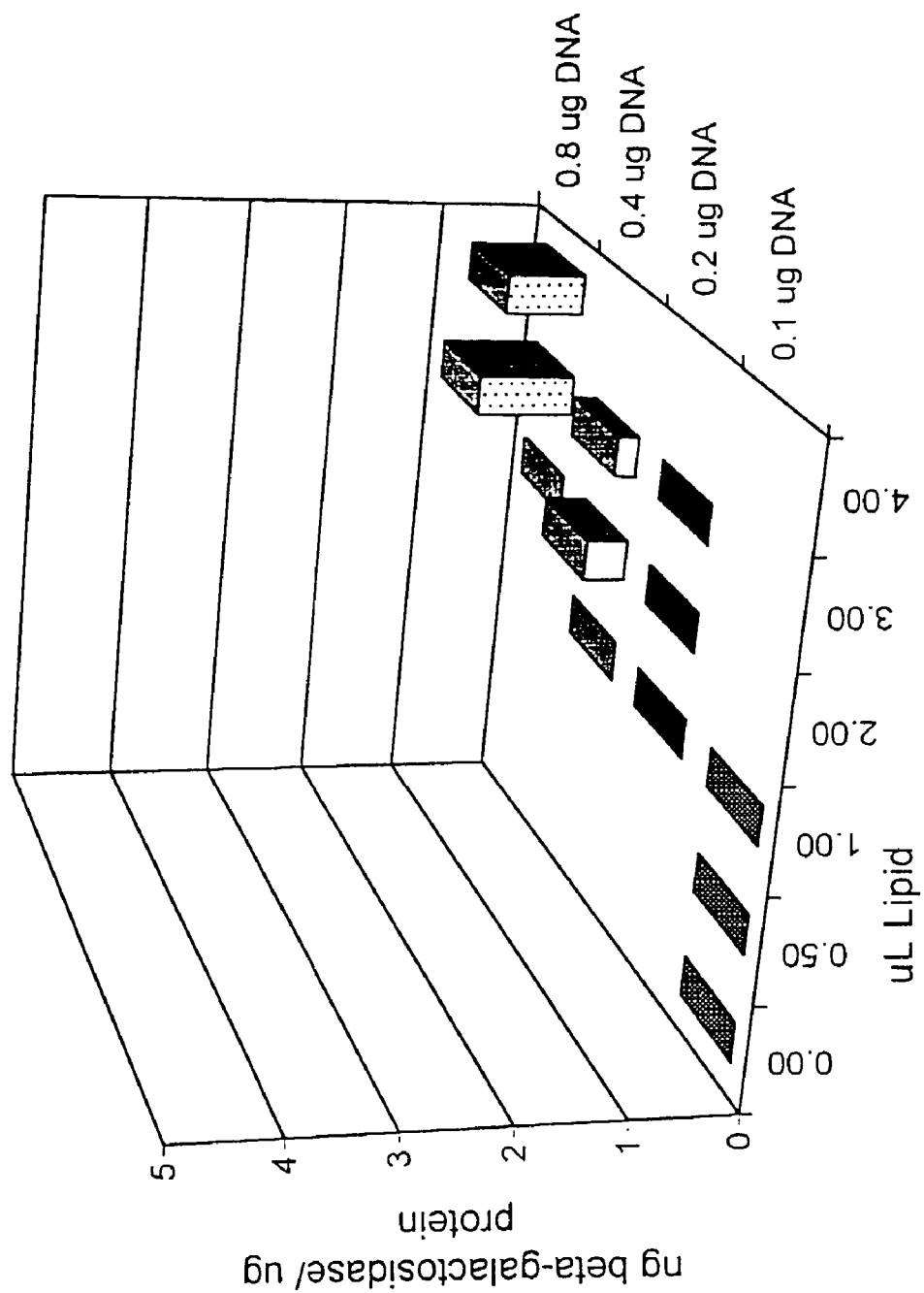
Figure 3F:
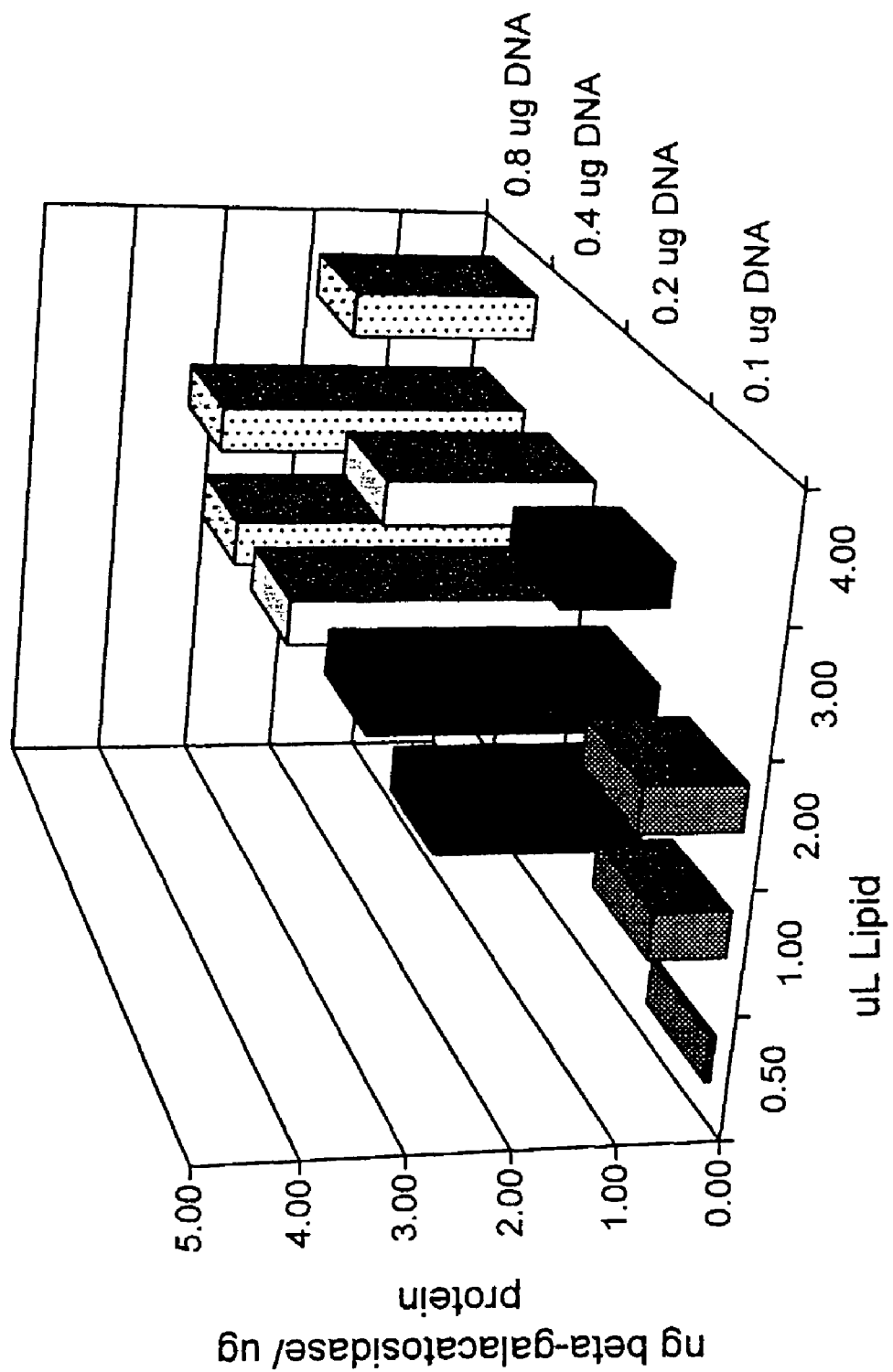
Figure 3G:
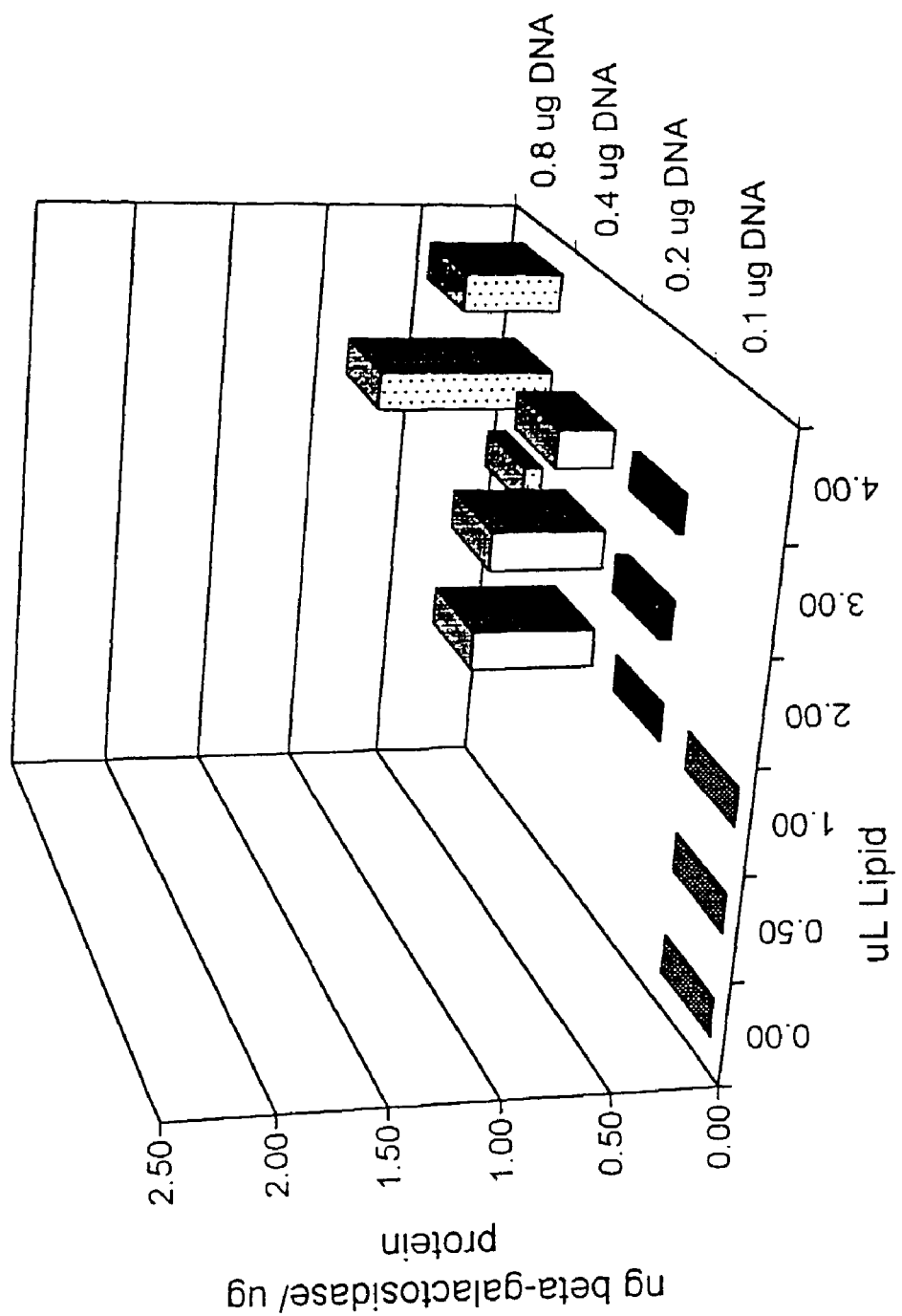
Figure 3H:
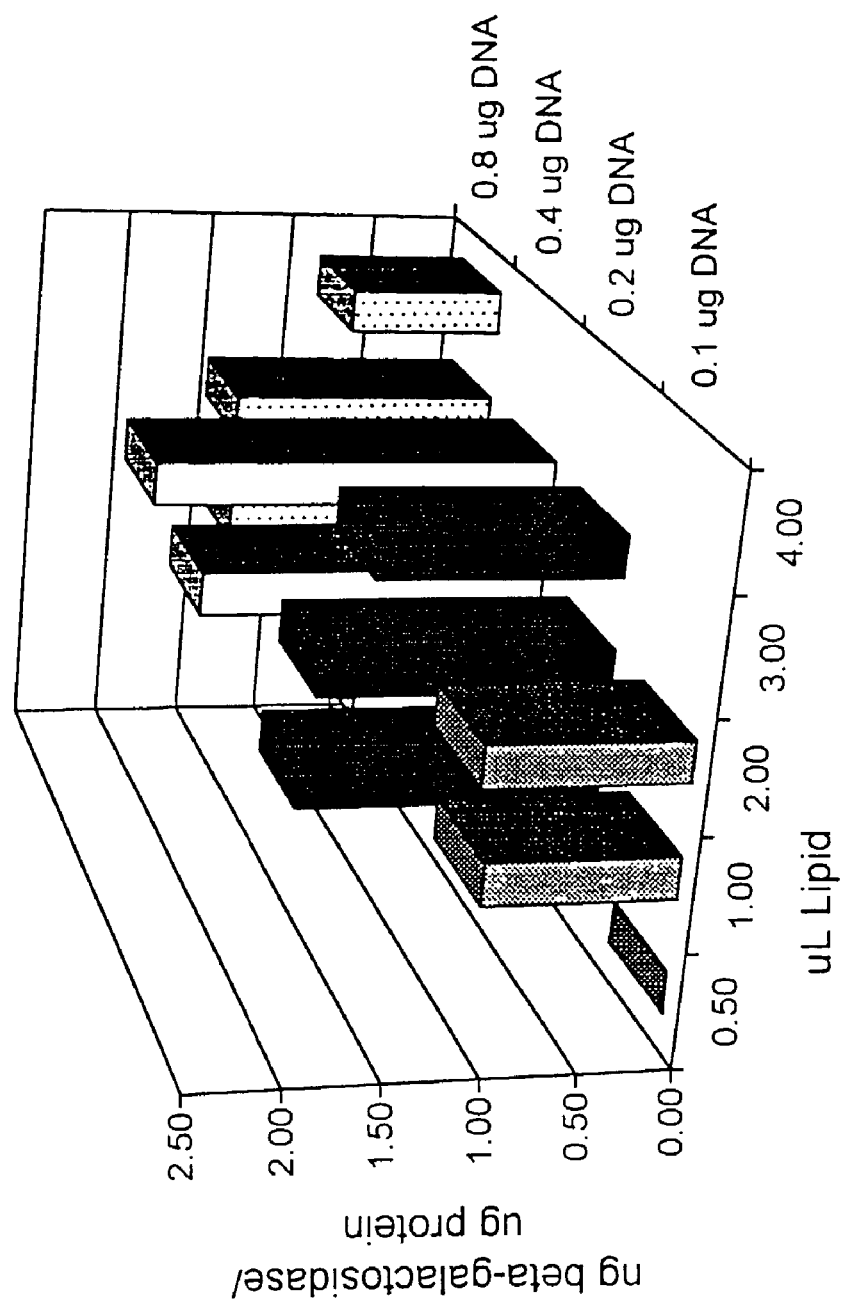

Table 6 illustrates this observation using data generated in the experiment graphed in FIGS. 3A and 3B. Peak activity of 0.07 ng β-gal/µg protein is achieved with "LIPOFECTAMINE" alone at 0.4 µg DNA and 2 µL "LIPOFECTAMINE". The protein yield (which is directly proportional to cell yield) for these conditions was 67.5 µg/well. By using Sp-NLSNLS 0.38 ng β-gal activity per µg protein (over 5-fold higher than the peak for "LIPOFECTAMINE" alone) can be achieved in a transfection with 0.1 µg DNA and 1 µl "LIPOFECTAMINE." The protein yield under these conditions is 85.5 µg/well, 25% more than at the peak with "LIPOFECTAMINE" alone. This difference is seen in other cell types, as well (data not shown). The enhanced yield is most likely due to the use of lower lipid and DNA concentrations, since similar yields are seen with "LIPOFECTAMINE" alone and with Sp-NLSNLS-precomplexed DNA at the same lipid and DNA concentrations (data not shown).

Example 4

Enhancement of "LIPOFECTAMINE" Transfection in Human Fibroblast Cells by Peptides and Peptide Derivatives Pre-Complexed to DNA.

Table 7 compares transfection activity for "LIPOFECTAMINE" combined with various peptides and peptide derivatives. Transfections were done in human fibroblasts (except as indicated) using pCMSPORTβgal or pCMVβ using the ONPG assay as described in Example 3. Experiments were done in 24-well plates using 0.4 µg DNA/transfection (except as indicated). The protocol described in Example 3 was used with the peptides added to DNA initially. The data in Table 7 are the fold-enhancement at peak activity for "LIPOFECTAMINE" and the peptide or modified peptide. During the purification of the peptides by HPLC in several instances, two peaks were isolated. K16NLS (peak 2) is incompletely deprotected material which is believed to retain the Mtr-protecting group on an arginine residue (R). Most preferred transfection enhancing agents are those peptides or peptide derivatives that give the highest fold enhancement (compared to cationic lipid alone) at the lowest amount of enhancing agent. Note that the reverse NLS peptide exhibited no enhancement of transfection with "LIPOFECTAMINE".

Example 5

Transfection Activity of DMRIE-C in the Presence of Certain Peptide Derivatives

Table 8 compares transfection activity for DMRIE-C combined with several different peptide (or peptide derivatives or combinations thereof) for transfection of suspension cell lines (K562 and Jurkat cells).

DMRIE-C is a 1:1 (M/M) liposome formulation with cation lipid DMRIE (1,2-dimyristyloxypropyl-1-3-dimethylhydroxyethyl ammonium bromide) and cholesterol in membrane-filtered water. See: K. Schifferli and V. Ciccarone (1996) "FOCUS" 18:45 and V. Ciccarone et al. (1995) "FOCUS" 17:84. Transfections were performed using pCMVSPORTCAT, and the assays were performed using CAT assay: varying amounts of peptide derivatives (or mixtures of such derivatives) were combined and pre-incubated with DNA for 15 minutes. The precomplexed DNA-peptide (and or peptide derivative) complex was then mixed with 1.6 µL DMRIE-C. The transfection composition was then mixed with $4 \times 10^5$ cells/well in 24-well plates. CAT assays were performed at 36-48 h after transfection.

The chloramphenicol acetyltransferase (CAT) assay was preformed as described in J. R. Neuman et al. (1987) *BioTechniques* 5:444. Briefly, harvested cells from a well were washed with PBS and pelleted by centrifugation at 1000 rpm (~600× G) for 5 m at RT for suspension cells. Pellets were put on ice and 1 mL of 0.1M Tris-HCl (pH 8.0) containing 0.1% TRITON X-100 was added and then frozen at −70° C. for 2 h. Pellets are thawed at 37° C., then chilled on ice. Cell lysates were centrifuged at maximum speed in a microcentifuge for 5 min. Supernatant was collected and heated for 10 m at 65° C. to inactivate deacetylases and other inhibitors of the CAT reaction. Heated supernatants (hereafter cell extracts) were centrifuged at maximum speed for 3 m and stored at −70° C.

For each cell extract sample, add 5-150 µL cell extract and make up to 150 µL with 0.1 M Tris-HCl (pH 8.0). Negative control is 150 µL 0.1 M Tris-HCl (pH 8.0); Positive control is CAT standard solution (1, 5, 10, 20, and 50 mU of CAT) made up to 150 µL with 0.1 M Tris-HCl (pH 8.0). Add 100 µL of a mixture: 10 µL 1 M Tris-HCl (pH 8.0); 1 µL 250 mM chloramphenicol (in 100% ethanol); 5 µL (50nCi) [$^{14}$C-butryl Coenzyme A (0.010 µCi/µL); 84 µL deionized, distilled water, to each sample and incubate at 37° C. for 2 h. Add 3 mL of "ECONOFLUOR" to each sample and incubate at RT for 2 h. Count each sample for 0.5 m in a liquid scintillation counter.

Table 8 lists the highest fold enhancement observed with peptide used and the amount of peptide (or derivative) needed to achieve that level of enhancement.

Example 6

Enhancement of Dendrimer-Mediated Transfection

"STARBURST" polyamidoamine (PAMAM) dendrimers: G7 (EDA), G9(EDA), and G6(EDA) modified with lysine [Lys DMER] or with arginine [Arg DMER], and a "COMB BURST" (Trademark, Dendritech Inc.) dendrigraft were obtained from Michigan Molecular Institute. The PAMAM dendrimers were prepared by now standard methods as described, for example, in Tomalia D. A. and Durst, H. D. (1993) in Weber E. (ed.) *Topics in Current Chemistry*, 165: "Supramolecular Chemistry I-Directed Synthesis and Molecular Recognition, Springer-Verlag, Berlin pp. 193-313 and Tomalia D. A. et al. (1990) Angew. Chem. Intl. Ed. Engl. 29:138-175. These modified dendrimers were stored as the trifluoroacetate salts. Lys DMER has a charge density of $2.07 \times 10^{15}$+charge/µg; Arg DMER has a charge density of $2.41 \times 10^{15}$+charge/µg. "COMB BURST" dendrigraft was grown to generation three and then modified with one layer of PAMAM repeat units to give a polymer with a molecular weight of 30,000, a polydispersity of 1.11 and a charge density of $2.68 \times 10^{15}$+charges/µg.

The effect of peptides and spermine-peptide conjugates on dendrimer-mediated transfection was assessed in transfections of COS-7 cells (ATCC). Dendrimer transfection was performed essentially as described in Kukowska-Latallo J. F. et al. (1996) Proc. Natl. Acad. Sci. USA 93:4897-4902. COS-7 cells were plated at $4 \times 10^4$ cells/well in 24 well plates. Two DNA plasmids were used: pCMVβ for X-gal staining and pGL3 (Promega) for luciferase assay both at 0.5 µg/well. All dendrimers were used at 3 µg/well and chloroquine was added to all dendrimer transfections at 25 µg/mL. Dendrimer transfections were compared with "LIPOFECTAMINE" transfections using 1 µL/well. The effect of three peptides: K16NLS (peak 2, incompletely deblocked) added at 1 µg/well, Sp-NLSNLS added at 1.5 µg/well, and NLS added at 20 µg/well was determined.

For the luciferase assay, each well was extracted in 0.15 ml lysis buffer (25 mM Tris HCl, pH 8.0, 0.1 mM EDTA, 10% glycerol, 0.1% Triton X 100), and 10 µL centrifuged extract supernate from each well was automatically mixed with 50 µL Luciferase Assay Reagent (Promega) and assayed in a luminometer for 5 seconds. The X-gal assay was performed as in Example 3.

The results of the luciferase assay are listed in Table 9. The transfection activity of each of the dendrimers in Table 11 was enhanced by the three peptides or peptide conjugates tested. The most active dendrimers for transfection of COS-7 cells were Arg DMER and "COMB BURST". In these experiments, transfection was not optimized for dendrimer concentration or the amount of peptide added. X-gal assays were consistent with the data given in Table 9.

Example 7

Effect of Sp-NLSNLS on Stable Transformation Frequency in NIH 3T3 Cells

Figure 4A:
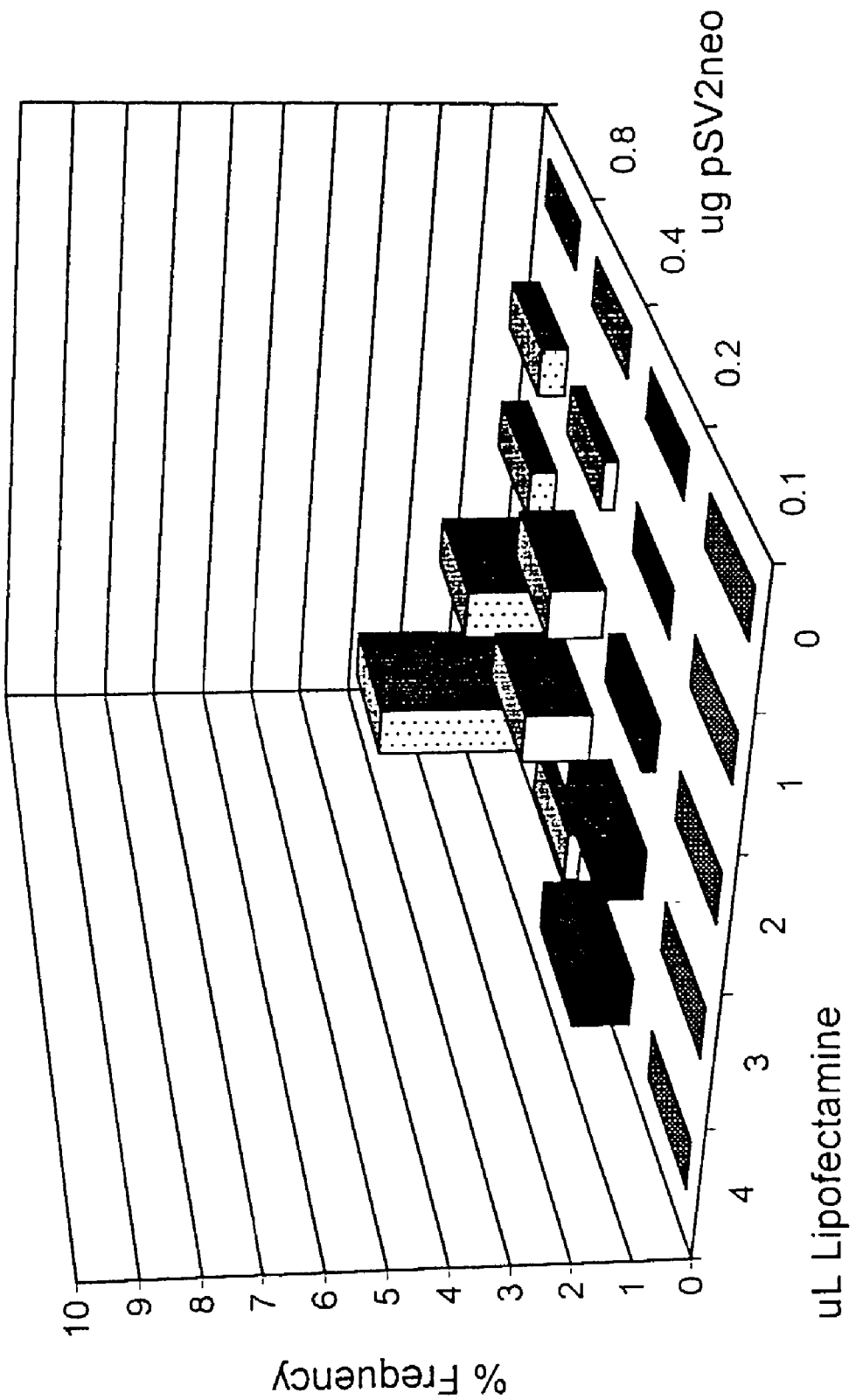
FIGS. 4A and 4B are three-dimensional graphs comparing "LIPOFECTAMINE" transfection in the presence of varying amounts of Sp-NLSNLS with varying amounts of DNA (pS-Vneo) with transfection with and without peptide in FIGS. 4B and 4A, respectively. The transfections were performed in NM 3T3 cells.
Figure 4B:
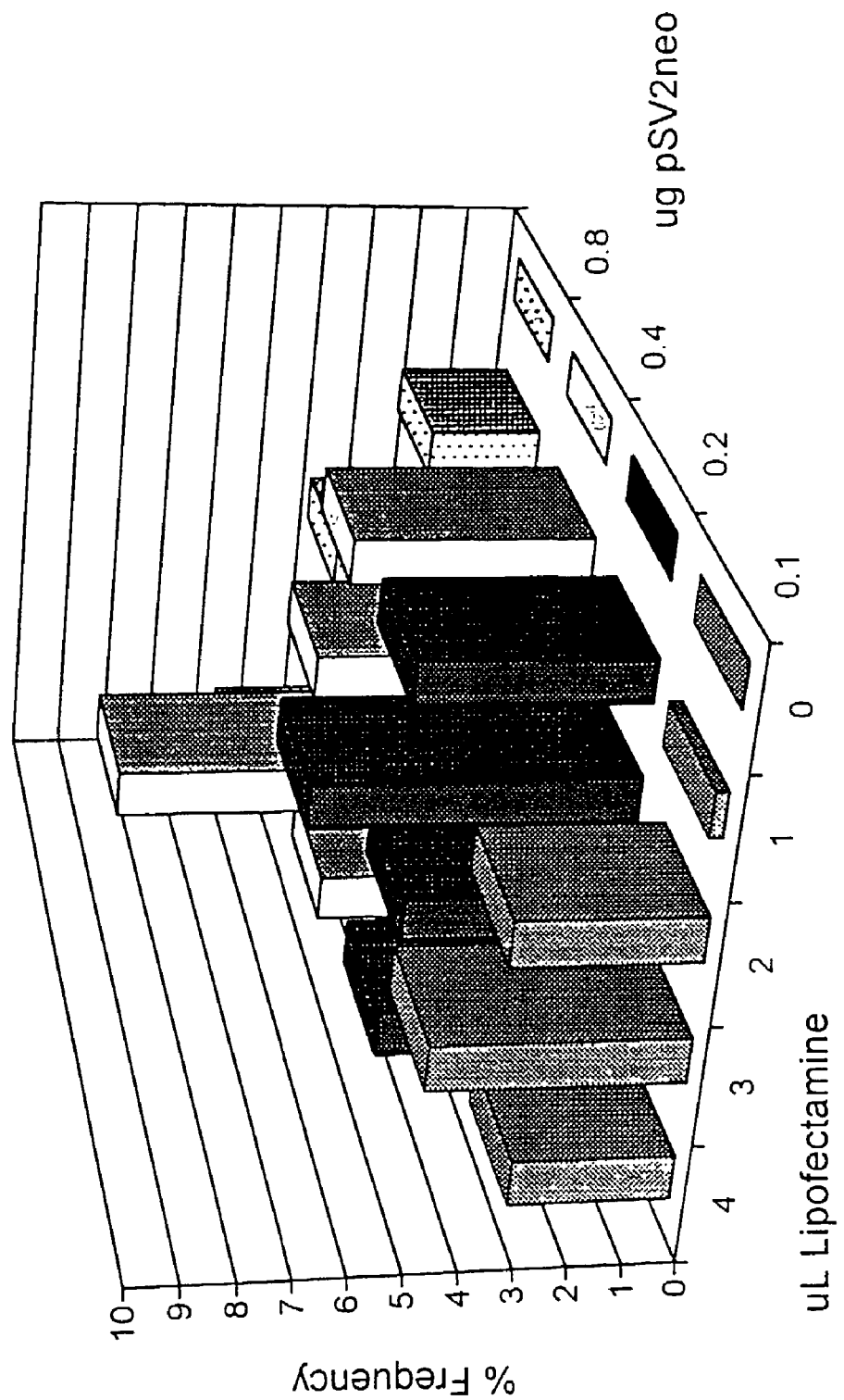

NIH 3T3 cells were seeded at $6\times10^4$ cells/well in 24 well plates, in DMEM supplemented with 10% Calf Serum, and allowed to grow overnight. Cells were transfected in matrix format using 0, 1, 2, 3, and 4 µL "LIPOFECTAMINE", and 0.1, 0.2, 0.4, and 0.8 µg pSV2neo (obtained from ATCC, carrying a neomycin resistance gene, see: Berg et al. (1982) J. Mol. Appl. Genet. 1: 327-341. DNA was pre-incubated with 2 µg (for 0.1-0.4 µg DNA) or 4 µg (for 0.8 µg DNA) peptide. Control DNA was provided with no peptide (here Sp-NLSNLS, see Table 5 for sequence). At 24 h after transfection, cells were split 1:150 into 35 mm plates containing growth medium, and allowed to grow overnight. The next day cells were put in selection medium containing 0.6 mg/ml "GENETICIN" (G418 sulfate, Gibco/BRL: Life Technologies, Inc., Gaithersburg, Md.)). After 10 days plates were fixed and stained with 10% formalin/PBS containing 0.4% toluidine blue. G418-resistant colonies were counted and expressed as % of initial number of cells plated. FIGS. 4A (no peptide control) and 4B (with added Sp-NLSNLS) show the results of this experiment. Significant enhancement of transfection by Sp-NLSNLS is observed in almost all cases.

Example 8

Effect of Sp-NLSNLS on Transfection by Monocationic Lipid Reagents

In separate experiments, BHK-21 cells were seeded at $2\times10^4$ cells/well, COS-7 cells were seeded at $5\times10^4$ cells/well, CHO-K1 cells were seeded at $6\times10^4$ cells/well, human fibroblasts were seeded at $8\times10^4$ cells/well, and HT29 cells were seeded at $1\times10^5$ cells/well in 24-well plates in DMEM supplemented with 10% fetal bovine serum and allowed to grow overnight. Cells were transfected as described in example 3, using 0-4 ml "LIPOFECTIN", "LIPOFECTACE" (1:2.5 w:w ratio of dimethyl-dioctadecyl-ammonium bromide (DDAB) and DOPE), or DMRIE-DOPE (1:1 molar ratio, 1 mg/ml) and 0.4 mg pCMVSPORTbgal plasmid DNA precomplexed with 0-15 mg Sp-NLSNLS peptide. At 24 h after transfection, cells were harvested as described in example 2. Lysates were assayed for b-galactosidase activity using the luminescent assay from Tropix (V. K. Jain and I. T. Magrath (1991) Anal. Biochem. 199:119-124). Table 10 shows the peak activities of transfection with a range of concentrations of the monocationic lipid with DNA alone or with DNA precomplexed to Sp-NLSNLS peptide. A clear enhancement is seen in most cases.

Example 9

Effect of Sp-NLSNLS on transfection by polycationic lipid reagents other than DOSPA-DOPE In separate experiments, CHO-K1 and NIH3T3 cells were seeded at $6\times10^4$ cells/well, and human fibroblasts were seeded at $8\times10^4$ cells/well in 24-well plates in DMEM supplemented with 10% fetal bovine serum (10% calf serum for NIH3T3) and allowed to grow overnight. Cells were transfected as described in example 3, using 0-4 ml "CELLFECTIN," TMDOS, "DOSPER" or "MULTIFECTOR" and 0.4 mg pCMVSPORTbgal plasmid DNA precomplexed with 0-40 mg Sp-NLSNLS peptide. At 24 h after transfection, cells were harvested as described in example 2. Lysates were assayed for b-galactosidase activity using ONPG (see Example 2) or the luminescent assay from Tropix (see Example 8). Table 11 shows the peak activities of transfection with a range of concentrations of the polycationic lipids with DNA alone or with DNA precomplexed to Sp-NLSNLS peptide. A clear enhancement is seen.

Example 10

Effect of Sp-NLSNLS on Transfection by the Activated Dendrimer "SUPERFECT"

COS-7 cells were seeded at $4\times10^4$ cells/well in 24-well plates in DMEM supplemented with 10% fetal bovine serum and allowed to grow overnight. Cells were transfected as described in example 3, using 0-4 ml "SUPERFECT" and 0.4 mg pCMVSPORTbgal plasmid DNA precomplexed with 0-5 mg Sp-NLSNLS peptide. At 24 h after transfection, cells were harvested as described in Example 2. Lysates were assayed for b-galactosidase activity using the luminescent assay from Tropix (see Example 8). Table 12 shows the peak activities of transfection with a range of concentrations of the dendrimers with DNA alone or with DNA precomplexed to Sp-NLSNLS peptide. A clear enhancement is seen.

Example 11

Effect of TAT and TAT-Spermine Peptides on Transfection by "LIPOFECTAMINE"

Two versions of the Tat peptide were synthesized: one with the DNA-binding group carboxyspermine on the N-terminus and one without. The core TAT sequence employed was CGYGRKKRRQRRRG [SEQ ID NO:123]. The ability of the TAT peptide and the carboxyspermine-modified TAT peptide to enhance cationic lipid-mediated transfection was tested.

Transfection was performed in NIH/3T3 cells, in 24-well plates. Seeding density was $6\times10^4$ cells/well. For each condition, the standard PLUS protocol was used (see example 3) for complexing. All complexes were prepared in OptiMEM reduced serum media. Cells were harvested and assayed for β-galactosidase acivity in the soluble extracts by luminescent assay (see example 8). Table 13 shows the peak activities of transfection with a range of concentrations of "LIPOFECTAMINE" with DNA alone or precomplexed to the Tat or Tat-spermine peptides. A clear enhancement is seen.

Example 12

Effect of Including Receptor-Ligand Proteins with Sp-NLSNLS in DNA Pre-Complexes on Transfection by "LIPOFECTAMINE" and "LIPOFECTIN"

In separate experiments, CHO-K1 cells were seeded at $6\times10^4$ cells/well, and human fibroblasts were seeded at $8\times10^4$ cells/well in 24-well plates in DMEM supplemented with 10% fetal bovine serum and allowed to grow overnight. Cells were transfected as described in Example 3, using 0-5 µl "LIPOFECTAMINE," "LIPOFECTIN," or "DMRIE-DOPE" and 0.4 µg pCMVSPORTβgal plasmid DNA precomplexed with 0-40 µg Sp-NLSNLS peptide or mixtures of Sp-NLSNLS peptide and 1-2 µg Insulin or 2-4 µg Transferrin, or both 1-4 µg both Insulin and Transferrin. At 24 h after transfection, cells were harvested as described in Example 2. Lysates were assayed for β-galactosidase activity using ONPG (see Example 2) or the luminescent assay from Tropix (see Example 8). Table 14 shows the peak activities of transfection with a range of concentrations of the lipids with DNA alone or with DNA precomplexed to Sp-NLSNLS peptide +/− the ligand proteins. A clear enhancement is seen resulting from the inclusion of the ligand proteins in the mixture.

Example 13

Effect of an Adhesion Protein Fragment on Transfection by LipofectAMINE Reagent

COS-7 cells were seeded at 5×10⁴ cells/well in 24-well plates in DMEM supplemented with 10% fetal bovine serum and allowed to grow overnight. Cells were transfected as described in Example 3, using 0-2.4 µl "LIPOFECTAMINE" and 0.8 µg pCMVSPORTβgal plasmid DNA precomplexed with 0 or 10 µg "RETRONECTIN". At 24 hours after transfection, cells were harvested as described in example 2. Lysates were assayed for β-galactosidase activity using ONPG (see Example 2). Table 15 shows the peak activities of transfection with a range of concentrations of the "LIPOFECTAMINE" with DNA alone or with DNA precomplexed to "RETRONECTIN". A clear enhancement is seen.

Those of ordinary skill in the art will appreciate that reagents starting materials, growth media, techniques and methods other than those specifically described herein can be employed in the preparation and use of the transfection compositions, kits, lipid aggregates, peptide and protein conjugates, modified peptides and proteins, lipids, dendrimers and peptide and protein conjugates thereof of this invention without departing from the spirit and scope of this invention.

TABLE 1

Examples of Cell Adhesion Proteins

| LIGAND | BINDING REGION | REFERENCE |
| --- | --- | --- |
| Fibronectin | RGD cell binding region (RGDSPC) (SEQ ID NO: 14)- (all motifs) | Pierschbacher & Ruoslahti (1987) *J. Biol. Chem.* 262, 17294-17298 |
| Fibronectin 1 | including all cell binding regions RGD cell binding region (all motifs) | Pierschbacher & Ruoslahti (1984) *Nature* 309, 30-33 |
| Fibronectin 2 | RGD cell binding region (REDV [SEQ ID NO: 15]/RGDV) [SEQ ID NO: 16] | Humphries et al., (1986) *J. Cell Biol.* 103, 2637-2647 |
| Fibronectin 3 | CS1 Fragment [SEQ ID NO. 17][1] | Humphries et al., (1987) *J. Biol. Chem.* 262, 6886-6892 |
| Vitronectin | RGD cell binding region (RGDV) [SEQ ID NO: 16] | Suzuki et al., (1985) *EMBO J.* 4, 2519-2524 |
| Laminin 3 | RGD cell binding region (RGDN) [SEQ ID NO: 18] | Grant et al., (1989) *Cell* 58, 933-943 |
| Tenascin 1 | RGD cell binding region (RGDM) [SEQ ID NO: 19] | Friedlander et al., (1988) *J. Cell Biol.* 107, 2329-2340 |
| Collagen 1 | RGD cell binding region (RGDT) [SEQ ID NO: 20] | Dedhar et al., (1988) *J. Cell Biol.* 104, 585-593 |
| Collagen 6 | RGD cell binding region (RGDX*) [SEQ ID NO: 21] | Aumailley et al., (1989) *Cell Res.* 181, 463-474 |
| von Willebrand Factor | RGD cell binding region (RGDS) [SEQ ID NO: 22] | Haverstick et al, (1985) *Blood* 66, 946-952 |
| Fibrinogen 1 | RGD cell binding region (RGDS) [SEQ ID NO: 22] | Gardner and Hynes et al., (1985) *Cell* 42, 439-448 |
| Thrombo-spondin 1 | RGD cell binding region (RGDA) [SEQ ID NO: 23] | Lawler et al., (1988) *J. Cell Biol.* 107, 2351-2361 |

[1]CS1 peptide sequence: DELPQLVTLPHPNLHGPEILDVPST
*X = various amino acids.

TABLE 2

Exemplary Peptides For Enhancement of Transfection[1]

NLS-BASED

| | |
| --- | --- |
| PKKKRKV | [SEQ ID NO: 2] |
| (±C)G(Y or W or -)GPKKKRKVGG | [SEQ ID NO: 25] |
| C(±Y or W)PKKKRKVGG | [SEQ ID NO: 25] |
| (±C)G(±Y or W)GPKKKRKVGG(±G$_n$) | [SEQ ID NO: 25] |
| (Xaa)$_x$PKKKRKV(Zaa)$_z$ | [SEQ ID NO: 24] |
| (Xaa)$_x$(±Y or W)PKKKRKV(Zaa)$_z$ | [SEQ ID NO: 24] |
| (Xaa)$_x$(±Y or W)(Jaa)$_j$PKKKRKV(Zaa)$_z$ | [SEQ ID NO: 24] |
| (Xaa)$_x$PKKKRKV(±Y or W)(Zaa)$_z$ | [SEQ ID NO: 24] |
| (Xaa)$_x$(±C)(±Y or W)(Jaa)$_j$PKKKRKV(±C)(Zaa)$_z$ | [SEQ ID NO: 24] |
| (Xaa)$_x$(±C)(±Y or W)(Jaa)$_j$PKKKRKV(±C)(Zaa)$_z$(Uaa or Sp or Poly)$_u$ | [SEQ ID NO: 24] |
| (±C)(Xaa)$_x$(±Y or W)(Jaa)$_j$PKKKRKV(Zaa)$_z$(±C) | [SEQ ID NO: 24] |
| (±C)(Xaa)$_x$(±Y or W)(Jaa)$_j$PKKKRKV(±C)(Zaa)$_z$(Uaa or Sp or Poly)$_u$ | [SEQ ID NO: 24] |
| Uaa or Sp or Poly)$_u$(Xaa)$_x$(±C)(±Y or W)(Jaa)$_j$PKKKRKV(Zaa)$_z$(±C) | [SEQ ID NO: 24] |
| (Uaa or Sp or Poly)$_u$(Xaa)$_x$(±C)(±Y or W)(Jaa)$_j$PKKKRKV(±C)(Zaa)$_z$ | [SEQ ID NO: 24] |

NLS-CONCATEMERS

| | |
| --- | --- |
| [(Xaa)$_x$(±C)(±Y or W)(Jaa)$_j$PKKKRKV(±C)(Zaa)$_z$]$_p$ | [SEQ ID NO: 24] |
| [(Xaa)$_x$(±C)(±Y or W)(Jaa)$_j$PKKKRKV(±C)(Zaa)$_z$]$_n$(Uaa or Sp or Poly)$_j$ | [SEQ ID NO: 24] |
| (Uaa or Sp or Poly)$_u$[(Xaa)$_x$(±C)(±Y or W)(Jaa)$_j$PKKKRKV(±C)(Zaa)$_z$]$_p$ | [SEQ ID NO: 24] |

RGD(SP)

| | |
| --- | --- |
| RGDSP | [SEQ ID NO: 26] |
| (±C)RGDSP(±C) | [SEQ ID NO: 26] |

TABLE 2-continued

Exemplary Peptides For Enhancement of Transfection[1]

| | |
|---|---|
| (±C)(±G)RGDSP(±C) | [SEQ ID NO: 26] |
| (Xaa)$_x$RGDSP(Zaa)$_z$ | [SEQ ID NO: 26] |
| (Xaa)$_x$(±C)(±G)RGDSP(±G)(±C)(Zaa)$_z$ | [SEQ ID NO: 26] |
| (±C)(Xaa)$_x$(±G)RGDSP(±G)(Zaa)$_z$(±C) | [SEQ ID NO: 26] |
| (Xaa)$_x$RGDSPC(Zaa)$_z$ | [SEQ ID NO: 26] |
| (Uaa or Sp or Poly)$_u$(Xaa)$_x$RGDSP(Zaa)$_z$ | [SEQ ID NO: 26] |
| (Uaa or Sp or Poly)$_u$(Xaa)$_x$(±C)(±G)RGDSP(±G)(±C)(Zaa)$_z$ | [SEQ ID NO: 26] |
| (Xaa)$_x$(±C)(±G)RGDSP(±G)(±C)(Zaa)$_z$(Uaa or Sp or Poly)$_u$ | [SEQ ID NO: 26] |
| (Uaa or Sp or Poly)$_u$(Xaa)$_x$(±C)(±G)RGDSP(±G)(Zaa)$_z$(±C) | [SEQ ID NO: 26] |
| (±C)(Xaa)$_x$(±G)RGDSP(±G)(±C)(Zaa)$_z$(Uaa or Sp or Poly)$_u$ | [SEQ ID NO: 26] |
| (Xaa)$_x$RGDSP(Zaa)$_z$(Uaa or Sp or Poly)$_u$ | [SEQ ID NO: 26] |

RGD(MF)

| | |
|---|---|
| RGDMF | [SEQ ID NO: 27] |
| (±C)GRGDMF(±C) | [SEQ ID NO: 27] |
| GRGDMFC | [SEQ ID NO: 27] |
| (±C)(±G)RGDMF(±G)(±C) | [SEQ ID NO: 27] |
| (Xaa)$_x$RGDMF(Zaa)$_z$ | [SEQ ID NO: 27] |
| (Xaa)$_x$(±C)(±G)RGDMF(±G)(±C)(Zaa)$_z$ | [SEQ ID NO: 27] |
| (±C)(Xaa)$_x$RGDMF(Zaa)$_z$(±C) | [SEQ ID NO: 27] |
| (Xaa)$_x$(±C)RGDMF(±C)(Zaa)$_z$ | [SEQ ID NO: 27] |
| (Uaa or Sp or Poly)$_u$(Xaa)$_x$(±C)(±G)RGDMF(±G)(Zaa)$_z$(±C) | [SEQ ID NO: 27] |
| (±C)(Xaa)$_x$(±G)RGDMF(±G)(±C)(Zaa)$_z$(Uaa or Sp or Poly)$_u$ | [SEQ ID NO: 27] |
| (Uaa or Sp or Poly)$_u$(Xaa)$_x$(±C)(±G)RGDMF(±G)(±C)(Zaa)$_z$ | [SEQ ID NO: 27] |
| (Xaa)$_x$(±C)(±G)RGDMF(±G)(±C)(Zaa)$_z$(Uaa or Sp or Poly)$_u$ | [SEQ ID NO: 27] |

CS-1 Peptide

| | |
|---|---|
| DELPQLVTLPHPNLHGPEILDVPST | [SEQ ID NO: 17] |
| (±C)DELPQLVTLPHPNLHGPEILDVPST(±C) | [SEQ ID NO: 28] |
| (Xaa)$_x$DELPQLVTLPHPNLHGPEILDVPST(Zaa)$_z$ | [SEQ ID NO: 28] |
| (Xaa)$_x$(±C)DELPQLVTLPHPNLHGPEILDVPST(±C)(Zaa)$_z$ | [SEQ ID NO: 28] |
| (±C)(Xaa)$_x$DELPQLVTLPHPNLHGPEILDVPST(Zaa)$_z$(±C) | [SEQ ID NO: 28] |
| (Uaa or Sp or Poly)$_u$(Xaa)$_x$(±C)DELPQLVTLPHPNLHGPEILDVPST(Zaa)$_z$(±C) | [SEQ ID NO: 28] |
| (Uaa or Sp or Poly)$_u$(Xaa)$_x$(±C)DELPQLVTLPHPNLHGPEILDVPST(Zaa)$_z$ | [SEQ ID NO: 28] |
| (±C)(Xaa)$_x$DELPQLVTLPHPNLHGPEILDVPST(±C)(Zaa)$_z$(Uaa or Sp or Poly)$_u$ | [SEQ ID NO: 28] |
| (Xaa)$_x$(±C)DELPQLVTLPHPNLHGPEILDVPST(±C)(Zaa)$_z$(Uaa or Sp or Poly)$_u$ | [SEQ ID NO: 28] |
| (Xaa)$_x$DELPQLVTLPHPNLHGPEILDVPST(Zaa)$_z$(Uaa or Sp or Poly)$_u$ | [SEQ ID NO: 28] |
| (Uaa or Sp or Poly)$_u$(Xaa)$_x$DELPQLVTLPHPNLHGPEILDVPST(Zaa)$_z$ | [SEQ ID NO: 28] |

LDV (active part of CS-1)

| | |
|---|---|
| EILDVPST | [SEQ ID NO: 29] |
| (±C)EILDVPST(±C) | [SEQ ID NO: 29] |
| (Xaa)$_x$EILDVPST(Zaa)$_z$ | [SEQ ID NO: 29] |
| (Xaa)$_x$(±C)EILDVPST(±C)(Zaa)$_z$ | [SEQ ID NO: 29] |
| (±C)(Xaa)$_x$EILDVPST(Zaa)$_z$(±C) | [SEQ ID NO: 29] |
| (Uaa or Sp or Poly)$_u$(Xaa)$_x$EILDVPST(Zaa)$_z$ | [SEQ ID NO: 29] |
| (Uaa or Sp or Poly)$_u$(Xaa)$_x$(±C)EILDVPST(±C)(Zaa)$_z$ | [SEQ ID NO: 29] |
| (Uaa or Sp or Poly)$_u$(Xaa)$_x$(±C)EILDVPST(Zaa)$_z$(±C) | [SEQ ID NO: 29] |
| (Xaa)$_x$EILDVPST(Zaa)$_z$(Uaa or Sp or Poly)$_u$ | [SEQ ID NO: 29] |
| (±C)(Xaa)$_x$EILDVPST(±C)(Zaa)$_z$(Uaa or Sp or Poly)$_u$ | [SEQ ID NO: 29] |
| (Xaa)$_x$(±C)EILDVPST(±C)(Zaa)$_z$(Uaa or Sp or Poly)$_u$ | [SEQ ID NO: 29] |

VSVG 6 mer

| | |
|---|---|
| KFTIVF | [SEQ ID NO: 30] |
| (±C)KFTIVF(±C) | [SEQ ID NO: 30] |
| (Xaa)$_x$KFTIVF(Zaa)$_z$ | [SEQ ID NO: 30] |
| (Xaa)$_x$(±C)KFTIVF(±C)(Zaa)$_z$ | [SEQ ID NO: 30] |
| (±C)(Xaa)$_x$KFTIVIF(Zaa)$_z$(±C) | [SEQ ID NO: 30] |
| (Uaa or Sp or Poly)$_u$(Xaa)$_x$KFTIVF(Zaa)$_z$ | [SEQ ID NO: 30] |
| (Uaa or Sp or Poly)$_u$(Xaa)$_x$(±C)KFTIVF(±C)(Zaa)$_z$ | [SEQ ID NO: 30] |
| (Uaa or Sp or Poly)$_u$(Xaa)$_x$(±C)KFTIVF(Zaa)$_z$(±C) | [SEQ ID NO: 30] |
| (Xaa)$_x$KFTIVF(Zaa)$_z$(Uaa or Sp or Poly)$_u$ | [SEQ ID NO: 30] |
| (±C)(Xaa)$_x$KFTIVF(±C)(Zaa)$_z$(UaaK or Sp or Poly)$_u$ | [SEQ ID NO: 30] |
| (Xaa)$_x$(±C)KFTIVF(±C)(Zaa)$_z$(UaaK or Sp or Poly)$_u$ | [SEQ ID NO: 30] |

CONCATEMERS

| | |
|---|---|
| [(Xaa)$_x$(±C)RGDSP(±C)(Zaa)$_z$]$_p$ | [SEQ ID NO: 26] |
| (Uaa or Sp or Poly)$_u$[(Xaa)$_x$(±C)RGDSP(±C)(Zaa)$_z$]$_p$ | [SEQ ID NO: 26] |
| [(Xaa)$_x$(±C)RGDMF(±C)(Zaa)$_z$]$_p$ | [SEQ ID NO: 27] |
| (Uaa or Sp or Poly)$_u$[(Xaa)$_m$(±C)RGDMF(±C)(Zaa)$_z$]$_p$ | [SEQ ID NO: 27] |
| [(Xaa)$_x$(±C)DELPQLVTLPHPNLHGPEILDVPST(±C)(Zaa)$_z$]$_p$ | [SEQ ID NO: 28] |
| (Uaa or Sp or Poly)$_u$[(Xaa)$_x$(±C)DELPQLVTLPHPNLHGPEILDVPST(±C)(Zaa)$_z$]$_p$ | [SEQ ID NO: 28] |
| [(Xaa)$_x$(±C)DELPQLVTLPHPNLHGPEILDVPST(±C)(Zaa)$_z$]$_p$(Uaa or Sp or Poly)$_u$ | [SEQ ID NO: 28] |

TABLE 2-continued

Exemplary Peptides For Enhancement of Transfection[1]

| | |
|---|---|
| $[(Xaa)_x(\pm C)EILDVPST(\pm C)(Zaa)_z]_p$ | [SEQ ID NO: 29] |
| $(Uaa\ or\ Sp\ or\ Poly)_u[(Xaa)_x(\pm C)EILDVPST(\pm C)(Zaa)_z]_p$ | [SEQ ID NO: 29] |
| $[(Xaa)_x(\pm C)KFTIVF(\pm C)(Zaa)_z]_p$ | [SEQ ID NO: 30] |
| $(Uaa\ or\ Sp\ or\ Poly)_u[(Xaa)_x(\pm C)KFTIVF(\pm C)(Zaa)_z]_p$ | [SEQ ID NO: 30] |
| $(\pm C)[(Xaa)_xRGDSP(Zaa)_z]_p(\pm C)$ | [SEQ ID NO: 26] |
| $(Uaa\ or\ Sp\ or\ Poly)_u[(Xaa)_x(\pm C)RGDSP(Zaa)_z]_p(\pm C)$ | [SEQ ID NO: 26] |
| $(\pm C)(Xaa)_xRGDMF(Zaa)_z]_p(\pm C)$ | [SEQ ID NO: 27] |
| $(Uaa\ or\ Sp\ or\ Poly)_u[(Xaa)_m(\pm C)RGDMF(Zaa)_z]_p(\pm C)$ | [SEQ ID NO: 27] |
| $(\pm C)[(Xaa)_xDELPQLVTLPHPNLHGPEILDVPST(Zaa)_z]_p(\pm C)$ | [SEQ ID NO: 28] |
| $(Uaa\ or\ Sp\ or\ Poly)_U[(Xaa)_x(\pm C)DELPQLVTLPHPNLHGPEILDVPST(Zaa)_z]_p(\pm C)$ | [SEQ ID NO: 28] |
| $(\pm C)(Xaa)_xDELPQLVTLPHPNLHGPEILDVPST(\pm C)(Zaa)_z]_p(Uaa\ or\ Sp\ or\ Poly)_u$ | [SEQ ID NO: 28] |
| $(\pm C)[(Xaa)_xEILDVPST(Zaa)_z]_p(\pm C)$ | [SEQ ID NO: 29] |
| $(Uaa\ or\ Sp\ or\ Poly)_u[(Xaa)_x(\pm C)EILDVPST(Zaa)_z]_p(\pm C)$ | [SEQ ID NO: 29] |
| $(\pm C)[(Xaa)_xKFTIVF(Zaa)_z]_p(\pm C)$ | [SEQ ID NO: 30] |
| $(Uaa\ or\ Sp\ or\ Poly)_u[(Xaa)_x(\pm C)KFTIVF(Zaa)_z]_p(\pm C)$ | [SEQ ID NO: 30] |

MIXED CONCATEMERS

| | |
|---|---|
| $[(Baa)_b(\pm C)(\pm Y\ or\ W)(Xaa)_xPKKXRKV(Jaa)_jRGDMF(\pm C)(Zaa)_z]_p$ | [SEQ ID NO: 31] |
| $(Uaa\ or\ Sp\ or\ Poly)_u[(Baa)_b(\pm C)(Xaa)_x(\pm Y\ or\ W)PKKKRKV(Jaa)_jRGDMF(\pm C)(Zaa)_z]_p$ | [SEQ ID NO: 31] |
| $[(Baa)_b(\pm C)(\pm Y\ or\ W)(Xaa)_xPKKKRKV(Jaa)_jGRDSP(\pm C)(Zaa)_z]_p$ | [SEQ ID NO: 32] |
| $(Uaa\ or\ Sp\ or\ Poly)_u[(Baa)_b(\pm C)(\pm Y\ or\ W)(Xaa)_xPKKKRKV(Jaa)_jRGDSP(\pm C)(Zaa)_z]_p$ | [SEQ ID NO: 33] |
| $[(Baa)_b(\pm C)KFTIVF(\pm C)(Xaa)_x(\pm C)(Jaa)_j(\pm Y\ or\ W)(Xaa)_xPKKKRKV(Zaa)_z]_p$ | [SEQ ID NO: 34] |
| $(Uaa\ or\ Sp\ or\ Poly)_u[(Baa)_b(\pm C)KFTIVF(\pm C)(Xaa)_x(\pm C)(Jaa)_j(\pm Y\ or\ W)PKKKRKV(Zaa)_z]_p$ | [SEQ ID NO: 34] |
| $[(Baa)_b(\pm C)(\pm Y\ or\ W)(Xaa)_xGPKKRKV(Jaa)_jEILDVSPT(\pm C)(Zaa)_z]_p$ | [SEQ ID NO: 35] |
| $(Uaa\ or\ Sp\ or\ Poly)_U[(Baa)_b(\pm C)(\pm Y\ or\ W)PKKKRKV(Jaa)_jEILDVSPT(\pm C)(Zaa)_z]_p$ | [SEQ ID NO: 36] |
| $[(Baa)_b(\pm C)KFTIVF(\pm C)(Xaa)_x(\pm C)EILDVPST(\pm C)(Zaa)_z]_p$ | [SEQ ID NO: 37] |
| $(Uaa\ or\ Sp\ or\ Poly)_u[(Baa)_b(\pm C)KETIVF(\pm C)(Xaa)_xEILDVPST(\pm C)(Zaa)_z]_p$ | [SEQ ID NO: 37] |
| $(\pm C)[(Baa)_b(\pm Y\ or\ W)(Xaa)_xPKKKRKV(Jaa)_jRGDMF(Zaa)_z]_p(\pm C)$ | [SEQ ID NO: 31] |
| $(Uaa\ or\ Sp\ or\ Poly)_u[(Baa)_b(\pm C)(Xaa)_x(\pm Y\ or\ W)PKKKRKV(Jaa)_jRGDMF(Zaa)_z]_p(\pm C)$ | [SEQ ID NO: 31] |
| $(\pm C)[(Baa)_b(\pm Y\ or\ W)(Xaa)_xPKKKRKV(Jaa)_jGRGDSP(Zaa)_z]_p(\pm C)$ | [SEQ ID NO: 32] |
| $(Uaa\ or\ Sp\ or\ Poly)_u[(Baa)_b(\pm C)(\pm Y\ or\ W)(Xaa)_xPKKKRKV(Jaa)_jRGDSP(Zaa)_z]_p(\pm C)$ | [SEQ ID NO: 33] |
| $(\pm C)[(Baa)_bKFTIVF(\pm C)(Xaa)_x(\pm C)(Jaa)_j(\pm Y\ or\ W)(Xaa)_xPKKKRKV(Zaa)_z]_p(\pm C)$ | [SEQ ID NO: 34] |
| $(Uaa\ or\ Sp\ or\ Poly)_u[(Baa)_b(\pm C)KFTIVF(\pm C)(Xaa)_x(\pm C)(Jaa)_j(\pm Y\ or\ W)PKKKRKV(Zaa)_z]_p(\pm C)$ | [SEQ ID NO: 34] |
| $(\pm C)[(Baa)_b(\pm Y\ or\ W)(Xaa)_xGPKKRKV(Jaa)_jEILDVSPT(Zaa)_z]_p(\pm C)$ | [SEQ ID NO: 35] |
| $(Uaa\ or\ Sp\ or\ Poly)_U[(Baa)_b(\pm C)(\pm Y\ or\ W)PKKKRKV(Jaa)_jEILDVSPT)(Zaa)_z]_p(\pm C)$ | [SEQ ID NO: 36] |
| $(\pm C)[(Baa)_bKFTIVF(\pm C)(Xaa)_xEILDVPST(Zaa)_z]_p(\pm C)$ | [SEQ ID NO: 37] |
| $(Uaa\ or\ Sp\ or\ Poly)_u[(Baa)_b(\pm C)KFTIVF(\pm C)(Xaa)_xEILDVPST)(Zaa)_z]_p(\pm C)$ | [SEQ ID NO: 37] |

CIRCULAR LDV

| | |
|---|---|
| $(Uaa\ or\ Sp\ or\ Poly)_u(Xaa)_xCEILDVPSTC(Zaa)_z$ | [SEQ ID NO: 38] |

CIRCULAR RGD, penton base

| | |
|---|---|
| $(Uaa\ or\ Sp\ or\ Poly)_u(Xaa)_xCHAIRGDTFAC(Zaa)_z$ | [SEQ ID NO: 39] |

TAT PEPTIDES

| | |
|---|---|
| CGYGRKKRRQRRRG | [SEQ ID NO: 40] |
| $(\pm C)CGYGRKKRRQRRRG(\pm C)$ | [SEQ ID NO: 40] |
| $(Xaa)_xCGYGRKKRRQRRRG(Zaa)_x$ | [SEQ ID NO: 40] |
| $(Xaa)_x(\pm C)CGYGRKKRRQRRRG(\pm C)(Zaa)_x$ | [SEQ ID NO: 40] |
| $(\pm C)(Xaa)_xCGYGRKKRRQRRRG(Zaa)_x(\pm C)$ | [SEQ ID NO: 40] |
| $(Uaa\ or\ Sp\ or\ Poly)_uCGYGRKKRRQRRRG$ | [SEQ ID NO: 40] |
| $(Uaa\ or\ Sp\ or\ Poly)_u(\pm C)(Xaa)_x(\pm C)CGYGRKKRRQRRRG(\pm C)(Zaa)_x(\pm C)$ | [SEQ ID NO: 40] |
| $(\pm C)(Xaa)_x(\pm C)CGYGRKKRRQRRRG(\pm C)(Zaa)_x(\pm C)(Uaa\ or\ Sp\ or\ Poly)_u$ | [SEQ ID NO: 40] |
| $CGYGRKKRRQRRRG(Jaa)_jCGYGRKKRRQRRRG$ | [SEQ ID NO: 41] |
| $(CGYGRKKRRQRRRG)_p$ | [SEQ ID NO: 40] |
| $[(Jaa)_jCGYGRKKRRQRRRG]_p$ | [SEQ ID NO: 40] |
| $[(\pm C)(Xaa)_x(\pm C)CGYGRKKRRQRRRG(\pm C)(Zaa)_x(\pm C)]_p$ | [SEQ ID NO: 40] |
| $(Uaa\ or\ Sp\ or\ Poly)_u[(\pm C)(Xaa)_x(\pm C)CGYGRKKRRQRRRG(\pm C)(Zaa)_x(\pm C)]_p$ | [SEQ ID NO: 40] |
| $[(\pm C)(Xaa)_x(\pm C)CGYGRKKRRQRRRG(\pm C)(Zaa)_x(\pm C)]_p(Uaa\ or\ Sp\ or\ Poly)_u$ | [SEQ ID NO: 40] |
| $K_{16}CGYGRKKRRQRRRG$ | [SEQ ID NO: 42] |
| $CGYGRKKRRQRRRGK_{16}$ | [SEQ ID NO: 43] |

TAT CONCATEMERS

| | |
|---|---|
| NLS-Tat: $(\pm K_{16})CGYGPKKKRK(Jaa)_jCGYGRKKRRQRRRG$ | [SEQ ID NO: 44] |
| Tat-NLS: $(\pm K_{16})CGYGRKKRRQRRRG(Jaa)_jCGYGPKKKRK$ | [SEQ ID NO: 45] |
| VSVG-Tat: $(\pm K_{16})KFTTIVFC(Jaa)_jCGYGRKKRRQRRRG$ | [SEQ ID NO: 46] |
| Tat-VSVG: $(\pm K_{16})CGYGRKKRRQRRRG(Jaa)_jKFTTIVFC$ | [SEQ ID NO: 47] |
| Tat-VSVGD6: $(\pm K_{16})CGYGRKKRRQRRRG(Jaa)_jKFTTIVFCDDDDDD(\pm G)$ | [SEQ ID NO: 48] |
| Tat-RGD: $(\pm K_{16})CGYGRKKRRQRRRG(Jaa)_jRGDSPC$ | [SEQ ID NO: 49] |
| RGD-Tat: $(\pm K_{16})RGDSPC(Jaa)_jCGYGRKKRRQRRRG$ | [SEQ ID NO: 50] |
| Tat-E5: $(\pm K_{16})CGYGRKKRRQRRRG(Jaa)_jGLFEAIAEFIEGGWEGLIEG$ | [SEQ ID NO: 51] |
| E5-Tat: $(\pm K_{16})GLFEAIAEFIEGGWEGLIEG(Jaa)_jCGYGRKKRRQRRRG$ | [SEQ ID NO: 52] |

TABLE 2-continued

Exemplary Peptides For Enhancement of Transfection[1]

| | | |
|---|---|---|
| HIS-TEV-Tat: | MSYYHHHHHHDYDIPTTENLYFQGS(Jaa)$_j$CGYGRKKRRQRRRG | [SEQ ID NO: 53] |
| 6HIS-Tat: | MSYYHHHHHH(Jaa)$_j$CGYGRKKRRQRRRG | [SEQ ID NO: 54] |

Where b, u, j, x, z, n and p are integers that can range from 0-20, Baa, Jaa, Xaa, and Zaa represent any amino acid and Uaa is used to represent any cationic amino acid, designations (Baa)$_b$, (Xaa)$_x$, (Jaa)$_j$, and (Zaa)$_z$ represent any combination of amino acids whether multiple, repeated or not repeated;

Where "±" indicates that any amino acid is optional;

Where Sp is a spermine (including carboxy spermine or spermines coupled to linkers)\;

Where Poly is any other polyamine; and

Where standard one-letter codes are used for amino acids.

TABLE 3

Additional Examples of Specific Peptides for Transfection Enhancement

| Designation | Sequence[1] | |
|---|---|---|
| VSVGD6 | GKFTIVFDDDDDD(±G) | [SEQ ID NO: 55] |
| VSVGE5 | KFTIVFGGGLFEAIAEFIEGGWEGLIEG | [SEQ ID NO: 56] |
| E5VSVG | GLFEAIAEFIEGGWEGLIEGCKFTIVF | [SEQ ID NO: 57] |
| NLSE5 | CGYGGGGGGPKKKRKVGGGLFEAIAEFIEGGWEGLIEG | [SEQ ID NO: 58] |
| E5NLS | GLFEAIAEFIEGGWEGLIEGGGYGGGGGGPKKKRKVGG | [SEQ ID NO: 59] |
| VSVGNLS | KFTTIVFCGYGPKKKRKVGG | [SEQ ID NO: 60] |
| NLSVSVG | CGYGPKKKRKVGGKFTIVF | [SEQ ID NO: 61] |
| K16VSVGD6 | K$_{16}$GKFTIVFDDDDDD(±G) | [SEQ ID NO: 62] |
| K16VSVGE5 | K$_{16}$KFTIVFGGGLFEAIAEFIEGGWEGLIEG | [SEQ ID NO: 63] |
| K16E5VSVG | K$_{16}$GLFEAIAEFIEGGWEGLIEGCKFTIVF | [SEQ ID NO: 64] |
| K16E5NLS | K$_{16}$GLFEAIAEFIEGGWEGLIEGGGYGGGGGGPKKKRKVGG | [SEQ ID NO: 65] |
| K16VSVGNLS | K$_{16}$KFTTIVFCGYGPKKKRKVGG | [SEQ ID NO: 66] |
| K16NLSVSVG | K$_{16}$GGCGYGGGPKKKRKVGGKFTIVF | [SEQ ID NO: 67] |
| K16NLSE5 | K$_{16}$GGCGYGGGGGGPKKKRKVGGGLFEAIAEFIEGGWEGLIEG | [SEQ ID NO: 68] |
| NLS | SSDDEATADSQHSTPPKKKRKVGG | [SEQ ID NO: 69] |
| phosphorylation | K$_{16}$SSDDEATADSQHSTPPKKKRKVGG | [SEQ ID NO: 70] |
| HIS-TEV-peptides: | MSYYHHHHHHDYDIPTTENLYFQGS-peptide | [SEQ ID NO: 71] |
| HIS-TEV-NLS | MSYYHHHHHHDYDIPTTENLYFQGSGYGPKKKRKVGG | [SEQ ID NO: 72] |
| HIS-TEV-VSVG | MSYYHHHHHHDYDIPTTENLYFQGSKFTIVF | [SEQ ID NO: 73] |
| HIS-TEV-E5 | MSYYHHHHHHDYDIPTTENLYFQGSGLFEAIAEFIEGGWEGLIEG | [SEQ ID NO: 74] |
| HIS-TEV-RGD | MSYYHHHHHHDYDIPTTENLYFQGSRGDSPC | [SEQ ID NO: 75] |
| 6HIS-peptides | MSYYHHHHHH-peptide | [SEQ ID NO: 76] |
| 6HIS-NLS | MSYYHHHHHHGYGPKKKRKVGG | [SEQ ID NO: 77] |
| 6HIS-VSVG | MSYYHHHHHHKFTIVF | [SEQ ID NO: 78] |
| 6HIS-E5 | MSYYHHHHHHGLFEAIAEFIEGGWEGLIEG | [SEQ ID NO: 79] |
| 6HIS-RGD | MSYYHHHHHHRGDSPC | [SEQ ID NO: 80] |
| peptide-6HIS | peptide-HHHHHH | [SEQ ID NO: 81] |

[1]Peptide sequences in this Table can be combined with polyamines, including spermine, or other nucleic acid-binding groups including strings of cationic amino acids at their N- or C-terminus.

TABLE 4

Examples of Spermine-Conjugated Peptides[1]

| Spermine-Conjugated Peptide | | Designation |
|---|---|---|
| Sp-5-CO-NH-CH$_2$-CO-GGGGYGPKKKRKVGG | [SEQ ID NO: 82] | Opf-GG-1 |
| Sp-5-CO-NH-CH$_2$-CO-GYGPKKKRKVG | [SEQ ID NO: 83] | Opf-GG-2 |
| Sp-5-CO-NH-CH$_2$-CO-CGYGPKKKRKVG | [SEQ ID NO: 84] | Opf-GG-2-CYS |
| Sp-5-CO-NH-CH$_2$-CO-GRGDMFGG | [SEQ ID NO: 85] | Sp-RGD |
| Sp-5-CO-NH-CH$_2$-CO-YGPKKKRKVGGGGRGDMFGG | [SEQ ID NO: 86] | Sp-NLSRGD |
| Sp-5-CO-NH-CH$_2$-CO-GYGPKKKRKVGGGGYGPKKKRKVGG | [SEQ ID NO: 13] | Sp-NLSNLS |
| Sp-5-CO-NH-CH((CH$_2$)$_4$-NH-5-CO-Sp)-CO-GGYGPKKKRKVGGGGYGPKKKRKVGG | [SEQ ID NO: 13] | Sp$_2$-NLSNLS |

[1]Prepared using automated solid phase peptide synthesis.

TABLE 5

Unmodified Peptides Tested for Enhancement of "LIPOFECTAMINE" Transfections in Human Fibroplasts by Inclusion in Transfection Medium

| Designation | Sequence | | Enhancement in Transfect. | Peptide Amount µM |
|---|---|---|---|---|
| E5 | GLFEAIAEFIEGGWEGLIEG | [SEQ ID NO: 88] | See FIG. 1 | 0.1 |
| K5 | GLFKAIAKFIKGGWKGLIKG | [SEQ ID NO: 89] | " | 5 |
| HApep | GLFGAIAGFIENGWEGMIDG | [SEQ ID NO: 87] | " | 10 |
| VSVG | KFTIVF | [SEQ ID NO: 30] | " | 1 |

TABLE 6

Comparison of "LIPOFECTAMINE" Transfection +/− Sp-NLSNLS

| | Transfection Conditions: | | Specific Activity | |
|---|---|---|---|---|
| Transfection Reagents | DNA (µg) | lipid (µl) | ng β-gal/ µg protein | Protein Yield µg/Well |
| "LIPOFECTAMINE" | 0.4 | 2 | 0.07 | 67.5 |
| "LIPOFECTAMINE" + Sp-NLSNLS | 0.1 | 1 | 0.38 | 85.5 |

TABLE 7

Enhancement of "LIPOFECTAMINE" Transfections in Human Fibroblasts for Peptides and Derivatized Peptides[1]

| Designation | Sequence | | Enhancement | Peptide Amount (mg per 0.4 mg DNA) |
|---|---|---|---|---|
| NLS | GYGPKKKRKVGG | [SEQ ID NO: 90] | 7-10 | 20 |
| Opf-GG-1 | Sp-5-CO-GGGGYGPKKKRKVGG | [SEQ ID NO: 82] | 4 | 6 |
| Opf-GG-2 (peak 1) | Sp-5-CO-GGYGPKKKRKVG | [SEQ ID NO: 83] | 5 | 10 |
| Opf-GG-2 (peak 2) | partially deblocked[2] Sp-5-CO-GGYGPKKKRKVG | [SEQ ID NO: 83] | 7 | 2 |
| Opf-GG-2-CYS (peak 1) | Sp-5-CO-GCGYGPKKKRKVG | [SEQ ID NO: 84] | 5 | 10 |

TABLE 7-continued

Enhancement of "LIPOFECTAMINE" Transfections in Human Fibroblasts for Peptides and Derivatized Peptides[1]

| Designation | Sequence | | Enhancement | Peptide Amount (mg per 0.4 mg DNA) |
|---|---|---|---|---|
| Opf-GG-2-CYS (peak 2) | partially deblocked[2] Sp-5-CO-GCGYGPKKKRKVG | [SEQ ID NO: 84] | 7 | 20 |
| SpRGD | Sp-5-CO-GGRGDMFGG | [SEQ ID NO: 85] | 5[3] | 12[3] |
| SpNLSRGD | Sp-5-CO-GYGPKKKRKVGGGGGRGDMFGG | [SEQ ID NO: 86] | 4 | 20 |
| SpNLSNLS | Sp-5-CO-GGYGPKKKRKVGGGGYGPKKKRKVGG | [SEQ ID NO: 13] | 7-10 | 4 |
| K16NLS (peak 1) | $K_{16}$GGCGYGPKKKRKVGG | [SEQ ID NO: 91] | 5 | 10 |
| K16NLS (peak 2) | partially deblocked[2] $K_{16}$GGCGYGPKKKRKVGG | [SEQ ID NO: 91] | 6 | 0.5 |
| K16NLSRGD | $K_{16}$CGYGPKKKRKVGGGGRGDSP | [SEQ ID NO: 92] | 10 | 2 |
| K16RGD | $K_{16}$GGRGDSPCG | [SEQ ID NO: 93] | 10 | 2 |
| RGDK16 | GRGDSPCGG$K_{16}$ | [SEQ ID NO: 94] | 6 | 5 |
| K16 | $K_{16}$ | [SEQ ID NO: 4] | 2 | 0.5 |
| G61934P NLSRGD | CGYGPKKKRKVGGGGRGDSPCG | [SEQ ID NO: 95] | 8 | 20 |

[1]The results in this table were compiled from a series of experiments, i.e., the peptides were not all compared in the same experiment. The data are the fold enhancement of "LIPOFECTAMINE" transfections at peak activity in human fibroblasts (unless otherwise noted) in 24-well plates, with 0.4 mg DNA per transfection. The DNA transfected was either pCMVSPORTβgal or pCMVβ, and the assays were all done with ONPG.
[2]These peptide were only partially deprotected following automatic peptide synthesis and were isolated as a side-product of the fully deprotected peptide as a separate peak on HPLC. These peptides carry one protecting group(Mtr) and that protecting group is believed to be on the R residue of the PKKKRK sequence (NLS). R-Mtr is generally more difficult to deprotect. The protecting (i.e., blocking group) that remains on the peptide is an Mtr group which is a conventional amino acid blocking group for automated peptide synthesis.
[3]This experiment was done with CHO-K1 cells and the amount of DNA used (either pCMVSPORTβgal or pCMVβ) is 0.2 mg DNA per well in 24-well plates.

TABLE 8

Enhancement of DMRIE-C Transfections by Peptides in Human Suspension Cells (K562 or JurkatCells)[1]

| Peptide/Cell Type | | Enhancement-Fold | Peptide Amount μg/0.4 μg DNA | DMRIE-C μL |
|---|---|---|---|---|
| E5: K562 | GLFEAIAIEFIEGGWEGLIEG [SEQ ID NO: 113] | 3 | 5 | 1.6 |
| Jurkat | | 1.2 | 5 | 1.6 |
| K16NLS (peak 2) K562 or Jurkat | | 1 | — | 1.6 |
| K16NLSRGD K562 or Jurkat | | 1 | — | 1.6 |
| K16NLSRGD + E5 K562 | | 1.8 | 2.5 + 2.5 | 1.6 |

[1]The results in this table were complied from a series of experiments.
The peptides were not all compared in the same experiment.
The data listed are the fold enhancement of DMRIE-C transfections at peak activity (both for DMRIE-C amone and for the peptide combination) in suspension cell lines as indicated.
Assays were done using either pCMVSPORTβ-gal or pCMVβ, assaying with CAT.

TABLE 9

Enhancement of Dendrimer-Mediated Transfection by Peptides and Spermine-Conjugated Peptides in COS-7 Cells

| Transfection Agent | Peptide Agent | RLU |
|---|---|---|
| Lipofectamine | None | 32971 |
| Lipofectamine | K16NLS (peak 2) | 164105 |
| Lipofectamine | Sp-NLSNLS | 200447 |
| Lipofectamine | NLS | 224029 |
| G7 (EDA) | None | 478 |
| G7 (EDA) | K16NLS (peak 2) | 3423 |
| G7 (EDA) | Sp-NLSNLS | 2832 |
| G7 (EDA) | NLS | 2749 |
| G9 (EDA) | None | 518 |
| G9 (EDA) | K16NLS (peak 2) | 2297 |
| G9 (EDA) | Sp-NLSNLS | 1702 |
| G9 (EDA) | NLS | 1747 |
| Arg DMER | None | 29139 |
| Arg DMER | K16NLS (peak 2) | 63307 |
| Arg DMER | Sp-NLSNLS | 56548 |
| Arg DMER | NLS | 84209 |
| Lys DMER | None | 2448 |
| Lys DMER | K16NLS (peak 2) | 20847 |
| Lys DMER | Sp-NLSNLS | 17203 |
| Lys DMER | NLS | 17689 |
| "COMB BURST" | None | 18453 |
| "COMB BURST" | K16NLS (peak 2) | 28562 |
| "COMB BURST" | Sp-NLSNLS | 23503 |
| "COMB BURST" | NLS | 29639 |

TABLE 10

Effect of Sp-NLSNLS on transfection by monocationic lipid reagents.

| Lipid | Cell | Peak activity (ng b-gal/cm$^2$) Lipid alone | Lipid + SpNLSNLS |
|---|---|---|---|
| Lipofectin | CHO-K1 | 70 | 805 |
| Lipofectin | CHO-K1 | 53 | 374 |
| Lipofectin | CHO-K1 | 20 | 388 |
| Lipofectin | CHO-K1 | 90 | 688 |
| Lipofectin | HT29 | 5 | 56 |
| Lipofectin | HT29 | 36 | 68 |
| Lipofectin | HT29 | 20 | 31 |
| Lipofectin | COS7 | 4.7 | 167 |
| Lipofectin | human fibroblasts | 1 | 97 |
| Lipofectin | human fibroblasts | 2 | 197 |
| Lipofectin | BHK-21 | 39 | 497 |
| LipofectACE | CHO-K1 | 0 | 53 |
| LipofectACE | HT29 | 0 | 4 |
| DMRIE-DOPE | human fibroblasts | 1.4 | 9.5 |

TABLE 11

Effect of Sp-NLSNLS on transfection by polycationic lipid reagents.

| Lipid | Cell | Peak activity (ng b-gal/cm$^2$) Lipid alone | Lipid + SpNLSNLS |
|---|---|---|---|
| "CELLFECTIN" | CHO-K1 | 21 | 48 |
| "CELLFECTIN" | CHO-K1 | 190 | 235 |
| "CELLFECTIN" | NIH3T3 | 3.5 | 14 |
| "CELLFECTIN" | human fibroblasts | 0.15 | 2.3 |
| TMDOS | CHO-K1 | 1.4 | 2.9 |
| TMDOS | NIH3T3 | 0.2 | 1.3 |
| TMDOS | human fibroblasts | 0.01 | 0.1 |
| DOSPER | human fibroblasts | 1.4 | 5.4 |
| "MULTIFECTOR" | human fibroblasts | 0.9 | 17.6 |

TABLE 12

Effect of Sp-NLSNLS on transfection by the dendrimer "SUPERFECT."

| | Peak activity (ng b-gal/cm$^2$) | |
|---|---|---|
| Cell | "SUPERFECT" alone | SUPERFECT + SpNLSNLS |
| COS-7 | 33 | 84 |

TABLE 13

Effect of TAT and spermine-TAT peptides on transfection by "LIPOFECTAMINE."

| Sample | ng b-Gal per ug Protein | ng b-Gal per cm2 | Peak lipid (ul) | Peak peptide (ug) |
|---|---|---|---|---|
| "LIPOFECTAMINE" alone | 0.93 | 104.47 | 1.0 | N/A |
| TAT alone | 0.00 | 0.1 | N/A | 2.0 |
| sp-TAT alone | 0.00 | 0.06 | N/A | 0.5 |
| TAT w/"LIPOFECTAMINE" | 3.73 | 433.05 | 1.0 | 1.0 |
| sp-TAT w/"LIPOFECTAMINE" | 3.07 | 312.77 | 2.0 | 0.5 |

TABLE 14

Effect of including receptor-ligand proteins with Sp-NLSNLS in DNA pre-complexes on transfection by LipofectAMINE and Lipofectin.

| Lipid: ligand | Cell | Peak activity (ng β-gal/cm$^2$) |
|---|---|---|
| "LIPOFECTAMINE:" | | |
| no ligand | human fibroblasts | 22.9 |
| Insulin | human fibroblasts | 24.3 |
| Transferrin | human fibroblasts | 24.5 |
| Insulin + Transferrin | human fibroblasts | 31.3 |
| no ligand | CHO-K1 | 358 |
| Insulin | CHO-K1 | 452 |
| Transferrin | CHO-K1 | 433 |
| Insulin + Transferrin | CHO-K1 | 460 |
| no ligand | human fibroblasts | 16.8 |
| Insulin | human fibroblasts | 34.1 |
| no ligand | human fibroblasts | 76.7 |
| Insulin | human fibroblasts | 86.9 |
| "LIPOFECTIN:" | | |
| no ligand | human fibroblasts | 17.7 |
| Insulin | human fibroblasts | 22.7 |
| Transferrin | human fibroblasts | 30.6 |
| Insulin + Transferrin | human fibroblasts | 37.0 |
| no ligand | CHO-K1 | 29 |
| Insulin | CHO-K1 | 31 |
| Transferrin | CHO-K1 | 44 |
| Insulin + Transferrin | CHO-K1 | 35 |
| DMRIE-DOPE: | | |
| no ligand | human fibroblasts | 9.5 |
| Insulin | human fibroblasts | 20.7 |

TABLE 15

Effect of an adhesion Protein Fragment on transfection by LipofectAMINE Reagent.

| Cell | Peak activity (ng β-gal/cm) | |
|---|---|---|
| | LipofectAMINE alone | LipofectAMINE + Retronectin |
| COS-7 | 39.5 | 138.4 |

We claim:

1. A purified peptide, wherein the peptide is Sp-NLSNLS.

2. A composition for transfecting a cell, the composition comprising one or more nucleic acid molecules, one or more peptides and one or more transfection agents, wherein each peptide in the composition comprises Sp-NLSNLS.

3. The composition of claim 2, wherein the composition comprises two or more transfection agents.

4. The composition of claim 2, wherein the transfection agent comprises one or more cationic lipids.

5. The composition of claim 4, wherein the transfection agent further comprises one or more neutral lipids.

6. The composition of claim 4, wherein the one or more cationic lipids comprise one or more monovalent cationic lipids.

7. The composition of claim 6, wherein the one or more monovalent cationic lipids are selected from the group consisting of N-[1-(2,3-dioleoyloxy)-propyl]-N,N,N-trimethyl ammonium chloride (DOTMA), 1,2-bis(oleoyloxy)-3-3-(trimethylammonium)propane (DOTAP), 1,2-dimyristyloxypropyl-3-dimethyl-hydroxy ethyl ammonium bromide (DMRIE), and dimethyl dioctadecyl ammonium bromide (DDAB).

8. The composition of claim 4, wherein the one or more cationic lipids comprise one or more polyvalent cationic lipids.

9. The composition of claim 8, wherein the one or more polyvalent cationic lipids are selected from the group consisting of 2,3-dioleyloxy-N-[2-(sperminecarboxamido)ethyl]-N,N-dimethyl-1-propanaminium trifluoro-acetate (DOSPA), 1,3-dioleoyloxy-2-(6-carboxy spermyl)-propylamide (DOSPER), 5-carboxyspermylglycine dioctadecyl-amide (DOGS), tetramethyltetrapalmitoyl spermine (TMTPS), tetramethyltetraoleyl spermine (TMTOS), tetramethlytetralauryl spermine (TMTLS), tetramethyltetramyristyl spermine (TMTMS), and tetramethyldioleyl spermine (TMDOS).

10. The composition of claim 5, wherein the one or more neutral lipids are selected from the group consisting of dioleoylphosphatidylethanolamine (DOPE), diphytanoylphosphatidylethanolamine (DPhPE), and cholesterol.

11. The composition of claim 2, further comprising DEAE-dextran, chloroquine or combinations thereof.

12. The composition of claim 2, wherein the composition can transfect a primary cell culture, a passaged cell culture or a cell line.

13. The composition of claim 12, wherein the cell line is a human cell line.

14. The composition of claim 12, wherein the cell line is an animal cell line.

15. The composition of claim 12, wherein the cell line is a fibroblast.

16. The composition of claim 2, wherein the one or more nucleic acid molecules is one or more DNA molecules or fragments thereof.

17. The composition of claim 2, wherein the one or more nucleic acid molecules is one or more RNA molecules or fragments thereof.

18. A transfection reagent kit which comprises a transfection agent and one or more peptides comprising Sp-NLSNLS.

19. The kit of claim 18, wherein the kit comprises a cationic lipid transfection agent.

20. The kit of claim 19, wherein the cationic lipid is a polyvalent cationic lipid.

21. The kit of claim 20, wherein the polyvalent cationic lipid is selected from the group consisting of 2,3-dioleyloxy-N-[2-(sperminecarboxamido)ethyl]-N,N-dimethyl-1-propanaminium trifluoro-acetate (DOSPA), 1,3-dioleoyloxy-2-(6-carboxy spermyl)-propylamide (DOSPER), 5-carboxyspermylglycine dioctadecyl-amide (DOGS), tetramethyltetrapalmitoyl spermine (TMTPS), tetramethyltetraoleyl spermine (TMTOS), tetramethlytetralauryl spermine (TMTLS), tetramethyltetramyristyl spermine (TMTMS), and tetramethyldioleyl spermine (TMDOS).

22. The kit of claim 18, wherein the kit further comprises one or more neutral lipids.

23. The kit of claim 22, wherein the one or more neutral lipids are selected from dioleoylphosphatidylethanolamine (DOPE), diphytanoylphosphatidylethanolamine (DPhPE) and cholesterol.

24. The kit of claim 18, wherein the kit comprises a 3:1 (w/w) mixture of the polycationic lipid 2,3-dioleyloxy-N-[2 (sperminecarboxamido)ethyl]-N,N-dimethyl-1-propaniminium trifluoroacetate and dioleoylphosphatidyl-ethanolamine.

25. A method for transfecting a cell with a nucleic acid, the method comprising the step of contacting the cell in vitro with the transfection composition of claim 2.

* * * * *

SEQUENCE LISTING (1) GENERAL INFORMATION:

(iii) NUMBER OF SEQUENCES: 123

(2) INFORMATION FOR SEQ ID NO: 1:

(i) SEQUENCE CHARACTERISTICS:
      (A) LENGTH: 10 amino acids
      (B) TYPE: amino acid
      (C) STRANDEDNESS: not relevant
      (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 1:

His Ala Ile Arg Gly Asp Thr Phe Ala Thr
1           5                   10

(2) INFORMATION FOR SEQ ID NO: 2:

(i) SEQUENCE CHARACTERISTICS:
      (A) LENGTH: 7 amino acids
      (B) TYPE: amino acid
      (C) STRANDEDNESS: not relevant
      (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 2:

Pro Lys Lys Lys Arg Lys Val
1           5

(2) INFORMATION FOR SEQ ID NO: 3:

(i) SEQUENCE CHARACTERISTICS:
      (A) LENGTH: 8 amino acids
      (B) TYPE: amino acid
      (C) STRANDEDNESS: not relevant
      (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 3:

Pro Lys Lys Lys Lys Arg Lys Val 1               5

(2) INFORMATION FOR SEQ ID NO: 4:

(i) SEQUENCE CHARACTERISTICS:
        (A) LENGTH: 20 amino acids
        (B) TYPE: amino acid
        (C) STRANDEDNESS: not relevant
        (D) TOPOLOGY: linear (ii) MOLECULE TYPE: peptide (iii) HYPOTHETICAL: NO (iv) ANTI-SENSE: NO (ix) FEATURE:
        (A) NAME/KEY: Modified-site
        (B) LOCATION: 2..20
        (D) OTHER INFORMATION: /product= "OTHER"
            /note= "ANY OR ALL OF THE AMINO ACIDS 2-20 CAN BE
            PRESENT OR ABSENT"

(xi) SEQUENCE DESCRIPTION: SEQ ID NO: 4:

Lys Lys Lys Lys Lys Lys Lys Lys Lys Lys Lys Lys Lys Lys Lys Lys
1               5                   10                  15

Lys Lys Lys Lys
            20

(2) INFORMATION FOR SEQ ID NO: 5:

(i) SEQUENCE CHARACTERISTICS:
        (A) LENGTH: 20 amino acids
        (B) TYPE: amino acid
        (C) STRANDEDNESS: not relevant
        (D) TOPOLOGY: linear (ii) MOLECULE TYPE: peptide (ix) FEATURE:
        (A) NAME/KEY: Modified-site
        (B) LOCATION: 2..20
        (D) OTHER INFORMATION: /product= "OTHER"
            /note= "ANY OR ALL OF THE AMINO ACIDS 2-20 CAN BE
            PRESENT OR ABSENT"

(xi) SEQUENCE DESCRIPTION: SEQ ID NO: 5:

Arg Arg Arg Arg Arg Arg Arg Arg Arg Arg Arg Arg Arg Arg Arg Arg
1               5                   10                  15

Arg Arg Arg Arg
            20

(2) INFORMATION FOR SEQ ID NO: 6:

(i) SEQUENCE CHARACTERISTICS:
        (A) LENGTH: 40 amino acids
        (B) TYPE: amino acid
        (C) STRANDEDNESS: not relevant
        (D) TOPOLOGY: linear (ii) MOLECULE TYPE: peptide (ix) FEATURE:
        (A) NAME/KEY: Modified-site
        (B) LOCATION: 3..40
        (D) OTHER INFORMATION: /product= "OTHER"
            /note= "ANY Lsy-Arg PAIR FROM AMINO ACID 3-40 CAN BE
            PRESENT OR ABSENT"

(xi) SEQUENCE DESCRIPTION: SEQ ID NO: 6:

Lys Arg Lys Arg Lys Arg Lys Arg Lys Arg Lys Arg Lys Arg Lys Arg
1               5                   10                  15

```
Lys Arg Lys Arg Lys Arg Lys Arg Lys Arg Lys Arg Lys Arg
            20                  25                  30

Lys Arg Lys Arg Lys Arg Lys Arg
            35                  40

(2) INFORMATION FOR SEQ ID NO: 7:

(i) SEQUENCE CHARACTERISTICS:
        (A) LENGTH: 20 amino acids
        (B) TYPE: amino acid
        (C) STRANDEDNESS: not relevant
        (D) TOPOLOGY: linear (ii) MOLECULE TYPE: peptide (ix) FEATURE:
        (A) NAME/KEY: Modified-site
        (B) LOCATION: 2..20
        (D) OTHER INFORMATION: /product= "OTHER"
            /note= "ANY OR ALL OF THE AMINO ACIDS 2-20 CAN BE
            PRESENT OR ABSENT"

(xi) SEQUENCE DESCRIPTION: SEQ ID NO: 7:

Gly Gly Gly Gly Gly Gly Gly Gly Gly Gly Gly Gly Gly Gly Gly
1               5                   10                  15

Gly Gly Gly Gly
            20

(2) INFORMATION FOR SEQ ID NO: 8:

(i) SEQUENCE CHARACTERISTICS:
        (A) LENGTH: 7 amino acids
        (B) TYPE: amino acid
        (C) STRANDEDNESS: not relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 8:

Gly Arg Gly Asp Ser Pro Cys
1               5

(2) INFORMATION FOR SEQ ID NO: 9:

(i) SEQUENCE CHARACTERISTICS:
        (A) LENGTH: 23 amino acids
        (B) TYPE: amino acid
        (C) STRANDEDNESS: not relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "ANY OR ALL OF THE AMINO ACIDS 1-20 CAN BE
            PRESENT OR ABSENT"

(xi) SEQUENCE DESCRIPTION: SEQ ID NO: 9:

Lys Lys Lys Lys Lys Lys Lys Lys Lys Lys Lys Lys Lys Lys Lys
1               5                   10                  15

Lys Lys Lys Lys Arg Gly Asp
            20
```

```
(2) INFORMATION FOR SEQ ID NO: 10:

(i) SEQUENCE CHARACTERISTICS:
            (A) LENGTH: 19 amino acids
            (B) TYPE: amino acid
            (C) STRANDEDNESS: not relevant
            (D) TOPOLOGY: linear (ii) MOLECULE TYPE: peptide (xi) SEQUENCE DESCRIPTION: SEQ ID NO: 10:

Lys Lys Lys Lys Lys Lys Lys Lys Lys Lys Lys Lys Lys Lys Lys
1               5                   10                  15

Arg Gly Asp (2) INFORMATION FOR SEQ ID NO: 11:

(i) SEQUENCE CHARACTERISTICS:
            (A) LENGTH: 7 amino acids
            (B) TYPE: amino acid
            (C) STRANDEDNESS: not relevant
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 11:

Lys Phe Thr Ile Val Phe Cys
1               5

(2) INFORMATION FOR SEQ ID NO: 12:

(i) SEQUENCE CHARACTERISTICS:
            (A) LENGTH: 12 amino acids
            (B) TYPE: amino acid
            (C) STRANDEDNESS: not relevant
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 12:

Cys Gly Trp Gly Pro Lys Lys Lys Arg Lys Val Gly
1               5                   10

(2) INFORMATION FOR SEQ ID NO: 13:

(i) SEQUENCE CHARACTERISTICS:
            (A) LENGTH: 26 amino acids
            (B) TYPE: amino acid
            (C) STRANDEDNESS: not relevant
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 13:

Gly Gly Tyr Gly Pro Lys Lys Lys Arg Lys Val Gly Gly Gly Tyr
1               5                   10                  15

Gly Pro Lys Lys Lys Arg Lys Val Gly Gly
            20                  25
```

(2) INFORMATION FOR SEQ ID NO: 14:

(i) SEQUENCE CHARACTERISTICS:
           (A) LENGTH: 6 amino acids
           (B) TYPE: amino acid
           (C) STRANDEDNESS: not relevant
           (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 14:

Arg Gly Asp Ser Pro Cys
1               5

(2) INFORMATION FOR SEQ ID NO: 15:

(i) SEQUENCE CHARACTERISTICS:
           (A) LENGTH: 4 amino acids
           (B) TYPE: amino acid
           (C) STRANDEDNESS: not relevant
           (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 15:

Arg Glu Asp Val
1

(2) INFORMATION FOR SEQ ID NO: 16:

(i) SEQUENCE CHARACTERISTICS:
           (A) LENGTH: 4 amino acids
           (B) TYPE: amino acid
           (C) STRANDEDNESS: not relevant
           (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 16:

Arg Gly Asp Val
1

(2) INFORMATION FOR SEQ ID NO: 17:

(i) SEQUENCE CHARACTERISTICS:
           (A) LENGTH: 25 amino acids
           (B) TYPE: amino acid
           (C) STRANDEDNESS: not relevant
           (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 17:

Asp Glu Leu Pro Gln Leu Val Thr Leu Pro His Pro Asn Leu His Gly
1               5                  10                  15

```
Pro Glu Ile Leu Asp Val Pro Ser Thr
        20                  25

(2) INFORMATION FOR SEQ ID NO: 18:

(i) SEQUENCE CHARACTERISTICS:
        (A) LENGTH: 4 amino acids
        (B) TYPE: amino acid
        (C) STRANDEDNESS: not relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 18:

Arg Gly Asp Asn
1

(2) INFORMATION FOR SEQ ID NO: 19:

(i) SEQUENCE CHARACTERISTICS:
        (A) LENGTH: 4 amino acids
        (B) TYPE: amino acid
        (C) STRANDEDNESS: not relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 19:

Arg Gly Asp Met
1

(2) INFORMATION FOR SEQ ID NO: 20:

(i) SEQUENCE CHARACTERISTICS:
        (A) LENGTH: 4 amino acids
        (B) TYPE: amino acid
        (C) STRANDEDNESS: not relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 20:

Arg Gly Asp Thr
1

(2) INFORMATION FOR SEQ ID NO: 21:

(i) SEQUENCE CHARACTERISTICS:
        (A) LENGTH: 4 amino acids
        (B) TYPE: amino acid
        (C) STRANDEDNESS: not relevant
        (D) TOPOLOGY: linear (ii) MOLECULE TYPE: peptide (iii) HYPOTHETICAL: NO (iv) ANTI-SENSE: NO (ix) FEATURE:
        (A) NAME/KEY: Modified-site
```

(B) LOCATION: 4
            (D) OTHER INFORMATION: /product= "OTHER"
                /note= "Xaa AT POSITION 4 CAN BE ANY AMINO ACID"

(xi) SEQUENCE DESCRIPTION: SEQ ID NO: 21:

Arg Gly Asp Xaa
1

(2) INFORMATION FOR SEQ ID NO: 22:

(i) SEQUENCE CHARACTERISTICS:
        (A) LENGTH: 4 amino acids
        (B) TYPE: amino acid
        (C) STRANDEDNESS: not relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 22:

Arg Gly Asp Ser
1

(2) INFORMATION FOR SEQ ID NO: 23:

(i) SEQUENCE CHARACTERISTICS:
        (A) LENGTH: 4 amino acids
        (B) TYPE: amino acid
        (C) STRANDEDNESS: not relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 23:

Arg Gly Asp Ala
1

(2) INFORMATION FOR SEQ ID NO: 24:

(i) SEQUENCE CHARACTERISTICS:
        (A) LENGTH: 33 amino acids
        (B) TYPE: amino acid
        (C) STRANDEDNESS: not relevant
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "C AT POSITION 1 CAN BE ABSENT"

(ix) FEATURE:
        (A) NAME/KEY: Modified-site
        (B) LOCATION: 3
        (D) OTHER INFORMATION: /product= "OTHER"
            /note= "Xaa AT POSITION 3 CAN BE TYR OR TRP OR CAN BE
            ABSENT"

(ix) FEATURE:
        (A) NAME/KEY: Modified-site
        (B) LOCATION: 14..33
        (D) OTHER INFORMATION: /product= "OTHER"
            /note= "ANY OR ALL OF THE GLY AT POSITIONS 14 TO 33 CAN
            BE ABSENT"

(xi) SEQUENCE DESCRIPTION: SEQ ID NO: 24:

Cys Gly Xaa Gly Pro Lys Lys Lys Arg Lys Val Gly Gly Gly Gly
1               5                   10                  15

Gly Gly Gly Gly Gly Gly Gly Gly Gly Gly Gly Gly Gly Gly Gly
            20                  25                  30

Gly (2) INFORMATION FOR SEQ ID NO: 25:

(i) SEQUENCE CHARACTERISTICS:
        (A) LENGTH: 48 amino acids
        (B) TYPE: amino acid
        (C) STRANDEDNESS: not relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa AT POSITIONS 1-20 CAN BE ANY AMINO ACIDS AND
            ANY OR ALL OF THESE AMINO ACIDS CAN BE ABSENT"

(ix) FEATURE:
        (A) NAME/KEY: Modified-site
        (B) LOCATION: 28
        (D) OTHER INFORMATION: /product= "OTHER"
            /note= "Xaa AT POSITION 28 CAN BE TYR OR TRP OR CAN BE
            ABSENT"

(ix) FEATURE:
        (A) NAME/KEY: Modified-site
        (B) LOCATION: 29..48
        (D) OTHER INFORMATION: /product= "OTHER"
            /note= "Xaa AT POSITIONS 29-48 CAN BE ANY AMINO ACIDS OR
            CAN BE ABSENT"

(xi) SEQUENCE DESCRIPTION: SEQ ID NO: 25:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Pro Lys Lys Lys Arg Lys Val Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

(2) INFORMATION FOR SEQ ID NO: 26:

(i) SEQUENCE CHARACTERISTICS:
        (A) LENGTH: 90 amino acids
        (B) TYPE: amino acid
        (C) STRANDEDNESS: not relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa AT POSITIONS 1-20 CAN BE ANY AMINO ACIDS OR
            ANY OF THESE AMINO ACIDS CAN BE ABSENT"

(ix) FEATURE:
        (A) NAME/KEY: Modified-site
        (B) LOCATION: 21
        (D) OTHER INFORMATION: /product= "OTHER"
            /note= "CYS AT POSITON 21 CAN BE ABSENT"

(ix) FEATURE:
        (A) NAME/KEY: Modified-site
        (B) LOCATION: 22

(D) OTHER INFORMATION: /product= "OTHER"
                /note= "Xaa AT POSITION 22 CAN BE TYR OR TRP OR CAN BE
                ABSENT"

(ix) FEATURE:
            (A) NAME/KEY: Modified-site
            (B) LOCATION: 23..42
            (D) OTHER INFORMATION: /product= "OTHER"
                /note= "Xaa AT POSITIONS 23-42 CAN BE ANY AMINO ACIDS OR
                ANY OF THESE AMINO ACIDS CAN BE ABSENT"

(ix) FEATURE:
            (A) NAME/KEY: Modified-site
            (B) LOCATION: 50
            (D) OTHER INFORMATION: /product= "OTHER"
                /note= "CYS AT POSITION 50 CAN BE ABSENT"

(ix) FEATURE:
            (A) NAME/KEY: Modified-site
            (B) LOCATION: 51..70
            (D) OTHER INFORMATION: /product= "OTHER"
                /note= "Xaa AT POSITIONS 51 TO 79 CAN BE ANY AMINO ACIDS
                OR ANY OF THESE AMINO ACIDS CAN BE ABSENT"

(ix) FEATURE:
            (A) NAME/KEY: Modified-site
            (B) LOCATION: 71..90
            (D) OTHER INFORMATION: /product= "OTHER"
                /note= "Xaa AT POSITIONS 71-90 CAN BE ANY CATIONIC AMINO
                ACIDS OR ANY OF THESE AMINO ACIDS CAN BE ABSENT"

(xi) SEQUENCE DESCRIPTION: SEQ ID NO: 26:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Cys Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Pro Lys Lys Lys Arg Lys
        35                  40                  45

Val Cys Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa
                85                  90

(2) INFORMATION FOR SEQ ID NO: 27:

(i) SEQUENCE CHARACTERISTICS:
            (A) LENGTH: 70 amino acids
            (B) TYPE: amino acid
            (C) STRANDEDNESS: not relevant
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /product= "OTHER"
                /note= "CYS AT POSITION 1 CAN BE ABSENT"

(ix) FEATURE:
            (A) NAME/KEY: Modified-site
            (B) LOCATION: 2..21
            (D) OTHER INFORMATION: /product= "OTHER"
                /note= "Xaa AT POSITIONS 2-21 CAN BE ANY AMINO ACIDS OR
                ANY OF THESE AMNION ACIDS CAN BE ABSENT"

(ix) FEATURE:
            (A) NAME/KEY: Modified-site
            (B) LOCATION: 22
            (D) OTHER INFORMATION: /product= "OTHER"
                /note= "Xaa AT POSITION 22 CAN BE TYR OR TRP OR CAN BE

ABSENT"

(ix) FEATURE:
          (A) NAME/KEY: Modified-site
          (B) LOCATION: 23..42
          (D) OTHER INFORMATION: /product= "OTHER"
              /note= "Xaa AT POSITIONS 23 TO 42 CAN BE ANY AMNIO ACIDS
              OR ANY OF THESE AMINO ACIDS CAN BE ABSENT"

(ix) FEATURE:
          (A) NAME/KEY: Modified-site
          (B) LOCATION: 50..69
          (D) OTHER INFORMATION: /product= "OTHER"
              /note= "Xaa AT POSITIONS 50 TO 69 CAN BE ANY AMINO ACIDS
              OR ANY OF THESE AMINO ACIDS CAN BE ABSENT"

(ix) FEATURE:
          (A) NAME/KEY: Modified-site
          (B) LOCATION: 70
          (D) OTHER INFORMATION: /product= "OTHER"
              /note= "CYS AT POSITION 70 CAN BE ABSENT"

(xi) SEQUENCE DESCRIPTION: SEQ ID NO: 27:

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Pro Lys Lys Lys Arg Lys
        35                  40                  45

Val Xaa Xaa Xaa Xaa Xaa Xaa Xaa Xaa Xaa Xaa Xaa Xaa Xaa Xaa
50                  55                  60

Xaa Xaa Xaa Xaa Xaa Cys
65                  70

(2) INFORMATION FOR SEQ ID NO: 28:

(i) SEQUENCE CHARACTERISTICS:
          (A) LENGTH: 90 amino acids
          (B) TYPE: amino acid
          (C) STRANDEDNESS: not relevant
          (D) TOPOLOGY: linear (ii) MOLECULE TYPE: peptide (ix) FEATURE:
          (A) NAME/KEY: Modified-site
          (B) LOCATION: 1
          (D) OTHER INFORMATION: /product= "OTHER"
              /note= "CYS AT POSITION 1 CAN BE ABSENT"

(ix) FEATURE:
          (A) NAME/KEY: Modified-site
          (B) LOCATION: 2..21
          (D) OTHER INFORMATION: /product= "OTHER"
              /note= "Xaa AT POSITIONS 2-21 CAN BE ANY AMINO ACIDS OR
              ANY OF THESE AMINO ACIDS CAN BE ABSENT"

(ix) FEATURE:
          (A) NAME/KEY: Modified-site
          (B) LOCATION: 22
          (D) OTHER INFORMATION: /product= "OTHER"
              /note= "Xaa AT POSITION 22 CAN BE TYR OR TRP OR CAN BE
              ABSENT"

(ix) FEATURE:
          (A) NAME/KEY: Modified-site
          (B) LOCATION: 23..42
          (D) OTHER INFORMATION: /product= "OTHER"
              /note= "Xaa AT POSITIONS 23-42 CAN BE ANY AMINO ACIDS OR
              CAN BE ABSENT"

(ix) FEATURE:
          (A) NAME/KEY: Modified-site
          (B) LOCATION: 50

```
            (D) OTHER INFORMATION: /product= "OTHER"
                /note= "CYS AT POSITION 50 CAN BE ABSENT"

(ix) FEATURE:
            (A) NAME/KEY: Modified-site
            (B) LOCATION: 51..70
            (D) OTHER INFORMATION: /product= "OTHER"
                /note= "Xaa AT POSITIONS 51 TO 70 CAN BE ANY AMINO ACIDS
                AND CAN BE ABSENT"

(ix) FEATURE:
            (A) NAME/KEY: Modified-site
            (B) LOCATION: 71..90
            (D) OTHER INFORMATION: /product= "OTHER"
                /note= "Xaa AT POSITIONS 71-90 CAN BE ANY CATIONIC AMINO
                ACIDS OR CAN BE ABSENT"

(xi) SEQUENCE DESCRIPTION: SEQ ID NO: 28:

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Pro Lys Lys Lys Arg Lys
        35                  40                  45

Val Cys Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa
            85                  90

(2) INFORMATION FOR SEQ ID NO: 29:

(i) SEQUENCE CHARACTERISTICS:
            (A) LENGTH: 90 amino acids
            (B) TYPE: amino acid
            (C) STRANDEDNESS: not relevant
            (D) TOPOLOGY: linear (ii) MOLECULE TYPE: peptide (ix) FEATURE:
            (A) NAME/KEY: Modified-site
            (B) LOCATION: 1..20
            (D) OTHER INFORMATION: /product= "OTHER"
                /note= "Xaa AT POSITIONS 1-20 CAN BE ANY CATIONIC AMINO
                ACIDS OR CAN BE AB..."

(ix) FEATURE:
            (A) NAME/KEY: Modified-site
            (B) LOCATION: 21..40
            (D) OTHER INFORMATION: /product= "OTHER"
                /note= "Xaa AT POSITIONS 21 TO 40 CAN BE ANY AMINO ACIDS
                OR CAN BE ABSENT"

(ix) FEATURE:
            (A) NAME/KEY: Modified-site
            (B) LOCATION: 41
            (D) OTHER INFORMATION: /product= "OTHER"
                /note= "CYS AT POSITION 41 CAN BE ABSENT"

(ix) FEATURE:
            (A) NAME/KEY: Modified-site
            (B) LOCATION: 42
            (D) OTHER INFORMATION: /product= "OTHER"
                /note= "Xaa AT POSITION 42 CAN BE TYR OT TRP OR CAN BE
                ABSENT"

(ix) FEATURE:
            (A) NAME/KEY: Modified-site
            (B) LOCATION: 43..62
            (D) OTHER INFORMATION: /product= "OTHER"
                /note= "Xaa AT POSITIONS 43 TO 62 CAN BE ANY AMINO ACIDS
```

```
                    OR CAN BE ABSENT"

(ix) FEATURE:
            (A) NAME/KEY: Modified-site
            (B) LOCATION: 70..89
            (D) OTHER INFORMATION: /product= "OTHER"
                /note= "Xaa AT POSITIONS 70 TO 89 CAN BE ANY AMINO ACIDS
                    OR CAN BE ABSENT"

(ix) FEATURE:
            (A) NAME/KEY: Modified-site
            (B) LOCATION: 90
            (D) OTHER INFORMATION: /product= "OTHER"
                /note= "CYS AT POSITION 90 CAN BE ABSENT"

(xi) SEQUENCE DESCRIPTION: SEQ ID NO: 29:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Cys Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Pro Lys
    50                  55                  60

Lys Lys Arg Lys Val Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Cys
            85                  90

(2) INFORMATION FOR SEQ ID NO: 30:

(i) SEQUENCE CHARACTERISTICS:
            (A) LENGTH: 90 amino acids
            (B) TYPE: amino acid
            (C) STRANDEDNESS: not relevant
            (D) TOPOLOGY: linear (ii) MOLECULE TYPE: peptide (ix) FEATURE:
            (A) NAME/KEY: Modified-site
            (B) LOCATION: 1..20
            (D) OTHER INFORMATION: /product= "OTHER"
                /note= "Xaa AT POSITIONS 1-20 CAN BE ANY CATIONIC AMINO
                    ACID OR CAN BE ABSENT"

(ix) FEATURE:
            (A) NAME/KEY: Modified-site
            (B) LOCATION: 21..40
            (D) OTHER INFORMATION: /product= "OTHER"
                /note= "Xaa AT POSITIONS 21 TO 40 CAN BE ANY AMINO ACIDS
                    OR CAN BE ABSENT"

(ix) FEATURE:
            (A) NAME/KEY: Modified-site
            (B) LOCATION: 41
            (D) OTHER INFORMATION: /product= "OTHER"
                /note= "CYS AT POSITION 41 CAN BE ABSENT"

(ix) FEATURE:
            (A) NAME/KEY: Modified-site
            (B) LOCATION: 42
            (D) OTHER INFORMATION: /product= "OTHER"
                /note= "Xaa AT POSITION 42 CAN BE TYR OR TRP OR CAN BE
                    ABSENT"

(ix) FEATURE:
            (A) NAME/KEY: Modified-site
            (B) LOCATION: 43..62
            (D) OTHER INFORMATION: /product= "OTHER"
                /note= "Xaa AT POSITIONS 43 TO 62 CAN BE ANY AMINO ACIDS
                    OR CAN BE ABSENT"
```

```
    (ix) FEATURE:
         (A) NAME/KEY: Modified-site
         (B) LOCATION: 70
         (D) OTHER INFORMATION: /product= "OTHER"
             /note= "CYS AT POSITION 70 CAN BE ABSENT"

(ix) FEATURE:
         (A) NAME/KEY: Modified-site
         (B) LOCATION: 71..90
         (D) OTHER INFORMATION: /product= "OTHER"
             /note= "Xaa AT POSITIONS 71 TO 90 CAN BE ANY AMINO ACIDS
             OR CAN BE ABSENT"

(xi) SEQUENCE DESCRIPTION: SEQ ID NO: 30:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Cys Xaa Xaa Xaa Xaa Xaa Xaa
        35                  40                  45

Xaa Xaa Xaa Xaa Xaa Xaa Xaa Xaa Xaa Xaa Xaa Xaa Xaa Pro Lys
    50                  55                  60

Lys Lys Arg Lys Val Cys Xaa Xaa Xaa Xaa Xaa Xaa Xaa Xaa Xaa
65                  70                  75                  80

Xaa Xaa Xaa Xaa Xaa Xaa Xaa Xaa Xaa Xaa
                85                  90

(2) INFORMATION FOR SEQ ID NO: 31:

(i) SEQUENCE CHARACTERISTICS:
        (A) LENGTH: 5 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 31:

Arg Gly Asp Ser Pro
1               5

(2) INFORMATION FOR SEQ ID NO: 32:

(i) SEQUENCE CHARACTERISTICS:
        (A) LENGTH: 69 amino acids
        (B) TYPE: amino acid
        (C) STRANDEDNESS: not relevant
        (D) TOPOLOGY: linear (ii) MOLECULE TYPE: peptide (ix) FEATURE:
         (A) NAME/KEY: Modified-site
         (B) LOCATION: 1..20
         (D) OTHER INFORMATION: /product= "OTHER"
             /note= "Xaa AT POSITIONS 1-20 CAN BE ANY CATIONIC AMINO
             ACIDS OR CAN BE AB..."

(ix) FEATURE:
         (A) NAME/KEY: Modified-site
         (B) LOCATION: 21..40
         (D) OTHER INFORMATION: /product= "OTHER"
             /note= "Xaa AT POSITIONS 21-40 CAN BE ANY AMINO ACIDS OR
             CAN BE ABSENT"

(ix) FEATURE:
         (A) NAME/KEY: Modified-site
         (B) LOCATION: 41
         (D) OTHER INFORMATION: /product= "OTHER"
             /note= "CYS AT POSITION 41 CAN BE ABSENT"
```

```
    (ix) FEATURE:
         (A) NAME/KEY: Modified-site
         (B) LOCATION: 42
         (D) OTHER INFORMATION: /product= "OTHER"
             /note= "GLY AT POSITION 42 CAN BE ABSENT"

(ix) FEATURE:
         (A) NAME/KEY: Modified-site
         (B) LOCATION: 48
         (D) OTHER INFORMATION: /product= "OTHER"
             /note= "GLY AT POSITION 48 CAN BE ABSENT"

(ix) FEATURE:
         (A) NAME/KEY: Modified-site
         (B) LOCATION: 49
         (D) OTHER INFORMATION: /product= "OTHER"
             /note= "CYS AT POSITION 49 CAN BE ABSENT"

(ix) FEATURE:
         (A) NAME/KEY: Modified-site
         (B) LOCATION: 50..69
         (D) OTHER INFORMATION: /product= "OTHER"
             /note= "Xaa AT POSITIONS 50-69 CAN BE ANY AMINO ACIDS OR
             CAN BE ABSENT"

(xi) SEQUENCE DESCRIPTION: SEQ ID NO: 32:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Cys Gly Arg Gly Asp Ser Pro Gly
        35                  40                  45

Cys Xaa Xaa Xaa Xaa Xaa Xaa Xaa Xaa Xaa Xaa Xaa Xaa Xaa Xaa
50                  55                  60

Xaa Xaa Xaa Xaa Xaa
65

(2) INFORMATION FOR SEQ ID NO: 33:

(i) SEQUENCE CHARACTERISTICS:
        (A) LENGTH: 69 amino acids
        (B) TYPE: amino acid
        (C) STRANDEDNESS: not relevant
        (D) TOPOLOGY: linear (ii) MOLECULE TYPE: peptide (ix) FEATURE:
         (A) NAME/KEY: Modified-site
         (B) LOCATION: 1..20
         (D) OTHER INFORMATION: /product= "OTHER"
             /note= "Xaa AT POSITIONS 1-20 CAN BE ANY AMINO ACIDS OR
             CAN BE ABSENT"

(ix) FEATURE:
         (A) NAME/KEY: Modified-site
         (B) LOCATION: 21
         (D) OTHER INFORMATION: /product= "OTHER"
             /note= "CYS AT POSITION 21 CAN BE ABSENT"

(ix) FEATURE:
         (A) NAME/KEY: Modified-site
         (B) LOCATION: 22
         (D) OTHER INFORMATION: /product= "OTHER"
             /note= "GLY AT POSITION 22 CAN BE ABSENT"

(ix) FEATURE:
         (A) NAME/KEY: Modified-site
         (B) LOCATION: 28
         (D) OTHER INFORMATION: /product= "OTHER"
             /note= "GLY AT POSITION 28 CAN BE ABSENT"

(ix) FEATURE:
         (A) NAME/KEY: Modified-site
```

```
        (B) LOCATION: 29
        (D) OTHER INFORMATION: /product= "OTHER"
            /note= "CYS AT POSITION 29 CAN BE ABSENT"

(ix) FEATURE:
        (A) NAME/KEY: Modified-site
        (B) LOCATION: 30..49
        (D) OTHER INFORMATION: /product= "OTHER"
            /note= "Xaa AT POSITIONS 30-49 CAN BE ANY AMINO ACIDS OR
            CAN BE ABSENT"

(ix) FEATURE:
        (A) NAME/KEY: Modified-site
        (B) LOCATION: 50..69
        (D) OTHER INFORMATION: /product= "OTHER"
            /note= "Xaa AT POSITIONS 50-69 CAN BE ANY CATIONIC AMINO
            ACIDS"

(xi) SEQUENCE DESCRIPTION: SEQ ID NO: 33:

Xaa Xaa Xaa Xaa Xaa Xaa Xaa Xaa Xaa Xaa Xaa Xaa Xaa Xaa Xaa
1               5                   10                  15

Xaa Xaa Xaa Xaa Cys Gly Arg Gly Asp Ser Pro Gly Cys Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa
65

(2) INFORMATION FOR SEQ ID NO: 34:

(i) SEQUENCE CHARACTERISTICS:
        (A) LENGTH: 69 amino acids
        (B) TYPE: amino acid
        (C) STRANDEDNESS: not relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa AT POSITIONS 1-20 CAN BE ANY CATIONIC AMINO
            ACIDS OR CAN BE AB..."

(ix) FEATURE:
        (A) NAME/KEY: Modified-site
        (B) LOCATION: 21..40
        (D) OTHER INFORMATION: /product= "OTHER"
            /note= "Xaa AT POSITIONS 21-40 CAN BE ANY AMINO ACIDS OR
            CAN BE ABSENT"

(ix) FEATURE:
        (A) NAME/KEY: Modified-site
        (B) LOCATION: 41
        (D) OTHER INFORMATION: /product= "OTHER"
            /note= "CYS AT POSITION 41 CAN BE ABSENT"

(ix) FEATURE:
        (A) NAME/KEY: Modified-site
        (B) LOCATION: 42
        (D) OTHER INFORMATION: /product= "OTHER"
            /note= "GLY AT POSITION 42 CAN BE ABSENT"

(ix) FEATURE:
        (A) NAME/KEY: Modified-site
        (B) LOCATION: 48
        (D) OTHER INFORMATION: /product= "OTHER"
            /note= "GLY AT POSITION 48 CAN BE ABSENT"

(ix) FEATURE:
        (A) NAME/KEY: Modified-site
```

(B) LOCATION: 49..68
            (D) OTHER INFORMATION: /product= "OTHER"
                /note= "Xaa AT POSITIONS 49-68 CAN BE ANY AMINO ACIDS OR
                CAN BE ABSENT"

(ix) FEATURE:
            (A) NAME/KEY: Modified-site
            (B) LOCATION: 69
            (D) OTHER INFORMATION: /product= "OTHER"
                /note= "CYS AT POSITION 69 CAN BE ABSENT"

(xi) SEQUENCE DESCRIPTION: SEQ ID NO: 34:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Cys Gly Arg Gly Asp Ser Pro Gly
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Cys
65

(2) INFORMATION FOR SEQ ID NO: 35:

(i) SEQUENCE CHARACTERISTICS:
            (A) LENGTH: 69 amino acids
            (B) TYPE: amino acid
            (C) STRANDEDNESS: not relevant
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /product= "OTHER"
                /note= "CYS AT POSITION 1 CAN BE ABSENT"

(ix) FEATURE:
            (A) NAME/KEY: Modified-site
            (B) LOCATION: 2..21
            (D) OTHER INFORMATION: /product= "OTHER"
                /note= "Xaa AT POSITIONS 2-21 CAN BE ANY AMINO ACID OR
                CAN BE ABSENT"

(ix) FEATURE:
            (A) NAME/KEY: Modified-site
            (B) LOCATION: 22
            (D) OTHER INFORMATION: /product= "OTHER"
                /note= "GLY AT POSITION 22 CAN BE ABSENT"

(ix) FEATURE:
            (A) NAME/KEY: Modified-site
            (B) LOCATION: 28
            (D) OTHER INFORMATION: /product= "OTHER"
                /note= "GLY AT POSITION 28 CAN BE ABSENT"

(ix) FEATURE:
            (A) NAME/KEY: Modified-site
            (B) LOCATION: 29
            (D) OTHER INFORMATION: /product= "OTHER"
                /note= "CYS AT POSITION 29 CAN BE ABSENT"

(ix) FEATURE:
            (A) NAME/KEY: Modified-site
            (B) LOCATION: 30..49
            (D) OTHER INFORMATION: /product= "OTHER"
                /note= "Xaa AT POSITIONS 30-49 CAN BE ANY AMINO ACIDS OR
                CAN BE ABSENT"

(ix) FEATURE:
            (A) NAME/KEY: Modified-site
            (B) LOCATION: 50..69

(D) OTHER INFORMATION: /product= "OTHER"
            /note= "Xaa AT POSITIONS 50-69 CAN BE ANY CATIONIC AMINO
            ACIDS OR CAN BE ABSENT"

(xi) SEQUENCE DESCRIPTION: SEQ ID NO: 35:

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Gly Arg Gly Asp Ser Pro Gly Cys Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa
65

(2) INFORMATION FOR SEQ ID NO: 36:

(i) SEQUENCE CHARACTERISTICS:
        (A) LENGTH: 5 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 36:

Arg Gly Asp Met Phe
1               5

(2) INFORMATION FOR SEQ ID NO: 37:

(i) SEQUENCE CHARACTERISTICS:
        (A) LENGTH: 49 amino acids
        (B) TYPE: amino acid
        (C) STRANDEDNESS: not relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa AT POSITIONS 1-20 CAN BE ANY AMINO ACIDS OR
            CAN BE ABSENT"

(ix) FEATURE:
        (A) NAME/KEY: Modified-site
        (B) LOCATION: 21
        (D) OTHER INFORMATION: /product= "OTHER"
            /note= "CYS AT POSITION 21 CAN BE ABSENT"

(ix) FEATURE:
        (A) NAME/KEY: Modified-site
        (B) LOCATION: 22
        (D) OTHER INFORMATION: /product= "OTHER"
            /note= "GLY AT POSITION 22 CAN BE ABSENT"

(ix) FEATURE:
        (A) NAME/KEY: Modified-site
        (B) LOCATION: 28
        (D) OTHER INFORMATION: /product= "OTHER"
            /note= "GLY AT POSITION 28 CAN BE ABSENT"

(ix) FEATURE:
        (A) NAME/KEY: Modified-site
        (B) LOCATION: 29
        (D) OTHER INFORMATION: /product= "OTHER"
            /note= "CYS AT POSITION 29 CAN BE ABSENT"

(ix) FEATURE:

(A) NAME/KEY: Modified-site
        (B) LOCATION: 30..49
        (D) OTHER INFORMATION: /product= "OTHER"
            /note= "Xaa AT POSITIONS 30-49 CAN BE ANY AMINO ACIDS OR
            CAN BE ABSENT"

(xi) SEQUENCE DESCRIPTION: SEQ ID NO: 37:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Cys Gly Arg Gly Asp Met Phe Gly Cys Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa (2) INFORMATION FOR SEQ ID NO: 38:

(i) SEQUENCE CHARACTERISTICS:
        (A) LENGTH: 47 amino acids
        (B) TYPE: amino acid
        (C) STRANDEDNESS: not relevant
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "CYS AT POSITION 1 CAN BE ABSENT"

(ix) FEATURE:
        (A) NAME/KEY: Modified-site
        (B) LOCATION: 2..21
        (D) OTHER INFORMATION: /product= "OTHER"
            /note= "Xaa AT POSITIONS 2-21 CAN BE ANY AMINO ACIDS OR
            CAN BE ABSENT"

(ix) FEATURE:
        (A) NAME/KEY: Modified-site
        (B) LOCATION: 27..46
        (D) OTHER INFORMATION: /product= "OTHER"
            /note= "Xaa AT POSITIONS 27-46 CAN BE ANY AMINO ACIDS OR
            CAN BE ABSENT"

(ix) FEATURE:
        (A) NAME/KEY: Modified-site
        (B) LOCATION: 47
        (D) OTHER INFORMATION: /product= "OTHER"
            /note= "CYS AT POSITION 47 CAN BE ABSENT"

(xi) SEQUENCE DESCRIPTION: SEQ ID NO: 38:

Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Arg Gly Asp Met Phe Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Cys
        35                  40                  45

(2) INFORMATION FOR SEQ ID NO: 39:

(i) SEQUENCE CHARACTERISTICS:
        (A) LENGTH: 69 amino acids
        (B) TYPE: amino acid
        (C) STRANDEDNESS: not relevant
        (D) TOPOLOGY: linear (ii) MOLECULE TYPE: peptide (ix) FEATURE:
        (A) NAME/KEY: Modified-site (B) LOCATION: 1..20
            (D) OTHER INFORMATION: /product= "OTHER"
                /note= "Xaa AT POSITIONS 1-20 CAN BE ANY CATIONIC AMINO
                ACIDS OR CAN BE AB..."

(ix) FEATURE:
            (A) NAME/KEY: Modified-site
            (B) LOCATION: 21..40
            (D) OTHER INFORMATION: /product= "OTHER"
                /note= "Xaa AT POSITIONS 21-40 CAN BE ANY AMINO ACIDS OR
                CAN BE ABSENT"

(ix) FEATURE:
            (A) NAME/KEY: Modified-site
            (B) LOCATION: 41
            (D) OTHER INFORMATION: /product= "OTHER"
                /note= "CYS AT POSITION 41 CAN BE ABSENT"

(ix) FEATURE:
            (A) NAME/KEY: Modified-site
            (B) LOCATION: 42
            (D) OTHER INFORMATION: /product= "OTHER"
                /note= "GLY AT POSITION 42 CAN BE ABSENT"

(ix) FEATURE:
            (A) NAME/KEY: Modified-site
            (B) LOCATION: 48
            (D) OTHER INFORMATION: /product= "OTHER"
                /note= "GLY AT POSITION 48 CAN BE ABSENT"

(ix) FEATURE:
            (A) NAME/KEY: Modified-site
            (B) LOCATION: 49..68
            (D) OTHER INFORMATION: /product= "OTHER"
                /note= "Xaa AT POSITIONS 49-68 CAN BE ANY AMINO ACIDS OR
                CAN BE ABSENT"

(ix) FEATURE:
            (A) NAME/KEY: Modified-site
            (B) LOCATION: 69
            (D) OTHER INFORMATION: /product= "OTHER"
                /note= "CYS AT POSITION 69 CAN BE ABSENT"

(xi) SEQUENCE DESCRIPTION: SEQ ID NO: 39:

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Cys Gly Arg Gly Asp Met Phe Gly
        35                  40                  45

Xaa Xaa Xaa Xaa Xaa Xaa Xaa Xaa Xaa Xaa Xaa Xaa Xaa Xaa Xaa
        50                  55                  60

Xaa Xaa Xaa Xaa Cys
65

(2) INFORMATION FOR SEQ ID NO: 40:

(i) SEQUENCE CHARACTERISTICS:
            (A) LENGTH: 69 amino acids
            (B) TYPE: amino acid
            (C) STRANDEDNESS: not relevant
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /product= "OTHER"
                /note= "CYS AT POSITION 1 CAN BE ABSENT"

(ix) FEATURE:
            (A) NAME/KEY: Modified-site
            (B) LOCATION: 2..21

(D) OTHER INFORMATION: /product= "OTHER"
                    /note= "Xaa AT POSITIONS 2-21 CAN BE ANY AMINO ACIDS OR
                    CAN BE ABSENT"

(ix) FEATURE:
                (A) NAME/KEY: Modified-site
                (B) LOCATION: 22
                (D) OTHER INFORMATION: /product= "OTHER"
                    /note= "GLY AT POSITION 22 CAN BE ABSENT"

(ix) FEATURE:
                (A) NAME/KEY: Modified-site
                (B) LOCATION: 28
                (D) OTHER INFORMATION: /product= "OTHER"
                    /note= "GLY AT POSITION 28 CAN BE ABSENT"

(ix) FEATURE:
                (A) NAME/KEY: Modified-site
                (B) LOCATION: 29
                (D) OTHER INFORMATION: /product= "OTHER"
                    /note= "CYS AT POSITION 29 CAN BE ABSENT"

(ix) FEATURE:
                (A) NAME/KEY: Modified-site
                (B) LOCATION: 30..49
                (D) OTHER INFORMATION: /product= "OTHER"
                    /note= "Xaa AT POSITIONS 30-49 CAN BE ANY AMINO ACIDS OR
                    CAN BE ABSENT"

(ix) FEATURE:
                (A) NAME/KEY: Modified-site
                (B) LOCATION: 50..69
                (D) OTHER INFORMATION: /product= "OTHER"
                    /note= "Xaa AT POSITIONS 50-69 CAN BE ANY CATIONIC AMINO
                    ACIDS OR CAN BE ABSENT"

(xi) SEQUENCE DESCRIPTION: SEQ ID NO: 40:

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Gly Arg Gly Asp Met Phe Gly Cys Xaa Xaa
                20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa
65

(2) INFORMATION FOR SEQ ID NO: 41:

(i) SEQUENCE CHARACTERISTICS:
                (A) LENGTH: 69 amino acids
                (B) TYPE: amino acid
                (C) STRANDEDNESS: not relevant
                (D) TOPOLOGY: linear (ii) MOLECULE TYPE: peptide (ix) FEATURE:
                (A) NAME/KEY: Modified-site
                (B) LOCATION: 1..20
                (D) OTHER INFORMATION: /product= "OTHER"
                    /note= "Xaa AT POSITIONS 1-20 CAN BE ANY CATIONIC AMINO
                    ACIDS OR CAN BE AB..."

(ix) FEATURE:
                (A) NAME/KEY: Modified-site
                (B) LOCATION: 21..40
                (D) OTHER INFORMATION: /product= "OTHER"
                    /note= "Xaa AT POSITIONS 21-40 CAN BE ANY AMINO ACIDS OR
                    CAN BE ABSENT"

(ix) FEATURE:
                (A) NAME/KEY: Modified-site

```
        (B) LOCATION: 41
        (D) OTHER INFORMATION: /product= "OTHER"
            /note= "CYS AT POSITION 41 CAN BE ABSENT"

(ix) FEATURE:
        (A) NAME/KEY: Modified-site
        (B) LOCATION: 42
        (D) OTHER INFORMATION: /product= "OTHER"
            /note= "GLY AT POSITION 42 CAN BE ABSENT"

(ix) FEATURE:
        (A) NAME/KEY: Modified-site
        (B) LOCATION: 48
        (D) OTHER INFORMATION: /product= "OTHRE"
            /note= "GLY AT POSITION 48 CAN BE ABSENT"

(ix) FEATURE:
        (A) NAME/KEY: Modified-site
        (B) LOCATION: 49
        (D) OTHER INFORMATION: /product= "OTHER"
            /note= "CYS AT POSITION 49 CAN BE ABSENT"

(ix) FEATURE:
        (A) NAME/KEY: Modified-site
        (B) LOCATION: 50..69
        (D) OTHER INFORMATION: /product= "OTHER"
            /note= "Xaa AT POSITIONS 50-69 CAN BE ANY AMINO ACIDS OR
            CAN BE ABSENT"

(xi) SEQUENCE DESCRIPTION: SEQ ID NO: 41:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Cys Gly Arg Gly Asp Met Phe Gly
        35                  40                  45

Cys Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa
65

(2) INFORMATION FOR SEQ ID NO: 42:

(i) SEQUENCE CHARACTERISTICS:
        (A) LENGTH: 69 amino acids
        (B) TYPE: amino acid
        (C) STRANDEDNESS: not relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa AT POSITIONS 1-20 CAN BE ANY AMINO ACIDS OR
            CAN BE ABSENT"

(ix) FEATURE:
        (A) NAME/KEY: Modified-site
        (B) LOCATION: 21
        (D) OTHER INFORMATION: /product= "OTHER"
            /note= "CYS AT POSITION 21 CAN BE ABSENT"

(ix) FEATURE:
        (A) NAME/KEY: Modified-site
        (B) LOCATION: 22
        (D) OTHER INFORMATION: /product= "OTHER"
            /note= "GLY AT POSITION 22 CAN BE ABSENT"

(ix) FEATURE:
        (A) NAME/KEY: Modified-site
        (B) LOCATION: 28
        (D) OTHER INFORMATION: /product= "OTHER"
```

/note= "GLY AT POSITION 28 CAN BE ABSENT"

(ix) FEATURE:
    (A) NAME/KEY: Modified-site
    (B) LOCATION: 29
    (D) OTHER INFORMATION: /product= "OTHER"
        /note= "CYS AT POSITION 29 CAN BE ABSENT"

(ix) FEATURE:
    (A) NAME/KEY: Modified-site
    (B) LOCATION: 30..49
    (D) OTHER INFORMATION: /product= "OTHER"
        /note= "Xaa AT POSITIONS 30-49 CAN BE ANY AMINO ACIDS OR
        CAN BE ABSENT"

(ix) FEATURE:
    (A) NAME/KEY: Modified-site
    (B) LOCATION: 50..69
    (D) OTHER INFORMATION: /product= "OTHER"
        /note= "Xaa AT POSITIONS 50-69 CAN BE ANY CATIONIC AMINO
        ACIDS OR CAN BE ABSENT"

(xi) SEQUENCE DESCRIPTION: SEQ ID NO: 42:

Xaa Xaa Xaa Xaa Xaa Xaa Xaa Xaa Xaa Xaa Xaa Xaa Xaa Xaa Xaa
1               5                   10                  15

Xaa Xaa Xaa Xaa Cys Gly Arg Gly Asp Met Phe Gly Cys Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa
65

(2) INFORMATION FOR SEQ ID NO: 43:

(i) SEQUENCE CHARACTERISTICS:
        (A) LENGTH: 67 amino acids
        (B) TYPE: amino acid
        (C) STRANDEDNESS: not relevant
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "CYS AT POSITION 1 CAN BE ABSENT"

(ix) FEATURE:
        (A) NAME/KEY: Modified-site
        (B) LOCATION: 2..21
        (D) OTHER INFORMATION: /product= "OTHER"
            /note= "Xaa AT POSITIONS 2-21 CAN BE ANY AMINO ACIDS OR
            CAN BE ABSENT"

(ix) FEATURE:
        (A) NAME/KEY: Modified-site
        (B) LOCATION: 47..66
        (D) OTHER INFORMATION: /product= "OTHER"
            /note= "Xaa AT POSITIONS 47-66 CAN BE ANY AMINO ACIDS OR
            CAN BE ABSENT"

(ix) FEATURE:
        (A) NAME/KEY: Modified-site
        (B) LOCATION: 67
        (D) OTHER INFORMATION: /product= "OTHER"
            /note= "CYS AT POSITION 67 CAN BE ABSENT"

(xi) SEQUENCE DESCRIPTION: SEQ ID NO: 43:

Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Asp Glu Leu Pro Gln Leu Val Thr Leu Pro His
            20                  25                  30

Pro Asn Leu His Gly Pro Glu Ile Leu Asp Val Pro Ser Thr Xaa Xaa
            35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Cys
65

(2) INFORMATION FOR SEQ ID NO: 44:

(i) SEQUENCE CHARACTERISTICS:
        (A) LENGTH: 87 amino acids
        (B) TYPE: amino acid
        (C) STRANDEDNESS: not relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa AT POSITIONS 1-20 CAN BE ANY CATIONIC AMINO
            ACID OR CAN BE ABSENT"

(ix) FEATURE:
        (A) NAME/KEY: Modified-site
        (B) LOCATION: 21..40
        (D) OTHER INFORMATION: /product= "OTHER"
            /note= "Xaa AT POSITIONS 21-40 CAN BE ANY AMINO ACIDS OR
            CAN BE ABSENT"

(ix) FEATURE:
        (A) NAME/KEY: Modified-site
        (B) LOCATION: 41
        (D) OTHER INFORMATION: /product= "OTHER"
            /note= "CYS AT POSITION 41 CAN BE ABSENT"

(ix) FEATURE:
        (A) NAME/KEY: Modified-site
        (B) LOCATION: 67..86
        (D) OTHER INFORMATION: /product= "OTHER"
            /note= "Xaa AT POSITIONS 67-86 CAN BE ANY AMINO ACIDS OR
            CAN BE ABSENT"

(ix) FEATURE:
        (A) NAME/KEY: Modified-site
        (B) LOCATION: 87
        (D) OTHER INFORMATION: /product= "OTHER"
            /note= "CYS AT POSITION 87 CAN BE ABSENT"

(xi) SEQUENCE DESCRIPTION: SEQ ID NO: 44:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Cys Asp Glu Leu Pro Gln Leu Val
            35                  40                  45

Thr Leu Pro His Pro Asn Leu His Gly Pro Glu Ile Leu Asp Val Pro
    50                  55                  60

Ser Thr Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Cys
            85

(2) INFORMATION FOR SEQ ID NO: 45:

```
    (i) SEQUENCE CHARACTERISTICS:
        (A) LENGTH: 87 amino acids
        (B) TYPE: amino acid
        (C) STRANDEDNESS: not relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa AT POSITIONS 1-20 CAN BE ANY CATIONIC AMINO
            ACIDS OR CAN BE AB..."

(ix) FEATURE:
        (A) NAME/KEY: Modified-site
        (B) LOCATION: 21..40
        (D) OTHER INFORMATION: /product= "OTHER"
            /note= "Xaa AT POSITIONS 21-40 CAN BE ANY AMINO ACIDS OR
            CAN BE ABSENT"

(ix) FEATURE:
        (A) NAME/KEY: Modified-site
        (B) LOCATION: 41
        (D) OTHER INFORMATION: /product= "OTHER"
            /note= "CYS AT POSTION 41 CAN BE ABSENT"

(ix) FEATURE:
        (A) NAME/KEY: Modified-site
        (B) LOCATION: 67
        (D) OTHER INFORMATION: /product= "OTHER"
            /note= "CYS AT POSITION 67 CAN BE ABSENT"

(ix) FEATURE:
        (A) NAME/KEY: Modified-site
        (B) LOCATION: 68..87
        (D) OTHER INFORMATION: /product= "OTHER"
            /note= "Xaa AT POSITIONS 68-87 CAN BE ANY AMINO ACIDS OR
            CAN BE ABSENT"

(xi) SEQUENCE DESCRIPTION: SEQ ID NO: 45:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Cys Asp Glu Leu Pro Gln Leu Val
            35                  40                  45

Thr Leu Pro His Pro Asn Leu His Gly Pro Glu Ile Leu Asp Val Pro
50                  55                  60

Ser Thr Cys Xaa Xaa Xaa Xaa Xaa Xaa Xaa Xaa Xaa Xaa Xaa Xaa Xaa
65              70                  75                  80

Xaa Xaa Xaa Xaa Xaa Xaa Xaa
            85

(2) INFORMATION FOR SEQ ID NO: 46:

(i) SEQUENCE CHARACTERISTICS:
        (A) LENGTH: 87 amino acids
        (B) TYPE: amino acid
        (C) STRANDEDNESS: not relevant
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "CYS AT POSITION 1 CAN BE ABSENT"

(ix) FEATURE:
        (A) NAME/KEY: Modified-site
```

```
        (B) LOCATION: 2..21
        (D) OTHER INFORMATION: /product= "OTHER"
            /note= "Xaa AT POSITIONS 2-21 CAN BE ANY AMINO ACID OR
            CAN BE ABSENT"

(ix) FEATURE:
        (A) NAME/KEY: Modified-site
        (B) LOCATION: 47
        (D) OTHER INFORMATION: /product= "OTHER"
            /note= "CYS AT POSITION 47 CAN BE ABSENT"

(ix) FEATURE:
        (A) NAME/KEY: Modified-site
        (B) LOCATION: 48..67
        (D) OTHER INFORMATION: /product= "OTHER"
            /note= "Xaa AT POSITIONS 48-67 CAN BE ANY AMINO ACIDS OR
            CAN BE ABSENT"

(ix) FEATURE:
        (A) NAME/KEY: Modified-site
        (B) LOCATION: 68..87
        (D) OTHER INFORMATION: /product= "OTHER"
            /note= "Xaa AT POSITIONS 68-87 CAN BE ANY CATIONIC AMINO
            ACIDS OR CAN BE ABSENT"

(xi) SEQUENCE DESCRIPTION: SEQ ID NO: 46:

Cys Xaa Xaa Xaa Xaa Xaa Xaa Xaa Xaa Xaa Xaa Xaa Xaa Xaa Xaa
 1               5                  10                  15

Xaa Xaa Xaa Xaa Xaa Asp Glu Leu Pro Gln Leu Val Thr Leu Pro His
            20                  25                  30

Pro Asn Leu His Gly Pro Glu Ile Leu Asp Val Pro Ser Thr Cys Xaa
                35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa
                85

(2) INFORMATION FOR SEQ ID NO: 47:

(i) SEQUENCE CHARACTERISTICS:
        (A) LENGTH: 87 amino acids
        (B) TYPE: amino acid
        (C) STRANDEDNESS: not relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa AT POSITIONS 1-20 CAN BE ANY AMINO ACIDS OR
            CAN BE ABSENT"

(ix) FEATURE:
        (A) NAME/KEY: Modified-site
        (B) LOCATION: 21
        (D) OTHER INFORMATION: /product= "OTHER"
            /note= "CYS AT POSITION 21 CAN BE ABSENT"

(ix) FEATURE:
        (A) NAME/KEY: Modified-site
        (B) LOCATION: 47
        (D) OTHER INFORMATION: /product= "OTHER"
            /note= "CYS AT POSITION 47 CAN BE ABSENT"

(ix) FEATURE:
        (A) NAME/KEY: Modified-site
        (B) LOCATION: 48..67
        (D) OTHER INFORMATION: /product= "OTHER"
            /note= "Xaa AT POSITIONS 48-67 CAN BE ANY AMINO ACIDS OR
```

(ix) FEATURE:
            (A) NAME/KEY: Modified-site
            (B) LOCATION: 68..87
            (D) OTHER INFORMATION: /product= "OTHER"
                /note= "Xaa AT POSITIONS 68-87 CAN BE ANY CATIONIC AMNIO
                ACIDS OR CAN BE ABSENT"

(xi) SEQUENCE DESCRIPTION: SEQ ID NO: 47:

Xaa Xaa Xaa Xaa Xaa Xaa Xaa Xaa Xaa Xaa Xaa Xaa Xaa Xaa Xaa
1               5                   10                  15

Xaa Xaa Xaa Xaa Cys Asp Glu Leu Pro Gln Leu Val Thr Leu Pro His
            20              25                  30

Pro Asn Leu His Gly Pro Glu Ile Leu Asp Val Pro Ser Thr Cys Xaa
            35              40                  45

Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa Xaa Xaa
65              70                  75                  80

Xaa Xaa Xaa Xaa Xaa Xaa Xaa
                85

(2) INFORMATION FOR SEQ ID NO: 48:

(i) SEQUENCE CHARACTERISTICS:
            (A) LENGTH: 8 amino acids
            (B) TYPE: amino acid
            (C) STRANDEDNESS: not relevant
            (D) TOPOLOGY: linear (ii) MOLECULE TYPE: peptide (xi) SEQUENCE DESCRIPTION: SEQ ID NO: 48:

Glu Ile Leu Asp Val Pro Ser Thr
1               5

(2) INFORMATION FOR SEQ ID NO: 49:

(i) SEQUENCE CHARACTERISTICS:
            (A) LENGTH: 50 amino acids
            (B) TYPE: amino acid
            (C) STRANDEDNESS: not relevant
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /product= "OTHER"
                /note= "CYS AT POSITION 1 CAN BE ABSENT"

(ix) FEATURE:
            (A) NAME/KEY: Modified-site
            (B) LOCATION: 21
            (D) OTHER INFORMATION: /product= "OTHER"
                /note= "Xaa AT POSITIONS 2-21 CAN BE ANY AMINO ACIDS OR
                CAN BE ABSENT"

(ix) FEATURE:
            (A) NAME/KEY: Modified-site
            (B) LOCATION: 30..49
            (D) OTHER INFORMATION: /product= "OTHER"
                /note= "Xaa AT POSITIONS 30-49 CAN BE ANY AMINO ACIDS OR
                CAN BE ABSENT"

(ix) FEATURE:
            (A) NAME/KEY: Modified-site
            (B) LOCATION: 50
            (D) OTHER INFORMATION: /product= "OTHER"

/note= "CYS AT POSITION 50 CAN BE ABSENT"

(xi) SEQUENCE DESCRIPTION: SEQ ID NO: 49:

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Glu Ile Leu Asp Val Pro Ser Thr Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Cys
    50

(2) INFORMATION FOR SEQ ID NO: 50:

(i) SEQUENCE CHARACTERISTICS:
        (A) LENGTH: 70 amino acids
        (B) TYPE: amino acid
        (C) STRANDEDNESS: not relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa AT POSITIONS 1-20 CAN BE ANY CATIONIC AMINO
            ACIDS OR CAN BE AB..."

(ix) FEATURE:
        (A) NAME/KEY: Modified-site
        (B) LOCATION: 21..40
        (D) OTHER INFORMATION: /product= "OTHER"
            /note= "Xaa AT POSITIONS 21-40 CAN BE ANY AMINO ACIDS OR
            CAN BE ABSENT"

(ix) FEATURE:
        (A) NAME/KEY: Modified-site
        (B) LOCATION: 41
        (D) OTHER INFORMATION: /product= "OTHER"
            /note= "CYS AT POSITION 41 CAN BE ABSENT"

(ix) FEATURE:
        (A) NAME/KEY: Modified-site
        (B) LOCATION: 50
        (D) OTHER INFORMATION: /product= "OTHER"
            /note= "CYS AT POSITION 50 CAN BE ABSENT"

(ix) FEATURE:
        (A) NAME/KEY: Modified-site
        (B) LOCATION: 51..70
        (D) OTHER INFORMATION: /product= "OTHER"
            /note= "Xaa AT POSITIONS 51-70 CAN BE ANY AMINO ACIDS OR
            CAN BE ABSENT"

(xi) SEQUENCE DESCRIPTION: SEQ ID NO: 50:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Cys Glu Ile Leu Asp Val Pro Ser
        35                  40                  45

Thr Cys Xaa Xaa Xaa Xaa Xaa Xaa Xaa Xaa Xaa Xaa Xaa Xaa Xaa
    50                  55                  60

Xaa Xaa Xaa Xaa Xaa Xaa
65                  70

(2) INFORMATION FOR SEQ ID NO: 51:

(i) SEQUENCE CHARACTERISTICS:
          (A) LENGTH: 70 amino acids
          (B) TYPE: amino acid
          (C) STRANDEDNESS: not relevant
          (D) TOPOLOGY: linear (ii) MOLECULE TYPE: peptide (ix) FEATURE:
          (A) NAME/KEY: Modified-site
          (B) LOCATION: 1..20
          (D) OTHER INFORMATION: /product= "OTHER"
              /note= "Xaa AT POSITIONS 1-20 CAN BE ANY CATIONIC AMINO
              ACIDS OR CAN BE AB..."

(ix) FEATURE:
          (A) NAME/KEY: Modified-site
          (B) LOCATION: 21..40
          (D) OTHER INFORMATION: /product= "OTHER"
              /note= "Xaa AT POSITIONS 21-40 CAN BE ANY AMINO ACIDS OR
              CAN BE ABSENT"

(ix) FEATURE:
          (A) NAME/KEY: Modified-site
          (B) LOCATION: 41
          (D) OTHER INFORMATION: /product= "OTHER"
              /note= "CYS AT POSITION 41 CAN BE ABSENT"

(ix) FEATURE:
          (A) NAME/KEY: Modified-site
          (B) LOCATION: 50..69
          (D) OTHER INFORMATION: /product= "OTHER"
              /note= "Xaa AT POSITIONS 50-69 CAN BE ANY AMINO ACIDS OR
              CAN BE ABSENT"

(ix) FEATURE:
          (A) NAME/KEY: Modified-site
          (B) LOCATION: 70
          (D) OTHER INFORMATION: /product= "OTHER"
              /note= "CYS AT POSITION 70 CAN BE ABSENT"

(xi) SEQUENCE DESCRIPTION: SEQ ID NO: 51:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Cys Glu Ile Leu Asp Val Pro Ser
        35                  40                  45

Thr Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Cys
65                  70

(2) INFORMATION FOR SEQ ID NO: 52:

(i) SEQUENCE CHARACTERISTICS:
          (A) LENGTH: 70 amino acids
          (B) TYPE: amino acid
          (C) STRANDEDNESS: not relevant
          (D) TOPOLOGY: linear (ii) MOLECULE TYPE: peptide (ix) FEATURE:
          (A) NAME/KEY: Modified-site
          (B) LOCATION: 1
          (D) OTHER INFORMATION: /product= "OTHER"
              /note= "CYS AT POSITION 1 CAN BE ABSENT"

(ix) FEATURE:
          (A) NAME/KEY: Modified-site
          (B) LOCATION: 2..21
          (D) OTHER INFORMATION: /product= "OTHER"
              /note= "Xaa AT POSITIONS 2-21 CAN BE ANY AMINO ACIDS OR

```
            CAN BE ABSENT"

(ix) FEATURE:
        (A) NAME/KEY: Modified-site
        (B) LOCATION: 30
        (D) OTHER INFORMATION: /product= "OTHER"
            /note= "CYS AT POSITION 30 CAN BE ABSENT"

(ix) FEATURE:
        (A) NAME/KEY: Modified-site
        (B) LOCATION: 31..50
        (D) OTHER INFORMATION: /product= "OTHER"
            /note= "Xaa AT POSITIONS 31-50 CAN BE ANY AMINO ACIDS OR
            CAN BE ABSENT"

(ix) FEATURE:
        (A) NAME/KEY: Modified-site
        (B) LOCATION: 51..70
        (D) OTHER INFORMATION: /product= "OTHER"
            /note= "Xaa AT POSITIONS 51-70 AN BE ANY CATIONIC AMINO
            ACIDS OR CAN BE AB..."

(xi) SEQUENCE DESCRIPTION: SEQ ID NO: 52:

Cys Xaa Xaa Xaa Xaa Xaa Xaa Xaa Xaa Xaa Xaa Xaa Xaa Xaa Xaa
 1               5                  10                  15

Xaa Xaa Xaa Xaa Xaa Glu Ile Leu Asp Val Pro Ser Thr Cys Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa
 65                  70

(2) INFORMATION FOR SEQ ID NO: 53:

(i) SEQUENCE CHARACTERISTICS:
        (A) LENGTH: 70 amino acids
        (B) TYPE: amino acid
        (C) STRANDEDNESS: not relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa AT POSITIONS 1-20 CAN BE ANY AMINO ACIDS OR
            CAN BE ABSENT"

(ix) FEATURE:
        (A) NAME/KEY: Modified-site
        (B) LOCATION: 21
        (D) OTHER INFORMATION: /product= "OTHER"
            /note= "CYS AT POSITION 21 CAN BE ABSENT"

(ix) FEATURE:
        (A) NAME/KEY: Modified-site
        (B) LOCATION: 30
        (D) OTHER INFORMATION: /product= "OTHER"
            /note= "CYS AT POSITION 50 CAN BE ABSENT"

(ix) FEATURE:
        (A) NAME/KEY: Modified-site
        (B) LOCATION: 31..50
        (D) OTHER INFORMATION: /product= "OTHER"
            /note= "Xaa AT POSITIONS 31-50 CAN BE ANY AMINO ACIDS OR
            CAN BE ABSENT"

(ix) FEATURE:
        (A) NAME/KEY: Modified-site
        (B) LOCATION: 51..70
        (D) OTHER INFORMATION: /product= "OTHER"
```

/note= "Xaa AT POSITIONS 51-70 CAN BE ANY CATIONIC AMINO
          ACIDS OR CAN BE ABSENT"

(xi) SEQUENCE DESCRIPTION: SEQ ID NO: 53:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Cys Glu Ile Leu Asp Val Pro Ser Thr Cys Xaa Xaa
            20                  25                  30

Xaa Xaa Xaa Xaa Xaa Xaa Xaa Xaa Xaa Xaa Xaa Xaa Xaa Xaa Xaa Xaa
                35                  40                  45

Xaa Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa
65                  70

(2) INFORMATION FOR SEQ ID NO: 54:

(i) SEQUENCE CHARACTERISTICS:
        (A) LENGTH: 6 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 54:

Lys Phe Thr Ile Val Phe
1               5

(2) INFORMATION FOR SEQ ID NO: 55:

(i) SEQUENCE CHARACTERISTICS:
        (A) LENGTH: 48 amino acids
        (B) TYPE: amino acid
        (C) STRANDEDNESS: not relevant
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "CYS AT POSITION 1 CAN BE ABSENT"

(ix) FEATURE:
        (A) NAME/KEY: Modified-site
        (B) LOCATION: 2..21
        (D) OTHER INFORMATION: /product= "OTHER"
            /note= "Xaa AT POSITIONS 2-21 CAN BE ANY AMINO ACIDS OR
            CAN BE ABSENT"

(ix) FEATURE:
        (A) NAME/KEY: Modified-site
        (B) LOCATION: 28..47
        (D) OTHER INFORMATION: /product= "OTHER"
            /note= "Xaa AT POSITIONS 28-47 CAN BE ANY AMINO ACIDS OR
            CAN BE ABSENT"

(ix) FEATURE:
        (A) NAME/KEY: Modified-site
        (B) LOCATION: 48
        (D) OTHER INFORMATION: /product= "OTHER"
            /note= "CYS AT POSITION 48 CAN BE ABSENT"

(xi) SEQUENCE DESCRIPTION: SEQ ID NO: 55:

Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Lys Phe Thr Ile Val Phe Xaa Xaa Xaa Xaa Xaa
            20                  25                  30

```
Xaa Xaa Xaa Xaa Xaa Xaa Xaa Xaa Xaa Xaa Xaa Xaa Xaa Xaa Cys
        35                  40                  45
```

(2) INFORMATION FOR SEQ ID NO: 56:

(i) SEQUENCE CHARACTERISTICS:
        (A) LENGTH: 68 amino acids
        (B) TYPE: amino acid
        (C) STRANDEDNESS: not relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa AT POSITIONS 1-20 CAN BE ANY CATIONIC AMINO
            ACIDS OR CAN BE AB..."

(ix) FEATURE:
        (A) NAME/KEY: Modified-site
        (B) LOCATION: 21..40
        (D) OTHER INFORMATION: /product= "OTHER"
            /note= "Xaa AT POSITIONS 21-40 CAN BE ANY AMINO ACIDS OR
            CAN BE ABSENT"

(ix) FEATURE:
        (A) NAME/KEY: Modified-site
        (B) LOCATION: 41
        (D) OTHER INFORMATION: /product= "OTHER"
            /note= "CYS AT POSITION 41 CAN BE ABSENT"

(ix) FEATURE:
        (A) NAME/KEY: Modified-site
        (B) LOCATION: 48
        (D) OTHER INFORMATION: /product= "OTHER"
            /note= "CYS AT POSITION 48 CAN BE ABSENT"

(ix) FEATURE:
        (A) NAME/KEY: Modified-site
        (B) LOCATION: 49..68
        (D) OTHER INFORMATION: /product= "OTHER"
            /note= "Xaa AT POSITIONS 49-68 CAN BE ANY AMINO ACIDS OR
            CAN BE ABSENT"

(xi) SEQUENCE DESCRIPTION: SEQ ID NO: 56:

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Cys Lys Phe Thr Ile Val Phe Cys
        35                  40                  45

Xaa Xaa Xaa Xaa Xaa Xaa Xaa Xaa Xaa Xaa Xaa Xaa Xaa Xaa Xaa
        50                  55                  60

Xaa Xaa Xaa Xaa
65
```

(2) INFORMATION FOR SEQ ID NO: 57:

(i) SEQUENCE CHARACTERISTICS:
        (A) LENGTH: 68 amino acids
        (B) TYPE: amino acid
        (C) STRANDEDNESS: not relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"

```
            /note= "Xaa AT POSITIONS 1-20 CAN BE ANY CATIONIC AMINO
            ACID OR CAN BE ABSENT"

(ix) FEATURE:
          (A) NAME/KEY: Modified-site
          (B) LOCATION: 21..40
          (D) OTHER INFORMATION: /product= "OTHER"
              /note= "Xaa AT POSITIONS 21-40 CAN BE ANY AMINO ACIDS OR
              CAN BE ABSENT"

(ix) FEATURE:
          (A) NAME/KEY: Modified-site
          (B) LOCATION: 41
          (D) OTHER INFORMATION: /product= "OTHER"
              /note= "CYS AT POSITION 41 CAN BE ABSENT"

(ix) FEATURE:
          (A) NAME/KEY: Modified-site
          (B) LOCATION: 48..67
          (D) OTHER INFORMATION: /product= "OTHER"
              /note= "Xaa AT POSITIONS 48-67 CAN BE ANY AMINO ACIDS OR
              CAN BE ABSENT"

(ix) FEATURE:
          (A) NAME/KEY: Modified-site
          (B) LOCATION: 68
          (D) OTHER INFORMATION: /product= "OTHER"
              /note= "CYS AT POSITION 68 CAN BE ABSENT"

(xi) SEQUENCE DESCRIPTION: SEQ ID NO: 57:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Cys Lys Phe Thr Ile Val Phe Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Cys
65

(2) INFORMATION FOR SEQ ID NO: 58:

(i) SEQUENCE CHARACTERISTICS:
          (A) LENGTH: 68 amino acids
          (B) TYPE: amino acid
          (C) STRANDEDNESS: not relevant
          (D) TOPOLOGY: linear (ii) MOLECULE TYPE: peptide (ix) FEATURE:
          (A) NAME/KEY: Modified-site
          (B) LOCATION: 1
          (D) OTHER INFORMATION: /product= "OTHER"
              /note= "CYS AT POSITION 1 CAN BE ABSENT"

(ix) FEATURE:
          (A) NAME/KEY: Modified-site
          (B) LOCATION: 2..21
          (D) OTHER INFORMATION: /product= "OTHER"
              /note= "Xaa AT POSITIONS 2-21 CAN BE ANY AMINO ACIDS OR
              CAN BE ABSENT"

(ix) FEATURE:
          (A) NAME/KEY: Modified-site
          (B) LOCATION: 28
          (D) OTHER INFORMATION: /product= "OTHER"
              /note= "CYS AT POSITION 28 CAN BE ABSENT"

(ix) FEATURE:
          (A) NAME/KEY: Modified-site
          (B) LOCATION: 29..48
          (D) OTHER INFORMATION: /product= "OTHER"
```

```
            /note= "Xaa AT POSITIONS 29-48 CAN BE ANY AMNINO ACIDS OR
            CAN BE ABSENT"

(ix) FEATURE:
         (A) NAME/KEY: Modified-site
         (B) LOCATION: 49..68
         (D) OTHER INFORMATION: /product= "OTHER"
            /note= "Xaa AT POSITIONS 49-68 CAN BE ANY CATIONIC AMINO
            ACIDS OR CAN BE ABSENT"

(xi) SEQUENCE DESCRIPTION: SEQ ID NO: 58:

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Lys Phe Thr Ile Val Phe Cys Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa
65

(2) INFORMATION FOR SEQ ID NO: 59:

(i) SEQUENCE CHARACTERISTICS:
        (A) LENGTH: 68 amino acids
        (B) TYPE: amino acid
        (C) STRANDEDNESS: not relevant
        (D) TOPOLOGY: linear (ii) MOLECULE TYPE: peptide (ix) FEATURE:
         (A) NAME/KEY: Modified-site
         (B) LOCATION: 1..20
         (D) OTHER INFORMATION: /product= "OTHER"
            /note= "Xaa AT POSITIONS 1-20 CAN BE ANY AMINO ACIDS OR
            CAN BE ABSENT"

(ix) FEATURE:
         (A) NAME/KEY: Modified-site
         (B) LOCATION: 21
         (D) OTHER INFORMATION: /product= "OTHER"
            /note= "CYS AT POSITION 21 CAN BE ABSENT"

(ix) FEATURE:
         (A) NAME/KEY: Modified-site
         (B) LOCATION: 28
         (D) OTHER INFORMATION: /product= "OTHER"
            /note= "CYS AT POSITION 28 CAN BE ABSENT"

(ix) FEATURE:
         (A) NAME/KEY: Modified-site
         (B) LOCATION: 29..48
         (D) OTHER INFORMATION: /product= "OTHER"
            /note= "Xaa AT POSITIONS 29-48 CAN BE ANY AMINO ACIDS OR
            CAN BE ABSENT"

(ix) FEATURE:
         (A) NAME/KEY: Modified-site
         (B) LOCATION: 49..68
         (D) OTHER INFORMATION: /product= "OTHER"
            /note= "Xaa AT POSITIONS 49-68 CAN BE ANY CATIONIC AMINO
            ACIDS OR CAN BE ABSENT"

(xi) SEQUENCE DESCRIPTION: SEQ ID NO: 59:

Xaa Xaa Xaa Xaa Xaa Xaa Xaa Xaa Xaa Xaa Xaa Xaa Xaa Xaa Xaa
1               5                   10                  15

Xaa Xaa Xaa Xaa Cys Lys Phe Thr Ile Val Phe Cys Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
```

```
                35                  40                  45
Xaa Xaa Xaa Xaa Xaa Xaa Xaa Xaa Xaa Xaa Xaa Xaa Xaa Xaa Xaa
        50                  55                  60

Xaa Xaa Xaa Xaa
65
```

(2) INFORMATION FOR SEQ ID NO: 60:

(i) SEQUENCE CHARACTERISTICS:
        (A) LENGTH: 95 amino acids
        (B) TYPE: amino acid
        (C) STRANDEDNESS: not relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa AT POSITIONS 1-20 CAN BE ANY AMINO ACIDS OR
            CAN BE ABSENT"

(ix) FEATURE:
        (A) NAME/KEY: Modified-site
        (B) LOCATION: 21
        (D) OTHER INFORMATION: /product= "OTHER"
            /note= "CYS AT POSITION 21 CAN BE ABSENT"

(ix) FEATURE:
        (A) NAME/KEY: Modified-site
        (B) LOCATION: 22
        (D) OTHER INFORMATION: /product= "OTHER"
            /note= "Xaa AT POSITION 22 CAN BE TYR OR TRP OR CAN BE
            ABSENT"

(ix) FEATURE:
        (A) NAME/KEY: Modified-site
        (B) LOCATION: 23..42
        (D) OTHER INFORMATION: /product= "OTHER"
            /note= "Xaa AT POSITIONS 23-42 ANC BE ANY AMINO ACIDS OR
            CAN BE ABSENT"

(ix) FEATURE:
        (A) NAME/KEY: Modified-site
        (B) LOCATION: 50..69
        (D) OTHER INFORMATION: /product= "OTHER"
            /note= "Xaa AT POSITIONS 50-69 CAN BE ANY AMINO ACIDS OR
            CAN BE ABSENT"

(ix) FEATURE:
        (A) NAME/KEY: Modified-site
        (B) LOCATION: 75
        (D) OTHER INFORMATION: /product= "OTHER"
            /note= "CYS AT POSITION 75 CAN BE ABSENT"

(ix) FEATURE:
        (A) NAME/KEY: Modified-site
        (B) LOCATION: 76..95
        (D) OTHER INFORMATION: /product= "OTHER"
            /note= "Xaa AT POSITIONS 76-95 CAN BE ANY AMINO ACIDS OR
            CAN BE ABSENT"

(xi) SEQUENCE DESCRIPTION: SEQ ID NO: 60:

```
Xaa Xaa Xaa Xaa Xaa Xaa Xaa Xaa Xaa Xaa Xaa Xaa Xaa Xaa Xaa
1               5                   10                  15

Xaa Xaa Xaa Xaa Cys Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Pro Lys Lys Arg Lys
        35                  40                  45

Val Xaa Xaa Xaa Xaa Xaa Xaa Xaa Xaa Xaa Xaa Xaa Xaa Xaa Xaa
        50                  55                  60
```

```
Xaa Xaa Xaa Xaa Xaa Arg Gly Asp Met Phe Cys Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95
```

(2) INFORMATION FOR SEQ ID NO: 61:

(i) SEQUENCE CHARACTERISTICS:
        (A) LENGTH: 95 amino acids
        (B) TYPE: amino acid
        (C) STRANDEDNESS: not relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa AT POSITIONS 1-20 CAN BE ANY AMINO ACIDS OR
            CAN BE ABSENT"

(ix) FEATURE:
        (A) NAME/KEY: Modified-site
        (B) LOCATION: 21
        (D) OTHER INFORMATION: /product= "OTHER"
            /note= "CYS AT POSITION 21 CAN BE ABSENT"

(ix) FEATURE:
        (A) NAME/KEY: Modified-site
        (B) LOCATION: 22..41
        (D) OTHER INFORMATION: /product= "OTHER"
            /note= "Xaa AT POSITIONS 22-41 CAN BE ANY AMINO ACIDS OR
            CAN BE ABSENT"

(ix) FEATURE:
        (A) NAME/KEY: Modified-site
        (B) LOCATION: 42
        (D) OTHER INFORMATION: /product= "OTHER"
            /note= "Xaa AT POSITION 42 CAN BE TYR OR TRP OR CAN BE
            ABSENT"

(ix) FEATURE:
        (A) NAME/KEY: Modified-site
        (B) LOCATION: 50..69
        (D) OTHER INFORMATION: /product= "OTHER"
            /note= "Xaa AT POSITIONS 50-69 CAN BE ANY AMINO ACIDS OR
            CAN BE ABSENT"

(ix) FEATURE:
        (A) NAME/KEY: Modified-site
        (B) LOCATION: 75
        (D) OTHER INFORMATION: /product= "OTHER"
            /note= "CYS AT POSITION 75 CAN BE ABSENT"

(ix) FEATURE:
        (A) NAME/KEY: Modified-site
        (B) LOCATION: 76..95
        (D) OTHER INFORMATION: /product= "OTHER"
            /note= "Xaa AT POSITIONS 76-95 CAN BE ANY AMINO ACIDS OR
            CAN BE ABSENT"

(xi) SEQUENCE DESCRIPTION: SEQ ID NO: 61:

```
Xaa Xaa Xaa Xaa Xaa Xaa Xaa Xaa Xaa Xaa Xaa Xaa Xaa Xaa Xaa
1                   5                   10                  15

Xaa Xaa Xaa Xaa Cys Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Pro Lys Lys Arg Lys
            35                  40                  45

Val Xaa Xaa Xaa Xaa Xaa Xaa Xaa Xaa Xaa Xaa Xaa Xaa Xaa Xaa
        50                  55                  60

Xaa Xaa Xaa Xaa Xaa Arg Gly Asp Met Phe Cys Xaa Xaa Xaa Xaa
65                  70                  75                  80
```

```
Xaa Xaa Xaa Xaa Xaa Xaa Xaa Xaa Xaa Xaa Xaa Xaa Xaa Xaa
            85                  90                  95

(2) INFORMATION FOR SEQ ID NO: 62:

(i) SEQUENCE CHARACTERISTICS:
         (A) LENGTH: 96 amino acids
         (B) TYPE: amino acid
         (C) STRANDEDNESS: not relevant
         (D) TOPOLOGY: linear (ii) MOLECULE TYPE: peptide (ix) FEATURE:
         (A) NAME/KEY: Modified-site
         (B) LOCATION: 1..20
         (D) OTHER INFORMATION: /product= "OTHER"
             /note= "Xaa AT POSITIONS 1-20 CAN BE ANY AMINO ACIDS OR
             CAN BE ABSENT"

(ix) FEATURE:
         (A) NAME/KEY: Modified-site
         (B) LOCATION: 21
         (D) OTHER INFORMATION: /product= "OTHER"
             /note= "CYS AT POSITION 21 CAN BE ABSENT"

(ix) FEATURE:
         (A) NAME/KEY: Modified-site
         (B) LOCATION: 22
         (D) OTHER INFORMATION: /product= "OTHER"
             /note= "Xaa AT POSITION 22 CAN BE TYR OR TRP OR CAN BE
             ABSENT"

(ix) FEATURE:
         (A) NAME/KEY: Modified-site
         (B) LOCATION: 23..42
         (D) OTHER INFORMATION: /product= "OTHER"
             /note= "Xaa AT POSITIONS 23-42 CAN BE ANY AMINO ACIDS OR
             CAN BE ABSENT"

(ix) FEATURE:
         (A) NAME/KEY: Modified-site
         (B) LOCATION: 50..69
         (D) OTHER INFORMATION: /product= "OTHER"
             /note= "Xaa AT POSITIONS 50-69 CAN BE ANY AMINO ACIDS OF
             CAN BE ABSENT"

(ix) FEATURE:
         (A) NAME/KEY: Modified-site
         (B) LOCATION: 76
         (D) OTHER INFORMATION: /product= "OTHER"
             /note= "CYS AT POSITION 76 CAN BE ABSENT"

(ix) FEATURE:
         (A) NAME/KEY: Modified-site
         (B) LOCATION: 77..96
         (D) OTHER INFORMATION: /product= "OTHER"
             /note= "Xaa AT POSITIONS 77-96 CAN BE ANY AMINO ACIDS OR
             CAN BE ABSENT"

(xi) SEQUENCE DESCRIPTION: SEQ ID NO: 62:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Cys Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Pro Lys Lys Lys Arg Lys
            35                  40                  45

Val Xaa Xaa Xaa Xaa Xaa Xaa Xaa Xaa Xaa Xaa Xaa Xaa Xaa Xaa Xaa
            50                  55                  60

Xaa Xaa Xaa Xaa Xaa Gly Arg Gly Asp Ser Pro Cys Xaa Xaa Xaa Xaa
65                  70                  75                  80

Xaa Xaa Xaa Xaa Xaa Xaa Xaa Xaa Xaa Xaa Xaa Xaa Xaa Xaa
```

-continued

```
                85                  90                  95

(2) INFORMATION FOR SEQ ID NO: 63:

(i) SEQUENCE CHARACTERISTICS:
        (A) LENGTH: 95 amino acids
        (B) TYPE: amino acid
        (C) STRANDEDNESS: not relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa AT POSITIONS 1-20 CAN BE ANY AMINO ACID OR
            CAN BE ABSENT"

(ix) FEATURE:
        (A) NAME/KEY: Modified-site
        (B) LOCATION: 21
        (D) OTHER INFORMATION: /product= "OTHER"
            /note= "CYS AT POSITION 21 CAN BE ABSENT"

(ix) FEATURE:
        (A) NAME/KEY: Modified-site
        (B) LOCATION: 22
        (D) OTHER INFORMATION: /product= "OTHER"
            /note= "Xaa AT POSITION 22 CAN BE TYR OR TRP OR CAN BE
            ABSENT"

(ix) FEATURE:
        (A) NAME/KEY: Modified-site
        (B) LOCATION: 23..42
        (D) OTHER INFORMATION: /product= "OTHER"
            /note= "Xaa AT POSITION 23-42 CAN BE ANY AMINO ACIDS OR
            CAN BE ABSENT"

(ix) FEATURE:
        (A) NAME/KEY: Modified-site
        (B) LOCATION: 50..69
        (D) OTHER INFORMATION: /product= "OTHER"
            /note= "Xaa AT POSITIONS 50-69 CAN BE ANY AMINO ACIDS OR
            CAN BE ABSENT"

(ix) FEATURE:
        (A) NAME/KEY: Modified-site
        (B) LOCATION: 75
        (D) OTHER INFORMATION: /product= "OTHER"
            /note= "CYS AT POSITION 75 CAN BE ABSENT"

(ix) FEATURE:
        (A) NAME/KEY: Modified-site
        (B) LOCATION: 76..95
        (D) OTHER INFORMATION: /product= "OTHER"
            /note= "Xaa AT POSITIONS 76-95 CAN BE ANY AMINO ACIDS OR
            CAN BE ABSENT"

(xi) SEQUENCE DESCRIPTION: SEQ ID NO: 63:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Cys Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Pro Lys Lys Lys Arg Lys
        35                  40                  45

Val Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Arg Gly Asp Ser Pro Cys Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
        85                  90                  95
```

(2) INFORMATION FOR SEQ ID NO: 64:

(i) SEQUENCE CHARACTERISTICS:
        (A) LENGTH: 117 amino acids
        (B) TYPE: amino acid
        (C) STRANDEDNESS: not relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa AT POSITIONS 1-20 CAN BE ANY AMINO ACID OR
            CAN BE ABSENT"

(ix) FEATURE:
        (A) NAME/KEY: Modified-site
        (B) LOCATION: 21
        (D) OTHER INFORMATION: /product= "OTHER"
            /note= "CYS AT POSITION 21 CAN BE ABSENT"

(ix) FEATURE:
        (A) NAME/KEY: Modified-site
        (B) LOCATION: 28
        (D) OTHER INFORMATION: /product= "OTHER"
            /note= "CYS AT POSITION 28 CAN BE ABSENT"

(ix) FEATURE:
        (A) NAME/KEY: Modified-site
        (B) LOCATION: 29..48
        (D) OTHER INFORMATION: /product= "OTHER"
            /note= "Xaa AT POSITIONS 29-48 CAN BE ANY AMINO ACIDS OR
            CAN BE ABSENT"

(ix) FEATURE:
        (A) NAME/KEY: Modified-site
        (B) LOCATION: 49
        (D) OTHER INFORMATION: /product= "OTHER"
            /note= "CYS AT POSITION 49 CAN BE ABSENT"

(ix) FEATURE:
        (A) NAME/KEY: Modified-site
        (B) LOCATION: 50..69
        (D) OTHER INFORMATION: /product= "OTHER"
            /note= "Xaa AT POSITIONS 50-69 CAN BE ANY AMINO ACIDS OR
            CAN BE ABSENT"

(ix) FEATURE:
        (A) NAME/KEY: Modified-site
        (B) LOCATION: 70
        (D) OTHER INFORMATION: /product= "OTHER"
            /note= "Xaa AT POSITION 70 CAN BE TYR OR TRP OR CAN BE
            ABSENT"

(ix) FEATURE:
        (A) NAME/KEY: Modified-site
        (B) LOCATION: 71..90
        (D) OTHER INFORMATION: /product= "OTHER"
            /note= "Xaa AT POSITIONS 71-90 CAN BE ANY AMINO ACIDS OR
            CAN BE ABSENT"

(ix) FEATURE:
        (A) NAME/KEY: Modified-site
        (B) LOCATION: 98..117
        (D) OTHER INFORMATION: /product= "OTHER"
            /note= "Xaa AT POSITIONS 98-117 CAN BE ANY AMINO ACIDS OR
            CAN BE ABSENT"

(xi) SEQUENCE DESCRIPTION: SEQ ID NO: 64:

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Cys Lys Phe Thr Ile Val Phe Cys Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
```

```
                35                  40                  45
Cys Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Pro Lys Lys Lys Arg Lys
            85                  90                  95

Val Xaa Xaa Xaa Xaa Xaa Xaa Xaa Xaa Xaa Xaa Xaa Xaa Xaa Xaa
            100                 105                 110

Xaa Xaa Xaa Xaa Xaa
        115
```

(2) INFORMATION FOR SEQ ID NO: 65:

(i) SEQUENCE CHARACTERISTICS:
        (A) LENGTH: 97 amino acids
        (B) TYPE: amino acid
        (C) STRANDEDNESS: not relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa AT POSITIONS 1-20 CAN BE ANY AMINO ACIDS OR
            CAN BE ABSENT"

(ix) FEATURE:
        (A) NAME/KEY: Modified-site
        (B) LOCATION: 21
        (D) OTHER INFORMATION: /product= "OTHER"
            /note= "CYS AT POSITION 21 CAN BE ABSENT"

(ix) FEATURE:
        (A) NAME/KEY: Modified-site
        (B) LOCATION: 28
        (D) OTHER INFORMATION: /product= "OTHER"
            /note= "CYS AT POSITION 28 CAN BE ABSENT"

(ix) FEATURE:
        (A) NAME/KEY: Modified-site
        (B) LOCATION: 29..48
        (D) OTHER INFORMATION: /product= "OTHER"
            /note= "Xaa AT POSITIONS 29-48 CAN BE ANY AMINO ACIDS OR
            CAN BE ABSENT"

(ix) FEATURE:
        (A) NAME/KEY: Modified-site
        (B) LOCATION: 49
        (D) OTHER INFORMATION: /product= "OTHER"
            /note= "CYS AT POSITION 49 CAN BE ABSENT"

(ix) FEATURE:
        (A) NAME/KEY: Modified-site
        (B) LOCATION: 50..69
        (D) OTHER INFORMATION: /product= "OTHER"
            /note= "Xaa AT POSITIONS 50-69 CAN BE ANY AMINO ACIDS OR
            CAN BE ABSENT"

(ix) FEATURE:
        (A) NAME/KEY: Modified-site
        (B) LOCATION: 70
        (D) OTHER INFORMATION: /product= "OTHER"
            /note= "Xaa AT POSITION 70 CAN BE TYR OR TRP OR CAN BE
            ABSENT"

(ix) FEATURE:
        (A) NAME/KEY: Modified-site
        (B) LOCATION: 78..97
        (D) OTHER INFORMATION: /product= "OTHER"
            /note= "Xaa AT POSITIONS 78-97 CAN BE ANY AMINO ACIDS OR
            CAN BE ABSENT"

(xi) SEQUENCE DESCRIPTION: SEQ ID NO: 65:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Cys Lys Phe Thr Ile Val Phe Cys Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Cys Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Pro Lys Lys Lys Arg Lys Val Xaa Xaa Xaa
65                  70                  75                  80

Xaa Xaa Xaa Xaa Xaa Xaa Xaa Xaa Xaa Xaa Xaa Xaa Xaa Xaa Xaa Xaa
            85                  90                  95

Xaa (2) INFORMATION FOR SEQ ID NO: 66:

(i) SEQUENCE CHARACTERISTICS:
        (A) LENGTH: 99 amino acids
        (B) TYPE: amino acid
        (C) STRANDEDNESS: not relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa AT POSITIONS 1-20 CAN BE ANY AMINO ACIDS OR
            CAN BE ABSENT"

(ix) FEATURE:
        (A) NAME/KEY: Modified-site
        (B) LOCATION: 21
        (D) OTHER INFORMATION: /product= "OTHER"
            /note= "CYS AT POSITION 21 CAN BE ABSENT"

(ix) FEATURE:
        (A) NAME/KEY: Modified-site
        (B) LOCATION: 22
        (D) OTHER INFORMATION: /product= "OTHER"
            /note= "Xaa AT POSITION 22 CAN BE TYR, TRP OR CAN BE
            ABSENT"

(ix) FEATURE:
        (A) NAME/KEY: Modified-site
        (B) LOCATION: 23..42
        (D) OTHER INFORMATION: /product= "OTHER"
            /note= "Xaa AT POSITIONS 23-42 CAN BE ANY AMINO ACIDS OR
            CAN BE ABSENT"

(ix) FEATURE:
        (A) NAME/KEY: Modified-site
        (B) LOCATION: 51..70
        (D) OTHER INFORMATION: /product= "OTHER"
            /note= "Xaa AT POSITIONS 51-70 CAN BE ANY AMINO ACIDS OR
            CAN BE ABSENT"

(ix) FEATURE:
        (A) NAME/KEY: Modified-site
        (B) LOCATION: 79
        (D) OTHER INFORMATION: /product= "OTHER"
            /note= "CYS AT POSITION 79 CAN BE ABSENT"

(ix) FEATURE:
        (A) NAME/KEY: Modified-site
        (B) LOCATION: 80..99
        (D) OTHER INFORMATION: /product= "OTHER"
            /note= "Xaa FROM 80-99 CAN BE ANY AMINO ACIDS OR CAN BE
            ABSENT"

(xi) SEQUENCE DESCRIPTION: SEQ ID NO: 66:

Xaa Xaa Xaa Xaa Xaa Xaa Xaa Xaa Xaa Xaa Xaa Xaa Xaa Xaa Xaa
1               5                   10                  15

Xaa Xaa Xaa Xaa Cys Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Gly Pro Lys Lys Arg
        35                  40                  45

Lys Val Xaa Xaa Xaa Xaa Xaa Xaa Xaa Xaa Xaa Xaa Xaa Xaa Xaa
50                  55                  60

Xaa Xaa Xaa Xaa Xaa Xaa Glu Ile Leu Asp Val Ser Pro Thr Cys Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa (2) INFORMATION FOR SEQ ID NO: 67:

(i) SEQUENCE CHARACTERISTICS:
        (A) LENGTH: 78 amino acids
        (B) TYPE: amino acid
        (C) STRANDEDNESS: not relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa FROM 1-20 CAN BE ANY AMINO ACIDS OR CAN BE
            ABSENT"

(ix) FEATURE:
        (A) NAME/KEY: Modified-site
        (B) LOCATION: 21
        (D) OTHER INFORMATION: /product= "OTHER"
            /note= "CYS AT POSITION 21 CAN BE ABSENT"

(ix) FEATURE:
        (A) NAME/KEY: Modified-site
        (B) LOCATION: 22
        (D) OTHER INFORMATION: /product= "OTHER"
            /note= "Xaa AT POSITION 22 CAN BE TYR, TRP OR CAN BE
            ABSENT"

(ix) FEATURE:
        (A) NAME/KEY: Modified-site
        (B) LOCATION: 30..49
        (D) OTHER INFORMATION: /product= "OTHER"
            /note= "Xaa AT POSITIONS 30-49 CAN BE ANY AMINO ACIDS OR
            CAN BE ABSENT"

(ix) FEATURE:
        (A) NAME/KEY: Modified-site
        (B) LOCATION: 58
        (D) OTHER INFORMATION: /product= "OTHER"
            /note= "CYS AT POSITION 58 CAN BE ABSENT"

(ix) FEATURE:
        (A) NAME/KEY: Modified-site
        (B) LOCATION: 59..78
        (D) OTHER INFORMATION: /product= "OTHER"
            /note= "Xaa AT POSITIONS 59-78 CAN BE ANY AMINO ACIDS OR
            CAN BE ABSENT"

(xi) SEQUENCE DESCRIPTION: SEQ ID NO: 67:

Xaa Xaa Xaa Xaa Xaa Xaa Xaa Xaa Xaa Xaa Xaa Xaa Xaa Xaa Xaa
1               5                   10                  15

Xaa Xaa Xaa Xaa Cys Xaa Pro Lys Lys Lys Arg Lys Val Xaa Xaa Xaa

```
                    20                  25                  30
Xaa Xaa Xaa Xaa Xaa Xaa Xaa Xaa Xaa Xaa Xaa Xaa Xaa Xaa Xaa
            35                  40                  45

Xaa Glu Ile Leu Asp Val Ser Pro Thr Cys Xaa Xaa Xaa Xaa Xaa
        50                  55                  60

Xaa Xaa Xaa Xaa Xaa Xaa Xaa Xaa Xaa Xaa Xaa Xaa Xaa
65                  70                  75

(2) INFORMATION FOR SEQ ID NO: 68:

(i) SEQUENCE CHARACTERISTICS:
        (A) LENGTH: 77 amino acids
        (B) TYPE: amino acid
        (C) STRANDEDNESS: not relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa AT POSITIONS 1-20 CAN BE ANY AMINO ACID OR
            CAN BE ABSENT"

(ix) FEATURE:
        (A) NAME/KEY: Modified-site
        (B) LOCATION: 21
        (D) OTHER INFORMATION: /product= "OTHER"
            /note= "CYS AT POSITION 21 CAN BE ABSENT"

(ix) FEATURE:
        (A) NAME/KEY: Modified-site
        (B) LOCATION: 28
        (D) OTHER INFORMATION: /product= "OTHER"
            /note= "CYS AT POSITION 28 CAN BE ABSENT"

(ix) FEATURE:
        (A) NAME/KEY: Modified-site
        (B) LOCATION: 29..48
        (D) OTHER INFORMATION: /product= "OTHER"
            /note= "Xaa AT POSITION 29-48 CAN BE ANY AMINO ACID OR
            CAN BE ABSENT"

(ix) FEATURE:
        (A) NAME/KEY: Modified-site
        (B) LOCATION: 57
        (D) OTHER INFORMATION: /product= "OTHER"
            /note= "CYS AT POSITION 57 CAN BE ABSENT"

(ix) FEATURE:
        (A) NAME/KEY: Modified-site
        (B) LOCATION: 58..77
        (D) OTHER INFORMATION: /product= "OTHER"
            /note= "Xaa AT POSITIONS 58-77 CAN BE ANY AMINO ACIDS OR
            CAN BE ABSENT"

(xi) SEQUENCE DESCRIPTION: SEQ ID NO: 68:

Xaa Xaa Xaa Xaa Xaa Xaa Xaa Xaa Xaa Xaa Xaa Xaa Xaa Xaa Xaa
1               5                   10                  15

Xaa Xaa Xaa Xaa Cys Lys Phe Thr Ile Val Phe Cys Xaa Xaa Xaa
            20                  25                  30

Xaa Xaa Xaa Xaa Xaa Xaa Xaa Xaa Xaa Xaa Xaa Xaa Xaa Xaa Xaa
            35                  40                  45

Glu Ile Leu Asp Val Pro Ser Thr Cys Xaa Xaa Xaa Xaa Xaa Xaa
        50                  55                  60

Xaa Xaa Xaa Xaa Xaa Xaa Xaa Xaa Xaa Xaa Xaa Xaa Xaa
65                  70                  75

(2) INFORMATION FOR SEQ ID NO: 69:
```

```
    (i) SEQUENCE CHARACTERISTICS:
        (A) LENGTH: 93 amino acids
        (B) TYPE: amino acid
        (C) STRANDEDNESS: not relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa AT POSITIONS 1-20 CAN BE ANY AMINO ACIDS OR
            CAN BE ABSENT"

(ix) FEATURE:
        (A) NAME/KEY: Modified-site
        (B) LOCATION: 21
        (D) OTHER INFORMATION: /product= "OTHER"
            /note= "Xaa AT POSITION 21 CAN BE TYR, TRP OR CAN BE
            ABSENT"

(ix) FEATURE:
        (A) NAME/KEY: Modified-site
        (B) LOCATION: 22..41
        (D) OTHER INFORMATION: /product= "OTHER"
            /note= "Xaa AT POSITIONS 22-41 CAN BE ANY AMINO ACIDS OR
            CAN BE ABSENT"

(ix) FEATURE:
        (A) NAME/KEY: Modified-site
        (B) LOCATION: 49..68
        (D) OTHER INFORMATION: /product= "OTHER"
            /note= "Xaa AT POSITIONS 49-68 CAN BE ANY AMINO ACIDS OR
            CAN BE ABSENT"

(ix) FEATURE:
        (A) NAME/KEY: Modified-site
        (B) LOCATION: 74..93
        (D) OTHER INFORMATION: /product= "OTHER"
            /note= "Xaa AT POSITIONS 74-93 CAN BE ANY AMINO ACIDS OR
            CAN BE ABSENT"

(xi) SEQUENCE DESCRIPTION: SEQ ID NO: 69:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Pro Lys Lys Lys Arg Lys Val
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Arg Gly Asp Met Phe Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa
                85                  90

(2) INFORMATION FOR SEQ ID NO: 70:

(i) SEQUENCE CHARACTERISTICS:
        (A) LENGTH: 94 amino acids
        (B) TYPE: amino acid
        (C) STRANDEDNESS: not relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa AT POSITIONS 1-20 CAN BE ANY AMINO ACIDS OR
```

```
            CAN BE ABSENT"

(ix) FEATURE:
         (A) NAME/KEY: Modified-site
         (B) LOCATION: 21
         (D) OTHER INFORMATION: /product= "OTHER"
             /note= "CYS AT POSITION 21 CAN BE ABSENT"

(ix) FEATURE:
         (A) NAME/KEY: Modified-site
         (B) LOCATION: 22..41
         (D) OTHER INFORMATION: /product= "OTHER"
             /note= "Xaa AT POSITIONS 22-41 CAN BE ANY AMINO ACIDS OR
             CAN BE ABSENT"

(ix) FEATURE:
         (A) NAME/KEY: Modified-site
         (B) LOCATION: 42
         (D) OTHER INFORMATION: /product= "OTHER"
             /note= "Xaa AT POSITION 42 CAN BE ANY AMINO ACID OR CAN
             BE ABSENT"

(ix) FEATURE:
         (A) NAME/KEY: Modified-site
         (B) LOCATION: 50..69
         (D) OTHER INFORMATION: /product= "OTHER"
             /note= "Xaa AT POSITIONS 50-69 CAN BE ANY AMINO ACID OR
             CAN BE ABSENT"

(ix) FEATURE:
         (A) NAME/KEY: Modified-site
         (B) LOCATION: 75..94
         (D) OTHER INFORMATION: /product= "OTHER"
             /note= "Xaa AT POSITIONS 75-94 CAN BE ANY AMINO ACIDS OR
             CAN BE ABSENT"

(xi) SEQUENCE DESCRIPTION: SEQ ID NO: 70:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Cys Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Pro Lys Lys Lys Arg Lys
        35                  40                  45

Val Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Arg Gly Asp Met Phe Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa
                85                  90

(2) INFORMATION FOR SEQ ID NO: 71:

(i) SEQUENCE CHARACTERISTICS:
        (A) LENGTH: 94 amino acids
        (B) TYPE: amino acid
        (C) STRANDEDNESS: not relevant
        (D) TOPOLOGY: linear (ii) MOLECULE TYPE: peptide (ix) FEATURE:
         (A) NAME/KEY: Modified-site
         (B) LOCATION: 1..20
         (D) OTHER INFORMATION: /product= "OTHER"
             /note= "Xaa CAN BE ANY AMINO ACID OR CAN BE ABSENT"

(ix) FEATURE:
         (A) NAME/KEY: Modified-site
         (B) LOCATION: 21
         (D) OTHER INFORMATION: /product= "OTHER"
             /note= "Xaa CAN BE TYR, TRP OR CAN BE ABSENT"

(ix) FEATURE:
```

(A) NAME/KEY: Modified-site
            (B) LOCATION: 22..41
            (D) OTHER INFORMATION: /product= "OTHER"
                /note= "Xaa CAN BE ANY AMINO ACIDS OR CAN BE ABSENT"

(ix) FEATURE:
            (A) NAME/KEY: Modified-site
            (B) LOCATION: 49..68
            (D) OTHER INFORMATION: /product= "OTHER"
                /note= "Xaa CAN BE ANY AMINO ACIDS OR CAN BE ABSENT"

(ix) FEATURE:
            (A) NAME/KEY: Modified-site
            (B) LOCATION: 75..94
            (D) OTHER INFORMATION: /product= "OTHER"
                /note= "Xaa CAN BE ANY AMINO ACIDS OR CAN BE ABSENT"

(xi) SEQUENCE DESCRIPTION: SEQ ID NO: 71:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Pro Lys Lys Lys Arg Lys Val
        35                  40                  45

Xaa Xaa Xaa Xaa Xaa Xaa Xaa Xaa Xaa Xaa Xaa Xaa Xaa Xaa Xaa
50                  55                  60

Xaa Xaa Xaa Xaa Gly Arg Gly Asp Ser Pro Xaa Xaa Xaa Xaa Xaa
65                  70                  75                  80

Xaa Xaa Xaa Xaa Xaa Xaa Xaa Xaa Xaa Xaa Xaa Xaa Xaa Xaa
                85                  90

(2) INFORMATION FOR SEQ ID NO: 72:

(i) SEQUENCE CHARACTERISTICS:
            (A) LENGTH: 94 amino acids
            (B) TYPE: amino acid
            (C) STRANDEDNESS: not relevant
            (D) TOPOLOGY: linear (ii) MOLECULE TYPE: peptide (ix) FEATURE:
            (A) NAME/KEY: Modified-site
            (B) LOCATION: 1..20
            (D) OTHER INFORMATION: /product= "OTHER"
                /note= "Xaa CAN BE ANY AMINO ACIDS OR CAN BE ABSENT"

(ix) FEATURE:
            (A) NAME/KEY: Modified-site
            (B) LOCATION: 21
            (D) OTHER INFORMATION: /product= "OTHER"
                /note= "CYS CAN BE ABSENT"

(ix) FEATURE:
            (A) NAME/KEY: Modified-site
            (B) LOCATION: 22
            (D) OTHER INFORMATION: /product= "OTHER"
                /note= "Xaa CAN BE TYR, TRP OR CAN BE ABSENT"

(ix) FEATURE:
            (A) NAME/KEY: Modified-site
            (B) LOCATION: 23..42
            (D) OTHER INFORMATION: /product= "OTHER"
                /note= "Xaa CAN BE ANY AMINO ACIDS OR CAN BE ABSENT"

(ix) FEATURE:
            (A) NAME/KEY: Modified-site
            (B) LOCATION: 50..69
            (D) OTHER INFORMATION: /product= "OTHER"
                /note= "Xaa CAN BE ANY AMINO ACIDS OR CAN BE ABSENT"

(ix) FEATURE:
            (A) NAME/KEY: Modified-site (B) LOCATION: 75..94
            (D) OTHER INFORMATION: /product= "OTHER"
                /note= "Xaa CAN BE ANY AMINO ACIDS OR CAN BE ABSENT"

(xi) SEQUENCE DESCRIPTION: SEQ ID NO: 72:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Cys Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Pro Lys Lys Lys Arg Lys
        35                  40                  45

Val Xaa Xaa Xaa Xaa Xaa Xaa Xaa Xaa Xaa Xaa Xaa Xaa Xaa Xaa
    50                  55                  60

Xaa Xaa Xaa Xaa Xaa Arg Gly Asp Ser Pro Xaa Xaa Xaa Xaa Xaa
65                  70                  75                  80

Xaa Xaa Xaa Xaa Xaa Xaa Xaa Xaa Xaa Xaa
                85                  90

(2) INFORMATION FOR SEQ ID NO: 73:

(i) SEQUENCE CHARACTERISTICS:
        (A) LENGTH: 116 amino acids
        (B) TYPE: amino acid
        (C) STRANDEDNESS: not relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "other"
            /note= "Xaa CAN BE ANY AMINO ACID OR CAN BE ABSENT"

(ix) FEATURE:
        (A) NAME/KEY: Modified-site
        (B) LOCATION: 27
        (D) OTHER INFORMATION: /product= "OTHER"
            /note= "CYS CAN BE ABSENT"

(ix) FEATURE:
        (A) NAME/KEY: Modified-site
        (B) LOCATION: 28..47
        (D) OTHER INFORMATION: /product= "OTHER"
            /note= "Xaa CAN BE ANY AMINO ACID OR CAN BE ABSENT"

(ix) FEATURE:
        (A) NAME/KEY: Modified-site
        (B) LOCATION: 48
        (D) OTHER INFORMATION: /product= "OTHER"
            /note= "CYS CAN BE ABSENT"

(ix) FEATURE:
        (A) NAME/KEY: Modified-site
        (B) LOCATION: 49..68
        (D) OTHER INFORMATION: /product= "OTHER"
            /note= "Xaa CAN BE ANY AMINO ACID OR CAN BE ABSENT"

(ix) FEATURE:
        (A) NAME/KEY: Modified-site
        (B) LOCATION: 69
        (D) OTHER INFORMATION: /product= "OTHER"
            /note= "Xaa AT POSITION 69 CAN BE TYR, TRP, OR CAN BE
            ABSENT"

(ix) FEATURE:
        (A) NAME/KEY: Modified-site
        (B) LOCATION: 70..89
        (D) OTHER INFORMATION: /product= "OTHER"
            /note= "Xaa CAN BE ANY AMINO ACIDS OR CAN BE ABSENT"

(ix) FEATURE:
        (A) NAME/KEY: Modified-site (B) LOCATION: 97..116
        (D) OTHER INFORMATION: /product= "OTHER"
            /note= "Xaa CAN BE ANY AMINO ACID OR CAN BE ABSENT"

(xi) SEQUENCE DESCRIPTION: SEQ ID NO: 73:

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Lys Phe Thr Ile Val Phe Cys Xaa Xaa Xaa Xaa
            20                  25                  30

Xaa Xaa Xaa Xaa Xaa Xaa Xaa Xaa Xaa Xaa Xaa Xaa Xaa Xaa Cys
        35                  40                  45

Xaa Xaa Xaa Xaa Xaa Xaa Xaa Xaa Xaa Xaa Xaa Xaa Xaa Xaa Xaa
 50                 55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Pro Lys Lys Lys Arg Lys Val
            85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa
        115

(2) INFORMATION FOR SEQ ID NO: 74:

(i) SEQUENCE CHARACTERISTICS:
        (A) LENGTH: 97 amino acids
        (B) TYPE: amino acid
        (C) STRANDEDNESS: not relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa CAN BE ANY AMINO ACID OR CAN BE ABSENT"

(ix) FEATURE:
        (A) NAME/KEY: Modified-site
        (B) LOCATION: 21
        (D) OTHER INFORMATION: /product= "OTHER"
            /note= "CYS CAN BE ABSENT"

(ix) FEATURE:
        (A) NAME/KEY: Modified-site
        (B) LOCATION: 28
        (D) OTHER INFORMATION: /product= "OTHER"
            /note= "CYS CAN BE ABSENT"

(ix) FEATURE:
        (A) NAME/KEY: Modified-site
        (B) LOCATION: 29..48
        (D) OTHER INFORMATION: /product= "OTHER"
            /note= "Xaa CAN BE ANY AMINO ACID OR CAN BE ABSENT"

(ix) FEATURE:
        (A) NAME/KEY: Active-site
        (B) LOCATION: 49
        (D) OTHER INFORMATION: /product= "OTHER"
            /note= "CYS CAN BE ABSENT"

(ix) FEATURE:
        (A) NAME/KEY: Modified-site
        (B) LOCATION: 50..69
        (D) OTHER INFORMATION: /product= "OTHER"
            /note= "Xaa CAN BE ANY AMINO ACID OR CAN BE ABSENT"

(ix) FEATURE:
        (A) NAME/KEY: Modified-site
        (B) LOCATION: 70

(D) OTHER INFORMATION: /product= "OTHER"
            /note= "Xaa CAN BE TYR, TRP OR CAN BE ABSENT"

(ix) FEATURE:
        (A) NAME/KEY: Modified-site
        (B) LOCATION: 78..97
        (D) OTHER INFORMATION: /product= "OTHER"
            /note= "Xaa CAN BE ANY AMINO ACID OR CAN BE ABSENT"

(xi) SEQUENCE DESCRIPTION: SEQ ID NO: 74:

Xaa Xaa Xaa Xaa Xaa Xaa Xaa Xaa Xaa Xaa Xaa Xaa Xaa Xaa Xaa
1               5                   10                  15

Xaa Xaa Xaa Xaa Cys Lys Phe Thr Ile Val Phe Cys Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Cys Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Pro Lys Lys Lys Arg Lys Val Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa (2) INFORMATION FOR SEQ ID NO: 75:

(i) SEQUENCE CHARACTERISTICS:
        (A) LENGTH: 97 amino acids
        (B) TYPE: amino acid
        (C) STRANDEDNESS: not relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa CAN BE ANY AMINO ACID OR CAN BE ABSENT"

(ix) FEATURE:
        (A) NAME/KEY: Modified-site
        (B) LOCATION: 21
        (D) OTHER INFORMATION: /product= "OTHER"
            /note= "Xaa CAN BE TYR, TRP OR CAN BE ABSENT"

(ix) FEATURE:
        (A) NAME/KEY: Modified-site
        (B) LOCATION: 22..41
        (D) OTHER INFORMATION: /product= "other"
            /note= "Xaa CAN BE ANY AMINO ACID OR CAN BE ABSENT"

(ix) FEATURE:
        (A) NAME/KEY: Modified-site
        (B) LOCATION: 50..69
        (D) OTHER INFORMATION: /product= "OTHER"
            /note= "Xaa CAN BE ANY AMINO ACID OR CAN BE ABSENT"

(ix) FEATURE:
        (A) NAME/KEY: Modified-site
        (B) LOCATION: 78..97
        (D) OTHER INFORMATION: /product= "OTHER"
            /note= "Xaa CAN BE ANY AMINO ACID OR CAN BE ABSENT"

(xi) SEQUENCE DESCRIPTION: SEQ ID NO: 75:

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

```
Xaa Xaa Xaa Xaa Xaa Xaa Xaa Xaa Xaa Gly Pro Lys Lys Lys Arg Lys
        35                  40                  45

Val Xaa Xaa Xaa Xaa Xaa Xaa Xaa Xaa Xaa Xaa Xaa Xaa Xaa Xaa
 50                  55                  60

Xaa Xaa Xaa Xaa Xaa Glu Ile Leu Asp Val Ser Pro Thr Xaa Xaa Xaa
 65                  70                  75                  80

Xaa Xaa Xaa Xaa Xaa Xaa Xaa Xaa Xaa Xaa Xaa Xaa Xaa Xaa Xaa
        85                  90                  95

Xaa
```

(2) INFORMATION FOR SEQ ID NO: 76:

(i) SEQUENCE CHARACTERISTICS:
        (A) LENGTH: 77 amino acids
        (B) TYPE: amino acid
        (C) STRANDEDNESS: not relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa CAN BE ANY AMINO ACIDS OR CAN BE ABSENT"

(ix) FEATURE:
        (A) NAME/KEY: Modified-site
        (B) LOCATION: 21
        (D) OTHER INFORMATION: /product= "OTHER"
            /note= "CYS CAN BE ABSENT"

(ix) FEATURE:
        (A) NAME/KEY: Modified-site
        (B) LOCATION: 22
        (D) OTHER INFORMATION: /product= "OTHER"
            /note= "Xaa CAN BE TYR, TRP OR CAN BE ABSENT"

(ix) FEATURE:
        (A) NAME/KEY: Modified-site
        (B) LOCATION: 30..49
        (D) OTHER INFORMATION: /product= "OTHER"
            /note= "Xaa CAN BE ANY AMINO ACID OR CAN BE ABSENT"

(ix) FEATURE:
        (A) NAME/KEY: Modified-site
        (B) LOCATION: 58..77
        (D) OTHER INFORMATION: /product= "OTHER"
            /note= "Xaa CAN BE ANY AMINO ACID OR CAN BE ABSENT"

(xi) SEQUENCE DESCRIPTION: SEQ ID NO: 76:

```
Xaa Xaa Xaa Xaa Xaa Xaa Xaa Xaa Xaa Xaa Xaa Xaa Xaa Xaa Xaa Xaa
 1                   5                  10                  15

Xaa Xaa Xaa Xaa Cys Xaa Pro Lys Lys Lys Arg Lys Val Xaa Xaa Xaa
                20                  25                  30

Xaa Xaa Xaa Xaa Xaa Xaa Xaa Xaa Xaa Xaa Xaa Xaa Xaa Xaa Xaa
        35                  40                  45

Xaa Glu Ile Leu Asp Val Ser Pro Thr Xaa Xaa Xaa Xaa Xaa Xaa Xaa
         50                  55                  60

Xaa Xaa Xaa Xaa Xaa Xaa Xaa Xaa Xaa Xaa Xaa Xaa Xaa
 65                  70                  75
```

(2) INFORMATION FOR SEQ ID NO: 77:

(i) SEQUENCE CHARACTERISTICS:
        (A) LENGTH: 75 amino acids
        (B) TYPE: amino acid
        (C) STRANDEDNESS: not relevant
        (D) TOPOLOGY: linear

```
    (ii) MOLECULE TYPE: peptide (ix) FEATURE:
         (A) NAME/KEY: Modified-site
         (B) LOCATION: 1..20
         (D) OTHER INFORMATION: /product= "OTHER"
             /note= "Xaa CAN BE ANY AMINO ACID OR CAN BE ABSENT"

(ix) FEATURE:
         (A) NAME/KEY: Modified-site
         (B) LOCATION: 27
         (D) OTHER INFORMATION: /product= "OTHER"
             /note= "CYS CAN BE ABSENT"

(ix) FEATURE:
         (A) NAME/KEY: Modified-site
         (B) LOCATION: 28..47
         (D) OTHER INFORMATION: /product= "OTHER"
             /note= "Xaa CAN BE ANY AMINO ACID AND CAN BE ABSENT"

(ix) FEATURE:
         (A) NAME/KEY: Modified-site
         (B) LOCATION: 56..75
         (D) OTHER INFORMATION: /product= "OTHER"
             /note= "Xaa CAN BE ANY AMINO ACID OR CAN BE ABSENT"

(xi) SEQUENCE DESCRIPTION: SEQ ID NO: 77:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Lys Phe Thr Ile Val Phe Cys Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Glu
        35                  40                  45

Ile Leu Asp Val Pro Ser Thr Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa
65                  70                  75

(2) INFORMATION FOR SEQ ID NO: 78:

(i) SEQUENCE CHARACTERISTICS:
        (A) LENGTH: 70 amino acids
        (B) TYPE: amino acid
        (C) STRANDEDNESS: not relevant
        (D) TOPOLOGY: circular (ii) MOLECULE TYPE: peptide (ix) FEATURE:
         (A) NAME/KEY: Modified-site
         (B) LOCATION: 1..20
         (D) OTHER INFORMATION: /product= "OTHER"
             /note= "Xaa CAN BE ANY CATIONIC AMINO ACIDS OR CAN BE
             ABSENT"

(ix) FEATURE:
         (A) NAME/KEY: Modified-site
         (B) LOCATION: 21..40
         (D) OTHER INFORMATION: /product= "OTHER"
             /note= "Xaa CAN BE ANY AMINO ACIDS OR CAN BE ABSENT"

(ix) FEATURE:
         (A) NAME/KEY: Modified-site
         (B) LOCATION: 51..70
         (D) OTHER INFORMATION: /product= "OTHER"
             /note= "Xaa CAN BE ANY AMINO ACIDS OR CAN BE ABSENT"

(xi) SEQUENCE DESCRIPTION: SEQ ID NO: 78:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
```

```
                    20                  25                  30
Xaa Xaa Xaa Xaa Xaa Xaa Xaa Xaa Cys Glu Ile Leu Asp Val Pro Ser
        35                  40                  45
Thr Cys Xaa Xaa Xaa Xaa Xaa Xaa Xaa Xaa Xaa Xaa Xaa Xaa Xaa Xaa
            50                  55                  60
Xaa Xaa Xaa Xaa Xaa Xaa
65                  70
```

(2) INFORMATION FOR SEQ ID NO: 79:

(i) SEQUENCE CHARACTERISTICS:
        (A) LENGTH: 71 amino acids
        (B) TYPE: amino acid
        (C) STRANDEDNESS: not relevant
        (D) TOPOLOGY: circular (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa CAN BE ANY CATIONIC AMINO ACID OR CAN BE
            ABSENT"

(ix) FEATURE:
        (A) NAME/KEY: Modified-site
        (B) LOCATION: 21..40
        (D) OTHER INFORMATION: /product= "OTHER"
            /note= "Xaa CAN BE ANY AMINO ACID OR CAN BE ABSENT"

(ix) FEATURE:
        (A) NAME/KEY: Modified-site
        (B) LOCATION: 52..71
        (D) OTHER INFORMATION: /product= "OTHER"
            /note= "Xaa CAN BE ANY AMINO ACID OR CAN BE ABSENT"

(xi) SEQUENCE DESCRIPTION: SEQ ID NO: 79:

```
Xaa Xaa Xaa Xaa Xaa Xaa Xaa Xaa Xaa Xaa Xaa Xaa Xaa Xaa Xaa Xaa
1                   5                  10                  15
Xaa Xaa Xaa Xaa Xaa Xaa Xaa Xaa Xaa Xaa Xaa Xaa Xaa Xaa Xaa Xaa
                    20                  25                  30
Xaa Xaa Xaa Xaa Xaa Xaa Xaa Xaa Cys His Ala Ile Arg Gly Asp Thr
        35                  40                  45
Phe Ala Cys Xaa Xaa Xaa Xaa Xaa Xaa Xaa Xaa Xaa Xaa Xaa Xaa Xaa
            50                  55                  60
Xaa Xaa Xaa Xaa Xaa Xaa Xaa
65                  70
```

(2) INFORMATION FOR SEQ ID NO: 80:

(i) SEQUENCE CHARACTERISTICS:
        (A) LENGTH: 14 amino acids
        (B) TYPE: amino acid
        (C) STRANDEDNESS: not relevant
        (D) TOPOLOGY: linear (ii) MOLECULE TYPE: peptide (iii) HYPOTHETICAL: NO (iv) ANTI-SENSE: NO (ix) FEATURE:
        (A) NAME/KEY: Modified-site
        (B) LOCATION: 14
        (D) OTHER INFORMATION: /product= "OTHER"
            /note= "G AT POSITION 14 CAN BE ABSENT"

(xi) SEQUENCE DESCRIPTION: SEQ ID NO: 80:

```
Gly Lys Phe Thr Ile Val Phe Asp Asp Asp Asp Asp Gly
1               5                   10
```

(2) INFORMATION FOR SEQ ID NO: 81:

(i) SEQUENCE CHARACTERISTICS:
        (A) LENGTH: 28 amino acids
        (B) TYPE: amino acid
        (C) STRANDEDNESS: not relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 81:

```
Lys Phe Thr Ile Val Phe Gly Gly Gly Leu Phe Glu Ala Ile Ala Glu
1               5                   10                  15
Phe Ile Glu Gly Gly Trp Glu Gly Leu Ile Glu Gly
            20                  25
```

(2) INFORMATION FOR SEQ ID NO: 82:

(i) SEQUENCE CHARACTERISTICS:
        (A) LENGTH: 27 amino acids
        (B) TYPE: amino acid
        (C) STRANDEDNESS: not relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 82:

```
Gly Leu Phe Glu Ala Ile Ala Glu Phe Ile Glu Gly Gly Trp Glu Gly
1               5                   10                  15
Leu Ile Glu Gly Cys Lys Phe Thr Ile Val Phe
            20                  25
```

(2) INFORMATION FOR SEQ ID NO: 83:

(i) SEQUENCE CHARACTERISTICS:
        (A) LENGTH: 38 amino acids
        (B) TYPE: amino acid
        (C) STRANDEDNESS: not relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 83:

```
Cys Gly Tyr Gly Gly Gly Gly Gly Pro Lys Lys Lys Arg Lys Val
1               5                   10                  15
Gly Gly Gly Leu Phe Glu Ala Ile Ala Glu Phe Ile Glu Gly Gly Trp
            20                  25                  30
Glu Gly Leu Ile Glu Gly
        35
```

(2) INFORMATION FOR SEQ ID NO: 84:

(i) SEQUENCE CHARACTERISTICS:

(A) LENGTH: 38 amino acids
        (B) TYPE: amino acid
        (C) STRANDEDNESS: not relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 84:

Gly Leu Phe Glu Ala Ile Ala Glu Phe Ile Glu Gly Gly Trp Glu Gly
1               5                   10                  15

Leu Ile Glu Gly Gly Tyr Gly Gly Gly Gly Gly Pro Lys Lys
            20                  25                  30

Lys Arg Lys Val Gly Gly
        35

(2) INFORMATION FOR SEQ ID NO: 85:

(i) SEQUENCE CHARACTERISTICS:
        (A) LENGTH: 20 amino acids
        (B) TYPE: amino acid
        (C) STRANDEDNESS: not relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 85:

Lys Phe Thr Thr Ile Val Phe Cys Gly Tyr Gly Pro Lys Lys Lys Arg
1               5                   10                  15

Lys Val Gly Gly
        20

(2) INFORMATION FOR SEQ ID NO: 86:

(i) SEQUENCE CHARACTERISTICS:
        (A) LENGTH: 19 amino acids
        (B) TYPE: amino acid
        (C) STRANDEDNESS: not relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 86:

Cys Gly Tyr Gly Pro Lys Lys Lys Arg Lys Val Gly Gly Lys Phe Thr
1               5                   10                  15

Ile Val Phe (2) INFORMATION FOR SEQ ID NO: 87:

(i) SEQUENCE CHARACTERISTICS:
        (A) LENGTH: 30 amino acids
        (B) TYPE: amino acid
        (C) STRANDEDNESS: not relevant
        (D) TOPOLOGY: linear (ii) MOLECULE TYPE: peptide (iii) HYPOTHETICAL: NO

```
        (iv) ANTI-SENSE: NO (ix) FEATURE:
              (A) NAME/KEY: Modified-site
              (B) LOCATION: 30
              (D) OTHER INFORMATION: /product= "OTHER"
                    /note= "G AT POSITION 30 CAN BE ABSENT"

(xi) SEQUENCE DESCRIPTION: SEQ ID NO: 87:

Lys Lys Lys Lys Lys Lys Lys Lys Lys Lys Lys Lys Lys Lys Lys Lys
  1               5                  10                  15

Gly Lys Phe Thr Ile Val Phe Asp Asp Asp Asp Asp Gly
             20                  25                  30

(2) INFORMATION FOR SEQ ID NO: 88:

(i) SEQUENCE CHARACTERISTICS:
              (A) LENGTH: 44 amino acids
              (B) TYPE: amino acid
              (C) STRANDEDNESS: not relevant
              (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 88:

Lys Lys Lys Lys Lys Lys Lys Lys Lys Lys Lys Lys Lys Lys Lys
  1               5                  10                  15

Lys Phe Thr Ile Val Phe Gly Gly Gly Leu Phe Glu Ala Ile Ala Glu
             20                  25                  30

Phe Ile Glu Gly Gly Trp Glu Gly Leu Ile Glu Gly
         35                  40

(2) INFORMATION FOR SEQ ID NO: 89:

(i) SEQUENCE CHARACTERISTICS:
              (A) LENGTH: 43 amino acids
              (B) TYPE: amino acid
              (C) STRANDEDNESS: not relevant
              (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 89:

Lys Lys Lys Lys Lys Lys Lys Lys Lys Lys Lys Lys Lys Lys Lys Lys
  1               5                  10                  15

Gly Leu Phe Glu Ala Ile Ala Glu Phe Ile Glu Gly Gly Trp Glu Gly
             20                  25                  30

Leu Ile Glu Gly Cys Lys Phe Thr Ile Val Phe
         35                  40

(2) INFORMATION FOR SEQ ID NO: 90:

(i) SEQUENCE CHARACTERISTICS:
              (A) LENGTH: 54 amino acids
              (B) TYPE: amino acid
              (C) STRANDEDNESS: not relevant
              (D) TOPOLOGY: linear (ii) MOLECULE TYPE: peptide (iii) HYPOTHETICAL: NO
```

(iv) ANTI-SENSE: NO (xi) SEQUENCE DESCRIPTION: SEQ ID NO: 90:

Lys Lys Lys Lys Lys Lys Lys Lys Lys Lys Lys Lys Lys Lys Lys
1               5                   10                  15

Gly Leu Phe Glu Ala Ile Ala Glu Phe Ile Glu Gly Trp Glu Gly
                20                  25                  30

Leu Ile Glu Gly Gly Gly Tyr Gly Gly Gly Gly Pro Lys Lys
            35                  40                  45

Lys Arg Lys Val Gly Gly
        50

(2) INFORMATION FOR SEQ ID NO: 91:

(i) SEQUENCE CHARACTERISTICS:
        (A) LENGTH: 36 amino acids
        (B) TYPE: amino acid
        (C) STRANDEDNESS: not relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 91:

Lys Lys Lys Lys Lys Lys Lys Lys Lys Lys Lys Lys Lys Lys Lys
1               5                   10                  15

Lys Phe Thr Thr Ile Val Phe Cys Gly Tyr Gly Pro Lys Lys Arg
                20                  25                  30

Lys Val Gly Gly
        35

(2) INFORMATION FOR SEQ ID NO: 92:

(i) SEQUENCE CHARACTERISTICS:
        (A) LENGTH: 37 amino acids
        (B) TYPE: amino acid
        (C) STRANDEDNESS: not relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 92:

Lys Lys Lys Lys Lys Lys Lys Lys Lys Lys Lys Lys Lys Lys Lys
1               5                   10                  15

Gly Gly Cys Gly Tyr Gly Pro Lys Lys Arg Lys Val Gly Gly Lys
                20                  25                  30

Phe Thr Ile Val Phe
        35

(2) INFORMATION FOR SEQ ID NO: 93:

(i) SEQUENCE CHARACTERISTICS:
        (A) LENGTH: 56 amino acids
        (B) TYPE: amino acid
        (C) STRANDEDNESS: not relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 93:

Lys Lys Lys Lys Lys Lys Lys Lys Lys Lys Lys Lys Lys Lys Lys
1               5                   10                  15

Gly Gly Cys Gly Tyr Gly Gly Gly Gly Gly Pro Lys Lys Lys Arg
            20                  25                  30

Lys Val Gly Gly Gly Leu Phe Glu Ala Ile Ala Glu Phe Ile Glu Gly
        35                  40                  45

Gly Trp Glu Gly Leu Ile Glu Gly
    50                  55

(2) INFORMATION FOR SEQ ID NO: 94:

(i) SEQUENCE CHARACTERISTICS:
        (A) LENGTH: 24 amino acids
        (B) TYPE: amino acid
        (C) STRANDEDNESS: not relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 94:

Ser Ser Asp Asp Glu Ala Thr Ala Asp Ser Gln His Ser Thr Pro Pro
1               5                   10                  15

Lys Lys Lys Arg Lys Val Gly Gly
                20

(2) INFORMATION FOR SEQ ID NO: 95:

(i) SEQUENCE CHARACTERISTICS:
        (A) LENGTH: 40 amino acids
        (B) TYPE: amino acid
        (C) STRANDEDNESS: not relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 95:

Lys Lys Lys Lys Lys Lys Lys Lys Lys Lys Lys Lys Lys Lys Lys
1               5                   10                  15

Ser Ser Asp Asp Glu Ala Thr Ala Asp Ser Gln His Ser Thr Pro Pro
            20                  25                  30

Lys Lys Lys Arg Lys Val Gly Gly
        35                  40

(2) INFORMATION FOR SEQ ID NO: 96:

(i) SEQUENCE CHARACTERISTICS:
        (A) LENGTH: 25 amino acids
        (B) TYPE: amino acid
        (C) STRANDEDNESS: not relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 96:

Met Ser Tyr Tyr His His His His His His Asp Tyr Asp Ile Pro Thr
1               5                   10                  15

Thr Glu Asn Leu Tyr Phe Gln Gly Ser
            20                  25

(2) INFORMATION FOR SEQ ID NO: 97:

(i) SEQUENCE CHARACTERISTICS:
            (A) LENGTH: 37 amino acids
            (B) TYPE: amino acid
            (C) STRANDEDNESS: not relevant
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 97:

Met Ser Tyr Tyr His His His His His His Asp Tyr Asp Ile Pro Thr
1               5                   10                  15

Thr Glu Asn Leu Tyr Phe Gln Gly Ser Gly Tyr Gly Pro Lys Lys Lys
            20                  25                  30

Arg Lys Val Gly Gly
        35

(2) INFORMATION FOR SEQ ID NO: 98:

(i) SEQUENCE CHARACTERISTICS:
            (A) LENGTH: 30 amino acids
            (B) TYPE: amino acid
            (C) STRANDEDNESS: not relevant
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 98:

Met Ser Tyr Tyr His His His His His His Asp Tyr Asp Ile Pro Thr
1               5                   10                  15

Thr Glu Asn Leu Tyr Phe Gln Ser Lys Phe Thr Ile Val Phe
            20                  25                  30

(2) INFORMATION FOR SEQ ID NO: 99:

(i) SEQUENCE CHARACTERISTICS:
            (A) LENGTH: 44 amino acids
            (B) TYPE: amino acid
            (C) STRANDEDNESS: not relevant
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 99:

Met Ser Tyr Tyr His His His His His His Asp Tyr Asp Ile Pro Thr
1               5                   10                  15

Thr Glu Asn Leu Tyr Phe Gln Ser Gly Leu Phe Glu Ala Ile Ala Glu

```
                    20                  25                  30

Phe Ile Glu Gly Gly Trp Glu Gly Leu Ile Glu Gly
        35                  40

(2) INFORMATION FOR SEQ ID NO: 100:

(i) SEQUENCE CHARACTERISTICS:
        (A) LENGTH: 30 amino acids
        (B) TYPE: amino acid
        (C) STRANDEDNESS: not relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 100:

Met Ser Tyr Tyr His His His His His His Asp Tyr Asp Ile Pro Thr
1               5                   10                  15

Thr Glu Asn Leu Tyr Phe Gln Ser Arg Gly Asp Ser Pro Cys
            20                  25                  30

(2) INFORMATION FOR SEQ ID NO: 101:

(i) SEQUENCE CHARACTERISTICS:
        (A) LENGTH: 10 amino acids
        (B) TYPE: amino acid
        (C) STRANDEDNESS: not relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 101:

Met Ser Tyr Tyr His His His His His His
1               5                   10

(2) INFORMATION FOR SEQ ID NO: 102:

(i) SEQUENCE CHARACTERISTICS:
        (A) LENGTH: 22 amino acids
        (B) TYPE: amino acid
        (C) STRANDEDNESS: not relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 102:

Met Ser Tyr Tyr His His His His His His Gly Tyr Gly Pro Lys Lys
1               5                   10                  15

Lys Arg Lys Val Gly Gly
            20

(2) INFORMATION FOR SEQ ID NO: 103:

(i) SEQUENCE CHARACTERISTICS:
        (A) LENGTH: 16 amino acids
        (B) TYPE: amino acid
        (C) STRANDEDNESS: not relevant
        (D) TOPOLOGY: linear
```

(ii) MOLECULE TYPE: peptide (iii) HYPOTHETICAL: NO (iv) ANTI-SENSE: NO (xi) SEQUENCE DESCRIPTION: SEQ ID NO: 103:

Met Ser Tyr Tyr His His His His His His Lys Phe Thr Ile Val Phe
1               5                   10                  15

(2) INFORMATION FOR SEQ ID NO: 104:

(i) SEQUENCE CHARACTERISTICS:
            (A) LENGTH: 30 amino acids
            (B) TYPE: amino acid
            (C) STRANDEDNESS: not relevant
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 104:

Met Ser Tyr Tyr His His His His His His Gly Leu Phe Glu Ala Ile
1               5                   10                  15

Ala Glu Phe Ile Glu Gly Gly Trp Glu Gly Leu Ile Glu Gly
            20                  25                  30

(2) INFORMATION FOR SEQ ID NO: 105:

(i) SEQUENCE CHARACTERISTICS:
            (A) LENGTH: 16 amino acids
            (B) TYPE: amino acid
            (C) STRANDEDNESS: not relevant
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 105:

Met Ser Tyr Tyr His His His His His His Arg Gly Asp Ser Pro Cys
1               5                   10                  15

(2) INFORMATION FOR SEQ ID NO: 106:

(i) SEQUENCE CHARACTERISTICS:
            (A) LENGTH: 6 amino acids
            (B) TYPE: amino acid
            (C) STRANDEDNESS: not relevant
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 106:

His His His His His His
1               5

(2) INFORMATION FOR SEQ ID NO: 107:

(i) SEQUENCE CHARACTERISTICS:
            (A) LENGTH: 16 amino acids
            (B) TYPE: amino acid (C) STRANDEDNESS: not relevant
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 107:

Gly Gly Gly Gly Gly Tyr Gly Pro Lys Lys Lys Arg Lys Val Gly Gly
1               5                   10                  15

(2) INFORMATION FOR SEQ ID NO: 108:

(i) SEQUENCE CHARACTERISTICS:
            (A) LENGTH: 12 amino acids
            (B) TYPE: amino acid
            (C) STRANDEDNESS: not relevant
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 108:

Gly Gly Tyr Gly Pro Lys Lys Lys Arg Lys Val Gly
1               5                   10

(2) INFORMATION FOR SEQ ID NO: 109:

(i) SEQUENCE CHARACTERISTICS:
            (A) LENGTH: 14 amino acids
            (B) TYPE: amino acid
            (C) STRANDEDNESS: not relevant
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 109:

Gly Cys Gly Tyr Gly Pro Lys Lys Lys Arg Lys Val Gly Gly
1               5                   10

(2) INFORMATION FOR SEQ ID NO: 110:

(i) SEQUENCE CHARACTERISTICS:
            (A) LENGTH: 9 amino acids
            (B) TYPE: amino acid
            (C) STRANDEDNESS: not relevant
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 110:

Gly Gly Arg Gly Asp Met Phe Gly Gly
1               5

(2) INFORMATION FOR SEQ ID NO: 111:

(i) SEQUENCE CHARACTERISTICS:
            (A) LENGTH: 22 amino acids
            (B) TYPE: amino acid (C) STRANDEDNESS: not relevant
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 111:

Gly Tyr Gly Pro Lys Lys Lys Arg Lys Val Gly Gly Gly Gly Gly Arg
1               5                   10                  15

Gly Asp Met Phe Gly Gly
            20

(2) INFORMATION FOR SEQ ID NO: 112:

(i) SEQUENCE CHARACTERISTICS:
            (A) LENGTH: 20 amino acids
            (B) TYPE: amino acid
            (C) STRANDEDNESS: not relevant
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 112:

Gly Leu Phe Gly Ala Ile Ala Gly Phe Ile Glu Asn Gly Trp Glu Gly
1               5                   10                  15

Met Ile Asp Gly
            20

(2) INFORMATION FOR SEQ ID NO: 113:

(i) SEQUENCE CHARACTERISTICS:
            (A) LENGTH: 20 amino acids
            (B) TYPE: amino acid
            (C) STRANDEDNESS: not relevant
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 113:

Gly Leu Phe Glu Ala Ile Ala Glu Phe Ile Glu Gly Gly Trp Glu Gly
1               5                   10                  15

Leu Ile Glu Gly
            20

(2) INFORMATION FOR SEQ ID NO: 114:

(i) SEQUENCE CHARACTERISTICS:
            (A) LENGTH: 20 amino acids
            (B) TYPE: amino acid
            (C) STRANDEDNESS: not relevant
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 114:

```
Gly Leu Phe Lys Ala Ile Ala Lys Phe Ile Lys Gly Gly Trp Lys Gly
1               5                   10                  15
Leu Ile Lys Gly
            20
```

(2) INFORMATION FOR SEQ ID NO: 115:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: <Unknown>

(ii) MOLECULE TYPE: peptide (iii) HYPOTHETICAL: NO (iv) ANTI-SENSE: NO (xi) SEQUENCE DESCRIPTION: SEQ ID NO: 115:

```
Gly Tyr Gly Pro Lys Lys Lys Arg Lys Val Gly Gly
1               5                   10
```

(2) INFORMATION FOR SEQ ID NO: 116:

(i) SEQUENCE CHARACTERISTICS:
        (A) LENGTH: 31 amino acids
        (B) TYPE: amino acid
        (C) STRANDEDNESS: not relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 116:

```
Lys Lys Lys Lys Lys Lys Lys Lys Lys Lys Lys Lys Lys Lys Lys
1               5                   10                  15
Gly Gly Cys Gly Tyr Gly Pro Lys Lys Lys Arg Lys Val Gly Gly
                20                  25                  30
```

(2) INFORMATION FOR SEQ ID NO: 117:

(i) SEQUENCE CHARACTERISTICS:
        (A) LENGTH: 36 amino acids
        (B) TYPE: amino acid
        (C) STRANDEDNESS: not relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 117:

```
Lys Lys Lys Lys Lys Lys Lys Lys Lys Lys Lys Lys Lys Lys Lys Lys
1               5                   10                  15
Cys Gly Tyr Gly Pro Lys Lys Arg Lys Val Gly Gly Gly Arg
                20                  25                  30
Gly Asp Ser Pro
            35
```

(2) INFORMATION FOR SEQ ID NO: 118:

(i) SEQUENCE CHARACTERISTICS:
        (A) LENGTH: 25 amino acids (B) TYPE: amino acid
            (C) STRANDEDNESS: not relevant
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 118:

Lys Lys Lys Lys Lys Lys Lys Lys Lys Lys Lys Lys Lys Lys Lys
1               5                   10                  15
Gly Gly Arg Gly Asp Ser Pro Cys Gly
            20                  25

(2) INFORMATION FOR SEQ ID NO: 119:

(i) SEQUENCE CHARACTERISTICS:
            (A) LENGTH: 25 amino acids
            (B) TYPE: amino acid
            (C) STRANDEDNESS: not relevant
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 119:

Gly Arg Gly Asp Ser Pro Cys Gly Gly Lys Lys Lys Lys Lys Lys
1               5                   10                  15
Lys Lys Lys Lys Lys Lys Lys Lys Lys
            20                  25

(2) INFORMATION FOR SEQ ID NO: 120:

(i) SEQUENCE CHARACTERISTICS:
            (A) LENGTH: 22 amino acids
            (B) TYPE: amino acid
            (C) STRANDEDNESS: not relevant
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 120:

Cys Gly Tyr Gly Pro Lys Lys Lys Arg Lys Val Gly Gly Gly Arg
1               5                   10                  15
Gly Asp Ser Pro Cys Gly
            20

(2) INFORMATION FOR SEQ ID NO: 121:

(i) SEQUENCE CHARACTERISTICS:
            (A) LENGTH: 7 amino acids
            (B) TYPE: amino acid
            (C) STRANDEDNESS: not relevant
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 121:

```
Asn Leu Ser Val Ser Val Gly
1               5
```

(2) INFORMATION FOR SEQ ID NO: 122:

(i) SEQUENCE CHARACTERISTICS:
        (A) LENGTH: 6 amino acids
        (B) TYPE: amino acid
        (C) STRANDEDNESS: not relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 122:

```
Arg Gly Asp Asn Leu Ser
1               5
```

(2) INFORMATION FOR SEQ ID NO: 123:

(i) SEQUENCE CHARACTERISTICS:
        (A) LENGTH: 14 amino acids
        (B) TYPE: amino acid
        (C) STRANDEDNESS: not relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 123:

```
Cys Gly Tyr Gly Arg Lys Lys Arg Arg Gln Arg Arg Arg Gly
1               5                   10
```